US011186647B2

(12) United States Patent
Fan et al.

(10) Patent No.: US 11,186,647 B2
(45) Date of Patent: *Nov. 30, 2021

(54) CHIMERIC ANTIGEN RECEPTORS TARGETING BCMA AND METHODS OF USE THEREOF

(71) Applicant: Legend Biotech USA Inc., Wilmington, DE (US)

(72) Inventors: Xiaohu Fan, Edmonton (CA); Qiuchuan Zhuang, Jiangsu (CN); Pingyan Wang, Anhui (CN); Lin Wang, Jiangsu (CN); Lei Yang, Anhui (CN); Jiaying Hao, Jiangsu (CN)

(73) Assignee: LEGEND BIOTECH USA INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/168,100

(22) Filed: Feb. 4, 2021

(65) Prior Publication Data

US 2021/0163615 A1 Jun. 3, 2021

Related U.S. Application Data

(63) Continuation of application No. 16/303,587, filed as application No. PCT/CN2017/096938 on Aug. 10, 2017.

(30) Foreign Application Priority Data

Aug. 10, 2016 (WO) ................ PCT/CN2016/094408

(51) Int. Cl.
*C07K 16/28* (2006.01)
*C07K 14/725* (2006.01)
*C07K 14/705* (2006.01)
*C07K 16/30* (2006.01)
*A61K 35/17* (2015.01)
*C12N 5/0783* (2010.01)
*C07K 19/00* (2006.01)
*C12N 5/10* (2006.01)
*C12N 15/62* (2006.01)
*C12N 15/63* (2006.01)

(52) U.S. Cl.
CPC .......... *C07K 16/2878* (2013.01); *A61K 35/17* (2013.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/70596* (2013.01); *C07K 16/2803* (2013.01); *C07K 16/2887* (2013.01); *C07K 16/2896* (2013.01); *C07K 16/30* (2013.01); *C07K 16/3061* (2013.01); *C07K 19/00* (2013.01); *C12N 5/0636* (2013.01); *C12N 5/10* (2013.01); *C12N 15/62* (2013.01); *C12N 15/63* (2013.01); *C07K 2317/22* (2013.01); *C07K 2317/31* (2013.01); *C07K 2317/35* (2013.01); *C07K 2317/569* (2013.01); *C07K 2317/622* (2013.01); *C07K 2319/02* (2013.01); *C07K 2319/03* (2013.01); *C07K 2319/21* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| 10,934,363 | B2 | 3/2021 | Fan et al. |
|---|---|---|---|
| 2010/0136018 | A1 | 6/2010 | Dolk et al. |
| 2012/0034160 | A1 | 2/2012 | Ghayur et al. |
| 2013/0156769 | A1 | 6/2013 | Kufer et al. |
| 2014/0099340 | A1 | 4/2014 | June et al. |
| 2014/0161828 | A1 | 6/2014 | Armitage et al. |
| 2015/0038684 | A1 | 2/2015 | Jensen |
| 2016/0046724 | A1 | 2/2016 | Brogdon et al. |
| 2018/0230225 | A1 | 8/2018 | Fan et al. |
| 2020/0078399 | A1 | 3/2020 | Fan et al. |
| 2021/0261675 | A1 | 8/2021 | Fan et al. |

FOREIGN PATENT DOCUMENTS

| AU | 2016305075 B2 | 10/2019 |
|---|---|---|
| CN | 103483453 A | 1/2014 |
| CN | 104136458 A | 11/2014 |
| CN | 104379179 A | 2/2015 |
| CN | 104583230 A | 4/2015 |
| CN | 105143263 A | 12/2015 |
| CN | 105384825 A | 3/2016 |
| CN | 105658671 A | 6/2016 |

(Continued)

OTHER PUBLICATIONS

Agaugue et al., 2015, "Development of Safer & Optimized CAR-T Cells Using Lentiviral Vectors", Cancer—Immunotherapy, Cancer Vaccines I, Abstract 224, Molecular Therapy (May 2015), vol. 23, Supplement 1, p. S88.

(Continued)

*Primary Examiner* — Brad Duffy
(74) *Attorney, Agent, or Firm* — Jones Day

(57) ABSTRACT

The present application provides single-domain antibodies targeting BCMA, and chimeric antigen receptors (such as monovalent CAR, and multivalent CAR including bi-epitope CAR) comprising one or more anti-BCMA single-domain antibodies. Further provided are engineered immune effector cells (such as T cells) comprising the chimeric antigen receptors. Pharmaceutical compositions, kits and methods of treating cancer are also provided.

21 Claims, 25 Drawing Sheets

Specification includes a Sequence Listing.

(56) References Cited

FOREIGN PATENT DOCUMENTS

| | | |
|---|---|---|
| CN | 105777911 A | 7/2016 |
| CN | 108395481 A | 8/2018 |
| CN | 109306014 A | 2/2019 |
| EP | 3029067 A1 | 6/2016 |
| JP | 2015-504306 A | 2/2015 |
| JP | 2015-513394 A | 5/2015 |
| WO | WO 1998024893 A2 | 6/1998 |
| WO | WO 2008074867 A2 | 6/2008 |
| WO | WO 2008074867 A3 | 6/2008 |
| WO | WO 2011154453 A1 | 12/2011 |
| WO | WO 2013123061 A1 | 8/2013 |
| WO | WO 2013126729 A1 | 8/2013 |
| WO | WO 2013154760 A1 | 10/2013 |
| WO | WO 2014011988 A2 | 1/2014 |
| WO | WO 2014011988 A3 | 1/2014 |
| WO | WO 2014089335 A2 | 6/2014 |
| WO | WO 2014089335 A3 | 6/2014 |
| WO | WO 2014122143 A1 | 8/2014 |
| WO | WO 2014153270 A1 | 9/2014 |
| WO | WO 2014165707 A2 | 10/2014 |
| WO | WO 2014165707 A3 | 10/2014 |
| WO | WO 2015052538 A1 | 4/2015 |
| WO | WO 2015120187 A1 | 8/2015 |
| WO | WO 2015142675 A2 | 9/2015 |
| WO | WO 2015142675 A3 | 9/2015 |
| WO | WO 2016014565 A2 | 1/2016 |
| WO | WO 2016014565 A3 | 1/2016 |
| WO | WO 2016014789 A2 | 1/2016 |
| WO | WO 2016094304 A2 | 6/2016 |
| WO | WO 2017025038 A1 | 2/2017 |
| WO | WO 2018028647 A1 | 2/2018 |
| WO | WO 2018193394 A1 | 10/2018 |
| WO | WO 2019001474 A1 | 1/2019 |
| WO | WO 2019133969 A2 | 7/2019 |
| WO | WO 2019133969 A3 | 7/2019 |
| WO | WO 2019157496 A1 | 8/2019 |
| WO | WO 2021037221 A1 | 3/2021 |
| WO | WO 2021037222 A1 | 3/2021 |
| WO | WO 2021121228 A1 | 6/2021 |

OTHER PUBLICATIONS

Chang et al 2015, "Chimeric antigen receptor-modified T cells against several target antigens in multiple myeloma", Cancer Research, (Aug. 1, 2015) vol. 75, No. 15, Supp. Suppl. 1, Abstract No. 3149, 106th Annual Meeting of the American Association for Cancer Research, AACR 2015, Philadelphia, PA, United States.
Deaglio et al., 2007, "CD38/CD19: a lipid raft-dependent signaling complex in human B cells", Blood, 109(12):5390-5398.
Grada et al., 2013, "TanCAR: A Novel Bispecific Chimeric Antigen Receptor for Cancer Immunotherapy", Mol Ther Nucleic Acids, 2(7):e105.
Hegde et al., 2016, "Tandem CAR T cells targeting HER2 and IL13Rα2 mitigate tumor antigen escape", J Clin Invest, 126(8):3036-3052.
Hoffmann et al., 2005, "Serial killing of tumor cells by cytotoxic T cells redirected with a CD19-/CD3-bispecific single-chain antibody construct", Int J Cancer, 115(1):98-104.
International Preliminary Report on Patentability Chapter I for International Patent Application No. PCT/CN2016/094408 (Pub No. WO 2017025038) dated Feb. 13, 2018.
International Preliminary Report on Patentability Chapter I for International Patent Application No. PCT/CN2017/096938 (Pub No. WO 2018028647) dated Feb. 12, 2019.
International Search Report and Written Opinion for International Patent Application No. PCT/CN2016/094408 (Pub No. WO 2017025038) dated Nov. 18, 2016.
International Search Report and Written Opinion for International Patent Application No. PCT/CN2017/096938 (Pub No. WO 2018028647) dated Nov. 8, 2017.
Jamnani et al., 2014, "T cells expressing VHH-directed oligoclonal chimeric HER2 antigen receptors: towards tumor-directed oligoclonal T cell therapy", Biochim Biophys Acta., 1840(1):378-386 (Epub 2013).
Kalled, 2005, "The role of BAFF in immune function and implications for autoimmunity", Immunol Rev., 204:43-54.
Knonpleva et al., 1998, "Ligation of cell surface CD38 protein with agonistic monoclonal antibody induces a cell growth signal in myeloid leukemia cells", J Immunol., 161(9):4702-4708.
Lin et al., 2004, "Flow cytometric immunophenotypic analysis of 306 cases of multiple myeloma", Am J Clin Pathol., 121(4):482-488.
Lokhorst et al., 2015, "Targeting CD38 with Daratumumab Monotherapy in Multiple Myeloma", N Engl J Med., 373(13):1207-1219.
Mackay et al., 2003, "BAFF and APRIL: a tutorial on B cell survival", Annu Rev Immunol, 21:231-264 (Epub 2001).
Neri et al., 2007, "Neutralizing B-cell activating factor antibody improves survival and inhibits osteoclastogenesis in a severe combined immunodeficient human multiple myeloma model", Clin Cancer Res., 13(19):5903-5909.
Novak et al., 2004, "Expression of BCMA, TACI, and BAFF-R in multiple myeloma: a mechanism for growth and survival", Blood, 103(2):689-694 (Epub 2003).
Oden et al., 2015, "Potent anti-tumor response by targeting B cell maturation antigen (BCMA) in a mouse model of multiple myeloma", Mol Oncol., 9(7):1348-1358.
Ramadoss et al., 2015, "An anti-B cell maturation antigen bispecific antibody for multiple myeloma", J Am Chem Soc., 137(16):5288-5291.
Thompson et al., 2000, "BAFF binds to the tumor necrosis factor receptor-like molecule B cell maturation antigen and is important for maintaining the peripheral B cell population", J Exp Med., 192(1):129-135.
Brentjens et al., 2013, "CD19-targeted T cells rapidly induce molecular remissions in adults with chemotherapy-refractory acute lymphoblastic leukemia", Sci Transl Med., 5(177):177ra38 (11 pages).
De Munter et al., 2018, "Nanobody Based Dual Specific CARs", Int J Mol Sci., 19(2):403 (11 pages).
Grupp et al., 2013, "Chimeric antigen receptor-modified T cells for acute lymphoid leukemia", N Engl J Med., 368(16):1509-1518.
Kalos et al., 2011, "T cells with chimeric antigen receptors have potent antitumor effects and can establish memory in patients with advanced leukemia", Sci Transl Med., 3(95):95ra73 (13 pages).
Kijanka et al., 2015, "Nanobody-based cancer therapy of solid tumors", Nanomedicine (Lond), 10(1):161-174.
Liu et al., 2014, "Thermal stability and refolding capability of shark derived single domain antibodies", Mol Immunol., 59(2):194-199.
Wang et al., 2013, "Construction and selection of camelized human sdAbs library against TNF-α", Military Medical Sciences, 37(5):339-344, English abstract only.
Yan et al., 2015, "Characterization and applications of Nanobodies against human procalcitonin selected from a novel naïve Nanobody phage display library", J Nanobiotechnology, 13:33 (11 pages).
Revets et al., 2005, "Nanobodies as novel agents for cancer therapy," Expert Opin. Biol. Ther., 5(1):111-124.
Schmitz et al., 2013, "Structural evaluation of EGFR inhibition mechanisms for nanobodies/VHH domains," Structure, 21(7):1214-1224.
Ajina et al., 2018, "Strategies to Address Chimeric Antigen Receptor Tonic Signaling," Mol. Cancer Ther., 17(9):1795-1815.
Bluhm et al., 2018, "CAR T Cells with Enhanced Sensitivity to B Cell Maturation Antigen for the Targeting of B Cell Non-Hodgkin's Lymphoma and Multiple Myeloma," Mol. Ther., 26(8):1906-1920.
Fan et al., 2019, "FP-182: Preclinical assessment of LCAR-B38M, a novel BCMA-targeting chimeric antigen receptor (CAR)-T cell therapy in relapsed/refractory multiple myeloma," 17th International Myeloma Workshop, Sep. 12-15, 2019, Clinical Lymphoma, Myeloma & Leukemia, 19(10):e160.
GenBank Reference NP_054373.1, nef protein [Simian immunodeficiency virus], Aug. 13, 2018 (2 pages).

(56) References Cited

OTHER PUBLICATIONS

International Search Report and Written Opinion for International Patent Application No. PCT/CN2020/136570 (Pub No. WO 2021121228) dated Mar. 11, 2021 (15 pages).

International Search Report and Written Opinion for International Patent Application No. PCT/CN2020/112181 (Pub No. WO 2021037221) dated Oct. 28, 2020 (12 pages).

International Search Report and Written Opinion for International Patent Application No. PCT/CN2020/112182 (Pub No. WO 2021037222) dated Dec. 3, 2020 (11 pages).

Lee et al., 1998, "Identification of an immunoreceptor tyrosine-based activation motif of K1 transforming protein of Kaposi's sarcoma-associated herpesvirus," Mol. Cell Biol., 18(9):5219-5228.

Loskog et al., 2006, "Addition of the CD28 signaling domain to chimeric T-cell receptors enhances chimeric T-cell resistance to T regulatory cells," Leukemia, ;20(10):1819-1828.

Manrique et al., 2017, "Endocytic sorting motif interactions involved in Nef-mediated downmodulation of CD4 and CD3," Nat. Commun., 8(1):442 (14 pages).

Nomura et al., 2014, "Identification of SIV Nef CD8(+) T cell epitopes restricted by a MHC class I haplotype associated with lower viral loads in a macaque AIDS model," Biochem. Biophys. Res. Commun., 450(2):942-947.

Schaefer et al., 2002, "The conserved process of TCR/CD3 complex down-modulation by SIV Nef is mediated by the central core, not endocytic motifs," Virology, 302(1):106-122.

Yu et al., 2019, "Next generation chimeric antigen receptor T cells: safety strategies to overcome toxicity," Mol. Cancer, 18(1):125 (13 pages).

|  |  | 1 | 11 | 21 | 31 | 41 | 51 |
|---|---|---|---|---|---|---|---|
| (SEQ ID NO: 396) | | MLQMAGQCSQ | NEYFDSLLHA | CIPCQLRCSS | NTPPLTCQRY | CNASVTNSVK | GTNA |

Disulfide bonds

| Code | Position | | | | | | |
|---|---|---|---|---|---|---|---|
| 269EP001 | 1-10 | MLQMAGQCSQ | (SEQ ID NO: 389) | | | | |
| 269EP002 | 8-21 | CSQ | NEYFDSLLHA | C | (SEQ ID NO: 390) | | |
| 269EP003 | 11-23 | | NEYFDSLLHA | CIP | (SEQ ID NO: 391) | | |
| 269EP004 | 20-30 | | A | CIPCQLRCSS | (SEQ ID NO: 392) | | |
| 269EP005 | 24-42 | | | CQLRCSS | NTPPLTCQRY | CN | (SEQ ID NO: 393) |
| 269EP006 | 36-43 | | | | TCQRY | CNA | (SEQ ID NO: 394) |
| 269EP007 | 43-54 | | | | | ASVTNSVK | GTNA (SEQ ID NO: 395) |

SEQUENCE LISTING

<160> NUMBER OF SEQ ID NOS: 399

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Asp Tyr Tyr Ala Ile Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Thr Tyr Gly Met Ala
1               5

<210> SEQ ID NO 3
<211> LENGTH: 5
<212> TYPE: PRT
<213> ORGANISM: Artificial Sequence
<220> FEATURE:

```
<223> OTHER INFORMATION: Synthetic Construct

<400> SEQUENCE: 3

Thr Phe Thr Met Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ile Asn Ala Met Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ser Ile Val Met Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Arg Ala Val Ile Val
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Asp Val Met Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asn Asp His Met Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 9

Lys Asn Thr Val Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ser His Val Met Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Thr Tyr Phe Met Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Ile Asn Val Met Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Thr Phe Thr Met Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Ile Asn Ala Met Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 15

Lys Asn Thr Val Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Ser Ile Val Met Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Thr Phe Thr Met Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Lys Asn Thr Val Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ile Asn Thr Met Asp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Lys Asn Thr Val Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21
```

```
Asp Tyr Trp Met His
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Ser Asn Thr Met Ala
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Thr Phe Thr Met Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Val Ala Ala Ile Ser Leu
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Lys Asn Thr Val Ala
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Thr Phe Thr Met Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27
```

```
Thr Phe Thr Met Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Ser Ile Val Met Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Thr Phe Thr Met Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Thr Phe Thr Met Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Thr Phe Thr Met Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct

<400> SEQUENCE: 32

Thr Phe Thr Met Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Thr Phe Thr Met Gly
```

```
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Asn His Val Met Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asn Tyr Ile Leu Ala
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Thr Phe Thr Met Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Thr Phe Thr Met Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Construct

<400> SEQUENCE: 38

Asn Asn Phe Val Met Gly
1               5

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Cys Ile Ser Arg Ser Asp Gly Ser Thr Tyr Tyr Ala Asp Ser Val Lys
1               5                   10                  15
```

Gly

<210> SEQ ID NO 40
<211> LENGTH: 19
<212> TYPE: PRT
<213> ORGANISM: Artificial Sequence
<220> FEATURE:
<223> OTHER INFORMATION: Synthetic Construct

<400> SEQUENCE: 40

Ser Lys Ala Ser Met Asn Tyr Ser Gly Arg Thr Tyr Tyr Ala Asp Ser
1               5                   10                  15

Val Lys Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Ala Ile Ser Leu Ser Pro Thr Leu Ala Tyr Tyr Ala Glu Ser Val Lys
1               5                   10                  15

Gly

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Ser Ile Arg Gly Leu Gly Arg Thr Asn Tyr Asp Asp Ser Val Lys Gly
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Synthetic Construct

<400> SEQUENCE: 43

Ala Ile Met Trp Asn Asp Gly Ile Thr Tyr Leu Gln Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Phe Ile Lys Pro Ser Asp Gly Thr Ile Tyr Tyr Ile Asp Ser Leu Lys
1               5                   10                  15

Gly

<210> SEQ ID NO 45
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 45

Ala Ile Met Trp Asn Asp Gly Ile Thr Tyr Leu Gln Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Ala Ile Asp Trp Ser Gly Arg Thr Thr Asn Tyr Ala Asp Pro Val Glu
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic Construct

<400> SEQUENCE: 47

Ser Ile Thr Trp Asp Gly Arg Thr Thr Tyr Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Val Ile Gly Trp Arg Asp Ile Ser Thr Ser Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Gly Ile Ala Trp Ser Gly Gly Ser Thr Ala Tyr Ala Asp Ser Val Lys
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct
```

-continued

<400> SEQUENCE: 50

Ala Val Thr Arg Asp Gly Arg Lys Ser Cys Gly Asp Ser Val Lys Gly
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Ser Ile Thr Trp Asp Gly Arg Ser Ala Tyr Tyr Ala Glu Ser Val Lys
1               5                   10                  15

Gly

<210> SEQ ID NO 52
<211> LENGTH: 16
<212> TYPE: PRT
<213> ORGANISM: Artificial Sequence
<220> FEATURE:
<223> OTHER INFORMATION: Synthetic Construct

<400> SEQUENCE: 52

Thr Ile Thr Arg Gly Gly Ser Thr Asn Tyr Gly Pro Ser Val Lys Gly
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Ser Ile Thr Cys Asp Gly Arg Thr Thr Tyr Tyr Ala Asn Ser Val Asn
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Ala Ile Met Trp Asn Asp Gly Leu Thr Tyr Leu Gln Gly Ser Val Lys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

Ala Ile Ser Leu Ser Pro Thr Leu Ala Tyr Tyr Ala Glu Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct

<400> SEQUENCE: 56

Ser Ile Thr Trp Asp Gly Arg Thr Thr Tyr Tyr Ala Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

Ala Ile Ser Leu Ser Pro Thr Leu Ala Tyr Tyr Ala Glu Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Ser Ile Thr Cys Asp Gly Arg Thr Thr Tyr Tyr Ala Asn Ser Val Lys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Ser Ile Asp Thr Ser Gly Gln Thr Thr Tyr Tyr Ala Asp Ser Leu Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

Ser Thr Thr Trp Asn Gly Arg Ser Thr Tyr Tyr Ala Asp Ser Val Lys
1               5                   10                  15

Gly

<210> SEQ ID NO 61
<211> LENGTH: 15
<212> TYPE: PRT

<213> ORGANISM: Artificial Sequence
<220> FEATURE:
<223> OTHER INFORMATION: Synthetic Construct

<400> SEQUENCE: 61

Asp Ile Ser Gly Gly Arg Thr Asn Tyr Ala Asp Ser Val Lys Gly
1               5                   10                  15

<210> SEQ ID NO 62
<211> LENGTH: 21
<212> TYPE: PRT
<213> ORGANISM: Artificial Sequence
<220> FEATURE:
<223> OTHER INFORMATION: Synthetic Construct

<400> SEQUENCE: 62

Phe Thr Ile Ser Arg Asp Asn Ala Lys Asn Thr Val Val Leu Gln Met
1               5                   10                  15

Asn Ser Leu Lys Pro
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct

<400> SEQUENCE: 63

Ser Ile Thr Trp Asp Gly Arg Thr Thr Tyr Tyr Ala Asp Ser Val Lys
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Ala Ile Ser Leu Ser Pro Thr Leu Ala Tyr Tyr Ala Glu Ser Val Lys
1               5                   10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: Synthetic Construct

<400> SEQUENCE: 65

Ala Ile Ser Leu Ser Pro Thr Leu Ala Tyr Tyr Ala Glu Ser Val Lys
1               5                   10                  15

Gly Lys Gly

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

```
Ala Ile Met Trp Asn Asp Gly Ile Thr Tyr Leu Gln Asp Ser Val Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Synthetic Construct

<400> SEQUENCE: 67

Ala Ile Asn Leu Ser Pro Thr Leu Thr Tyr Tyr Ala Glu Ser Val Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Ser Ile Thr Leu Ile Pro Thr Phe Pro Tyr Tyr Ala Tyr Ser Val Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic Construct

<400> SEQUENCE: 69

Ala Ile Ser Leu Ser Pro Thr Leu Ala Tyr Tyr Ala Glu Ser Val Lys
1               5                   10                  15

Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Ala Ile Ser Leu Ser Pro Thr Leu Ala Tyr Tyr Ala Glu Ser Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct

<400> SEQUENCE: 71

Val Ile Gly Trp Arg Asp Ile Asn Ala Ser Tyr Ala Asp Ser Val Lys
1               5                   10                  15
```

Gly

<210> SEQ ID NO 72
<211> LENGTH: 17
<212> TYPE: PRT
<213> ORGANISM: Artificial Sequence
<220> FEATURE:
<223> OTHER INFORMATION: Synthetic Construct

<400> SEQUENCE: 72

Val Ile Gly Trp Arg Asp Ile Ser Thr Ser Tyr Ala Asp Ser Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

<400> SEQUENCE: 73

His Ile Ser Arg Ser Gly Gly Lys Ser Gly Tyr Gly Asp Ser Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Ala Ile Ser Leu Ser Pro Thr Leu Ala Tyr Tyr Ala Glu Ser Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

Ala Ile Ser Leu Ser Pro Thr Leu Ala Tyr Tyr Ala Glu Pro Val Lys
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic Construct

<400> SEQUENCE: 76

Ala Ile Ser Leu Ser Pro Thr Leu Ala Tyr Tyr Val Glu Ser Val Lys
1               5                   10                  15

Gly

<210> SEQ ID NO 77

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Ala Gly Ala Asp Cys Ser Gly Tyr Leu Arg Asp Tyr Glu Phe
1               5                   10

<210> SEQ ID NO 78
<211> LENGTH: 18
<212> TYPE: PRT
<213> ORGANISM: Artificial Sequence
<220> FEATURE:
<223> OTHER INFORMATION: Synthetic Construct

<400> SEQUENCE: 78

Ala Gly Thr Gly Cys Ser Thr Tyr Gly Cys Phe Asp Ala Gln Ile Ile
1               5                   10                  15

Asp Tyr

<210> SEQ ID NO 79
<211> LENGTH: 13
<212> TYPE: PRT
<213> ORGANISM: Artificial Sequence
<220> FEATURE:
<223> OTHER INFORMATION: Synthetic Construct

<400> SEQUENCE: 79

Ala Asp Arg Lys Ser Val Met Ser Ile Arg Pro Asp Tyr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic Construct

<400> SEQUENCE: 80

Val Tyr Val Thr Leu Leu Gly Gly Val Asn Arg Asp Tyr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Ala Ser Lys Gly Arg Tyr Ser Glu Tyr Glu Tyr
1               5                   10

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

Ala Ser Pro Glu Asp Trp Tyr Thr Asp Trp Ile Asp Trp Ser Ile Tyr
1               5                   10                  15

Arg
```

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Ala Ser Lys Gly Arg Tyr Ser Glu Tyr Glu Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic Construct

<400> SEQUENCE: 84

Val Leu Arg Ala Trp Ile Ser Tyr Asp Asn Asp Tyr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Construct

<400> SEQUENCE: 85

Asp Leu Gly Lys Trp Pro Ala Gly Pro Ala Asp Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Ala Arg Arg Ile Asp Ala Ala Asp Phe Asp Ser
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Construct

<400> SEQUENCE: 87

Ser Arg Gly Ile Glu Val Glu Glu Phe Gly Ala
1               5                   10

<210> SEQ ID NO 88
<211> LENGTH: 16
<212> TYPE: PRT
<213> ORGANISM: Artificial Sequence
<220> FEATURE:
<223> OTHER INFORMATION: Synthetic Construct

<400> SEQUENCE: 88

Asp Gly Trp Gly Ala Thr Thr Leu Asp Tyr Thr Tyr Gly Met Asp Tyr
1               5                   10                  15

```
<210> SEQ ID NO 89
<211> LENGTH: 12
<212> TYPE: PRT
<213> ORGANISM: Artificial Sequence
<220> FEATURE:
<223> OTHER INFORMATION: Synthetic Construct

<400> SEQUENCE: 89

Asp Arg Lys Ser Val Met Ser Ile Arg Pro Asp Tyr
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct

<400> SEQUENCE: 90

Glu Arg Leu Asp Gly Ser Gly Tyr Gly Tyr Glu Tyr Asp Tyr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic Construct

<400> SEQUENCE: 91

Tyr Arg Lys Ser Ile Met Ser Ile Gln Pro Asp Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Construct

<400> SEQUENCE: 92

Asp Arg Lys Ser Val Met Ser Ile Arg Pro Asp Tyr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic Construct

<400> SEQUENCE: 93

Arg Arg Ile Asp Ala Ala Asp Phe Asp Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic Construct

<400> SEQUENCE: 94

Leu Gly Lys Trp Pro Ala Gly Pro Ala Asp Tyr
1               5                   10
```

```
<210> SEQ ID NO 95
<211> LENGTH: 12
<212> TYPE: PRT
<213> ORGANISM: Artificial Sequence
<220> FEATURE:
<223> OTHER INFORMATION: Synthetic Construct

<400> SEQUENCE: 95

Asp Arg Lys Ser Val Met Ser Ile Arg Pro Asp Tyr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic Construct

<400> SEQUENCE: 96

Leu Gly Lys Trp Pro Ala Gly Ser Ala Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic Construct

<400> SEQUENCE: 97

Arg Tyr Arg Gly Gly Thr Trp Tyr Gly Met Ala Asn
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Construct

<400> SEQUENCE: 98

Leu Gly Lys Trp Pro Ala Gly Pro Ala Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic Construct

<400> SEQUENCE: 99

Asp Arg Lys Ser Val Met Ser Ile Arg Pro Asp Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic Construct

<400> SEQUENCE: 100

Asp Arg Lys Ser Val Met Ser Ile Arg Pro Asp Tyr
1               5                   10

<210> SEQ ID NO 101
```

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 101

Thr Ala Ser Cys His Leu Phe Gly Leu Gly Ser Gly Ala Phe Val Ser
1               5                   10                  15

<210> SEQ ID NO 102
<211> LENGTH: 10
<212> TYPE: PRT
<213> ORGANISM: Artificial Sequence
<220> FEATURE:
<223> OTHER INFORMATION: Synthetic Construct

<400> SEQUENCE: 102

Ser Lys Asp Arg Tyr Ser Glu Tyr Glu Tyr
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 103

Lys Asn Gly Gly Pro Val Asp Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Ser Lys Gly Arg Tyr Ser Glu Tyr Glu Tyr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic Construct

<400> SEQUENCE: 105

Glu Arg Lys Ser Val Met Ala Ile Pro Pro Asp Tyr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic Construct

<400> SEQUENCE: 106

Tyr Arg Lys Tyr Leu Met Ser Ile Leu Pro Asp Tyr
1               5                   10

<210> SEQ ID NO 107
<211> LENGTH: 18
```

```
<212> TYPE: PRT
<213> ORGANISM: Artificial Sequence
<220> FEATURE:
<223> OTHER INFORMATION: Synthetic Construct

<400> SEQUENCE: 107

Asn Arg Asn Ser Gln Arg Val Ile Ala Ala Leu Ser Trp Ile Gly Met
1               5                   10                  15

Asn Tyr

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct

<400> SEQUENCE: 108

Arg Arg Ile Asp Ala Ala Asp Phe Asp Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Arg Arg Ile Asp Ala Thr Asp Phe Asp Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Arg Arg Ile Asp Ala Ala Asp Phe Asp Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct

<400> SEQUENCE: 111

Pro Leu Trp Tyr Gly Ser Pro Thr Leu Ile Asp Tyr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic Construct

<400> SEQUENCE: 112

Asp Arg Lys Ser Val Met Ser Ile Arg Pro Asp Tyr
1               5                   10

<210> SEQ ID NO 113
```

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 113

Asp Arg Lys Ser Val Met Ser Ile Arg Pro Asp Tyr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Construct

<400> SEQUENCE: 114

Asp Arg Lys Ser Val Met Ser Ile Arg Pro Asp Tyr
1               5                   10

<210> SEQ ID NO 115
<211> LENGTH: 122
<212> TYPE: PRT
<213> ORGANISM: Artificial Sequence
<220> FEATURE:
<223> OTHER INFORMATION: Synthetic Construct

<400> SEQUENCE: 115

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser
        115                 120

<210> SEQ ID NO 116
<211> LENGTH: 128
<212> TYPE: PRT
<213> ORGANISM: Artificial Sequence
<220> FEATURE:
<223> OTHER INFORMATION: Synthetic Construct

<400> SEQUENCE: 116

Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60
```

```
Ser Val Lys Gly Arg Phe Thr Ile Ala Arg Asp Asn Ala Lys Asn Met
 65                  70                  75                  80

Val Phe Leu Gln Met Asn Asn Leu Lys Pro Glu Asp Thr Ala Val Tyr
                 85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
        115                 120                 125
```

<210> SEQ ID NO 117
<211> LENGTH: 118
<212> TYPE: PRT
<213> ORGANISM: Artificial Sequence
<220> FEATURE:
<223> OTHER INFORMATION: Synthetic Construct

<400> SEQUENCE: 117

```
Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Phe Thr Met Gly
             20                  25                  30

Trp Phe Arg Gln Ala Pro Gly Lys Glu Arg Glu Phe Val Ala Ala Ile
         35                  40                  45

Ser Leu Ser Pro Thr Leu Ala Tyr Tyr Ala Glu Ser Val Lys Gly Arg
     50                  55                  60

Phe Thr Ile Ser Arg Asp Asn Ala Lys Asn Thr Val Val Leu Gln Met
 65                  70                  75                  80

Asn Ser Leu Lys Pro Glu Asp Thr Ala Leu Tyr Tyr Cys Ala Ala Asp
                 85                  90                  95

Arg Lys Ser Val Met Ser Ile Arg Pro Asp Tyr Trp Gly Gln Gly Thr
            100                 105                 110

Gln Val Thr Val Ser Ser
        115
```

<210> SEQ ID NO 118
<211> LENGTH: 120
<212> TYPE: PRT
<213> ORGANISM: Artificial Sequence
<220> FEATURE:
<223> OTHER INFORMATION: Synthetic Construct

<400> SEQUENCE: 118

```
Ala Val Gln Leu Val Asp Ser Gly Gly Gly Leu Val Gln Pro Gly Gly
  1               5                  10                  15

Ser Leu Arg Leu Ser Cys Val Ala Ser Gly Gly Ile Phe Val Ile Asn
             20                  25                  30

Ala Met Gly Trp Tyr Arg Gln Ala Pro Gly Lys Gln Arg Glu Leu Val
         35                  40                  45

Ala Ser Ile Arg Gly Leu Gly Thr Asn Tyr Asp Asp Ser Val Lys
     50                  55                  60

Gly Arg Phe Thr Ile Ser Arg Asp Asn Ala Asn Asn Thr Val Tyr Leu
 65                  70                  75                  80

Gln Met Asn Ser Leu Glu Pro Glu Asp Thr Ala Val Tyr Tyr Cys Thr
                 85                  90                  95

Val Tyr Val Thr Leu Leu Gly Gly Val Asn Arg Asp Tyr Trp Gly Gln
            100                 105                 110

Gly Thr Gln Val Thr Val Ser Ser
        115
```

<210> SEQ ID NO 119
<211> LENGTH: 119
<212> TYPE: PRT
<213> ORGANISM: Artificial Sequence
<220> FEATURE:
<223> OTHER INFORMATION: Synthetic Construct

<400> SEQUENCE: 119

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Tyr Glu Tyr Trp Gly Gln Gly
            100                 105                 110

Thr Gln Val Thr Val Ser Ser
        115
```

<210> SEQ ID NO 120
<211> LENGTH: 128
<212> TYPE: PRT
<213> ORGANISM: Artificial Sequence
<220> FEATURE:
<223> OTHER INFORMATION: Synthetic Construct

<400> SEQUENCE: 120

```
Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
            20                  25                  30

Val Ile Val Trp Phe Arg Gln Ala Pro Gly Lys Gly Arg Glu Gly Val
        35                  40                  45

Ser Phe Ile Lys Pro Ser Asp Gly Thr Ile Tyr Tyr Ile Asp Ser Leu
    50                  55                  60

Lys Gly Arg Phe Thr Ile Ser Ser Asp Ile Ala Lys Asn Thr Val Tyr
65                  70                  75                  80

Leu Gln Met Lys Ser Leu Glu Ser Glu Asp Ser Ala Val Tyr Tyr Cys
                85                  90                  95

Ala Ala Ser Pro Glu Asp Trp Tyr Thr Asp Trp Ile Asp Trp Ser Ile
            100                 105                 110

Tyr Arg Trp Gln His Trp Gly Gln Gly Thr Gln Val Thr Val Ser Ser
        115                 120                 125
```

<210> SEQ ID NO 121
<211> LENGTH: 119
<212> TYPE: PRT
<213> ORGANISM: Artificial Sequence
<220> FEATURE:
<223> OTHER INFORMATION: Synthetic Construct

<400> SEQUENCE: 121

```
Glu Val Gln Leu Val Glu Ser Gly Gly Gly Met Val Gln Ala Gly Asp
1               5                   10                  15

Ser Leu Arg Leu Ser Cys Val Gln Ser Thr Tyr Thr Val Asn Ser Asp
            20                  25                  30

Val Met Gly Trp Phe Arg Gln Ala Pro Gly Lys Glu Arg Glu Phe Val
            35                  40                  45

Gly Ala Ile Met Trp Asn Asp Gly Ile Thr Tyr Leu Gln Asp Ser Val
        50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser
        115
```

<210> SEQ ID NO 122
<211> LENGTH: 120
<212> TYPE: PRT
<213> ORGANISM: Artificial Sequence
<220> FEATURE:
<223> OTHER INFORMATION: Synthetic Construct

<400> SEQUENCE: 122

```
Ala Val Gln Leu Val Glu Ser Gly Gly Gly Leu Val Gln Ala Gly Asp
1               5                   10                  15

Ser Leu Arg Leu Ser Cys Thr Ala Ser Gly Ala Thr Leu Thr Asn Asp
            20                  25                  30

His Met Ala Trp Phe Arg Gln Ala Pro Gly Lys Gly Arg Glu Phe Val
            35                  40                  45

Ala Ala Ile Asp Trp Ser Gly Arg Thr Thr Asn Tyr Ala Asp Pro Val
        50                  55                  60

Glu Gly Arg Phe Thr Ile Ser Arg Asn Asn Ala Lys Asn Thr Val Tyr
65                  70                  75                  80

Leu Glu Met Asn Ser Leu Lys Leu Glu Asp Thr Ala Val Tyr Tyr Cys
                85                  90                  95

Ala Val Leu Arg Ala Trp Ile Ser Tyr Asp Asn Asp Tyr Trp Gly Gln
            100                 105                 110

Gly Thr Gln Val Thr Val Ser Ser
        115                 120
```

<210> SEQ ID NO 123
<211> LENGTH: 120
<212> TYPE: PRT
<213> ORGANISM: Artificial Sequence
<220> FEATURE:
<223> OTHER INFORMATION: Synthetic Construct

<400> SEQUENCE: 123

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
            35                  40                  45

Ala Ser Ile Thr Trp Asp Gly Arg Thr Thr Tyr Tyr Ala Asp Ser Val
```

```
                50              55              60
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                 85                  90                  95

Ala Asp Leu Gly Lys Trp Pro Ala Gly Pro Ala Asp Tyr Trp Gly Gln
                100                 105                 110

Gly Thr Gln Val Thr Val Ser Ser
            115                 120

<210> SEQ ID NO 124
<211> LENGTH: 119
<212> TYPE: PRT
<213> ORGANISM: Artificial Sequence
<220> FEATURE:
<223> OTHER INFORMATION: Synthetic Construct

<400> SEQUENCE: 124

Gln Val Lys Leu Glu Glu Ser Gly Gly Gly Leu Val Gln Ala Gly Arg
  1               5                  10                  15

Ser Leu Arg Leu Ser Cys Ala Ala Ser Glu His Thr Phe Ser Ser His
                 20                  25                  30

Val Met Gly Trp Phe Arg Gln Ala Pro Gly Lys Glu Arg Glu Ser Val
             35                  40                  45

Ala Val Ile Gly Trp Arg Asp Ile Ser Thr Ser Tyr Ala Asp Ser Val
         50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Ala Asp Phe Asp Ser Trp Gly Gln Gly
                100                 105                 110

Thr Gln Val Thr Val Ser Ser
            115

<210> SEQ ID NO 125
<211> LENGTH: 119
<212> TYPE: PRT
<213> ORGANISM: Artificial Sequence
<220> FEATURE:
<223> OTHER INFORMATION: Synthetic Construct

<400> SEQUENCE: 125

Ala Val Gln Leu Val Glu Ser Gly Gly Gly Leu Val Gln Ala Gly Asp
  1               5                  10                  15

Ser Leu Arg Leu Thr Cys Thr Ala Ser Gly Arg Ala Phe Ser Thr Tyr
                 20                  25                  30

Phe Met Ala Trp Phe Arg Gln Ala Pro Gly Lys Glu Arg Glu Phe Val
             35                  40                  45

Ala Gly Ile Ala Trp Ser Gly Ser Thr Ala Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Ala Val Tyr Tyr Cys
                 85                  90                  95

Ala Ser Arg Gly Ile Glu Val Glu Glu Phe Gly Ala Trp Gly Gln Gly
                100                 105                 110
```

Thr Gln Val Thr Val Ser Ser
            115

<210> SEQ ID NO 126
<211> LENGTH: 124
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Glu Ser Gly Gly Gly Leu Val Pro Pro Gly Gly
1               5                   10                  15

Ser Leu Arg Leu Ser Cys Thr Ala Ser Gly Ser Thr Val Ser Ile Asn
            20                  25                  30

Val Met Ala Trp Tyr Arg Gln Val Ser Gly Lys Gln Arg Glu Leu Val
        35                  40                  45

Ala Ala Val Thr Arg Asp Gly Arg Lys Ser Cys Gly Asp Ser Val Lys
    50                  55                  60

Gly Arg Phe Thr Ile Ser Arg Asp Gly Ala Lys Asn Ala Val Tyr Leu
65                  70                  75                  80

Gln Met Asn Ser Leu Lys Pro Glu Asp Thr Ala Val Tyr Leu Cys Gly
                85                  90                  95

Ala Asp Gly Trp Gly Ala Thr Thr Leu Asp Tyr Thr Tyr Gly Met Asp
            100                 105                 110

Tyr Trp Gly Lys Gly Thr Gln Val Thr Val Ser Ser
            115                 120

<210> SEQ ID NO 127
<211> LENGTH: 118
<212> TYPE: PRT
<213> ORGANISM: Artificial Sequence
<220> FEATURE:
<223> OTHER INFORMATION: Synthetic Construct

<400> SEQUENCE: 127

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Gly Phe Val Ala Ser Ile
        35                  40                  45

Thr Trp Asp Gly Arg Ser Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 128
<211> LENGTH: 122
<212> TYPE: PRT
<213> ORGANISM: Artificial Sequence
<220> FEATURE:
<223> OTHER INFORMATION: Synthetic Construct

<400> SEQUENCE: 128

```
Gln Val Gln Leu Val Glu Ser Gly Gly Gly Leu Val Gln Pro Gly Gly
1               5                   10                  15

Ser Leu Arg Leu Ala Cys Glu Ala Pro Gly Ser Gly Asn Ser Ile Asn
            20                  25                  30

Ala Met Gly Trp Tyr Arg Gln Thr Pro Gly Lys Arg Arg Glu Leu Val
        35                  40                  45

Ala Thr Ile Thr Arg Gly Gly Ser Thr Asn Tyr Gly Pro Ser Val Lys
    50                  55                  60

Gly Arg Phe Thr Ile Thr Arg Asp Asn Val Lys Asn Thr Val His Leu
65                  70                  75                  80

Gln Met Asn Ser Leu Lys Pro Asp Asp Thr Ala Val Tyr Tyr Cys Asn
                85                  90                  95

Ala Glu Arg Leu Asp Gly Ser Gly Tyr Gly Tyr Glu Tyr Asp Tyr Trp
            100                 105                 110

Gly Gln Gly Thr Gln Val Thr Val Ser Ser
        115                 120
```

<210> SEQ ID NO 129
<211> LENGTH: 121
<212> TYPE: PRT
<213> ORGANISM: Artificial Sequence
<220> FEATURE:
<223> OTHER INFORMATION: Synthetic Construct

<400> SEQUENCE: 129

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Asn Gly Arg Phe Pro Ile Asn Arg Asn Asn Ala Glu Asn Leu Val Val
65                  70                  75                  80

Leu Gln Met Asn Ser Leu Lys Pro Asp Asp Thr Ala Leu Tyr Tyr Cys
                85                  90                  95

Ala Ala Tyr Arg Lys Ser Ile Met Ser Ile Gln Pro Asp Tyr Trp Gly
            100                 105                 110

Gln Gly Thr Gln Val Thr Val Ser Ser
        115                 120
```

<210> SEQ ID NO 130
<211> LENGTH: 121
<212> TYPE: PRT
<213> ORGANISM: Artificial Sequence
<220> FEATURE:
<223> OTHER INFORMATION: Synthetic Construct

<400> SEQUENCE: 130

```
Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45
```

```
Gly Ala Ile Met Trp Asn Asp Gly Leu Thr Tyr Leu Gln Gly Ser Val
    50              55                  60

Lys Gly Arg Phe Thr Ile Ser Arg Asp Asn Ala Lys Asn Thr Val Val
 65              70                  75                  80

Leu Gln Met Asn Ser Leu Lys Pro Glu Asp Thr Ala Leu Tyr Tyr Cys
                85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
            115                 120
```

<210> SEQ ID NO 131
<211> LENGTH: 116
<212> TYPE: PRT
<213> ORGANISM: Artificial Sequence
<220> FEATURE:
<223> OTHER INFORMATION: Synthetic Construct

<400> SEQUENCE: 131

```
Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Thr Met Gly
                20                  25                  30

Trp Phe Arg Gln Ala Pro Gly Lys Glu Arg Glu Phe Val Ala Ala Ile
            35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
 65                  70                  75                  80

Asn Ser Leu Lys Pro Glu Asp Thr Ala Val Tyr Tyr Cys Ala Ala Arg
                85                  90                  95

Arg Ile Asp Ala Ala Asp Phe Asp Ser Trp Gly Gln Gly Thr Gln Val
            100                 105                 110

Thr Val Ser Ser
    115
```

<210> SEQ ID NO 132
<211> LENGTH: 120
<212> TYPE: PRT
<213> ORGANISM: Artificial Sequence
<220> FEATURE:
<223> OTHER INFORMATION: Synthetic Construct

<400> SEQUENCE: 132

```
Gln Val Gln Leu Val Glu Ser Gly Gly Gly Leu Val Gln Ala Gly Gly
 1               5                  10                  15

Ser Leu Arg Leu Ser Cys Ala Ala Ser Gly Gly Thr Leu Ser Lys Asn
                20                  25                  30

Thr Val Ala Trp Phe Arg Gln Ala Pro Gly Lys Glu Arg Gly Phe Val
            35                  40                  45

Ala Ser Ile Thr Trp Asp Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                85                  90                  95

Ala Asp Leu Gly Lys Trp Pro Ala Gly Pro Ala Asp Tyr Trp Gly Gln
            100                 105                 110
```

```
Gly Thr Gln Val Thr Val Ser Ser
        115                 120

<210> SEQ ID NO 133
<211> LENGTH: 121
<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Val Glu Ser Gly Gly Gly Leu Val Gln Pro Gly Gly
1               5                   10                  15

Ser Leu Thr Leu Ser Cys Ala Ala Ser Gly Ser Ile Asp Ser Ile Asn
            20                  25                  30

Thr Met Asp Trp Phe Arg Gln Ala Pro Gly Lys Glu Arg Glu Phe Val
        35                  40                  45

Ala Ala Ile Ser Leu Ser Pro Thr Leu Ala Tyr Tyr Ala Glu Ser Val
    50                  55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Leu Tyr Tyr Cys
                85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 134
<211> LENGTH: 120
<212> TYPE: PRT
<213> ORGANISM: Artificial Sequence
<220> FEATURE:
<223> OTHER INFORMATION: Synthetic Construct

<400> SEQUENCE: 134

Asp Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Lys Gly Arg Phe Pro Ile Ser Arg Asp Asn Ala Glu Asn Thr Val Tyr
65                  70                  75                  80

Leu Gln Met Asn Ser Leu Lys Pro Glu Asp Thr Ala Gly Tyr Val Cys
                85                  90                  95

Ala Asp Leu Gly Lys Trp Pro Ala Gly Ser Ala Asp Tyr Trp Gly Gln
            100                 105                 110

Gly Thr His Val Thr Val Ser Ser
        115                 120

<210> SEQ ID NO 135
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 135

Gln Val Lys Leu Glu Glu Ser Gly Gly Gly Leu Val Gln Pro Gly Gly
1               5                   10                  15

Ser Leu Arg Leu Ser Cys Thr Ala Ser Glu Phe Thr Phe Ser Asp Tyr
            20                  25                  30

Trp Met His Trp Val Arg Gln Ala Pro Gly Lys Gly Leu Glu Trp Val
        35                  40                  45

Ala Ser Ile Asp Thr Ser Gly Gln Thr Thr Tyr Tyr Ala Asp Ser Leu
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Ser Glu Asp Thr Gly Val Tyr Phe Cys
                85                  90                  95

Ala Lys Arg Tyr Arg Gly Gly Thr Trp Tyr Gly Met Ala Asn Trp Gly
            100                 105                 110

Lys Gly Thr Gln Val Thr Val Ser Ser
        115                 120

<210> SEQ ID NO 136
<211> LENGTH: 120
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Ser Asn
            20                  25                  30

Thr Met Ala Trp Phe Arg Gln Ala Pro Gly Lys Glu Arg Glu Phe Val
        35                  40                  45

Ala Ser Thr Thr Trp Asn Gly Arg Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Val Cys
                85                  90                  95

Ala Asp Leu Gly Lys Trp Pro Ala Gly Pro Ala Asp Tyr Trp Gly Gln
            100                 105                 110

Gly Thr Gln Val Thr Val Ser Ser
        115                 120

<210> SEQ ID NO 137
<211> LENGTH: 116
<212> TYPE: PRT
<213> ORGANISM: Artificial Sequence
<220> FEATURE:
<223> OTHER INFORMATION: Synthetic Construct

<400> SEQUENCE: 137

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Gln Arg Glu Leu Val Ala Asp Ile
        35                  40                  45

Ser Gly Gly Arg Thr Asn Tyr Ala Asp Ser Val Lys Gly Arg Phe Thr
        50                  55                  60

Ile Ser Arg Asp Asn Ala Lys Asn Thr Val Tyr Leu Gln Met Asn Ser
65                  70                  75                  80

Leu Lys Pro Glu Asp Thr Ala Val Tyr Tyr Cys Ala Ala Asp Arg Lys
                85                  90                  95

Ser Val Met Ser Ile Arg Pro Asp Tyr Trp Gly Gln Gly Thr Gln Val
            100                 105                 110

Thr Val Ser Ser
        115

<210> SEQ ID NO 138
<211> LENGTH: 104
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Thr Val Ala
            20                  25                  30

Ala Ile Ser Leu Ser Pro Thr Leu Ala Tyr Tyr Ala Glu Ser Val Lys
        35                  40                  45

Gly Arg Phe Thr Ile Ser Arg Asp Asn Ala Lys Asn Thr Val Val Leu
    50                  55                  60

Gln Met Asn Ser Leu Lys Pro Glu Asp Thr Ala Leu Tyr Tyr Cys Ala
65                  70                  75                  80

Ala Asp Arg Lys Ser Val Met Ser Ile Arg Pro Asp Tyr Trp Gly Gln
                85                  90                  95

Gly Thr Gln Val Thr Val Ser Ser
            100

<210> SEQ ID NO 139
<211> LENGTH: 125
<212> TYPE: PRT
<213> ORGANISM: Artificial Sequence
<220> FEATURE:
<223> OTHER INFORMATION: Synthetic Construct

<400> SEQUENCE: 139

Asp Val Gln Leu Val Glu Ser Gly Gly Gly Leu Glu Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
        35                  40                  45

Ala Ser Ile Thr Trp Asp Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Thr Ala Ser Cys His Leu Phe Gly Leu Gly Ser Gly Ala Phe
            100                 105                 110

Val Ser Trp Gly Arg Gly Thr Gln Val Thr Val Ser Ser

-continued

```
                115                 120                 125

<210> SEQ ID NO 140
<211> LENGTH: 116
<212> TYPE: PRT
<213> ORGANISM: Artificial Sequence
<220> FEATURE:
<223> OTHER INFORMATION: Synthetic Construct

<400> SEQUENCE: 140

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe His Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Ser
                85                  90                  95

Lys Asp Arg Tyr Ser Glu Tyr Glu Tyr Trp Gly Gln Gly Thr Gln Val
            100                 105                 110

Thr Val Ser Ser
        115

<210> SEQ ID NO 141
<211> LENGTH: 114
<212> TYPE: PRT
<213> ORGANISM: Artificial Sequence
<220> FEATURE:
<223> OTHER INFORMATION: Synthetic Construct

<400> SEQUENCE: 141

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Lys Lys
                85                  90                  95

Asn Gly Gly Pro Val Asp Tyr Trp Gly Lys Gly Thr Gln Val Thr Val
            100                 105                 110

Ser Ser

<210> SEQ ID NO 142
<211> LENGTH: 119
<212> TYPE: PRT
<213> ORGANISM: Artificial Sequence
<220> FEATURE:
<223> OTHER INFORMATION: Synthetic Construct

<400> SEQUENCE: 142
```

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser
        115
```

<210> SEQ ID NO 143
<211> LENGTH: 118
<212> TYPE: PRT
<213> ORGANISM: Artificial Sequence
<220> FEATURE:
<223> OTHER INFORMATION: Synthetic Construct

<400> SEQUENCE: 143

```
Gln Val Lys Leu Glu Glu Ser Gly Gly Arg Leu Val Gln Ala Gly Gly
1               5                   10                  15

Ser Leu Lys Leu Ser Trp Ala Ala Ser Gly Arg Thr Phe Thr Met Gly
            20                  25                  30

Trp Phe Arg Gln Ala Pro Gly Lys Glu Arg Glu Phe Val Thr Ala Ile
        35                  40                  45

Asn Leu Ser Pro Thr Leu Thr Tyr Tyr Ala Glu Ser Val Lys Gly Arg
    50                  55                  60

Phe Pro Ile Ser Arg Asn Asn Ala Gln Asn Thr Val Val Leu Gln Met
65                  70                  75                  80

Asn Ser Leu Lys Pro Glu Asp Thr Ala Leu Tyr Tyr Cys Ala Ala Glu
                85                  90                  95

Arg Lys Ser Val Met Ala Ile Pro Pro Asp Tyr Trp Gly Gln Gly Thr
            100                 105                 110

Gln Val Thr Val Ser Ser
        115
```

<210> SEQ ID NO 144
<211> LENGTH: 118
<212> TYPE: PRT
<213> ORGANISM: Artificial Sequence
<220> FEATURE:
<223> OTHER INFORMATION: Synthetic Construct

<400> SEQUENCE: 144

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Thr Met Gly
            20                  25                  30

Gly Phe Arg Arg Val Pro Arg Asp Glu Arg Glu Phe Val Ala Ser Ile
        35                  40                  45

Thr Leu Ile Pro Thr Phe Pro Tyr Ala Tyr Ser Val Lys Gly Arg
    50                  55                  60
```

Phe Ala Leu Phe Arg Asp Asn Pro Asn Asn Thr Val Ile Leu Leu Met
65                  70                  75                  80

Ile Ser Leu Lys Pro Glu Asp Pro Asp Leu Tyr Tyr Cys Ala Ser Tyr
                85                  90                  95

Arg Lys Tyr Leu Met Ser Ile Leu Pro Asp Tyr Trp Gly Gln Gly Thr
            100                 105                 110

Gln Gly Thr Val Ser Ser
        115

<210> SEQ ID NO 145
<211> LENGTH: 124
<212> TYPE: PRT
<213> ORGANISM: Artificial Sequence
<220> FEATURE:
<223> OTHER INFORMATION: Synthetic Construct

<400> SEQUENCE: 145

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Asp Leu Gln Met
65                  70                  75                  80

Asn Ser Leu Lys Pro Glu Asp Thr Ala Val Tyr Phe Cys Ala Ala Asn
                85                  90                  95

Arg Asn Ser Gln Arg Val Ile Ala Ala Leu Ser Trp Ile Gly Met Asn
            100                 105                 110

Tyr Trp Gly Glu Trp Thr Gln Val Thr Val Ser Ser
        115                 120

<210> SEQ ID NO 146
<211> LENGTH: 116
<212> TYPE: PRT
<213> ORGANISM: Artificial Sequence
<220> FEATURE:
<223> OTHER INFORMATION: Synthetic Construct

<400> SEQUENCE: 146

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Lys Thr Leu Tyr Leu Arg Met
65                  70                  75                  80

Asn Ser Leu Lys Pro Glu Asp Thr Ala Val Tyr Tyr Cys Ala Ala Arg
                85                  90                  95

Arg Ile Asp Ala Ala Asp Phe Asp Ser Trp Gly Gln Gly Thr Gln Val
            100                 105                 110

Thr Val Ser Ser

<210> SEQ ID NO 147
<211> LENGTH: 116
<212> TYPE: PRT
<213> ORGANISM: Artificial Sequence
<220> FEATURE:
<223> OTHER INFORMATION: Synthetic Construct

<400> SEQUENCE: 147

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Arg Ala Pro Gly Lys Glu Arg Glu Ser Val Ala Val Ile
        35                  40                  45

Gly Trp Arg Asp Ile Asn Ala Ser Tyr Ala Asp Ser Val Lys Gly Arg
    50                  55                  60

Phe Ala Ile Ser Arg Asp Asn Ala Lys Lys Thr Leu Tyr Leu Gln Met
65                  70                  75                  80

Asn Ser Leu Lys Pro Glu Asp Thr Ala Val Tyr Tyr Cys Ala Ala Arg
                85                  90                  95

Arg Ile Asp Ala Thr Asp Phe Asp Ser Trp Gly Gln Gly Thr Gln Val
            100                 105                 110

Thr Val Ser Ser
        115

<210> SEQ ID NO 148
<211> LENGTH: 119
<212> TYPE: PRT
<213> ORGANISM: Artificial Sequence
<220> FEATURE:
<223> OTHER INFORMATION: Synthetic Construct

<400> SEQUENCE: 148

Gln Val Lys Leu Glu Glu Ser Gly Gly Gly Leu Val Gln Thr Gly Gly
1               5                   10                  15

Ser Leu Arg Leu Ser Cys Ala Ala Ser Glu His Thr Phe Ser Asn His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Arg Gly Gln Gly
            100                 105                 110

Thr Gln Val Thr Val Ser Ser
        115

<210> SEQ ID NO 149
<211> LENGTH: 123
<212> TYPE: PRT
<213> ORGANISM: Artificial Sequence
<220> FEATURE:
<223> OTHER INFORMATION: Synthetic Construct

<400> SEQUENCE: 149

Ala Val Gln Leu Val Asp Ser Gly Gly Gly Leu Val Gln Ala Gly Gly
1               5                   10                  15

Ser Leu Arg Ile Ser Cys Ala Val Ser Gly Arg Thr Ser Ser Asn Tyr
            20                  25                  30

Ile Leu Ala Trp Phe Arg Gln Ala Pro Gly Lys Glu Arg Asp Phe Val
            35                  40                  45

Ala His Ile Ser Arg Ser Gly Gly Lys Ser Gly Tyr Gly Asp Ser Val
        50                  55                  60

Lys Gly Arg Phe Thr Ile Ser Arg Asp Asn Ala Glu Asn Thr Val Arg
65                  70                  75                  80

Val Tyr Leu Gln Met Asn Ser Leu Lys Pro Gly Asp Thr Ala Val Tyr
                85                  90                  95

Tyr Cys Asn Arg Pro Leu Trp Tyr Gly Ser Pro Thr Leu Ile Asp Tyr
            100                 105                 110

Trp Gly Gln Gly Thr Gln Val Thr Val Ser Ser
            115                 120

<210> SEQ ID NO 150
<211> LENGTH: 118
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
            35                  40                  45

Ser Leu Ser Pro Thr Leu Ala Tyr Tyr Ala Glu Ser Val Lys Gly Arg
        50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 151
<211> LENGTH: 118
<212> TYPE: PRT
<213> ORGANISM: Artificial Sequence
<220> FEATURE:
<223> OTHER INFORMATION: Synthetic Construct

<400> SEQUENCE: 151

Ala Val Gln Leu Val Asp Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
            35                  40                  45

Ser Leu Ser Pro Thr Leu Ala Tyr Tyr Ala Glu Pro Val Lys Gly Arg

```
                    50                  55                  60
Phe Thr Ile Ser Arg Asp Asn Ala Lys Asn Thr Val Val Leu Gln Met
 65                  70                  75                  80

Asn Ser Leu Lys Pro Glu Asp Thr Ala Leu Tyr Tyr Cys Ala Ala Asp
                 85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 152
<211> LENGTH: 121
<212> TYPE: PRT
<213> ORGANISM: Artificial Sequence
<220> FEATURE:
<223> OTHER INFORMATION: Synthetic Construct

<400> SEQUENCE: 152

Asp Val Gln Leu Val Glu Ser Gly Gly Gly Ser Val Gln Thr Gly Gly
 1               5                  10                  15

Ser Leu Arg Leu Ser Cys Thr Ala Ser Gly Arg Thr Leu Asn Asn Phe
            20                  25                  30

Val Met Gly Trp Phe Arg Gln Ala Pro Gly Lys Glu Arg Glu Phe Val
        35                  40                  45

Ala Ala Ile Ser Leu Ser Pro Thr Leu Ala Tyr Tyr Val Glu Ser Val
     50                  55                  60

Lys Gly Arg Phe Thr Ile Ser Arg Asp Asn Ala Lys Asn Thr Val Val
 65                  70                  75                  80

Leu Gln Met Asn Ser Leu Lys Pro Glu Asp Thr Ala Leu Tyr Tyr Cys
                 85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 153
<211> LENGTH: 366
<212> TYPE: DNA
<213> ORGANISM: Artificial Sequence
<220> FEATURE:
<223> OTHER INFORMATION: Synthetic Construct

<400> SEQUENCE: 153
caggtgcagc tggtggagtc tgggggaggc ttggtgcagc tggggggttc tctgaggctc      60
tcctgtgaag cctctggatt cactttggat tattatgcca taggctggtt ccgccaggcc     120
ccagggaagg agcgcgaggg ggtcatatgt attagtagaa gtgatggtag cacatactat     180
gcagactccg tgaagggccg attcaccatc tccagagaca cgccaagaa acggtgtat      240 ctgcaaatga tcagcctgaa acctgaggac acggccgctt attactgtgc agcagggcc      300 gattgttcgg ggtacctacg agattatgag ttcggggggc aggggaccca ggtcaccgtc     360
tcctca                                                                366

<210> SEQ ID NO 154
<211> LENGTH: 384
<212> TYPE: DNA
<213> ORGANISM: Artificial Sequence
<220> FEATURE:
<223> OTHER INFORMATION: Synthetic Construct
```

<400> SEQUENCE: 154

```
caggtaaagc tggaggagtc tgggggacga ttggtgcagc caaggggctc tctgagactc    60
tcctgtgcag gctctggacg cactttcagt acctatggta tggcctggtt ccgccaggct   120
ccagggaagg agcgtgagtt cgtagcgtct aaagcatcga tgaattacag cggtagaaca   180
tactatgcag actccgtgaa gggccgattc accatcgcca gagacaacgc caagaacatg   240
gtgtttctgc aaatgaacaa cctgaagcct gaggacacgg ccgtttatta ctgtgcagcg   300
ggcactggat gctcaacata tgggtgtttt gacgcccaga taatagacta ctggggcaaa   360
gggaccctgg tcaccgtctc ctca                                          384
```

<210> SEQ ID NO 155
<211> LENGTH: 354
<212> TYPE: DNA
<213> ORGANISM: Artificial Sequence
<220> FEATURE:
<223> OTHER INFORMATION: Synthetic Construct

<400> SEQUENCE: 155

```
gaggtgcagc tggtggagtc tgggggaggc ttggtgcagg ctgggggtc tctgagactc     60
tcctgtgcag cctctggacg caccttcacc atggggtggt tccgtcaggc tccagggaag   120
gagcgtgagt ttgtagcagc tattagtttg agtcctactt tagcatatta tgcagagtcc   180
gtgaagggcc gattcaccat cagccgagac aacgccaaga acacggtggt tttgcaaatg   240
aacagcctga acctgaggac acgccctt tattactgtg cagcagaccg gaaatcagta   300
atgtctattc ggcccgacta ctggggccag gggacccagg tcaccgtctc ctca         354
```

<210> SEQ ID NO 156
<211> LENGTH: 360
<212> TYPE: DNA
<213> ORGANISM: Artificial Sequence
<220> FEATURE:
<223> OTHER INFORMATION: Synthetic Construct

<400> SEQUENCE: 156

```
gccgtgcagc tggtggattc tgggggaggc ttggtgcagc ctgggggtc tctgagactc     60
tcctgtgtag cctctggagg tatcttcgtc atcaatgcca tgggctggta ccgccaggct   120
ccaggaaagc agcgcgagtt ggtcgcatct attcgtggac taggcagaac aaactatgac   180
gactccgtga agggccgatt caccatctcc agagacaacg ccaacaacac ggtgtatctg   240
cagatgaaca gcctggaacc tgaggacacg gccgtctact actgtacagt ctacgttaca   300
ctacttggtg gggttaatag ggactactgg ggccagggga cccaggtcac cgtctcctca   360
```

<210> SEQ ID NO 157
<211> LENGTH: 357
<212> TYPE: DNA
<213> ORGANISM: Artificial Sequence
<220> FEATURE:
<223> OTHER INFORMATION: Synthetic Construct

<400> SEQUENCE: 157

```
gaggtgcagc tggtggagtc tgggggagga ttggtgcagg ctgggggctc tctgagactc     60
tcctgtgcag cctctggacg gaccttcagt agcattgtca tggctggtt ccgccaggct   120
ccagggaagg agcgtgagtt tgtaggagcg attatgtgga atgatggtat tacatacttg   180
caagactccg tgaagggccg atttaccatc ttcagagaca atgccaagaa cacggtgtat   240
```

```
ctgcaaatga acagcctgaa acttgaggat acggccgttt attactgtgc agcatccaag    300
ggtagatact cggaatatga gtactggggc aggggaccc aggtcaccgt ctcctca        357
```

<210> SEQ ID NO 158
<211> LENGTH: 384
<212> TYPE: DNA
<213> ORGANISM: Artificial Sequence
<220> FEATURE:
<223> OTHER INFORMATION: Synthetic Construct

<400> SEQUENCE: 158

```
gaggtgcagc tggtggagtc tgggggaggc gtggtgcagg ctgggggtc tctgacagtc     60 tcctgtacag cctctggatt cactttcgac cgtgctgtca tagtctggtt ccgccaggcc   120
cccgggaagg gccgtgaggg ggtctcattt attaaaccta gtgatggcac catatactac   180
attgactccc tgaagggccg attcacgatc tccagtgaca tcgccaagaa tacggtatat   240
ctgcaaatga aaagtctgga atcggaggac tcggccgttt attactgtgc ggcctcgcct   300
gaggactggt acacggattg gatcgactgg agtatatatc ggtggcagca ctggggccag   360
gggacccagg tcactgtctc ctca                                           384
```

<210> SEQ ID NO 159
<211> LENGTH: 357
<212> TYPE: DNA
<213> ORGANISM: Artificial Sequence
<220> FEATURE:
<223> OTHER INFORMATION: Synthetic Construct

<400> SEQUENCE: 159

```
gaggtgcagc tggtggagtc tgggggagga atggtgcagg ctggggactc tctgagacta    60
tcctgtgtgc agtctactta caccgtcaat agcgatgtca tgggctggtt ccgccaggct   120
ccagggaagg agcgtgagtt tgtaggagcg attatgtgga atgatggtat tacatacttg   180
caagactccg tgaagggccg atttaccatc ttcagagaca cgccaagaa cacggtgtat   240 ctgcaaatga acagcctgaa acttgaggat acggccgttt attactgtgc agcatccaag   300
ggtagatact cggaatatga gtactggggc aggggaccc aggtcaccgt ctcctca      357
```

<210> SEQ ID NO 160
<211> LENGTH: 360
<212> TYPE: DNA
<213> ORGANISM: Artificial Sequence
<220> FEATURE:
<223> OTHER INFORMATION: Synthetic Construct

<400> SEQUENCE: 160

```
gcggtgcagc tggtggagtc tgggggagga ttggtgcagg ctggggactc tctgagactc    60
tcctgtacag cctctggtgc aaccttgact aacgatcaca tggcatggtt ccgccaggct   120
ccagggaagg ggcgtgaatt tgtagcagct attgactgga gtggtcgtac cacaaattac   180
gcagaccccg tagagggccg attcaccatc tccagaaaca cgccaagaa cacggtgtat   240 ctggaaatga acagcctgaa acttgaggac acggccgttt attactgtgc ggtcctccgc   300
gcttggatct catatgacaa tgactactgg ggccagggga cccaggtcac cgtctcctca   360
```

<210> SEQ ID NO 161
<211> LENGTH: 360
<212> TYPE: DNA
<213> ORGANISM: Artificial Sequence
<220> FEATURE:
<223> OTHER INFORMATION: Synthetic Construct

<400> SEQUENCE: 161

```
caggtgcagc tggtggagtc tgggggagga ttggtgcagg ctgggggctc tctgagactc    60
tcctgtgcag cctctggagg caccttaagt aaaaataccg tggcttggtt ccgccaggct   120
ccagggaagg agcgtgggtt tgtagcgtct attacctggg atggtcgtac gacatactat   180
gcagactccg tgaagggccg attcaccatc tccagagaca cgccaagaa cacagtgtat    240
ctgcaaatga acagcctgaa acctgaggat acggccgttt atgtctgtgc agacttaggg   300
aaatggcctg cgggcccggc ggactactgg ggccagggga cccaggtcac cgtctcctca   360
```

<210> SEQ ID NO 162
<211> LENGTH: 357
<212> TYPE: DNA
<213> ORGANISM: Artificial Sequence
<220> FEATURE:
<223> OTHER INFORMATION: Synthetic Construct

<400> SEQUENCE: 162

```
caggtaaagc tggaggagtc tgggggaggc ttggtgcagg ctgggcggtc tctgagactc    60
tcctgtgcag cctctgaaca caccttcagt agccatgtca tggctggtt ccgccaggct    120
ccagggaagg agcgtgagtc tgttgcagtt attggctgga gagatattag cacaagctat   180
gcagactccg tgaagggccg attcaccatc tccagagaca cgccaagaa gacgctgtat    240
ctgcaaatga atagcctgaa acctgaggac acggccgttt actactgtgc agcacgtcgg   300
atcgacgcag ctgactttga ttcctggggg caggggaccc aggtcaccgt ctcctcg      357
```

<210> SEQ ID NO 163
<211> LENGTH: 357
<212> TYPE: DNA
<213> ORGANISM: Artificial Sequence
<220> FEATURE:
<223> OTHER INFORMATION: Synthetic Construct

<400> SEQUENCE: 163

```
gcggtgcagc tggtggagtc tgggggagga ttggtgcagg ctggggactc tctgagactc    60
acctgtacag cctctggacg cgccttcagt acctatttca tggcctggtt ccgccaggct   120
ccagggaagg agcgtgagtt tgtagcagga attgcatgga gtggtggtag cacggcgtat   180
gcagactccg tgaagggccg attcaccatc tccagagaca cgccaagaa cacggtgtat    240
ctgcaaatga acagcctgaa atctgaggac acggccgttt attactgtgc agcaggggg    300
attgaggtcg aagagtttgg tgcctggggc caggggaccc aggtcaccgt ctcgtcg      357
```

<210> SEQ ID NO 164
<211> LENGTH: 372
<212> TYPE: DNA
<213> ORGANISM: Artificial Sequence
<220> FEATURE:
<223> OTHER INFORMATION: Synthetic Construct

<400> SEQUENCE: 164

```
gaggtgcagc tggtggagtc tgggggaggc ttggtgccgc ctgggggtc tctgagactc     60
tcctgtacag cctctggaag cacagtcagc atcaatgtca tggcctggta ccgccaggtt   120
tcagggaagc agcgcgagtt ggtcgcggcc gttactaggg atggtaggaa aagttgtgga   180
gactccgtga agggccgatt caccatttcc agagacggcg ccaagaatgc ggtatatttg   240
caaatgaaca gtctgaaacc tgaggacaca gcggtctatt tatgtggagc cgatggttgg   300
```

```
ggtgctacta ccttagatta tacctacggc atggactatt ggggcaaagg gacccaggtc    360
accgtctcct ca                                                        372

<210> SEQ ID NO 165
<211> LENGTH: 354
<212> TYPE: DNA
<213> ORGANISM: Artificial Sequence
<220> FEATURE:
<223> OTHER INFORMATION: Synthetic Construct

<400> SEQUENCE: 165
gcggtgcagc tggtggagtc tgggggagga ttggtgcagg ctgggggctc tctgagactc     60
tcctgtgcag cctctggacg caccttcacc atggggtggt ccgtcaggc tccagggaag    120 gagcgtgggt ttgtagcgtc tattacctgg gatggtcgtt cggcatacta tgcagagtcc   180
gtgaagggcc gattcaccat cagccgagac aacgccaaga cacggtggt tttgcaaatg    240 aacagcctga aacctgagga cacggcccctt tattactgtg cagcagaccg gaaatcagta   300
atgtctattc ggcccgacta ctggggccag gggacccagg tcaccgtctc ctca          354

<210> SEQ ID NO 166
<211> LENGTH: 366
<212> TYPE: DNA
<213> ORGANISM: Artificial Sequence
<220> FEATURE:
<223> OTHER INFORMATION: Synthetic Construct

<400> SEQUENCE: 166
caggtacagc tggtggagtc tgggggagga ttggtgcagc ctgggggtc tctaagactc      60 gcatgtgaag cgcctggaag cggcaatagt atcaatgcca tgggctggta ccggcagact   120
ccggggaagc ggcgcgagtt ggtcgcaact attactcggg gtggtagcac gaactatgga   180
ccctccgtga agggccgatt cacgatcacc agagacaatg tcaagaatac ggtgcatctg   240
cagatgaaca gcctgaaacc tgacgacacg gccgtctatt attgcaatgc ggagaggctg   300
gacggctcgg ggtacggata tgagtatgat tactggggcc aggggaccca ggtcaccgtc   360
tcctca                                                              366

<210> SEQ ID NO 167
<211> LENGTH: 363
<212> TYPE: DNA
<213> ORGANISM: Artificial Sequence
<220> FEATURE:
<223> OTHER INFORMATION: Synthetic Construct

<400> SEQUENCE: 167
caggtaaagc tggaggagtc tgggggagga ttggtgcagg ctgggggctc tctgagactc     60
tcctgtgcag cctctggagg caccttaagt aagaataccg tggcttgggt ccgccaggct   120
ccagggaagg agcgtgggtt tgtaacgtct attacctgtg atggtcgtac gacatactat   180
gcgaactccg taaacggccg attccccatc aaccgaaaca cgccgagaa tttggtggtt    240 ttgcaaatga acagcctgaa acctgacgac acggcccttt attactgtgc agcataccgg   300
aagtcaataa tgtctattca gcccgactac tggggccagg gacccaggt caccgtctcc     360 tca                                                                 363

<210> SEQ ID NO 168
<211> LENGTH: 363
<212> TYPE: DNA
<213> ORGANISM: Artificial Sequence
```

```
<220> FEATURE:
<223> OTHER INFORMATION: Synthetic Construct

<400> SEQUENCE: 168
gatgtgcagc tggtggagtc tgggggagga ttggtgcagg ctgggggctc tctgagactc    60
tcctgtgcag cctctggacg gaccttcagt agcattgtca tgggctggtt ccgccaggct   120
ccagggaagg agcgtgagtt tgtaggagcg attatgtgga atgatggtct gacatacttg   180
caagggtccg tgaagggccg attcaccatt tccagagaca cgccaagaa cacggtggtt    240 ttgcaaatga acagcctgaa acctgaggac acggcccttt attactgtgc agcagaccgg   300
aaatcagtaa tgtctattcg gcccgactac tggggccagg ggacccaggt caccgtctcc   360
tca                                                                 363

<210> SEQ ID NO 169
<211> LENGTH: 348
<212> TYPE: DNA
<213> ORGANISM: Artificial Sequence
<220> FEATURE:
<223> OTHER INFORMATION: Synthetic Construct

<400> SEQUENCE: 169
caggtacagc tggtggagtc tgggggagga ttggtgcagg ctgggggctc tctgagactc    60
tcctgtgcag cctctggacg caccttcacc atgggggtggt tccgtcaggc tccagggaag   120
gagcgtgagt ttgtagcagc tattagtttg agtcctactt tagcatatta tgcagagtcc   180
gtgaagggcc gattcaccat cagccgagac aacgccaaga acacggtggt tttgcaaatg   240
aacagcctga aacctgagga cacggccgtt tactactgtg cagcacgtcg gatcgacgca   300
gctgactttg attcctgggg gcaggggacc caggtcaccg tctcctca                348

<210> SEQ ID NO 170
<211> LENGTH: 360
<212> TYPE: DNA
<213> ORGANISM: Artificial Sequence
<220> FEATURE:
<223> OTHER INFORMATION: Synthetic Construct

<400> SEQUENCE: 170
caggtacagc tggtggagtc tgggggagga ttggtgcagg ctgggggctc tctgagactc    60
tcctgtgcag cctctggagg caccttaagt aaaaataccg tggcttggtt ccgccaggct   120
ccagggaagg agcgtgggtt tgtagcgtct attacctggg atggtcgtac gacatactat   180
gcagactccg tgaagggccg attcaccatc tccagagaca cgccaagaa cacagtgtat    240 ctgcaaatga acagcctgaa acctgaggat acggccgttt atgtctgtgc agacttaggg   300
aaatggcctg cgggcccggc ggactactgg ggccagggga cccaggtcac cgtctcctca   360

<210> SEQ ID NO 171
<211> LENGTH: 363
<212> TYPE: DNA
<213> ORGANISM: Artificial Sequence
<220> FEATURE:
<223> OTHER INFORMATION: Synthetic Construct

<400> SEQUENCE: 171
caggtgcagc tggtggagtc tgggggaggc ttggtgcagc ctgggggtc tctgacactc     60 tcctgtgcag cctctggaag catcgacagt atcaatacca tggactggtt ccgtcaggct   120
ccagggaagg agcgtgagtt tgtagcagct attagtttga gtcccacttt agcatattat   180
```

```
gcagagtccg tgaagggccg attcaccatc agccgagaca acgccaagaa cacggtggtt    240
ttgcaaatga acagcctgaa acctgaggac acggccctttt attactgtgc agcagaccgg   300
aaatcagtaa tgtctattcg gcccgactac tggggccagg ggacccaggt caccgtctcc    360
tca                                                                  363

<210> SEQ ID NO 172
<211> LENGTH: 360
<212> TYPE: DNA
<213> ORGANISM: Artificial Sequence
<220> FEATURE:
<223> OTHER INFORMATION: Synthetic Construct

<400> SEQUENCE: 172
gatgtgcagc tggtggagtc tgggggagga ttggtgcagg ctgggggctc tctgagactc     60
tcctgtgcag cctctggagg caccttaagt aagaataccg tggcttgggt ccgccaggct    120
ccagggaagg agcgtgggtt tgtaacgtct attacctgtg atggtcgtac gacatactat    180
gcgaactccg tgaagggccg attccccatc tccagagaca acgccgagaa cacagtgtat    240
ctgcaaatga acagcctgaa acctgaggat acggccggtt atgtctgtgc agacttaggg   300
aagtggcctg cgggttcggc ggactactgg ggccagggga cccacgtcac cgtctcctcc    360

<210> SEQ ID NO 173
<211> LENGTH: 363
<212> TYPE: DNA
<213> ORGANISM: Artificial Sequence
<220> FEATURE:
<223> OTHER INFORMATION: Synthetic Construct

<400> SEQUENCE: 173
caggtaaagc tggaggagtc tgggggaggc ttggtgcagc ctgggggtc tctgagactc      60 tcctgtacag cctcggaatt cacattcagt gactactgga tgcattgggt ccgtcaggct    120
ccggggaagg ggctcgagtg ggtcgcatct atagatacta gtggacagac cacatactat    180
gcagactccc tgaagggccg attcaccatc tccagagaca acgccaagag cacgttgtat    240
ctgcaaatga acagtctgaa atctgaagac acgggcgtgt atttctgtgc aaaacgatat    300
aggggtggta cctggtatgg catggccaac tggggcaaag gacccaggt caccgtctcc     360 tca                                                                  363

<210> SEQ ID NO 174
<211> LENGTH: 360
<212> TYPE: DNA
<213> ORGANISM: Artificial Sequence
<220> FEATURE:
<223> OTHER INFORMATION: Synthetic Construct

<400> SEQUENCE: 174
caggtgcagc tggtggagtc tgggggagga ttggtgcagg ctgggggctc tctgagactc     60
tcctgtgcag cctctggacg caccttaagt agtaatacca tggcttggtt ccgccaggct   120
ccagggaagg agcgtgagtt tgtagcgtct actacctgga atggtcgtag cacatactat    180
gcagactccg tgaagggccg attcaccatc tccagagaca acgccaagaa cacgatgtat    240
ctgcaaatga acagcctgaa acctgaggat acggccgttt atgtctgtgc agacttaggg    300
aaatggcctg cgggcccggc ggactactgg ggccagggga cccaggtcac cgtctcctca    360

<210> SEQ ID NO 175
<211> LENGTH: 348
```

```
<212> TYPE: DNA
<213> ORGANISM: Artificial Sequence
<220> FEATURE:
<223> OTHER INFORMATION: Synthetic Construct

<400> SEQUENCE: 175
caggtgcagc tggtggagtc tgggggagga ttggtgcagg ctgggggctc tctgagactc      60
tcctgtgcag cctctggacg caccttcacc atggggtggt ccgtcaggc tccagggaag      120 cagcgcgaat tggtcgcaga tattagtggt ggtcgcacaa actatgcaga ttccgtgaag     180
ggacgattca ccatctccag agacaacgcc aagaacacgg tatatctgca aatgaacagc    240
ctgaaacctg aggacacggc cgtttattac tgtgcagcag accggaaatc agtaatgtct    300
attcggcccg actactgggg ccaggggacc caggtcaccg tctcctca                 348

<210> SEQ ID NO 176
<211> LENGTH: 312
<212> TYPE: DNA
<213> ORGANISM: Artificial Sequence
<220> FEATURE:
<223> OTHER INFORMATION: Synthetic Construct

<400> SEQUENCE: 176
caggtgcagc tggtggagtc tgggggaggc ttggtgcagg ctggggcctc tctgagactc     60
tcctgtgcag cctctggacg caccttcacc gtggcagcta ttagtttgag tcctactttta   120 gcatattatg cagagtccgt gaagggccga ttcaccatca gccgagacaa cgccaagaac    180
acggtggttt tgcaaatgaa cagcctgaaa cctgaggaca cggccccttta ttactgtgca   240 gcagaccgga aatcagtaat gtctattcgg cccgactact ggggccaggg gacccaggtc   300
accgtctcct ca                                                       312

<210> SEQ ID NO 177
<211> LENGTH: 375
<212> TYPE: DNA
<213> ORGANISM: Artificial Sequence
<220> FEATURE:
<223> OTHER INFORMATION: Synthetic Construct

<400> SEQUENCE: 177
gatgtgcagc tggtggagtc tgggggagga ttggagcagg ctgggggctc tctgagactc     60
tcctgtgcag cctctggagg caccttaagt aaaaataccg tggcttggtt ccgccaggct   120
ccagggaagg agcgtgggtt tgtagcgtct attacctggg atggtcgtac gacatactat    180
gcagactccg tgaagggccg attcaccatc tccagagaca cgccaagaa cacagtgtat    240 ctgcaaatga acagcctgaa acctgaggat acggccgttt attactgtgc gtcgacggca   300
tcgtgccacc tcttcggatt ggggtccggg gcctttgtgt cctggggccg ggggacccag   360
gtcaccgtct cctca                                                    375

<210> SEQ ID NO 178
<211> LENGTH: 348
<212> TYPE: DNA
<213> ORGANISM: Artificial Sequence
<220> FEATURE:
<223> OTHER INFORMATION: Synthetic Construct

<400> SEQUENCE: 178
gcggtgcagc tggtggagtc tgggggagga ttggtgcagg ctgggggctc tctgagactc     60
tcctgtgcag cctctggacg caccttcacc atggggtggt ccatcaggc tccagggaag     120
```

```
gagcgtgagt ttgtagcagc tattagtttg agtcctactt tagcatatta tgcagagtcc    180
gtgaagggcc gattcaccat cagccgagac aacgccaaga acacggtggt tttgcaaatg    240
aacagcctga aacctgagga cacggccctt tattactgtg cagcatccaa ggatagatat    300
tcggaatatg agtactgggg ccaggggacc caggtcaccg tctcctca                 348

<210> SEQ ID NO 179
<211> LENGTH: 342
<212> TYPE: DNA
<213> ORGANISM: Artificial Sequence
<220> FEATURE:
<223> OTHER INFORMATION: Synthetic Construct

<400> SEQUENCE: 179
caggtaaagc tggaggagtc tgggggagga ttggtgcagg ctgggggctc tctgagactc    60
tcctgtgcag cctctggacg caccttcacc atggggtggt ccgtcaggc tccagggaag    120 gagcgtgagt ttgtagcagc tattagtttg agtcctactt tagcatatta tgcagagtcc    180
gtgaagggcc gattcaccat cagccgagac aacgccaaga acacggtggt tttgcaaatg    240
aacagcctga aacctgagga cacggccctt tattactgtg caaaaaaaaa cgggggggcct    300 gtggactact ggggcaaagg gacccaggtc accgtctcct ca                       342

<210> SEQ ID NO 180
<211> LENGTH: 357
<212> TYPE: DNA
<213> ORGANISM: Artificial Sequence
<220> FEATURE:
<223> OTHER INFORMATION: Synthetic Construct

<400> SEQUENCE: 180
gatgtgcagc tggtggagtc tgggggaggc ttggtgcagc ctggggggtc tctgagactc    60
tcctgtgcag cctctggacg gaccttcagt agcattgtca tgggctggtt ccgccaggct    120
ccagggaagg agcgtgagtt tgtaggagcg attatgtgga atgatggtat tacatacttg    180
caagactccg tgaagggccg atttaccatc ttcagagaca acgccaagaa cacggtgtat    240
ctgcaaatga acagcctgaa acttgaggat acggccgttt attactgtgc agcatccaag    300
ggtagatact cggaatatga gtactggggc caggggaccc aggtcaccgt ctcctca       357

<210> SEQ ID NO 181
<211> LENGTH: 354
<212> TYPE: DNA
<213> ORGANISM: Artificial Sequence
<220> FEATURE:
<223> OTHER INFORMATION: Synthetic Construct

<400> SEQUENCE: 181
caggtaaagc tggaggaatc tgggggaaga ttggtgcagg ctgggggctc tctgaaactc    60
tcctgggcag cctctggacg caccttcacc atggggtggt ccgtcaggc tccagggaag    120 gaacgtgagt ttgtaacagc tattaatttg agtcctactt taacatatta tgcagaatcc    180
gtgaagggcc gattccccat cagccgaaac aacgcccaga acacggtggt tttgcaaatg    240
aacagcctga aacctgagga cacggccctt tattactgtg cagcagaacg gaaatcagta    300
atggctattc cgcccgacta ctggggccag gggacccagg tcaccgtctc ctca          354

<210> SEQ ID NO 182
<211> LENGTH: 354
<212> TYPE: DNA
<213> ORGANISM: Artificial Sequence
```

```
<220> FEATURE:
<223> OTHER INFORMATION: Synthetic Construct

<400> SEQUENCE: 182
gaggtgcagc tggtggagtc tgggggagga ttggtgcagg ctgggggctc tctgagactc    60
tcctgtgcag cctctggacg caccttcacc atggggggt tccgtcgggt tcctcggat    120 gagcgggagt ttgtagcatc tattactttg attcctactt ttccttatta tgcatattcc   180
gtgaagggcc gattcgccct cttccgagac aaccccaaca acaccgtgat tttgctgatg   240
atcagcctga aacctgagga cccggacctt tattactgtg cttcataccg gaaataccta   300
atgtctattc tgcccgacta ctggggccag gggacccagg gcaccgtctc ctcc          354

<210> SEQ ID NO 183
<211> LENGTH: 372
<212> TYPE: DNA
<213> ORGANISM: Artificial Sequence
<220> FEATURE:
<223> OTHER INFORMATION: Synthetic Construct

<400> SEQUENCE: 183
caggtaaagc tggaggagtc tgggggagga ttggtgcagg ctgggggctc tctgagactc    60
tcctgtgcag cctctggacg caccttcacc atggggtggt tccgtcaggc tccagggaag   120
gagcgtgagt ttgtagcagc tattagtttg agtcctactt tagcatatta tgcagagtcc   180
gtgaagggcc gattcaccat cagccgagac aacgccaaga acacggtgga tctgcaaatg   240
aacagcctga aacctgagga cacggccgtc tatttctgtg cagcaaatcg gaactcccaa   300
cgggtaattg cggcactgtc ctggattggc atgaactact ggggcgaatg gacccaggtc   360
accgtctcct cc                                                      372

<210> SEQ ID NO 184
<211> LENGTH: 348
<212> TYPE: DNA
<213> ORGANISM: Artificial Sequence
<220> FEATURE:
<223> OTHER INFORMATION: Synthetic Construct

<400> SEQUENCE: 184
caggtgcagc tggtggagtc tgggggagga ttggtgcagg ctgggggctc tctgagactc    60
tcctgtgcag cctctggacg caccttcacc atggggtggt tccgtcaggc tccagggaag   120
gagcgtgagt ttgtagcagc tattagtttg agtcctactt tagcatatta tgcagagtcc   180
gtgaagggcc gattcaccat ctccagagac aacgccaaga gacgctgta tctgcgaatg   240 aatagcctga aacctgagga cacggccgtt tactactgtg cagcacgtcg gatcgacgca   300
gctgactttg attcctgggg gcaggggacc caggtcaccg tctcctca                348

<210> SEQ ID NO 185
<211> LENGTH: 348
<212> TYPE: DNA
<213> ORGANISM: Artificial Sequence
<220> FEATURE:
<223> OTHER INFORMATION: Synthetic Construct

<400> SEQUENCE: 185
caggtaaagc tggaggagtc tgggggagga ttggtgcagg ctgggggctc tctgagactc    60
tcctgtgcag cctctggacg caccttcacc atggggtggt tccgtcgggc tccagggaag   120
gagcgtgagt ctgttgcagt tattggctgg agagatatta acgcaagcta tgcagactcc   180
```

```
gtgaagggcc gattcgccat ctccagagac aacgccaaga agacgctgta tctgcagatg    240
aatagcctga aacctgagga cacggccgtt tactactgtg cagcacgtcg gatcgacgca    300
actgactttg attcctgggg gcagggggacc caggtcaccg tctcctca               348
```

<210> SEQ ID NO 186
<211> LENGTH: 357
<212> TYPE: DNA
<213> ORGANISM: Artificial Sequence
<220> FEATURE:
<223> OTHER INFORMATION: Synthetic Construct

<400> SEQUENCE: 186

```
caggtaaagc tggaggagtc tgggggagga ttggtgcaga ctgggggctc tctgagactc     60
tcctgtgcag cctctgaaca caccttcagt aaccatgtca tgggctggtt ccgccaggct    120
ccagggaagg agcgtgagtc tgttgcagtt attggctgga gagatattag cacaagctat    180
gcagactccg tgaagggccg attcaccatc tccagagaca acgccaagaa gacgctgtat    240
ctgcaaatga atagcctgaa acctgaggac acggccgttt actactgtgc agcacgtcgg    300
atcgacgcag ctgactttga ttcccgggggg caggggaccc aggtcaccgt ctcctca      357
```

<210> SEQ ID NO 187
<211> LENGTH: 369
<212> TYPE: DNA
<213> ORGANISM: Artificial Sequence
<220> FEATURE:
<223> OTHER INFORMATION: Synthetic Construct

<400> SEQUENCE: 187

```
gccgtgcagc tggtggattc tgggggagga ttggtgcagg ctgggggctc tctgagaatt     60
tcctgtgcag tctctggacg cacctccagt aactatatat tggcctggtt ccgtcaggct    120
ccaggaaaag agcgtgactt tgtagcacat attagccgga gtggtggtaa gtccggctat    180
ggagactccg tgaagggccg attcaccatc tccagagaca acgccgagaa cacggtcagg    240
gtgtatctgc aaatgaacag tctgaaacct ggggacacgg ccgtctatta ctgtaatcgc    300
cccctctggt acggaagtcc cacgttgatt gactactggg gccaggggac ccaggtcacc    360
gtctcctca                                                            369
```

<210> SEQ ID NO 188
<211> LENGTH: 354
<212> TYPE: DNA
<213> ORGANISM: Artificial Sequence
<220> FEATURE:
<223> OTHER INFORMATION: Synthetic Construct

<400> SEQUENCE: 188

```
gcggtgcagc tggtggagtc tgggggaggc ttggtgcagc ctggggggtc tctgagactc     60
tcctgtgcag cctctggacg cacctttcacc atgggtggt tccgtcaggc tccaggggaag    120 gagcgtgagt ttgtagcagc tattagtttg agtcctactt tagcatatta tgcagagtcc    180
gtgaagggcc gattcaccat cagccgagac aacgccaaga acacggtggt tttgcaaatg    240
aacagcctga aacctgagga cacggcccctt tattactgtg cagcagaccg gaaatcagta    300
atgtctattc ggcccgacta ctggggccag gggacccagg tcaccgtctc ctca          354
```

<210> SEQ ID NO 189
<211> LENGTH: 354
<212> TYPE: DNA
<213> ORGANISM: Artificial Sequence
<220> FEATURE:
<223> OTHER INFORMATION: Synthetic Construct

<400> SEQUENCE: 189

```
gcggtgcagc tggtggagtc tgggggagga ttggtgcagg ctgggggctc tctgagactc      60
tcctgtgcag cctctggacg caccttcacc atggggtggt ccgtcaggc tccaggggaag    120
gagcgtgagt ttgtagcagc tattagtttg agtcctactt tagcatatta tgcagagtcc    180
gtgaagggcc gattcaccat cagccgagac aacgccaaga acacggtggt tttgcaaatg    240
aacagcctga aacctgagga cacggccctt tattactgtg cagcagaccg gaaatcagta    300
atgtctattc ggcccgacta ctggggccag gggacccagg tcaccgtctc ctca          354
```

<210> SEQ ID NO 190
<211> LENGTH: 363
<212> TYPE: DNA
<213> ORGANISM: Artificial Sequence
<220> FEATURE:
<223> OTHER INFORMATION: Synthetic Construct

<400> SEQUENCE: 190

```
gatgtgcagc tggtggagtc tgggggagga tcggtgcaga ctgggggctc tctgagactc      60
tcctgtacag cctctggacg caccctcaat aactttgtca tgggctggtt ccgtcaggct    120
ccagggaagg agcgtgagtt tgtagcagct attagtttga gtcctacttt agcatattat    180
gtagagtccg tgaagggccg attcaccatc agccgagaca acgccaagaa cacggtggtt    240
ttgcaaatga acagcctgaa acctgaggac acggcccttt attactgtgc agcagaccgg    300
aaatcagtaa tgtctattcg gcccgactac tggggccagg gacccaggt caccgtctcc    360
tca                                                                 363
```

<210> SEQ ID NO 191
<211> LENGTH: 21
<212> TYPE: PRT
<213> ORGANISM: Artificial Sequence
<220> FEATURE:
<223> OTHER INFORMATION: Synthetic Construct

<400> SEQUENCE: 191

Met Ala Leu Pro Val Thr Ala Leu Leu Leu Pro Leu Ala Leu Leu Leu
1               5                   10                  15

His Ala Ala Arg Pro
            20

<210> SEQ ID NO 192
<211> LENGTH: 45
<212> TYPE: PRT
<213> ORGANISM: Artificial Sequence
<220> FEATURE:
<223> OTHER INFORMATION: Synthetic Construct

<400> SEQUENCE: 192

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 193
<211> LENGTH: 24

<212> TYPE: PRT
<213> ORGANISM: Artificial Sequence
<220> FEATURE:
<223> OTHER INFORMATION: Synthetic Construct

<400> SEQUENCE: 193

Ile Tyr Ile Trp Ala Pro Leu Ala Gly Thr Cys Gly Val Leu Leu
1               5                   10                  15

Ser Leu Val Ile Thr Leu Tyr Cys
            20

<210> SEQ ID NO 194
<211> LENGTH: 27
<212> TYPE: PRT
<213> ORGANISM: Artificial Sequence
<220> FEATURE:
<223> OTHER INFORMATION: Synthetic Construct

<400> SEQUENCE: 194

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 195
<211> LENGTH: 41
<212> TYPE: PRT
<213> ORGANISM: Artificial Sequence
<220> FEATURE:
<223> OTHER INFORMATION: Synthetic Construct

<400> SEQUENCE: 195

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 196
<211> LENGTH: 42
<212> TYPE: PRT
<213> ORGANISM: Artificial Sequence
<220> FEATURE:
<223> OTHER INFORMATION: Synthetic Construct

<400> SEQUENCE: 196

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 197
<211> LENGTH: 113
<212> TYPE: PRT
<213> ORGANISM: Artificial Sequence
<220> FEATURE:
<223> OTHER INFORMATION: Synthetic Construct

<400> SEQUENCE: 197

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 198
<211> LENGTH: 113
<212> TYPE: PRT
<213> ORGANISM: Artificial Sequence
<220> FEATURE:
<223> OTHER INFORMATION: Synthetic Construct

<400> SEQUENCE: 198

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 199
<211> LENGTH: 63
<212> TYPE: DNA
<213> ORGANISM: Artificial Sequence
<220> FEATURE:
<223> OTHER INFORMATION: Synthetic Construct

<400> SEQUENCE: 199
atggccttac cagtgaccgc cttgctcctg ccgctggcct tgctgctcca cgccgccagg    60
ccg                                                                 63

<210> SEQ ID NO 200
<211> LENGTH: 63
<212> TYPE: DNA
<213> ORGANISM: Artificial Sequence
<220> FEATURE:
<223> OTHER INFORMATION: Synthetic Construct

<400> SEQUENCE: 200
atggctctgc ccgtcactgc tctgctgctg cccctggctc tgctgctgca cgccgcaaga    60
ccc                                                                 63

<210> SEQ ID NO 201
<211> LENGTH: 135
<212> TYPE: DNA
<213> ORGANISM: Artificial Sequence
<220> FEATURE:
<223> OTHER INFORMATION: Synthetic Construct

<400> SEQUENCE: 201
accacgacgc cagcgccgcg accaccaaca ccggcgccca ccatcgcgtc gcagccctg    60 tccctgcgcc cagaggcgtg ccggccagcg gcggggggcg cagtgcacac gagggggctg   120
gacttcgcct gtgat                                                   135

<210> SEQ ID NO 202
<211> LENGTH: 72
<212> TYPE: DNA
<213> ORGANISM: Artificial Sequence
<220> FEATURE:
<223> OTHER INFORMATION: Synthetic Construct

<400> SEQUENCE: 202
atctacatct gggcgcccctt ggccgggact tgtggggtcc ttctcctgtc actggttatc    60 acccctttact gc                                                      72

<210> SEQ ID NO 203
<211> LENGTH: 81
<212> TYPE: DNA
<213> ORGANISM: Artificial Sequence
<220> FEATURE:
<223> OTHER INFORMATION: Synthetic Construct

<400> SEQUENCE: 203
ttttgggtgc tggtggtggt tggtggagtc ctggcttgct atagcttgct agtaacagtg    60
gcctttatta ttttctgggt g                                             81

<210> SEQ ID NO 204
<211> LENGTH: 123
<212> TYPE: DNA
<213> ORGANISM: Artificial Sequence
<220> FEATURE:
<223> OTHER INFORMATION: Synthetic Construct

<400> SEQUENCE: 204
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                123

<210> SEQ ID NO 205
<211> LENGTH: 126
<212> TYPE: DNA
<213> ORGANISM: Artificial Sequence
<220> FEATURE:
<223> OTHER INFORMATION: Synthetic Construct

<400> SEQUENCE: 205 aaacgggca gaaagaaact cctgtatata ttcaaacaac catttatgag accagtacaa     60
actactcaag aggaagatgg ctgtagctgc cgatttccag aagaagaaga aggaggatgt   120
gaactg                                                             126

<210> SEQ ID NO 206
<211> LENGTH: 336
<212> TYPE: DNA
<213> ORGANISM: Artificial Sequence
<220> FEATURE:
<223> OTHER INFORMATION: Synthetic Construct

<400> SEQUENCE: 206

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc    300
tacgacgccc ttcacatgca ggccctgccc cctcgc                              336
```

<210> SEQ ID NO 207
<211> LENGTH: 336
<212> TYPE: DNA
<213> ORGANISM: Artificial Sequence
<220> FEATURE:
<223> OTHER INFORMATION: Synthetic Construct

<400> SEQUENCE: 207

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc    300
tacgacgccc ttcacatgca ggccctgccc cctcgc                              336
```

<210> SEQ ID NO 208
<211> LENGTH: 5
<212> TYPE: PRT
<213> ORGANISM: Artificial Sequence
<220> FEATURE:
<223> OTHER INFORMATION: Synthetic Construct

<400> SEQUENCE: 208

Gly Gly Gly Gly Ser
1               5

<210> SEQ ID NO 209
<211> LENGTH: 10
<212> TYPE: PRT
<213> ORGANISM: Artificial Sequence
<220> FEATURE:
<223> OTHER INFORMATION: Synthetic Construct

<400> SEQUENCE: 209

Gly Gly Gly Gly Ser Gly Gly Gly Gly Ser
1               5                   10

<210> SEQ ID NO 210
<211> LENGTH: 16
<212> TYPE: PRT
<213> ORGANISM: Artificial Sequence
<220> FEATURE:
<223> OTHER INFORMATION: Synthetic Construct

<400> SEQUENCE: 210

```
Gly Gly Gly Ser Gly Gly Gly Ser Gly Gly Gly Ser Gly Gly Gly Ser
1               5                   10                  15
```

<210> SEQ ID NO 211
<211> LENGTH: 24
<212> TYPE: PRT
<213> ORGANISM: Artificial Sequence
<220> FEATURE:
<223> OTHER INFORMATION: Synthetic Construct

<400> SEQUENCE: 211

```
Gly Gly Gly Gly Ser Gly Gly Gly Gly Ser Gly Gly Gly Gly Gly
1               5                   10                  15

Ser Gly Ser Gly Gly Gly Gly Ser
            20
```

<210> SEQ ID NO 212
<211> LENGTH: 34
<212> TYPE: PRT
<213> ORGANISM: Artificial Sequence
<220> FEATURE:
<223> OTHER INFORMATION: Synthetic Construct

<400> SEQUENCE: 212

```
Gly Gly Gly Gly Ser Gly Gly Gly Gly Ser Gly Gly Gly Gly Gly
1               5                   10                  15

Ser Gly Ser Gly Gly Gly Ser Gly Gly Gly Ser Gly Gly Gly Gly
            20                  25                  30

Gly Ser
```

<210> SEQ ID NO 213
<211> LENGTH: 15
<212> TYPE: PRT
<213> ORGANISM: Artificial Sequence
<220> FEATURE:
<223> OTHER INFORMATION: Synthetic Construct

<400> SEQUENCE: 213

```
Gly Gly Gly Gly Ser Gly Gly Gly Gly Ser Gly Gly Gly Gly Ser
1               5                   10                  15
```

<210> SEQ ID NO 214
<211> LENGTH: 20
<212> TYPE: PRT
<213> ORGANISM: Artificial Sequence
<220> FEATURE:
<223> OTHER INFORMATION: Synthetic Construct

<400> SEQUENCE: 214

```
Gly Gly Gly Gly Ser Gly Gly Gly Gly Ser Gly Gly Gly Ser Gly
1               5                   10                  15

Gly Gly Gly Ser
            20
```

<210> SEQ ID NO 215
<211> LENGTH: 25
<212> TYPE: PRT
<213> ORGANISM: Artificial Sequence
<220> FEATURE:
<223> OTHER INFORMATION: Synthetic Construct

<400> SEQUENCE: 215

```
Gly Gly Gly Gly Ser Gly Gly Gly Gly Ser Gly Gly Gly Ser Gly
1               5                   10                  15
```

Gly Gly Gly Ser Gly Gly Gly Ser
            20              25

<210> SEQ ID NO 216
<211> LENGTH: 420
<212> TYPE: PRT
<213> ORGANISM: Artificial Sequence
<220> FEATURE:
<223> OTHER INFORMATION: Synthetic Construct

<400> SEQUENCE: 216

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
            20                  25                  30

Leu Val Glu Ser Gly Gly Gly Leu Val Gln Pro Gly Gly Ser Leu Arg
        35                  40                  45

Leu Ser Cys Glu Ala Ser Gly Phe Thr Leu Asp Tyr Tyr Ala Ile Gly
    50                  55                  60

Trp Phe Arg Gln Ala Pro Gly Lys Glu Arg Glu Gly Val Ile Cys Ile
65                  70                  75                  80

Ser Arg Ser Asp Gly Ser Thr Tyr Tyr Ala Asp Ser Val Lys Gly Arg
                85                  90                  95

Phe Thr Ile Ser Arg Asp Asn Ala Lys Lys Thr Val Tyr Leu Gln Met
            100                 105                 110

Ile Ser Leu Lys Pro Glu Asp Thr Ala Ala Tyr Tyr Cys Ala Ala Gly
        115                 120                 125

Ala Asp Cys Ser Gly Tyr Leu Arg Asp Tyr Glu Phe Arg Gly Gln Gly
    130                 135                 140

Thr Gln Val Thr Val Ser Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Phe Trp Val Leu Val Val Val Gly Gly Val
        195                 200                 205

Leu Ala Cys Tyr Ser Leu Leu Val Thr Val Ala Phe Ile Ile Phe Trp
    210                 215                 220

Val Arg Ser Lys Arg Ser Arg Leu Leu His Ser Asp Tyr Met Asn Met
225                 230                 235                 240

Thr Pro Arg Arg Pro Gly Pro Thr Arg Lys His Tyr Gln Pro Tyr Ala
                245                 250                 255

Pro Pro Arg Asp Phe Ala Ala Tyr Arg Ser Lys Arg Gly Arg Lys Lys
            260                 265                 270

Leu Leu Tyr Ile Phe Lys Gln Pro Phe Met Arg Pro Val Gln Thr Thr
        275                 280                 285

Gln Glu Glu Asp Gly Cys Ser Cys Arg Phe Pro Glu Glu Glu Glu Gly
    290                 295                 300

Gly Cys Glu Leu Arg Val Lys Phe Ser Arg Ser Ala Asp Ala Pro Ala
305                 310                 315                 320

Tyr Lys Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

```
Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
    370                 375                 380

Lys Gly Glu Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 217
<211> LENGTH: 426
<212> TYPE: PRT
<213> ORGANISM: Artificial Sequence
<220> FEATURE:
<223> OTHER INFORMATION: Synthetic Construct

<400> SEQUENCE: 217

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
                20                  25                  30

Leu Glu Glu Ser Gly Gly Arg Leu Val Gln Pro Arg Gly Ser Leu Arg
            35                  40                  45

Leu Ser Cys Ala Gly Ser Gly Arg Thr Phe Ser Thr Tyr Gly Met Ala
        50                  55                  60

Trp Phe Arg Gln Ala Pro Gly Lys Glu Arg Glu Phe Val Ala Ser Lys
65                  70                  75                  80

Ala Ser Met Asn Tyr Ser Gly Arg Thr Tyr Tyr Ala Asp Ser Val Lys
                85                  90                  95

Gly Arg Phe Thr Ile Ala Arg Asp Asn Ala Lys Asn Met Val Phe Leu
            100                 105                 110

Gln Met Asn Asn Leu Lys Pro Glu Asp Thr Ala Val Tyr Tyr Cys Ala
        115                 120                 125

Ala Gly Thr Gly Cys Ser Thr Tyr Gly Cys Phe Asp Ala Gln Ile Ile
    130                 135                 140

Asp Tyr Trp Gly Lys Gly Thr Leu Val Thr Val Ser Ser Thr Ser Thr
145                 150                 155                 160

Thr Thr Pro Ala Pro Arg Pro Pro Thr Pro Ala Pro Thr Ile Ala Ser
                165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Phe Trp Val Leu
        195                 200                 205

Val Val Val Gly Gly Val Leu Ala Cys Tyr Ser Leu Leu Val Thr Val
    210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
                245                 250                 255

His Tyr Gln Pro Tyr Ala Pro Pro Arg Asp Phe Ala Ala Tyr Arg Ser
            260                 265                 270

Lys Arg Gly Arg Lys Lys Leu Leu Tyr Ile Phe Lys Gln Pro Phe Met
        275                 280                 285
```

```
Arg Pro Val Gln Thr Thr Gln Glu Glu Asp Gly Cys Ser Cys Arg Phe
    290                 295                 300

Pro Glu Glu Glu Gly Gly Cys Glu Leu Arg Val Lys Phe Ser Arg
305                 310                 315                 320

Ser Ala Asp Ala Pro Ala Tyr Lys Gln Gly Gln Asn Gln Leu Tyr Asn
                325                 330                 335

Glu Leu Asn Leu Gly Arg Arg Glu Glu Tyr Asp Val Leu Asp Lys Arg
                340                 345                 350

Arg Gly Arg Asp Pro Glu Met Gly Gly Lys Pro Arg Arg Lys Asn Pro
                355                 360                 365

Gln Glu Gly Leu Tyr Asn Glu Leu Gln Lys Asp Lys Met Ala Glu Ala
                370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                405                 410                 415

Ala Leu His Met Gln Ala Leu Pro Pro Arg
                420                 425

<210> SEQ ID NO 218
<211> LENGTH: 416
<212> TYPE: PRT
<213> ORGANISM: Artificial Sequence
<220> FEATURE:
<223> OTHER INFORMATION: Synthetic Construct

<400> SEQUENCE: 218

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
                20                  25                  30

Leu Val Glu Ser Gly Gly Gly Leu Val Gln Ala Gly Gly Ser Leu Arg
            35                  40                  45

Leu Ser Cys Ala Ala Ser Gly Arg Thr Phe Thr Met Gly Trp Phe Arg
    50                  55                  60

Gln Ala Pro Gly Lys Glu Arg Glu Phe Val Ala Ala Ile Ser Leu Ser
65                  70                  75                  80

Pro Thr Leu Ala Tyr Tyr Ala Glu Ser Val Lys Gly Arg Phe Thr Ile
                85                  90                  95

Ser Arg Asp Asn Ala Lys Asn Thr Val Val Leu Gln Met Asn Ser Leu
                100                 105                 110

Lys Pro Glu Asp Thr Ala Leu Tyr Tyr Cys Ala Ala Asp Arg Lys Ser
            115                 120                 125

Val Met Ser Ile Arg Pro Asp Tyr Trp Gly Gln Gly Thr Gln Val Thr
    130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
                180                 185                 190

Cys Asp Phe Trp Val Leu Val Val Gly Gly Val Leu Ala Cys Tyr
            195                 200                 205

Ser Leu Leu Val Thr Val Ala Phe Ile Ile Phe Trp Val Arg Ser Lys
    210                 215                 220
```

```
Arg Ser Arg Leu Leu His Ser Asp Tyr Met Asn Met Thr Pro Arg Arg
225                 230                 235                 240

Pro Gly Pro Thr Arg Lys His Tyr Gln Pro Tyr Ala Pro Pro Arg Asp
            245                 250                 255

Phe Ala Ala Tyr Arg Ser Lys Arg Gly Arg Lys Lys Leu Leu Tyr Ile
        260                 265                 270

Phe Lys Gln Pro Phe Met Arg Pro Val Gln Thr Thr Gln Glu Glu Asp
    275                 280                 285

Gly Cys Ser Cys Arg Phe Pro Glu Glu Glu Gly Cys Glu Leu
290                 295                 300

Arg Val Lys Phe Ser Arg Ser Ala Asp Ala Pro Ala Tyr Lys Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415

<210> SEQ ID NO 219
<211> LENGTH: 418
<212> TYPE: PRT
<213> ORGANISM: Artificial Sequence
<220> FEATURE:
<223> OTHER INFORMATION: Synthetic Construct

<400> SEQUENCE: 219

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
            20                  25                  30

Leu Val Asp Ser Gly Gly Gly Leu Val Gln Pro Gly Gly Ser Leu Arg
        35                  40                  45

Leu Ser Cys Val Ala Ser Gly Gly Ile Phe Val Ile Asn Ala Met Gly
    50                  55                  60

Trp Tyr Arg Gln Ala Pro Gly Lys Gln Arg Glu Leu Val Ala Ser Ile
65                  70                  75                  80

Arg Gly Leu Gly Arg Thr Asn Tyr Asp Asp Ser Val Lys Gly Arg Phe
                85                  90                  95

Thr Ile Ser Arg Asp Asn Ala Asn Asn Thr Val Tyr Leu Gln Met Asn
            100                 105                 110

Ser Leu Glu Pro Glu Asp Thr Ala Val Tyr Tyr Cys Thr Val Tyr Val
        115                 120                 125

Thr Leu Leu Gly Gly Val Asn Arg Asp Tyr Trp Gly Gln Gly Thr Gln
    130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175
```

```
Ala Cys Arg Pro Ala Ala Gly Gly Ala Val His Thr Arg Gly Leu Asp
            180                 185                 190

Phe Ala Cys Asp Phe Trp Val Leu Val Val Val Gly Val Leu Ala
            195                 200                 205

Cys Tyr Ser Leu Leu Val Thr Val Ala Phe Ile Ile Phe Trp Val Arg
210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
            275                 280                 285

Glu Asp Gly Cys Ser Cys Arg Phe Pro Glu Glu Glu Glu Gly Gly Cys
            290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
            355                 360                 365

Gln Lys Asp Lys Met Ala Glu Ala Tyr Ser Glu Ile Gly Met Lys Gly
            370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 220
<211> LENGTH: 417
<212> TYPE: PRT
<213> ORGANISM: Artificial Sequence
<220> FEATURE:
<223> OTHER INFORMATION: Synthetic Construct

<400> SEQUENCE: 220

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
            20                  25                  30

Leu Val Glu Ser Gly Gly Gly Leu Val Gln Ala Gly Gly Ser Leu Arg
        35                  40                  45

Leu Ser Cys Ala Ala Ser Gly Arg Thr Phe Ser Ser Ile Val Met Gly
    50                  55                  60

Trp Phe Arg Gln Ala Pro Gly Lys Glu Arg Glu Phe Val Gly Ala Ile
65                  70                  75                  80

Met Trp Asn Asp Gly Ile Thr Tyr Leu Gln Asp Ser Val Lys Gly Arg
                85                  90                  95

Phe Thr Ile Phe Arg Asp Asn Ala Lys Asn Thr Val Tyr Leu Gln Met
            100                 105                 110
```

```
Asn Ser Leu Lys Leu Glu Asp Thr Ala Val Tyr Tyr Cys Ala Ala Ser
            115                 120                 125

Lys Gly Arg Tyr Ser Glu Tyr Glu Tyr Trp Gly Gln Gly Thr Gln Val
        130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
        210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
            290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 221
<211> LENGTH: 426
<212> TYPE: PRT
<213> ORGANISM: Artificial Sequence
<220> FEATURE:
<223> OTHER INFORMATION: Synthetic Construct

<400> SEQUENCE: 221

Met Ala Leu Pro Val Thr Ala Leu Leu Leu Pro Leu Ala Leu Leu Leu
1               5                   10                  15

His Ala Ala Arg Pro Val Asn Arg Thr Arg Met His Glu Val Gln
            20                  25                  30

Leu Val Glu Ser Gly Gly Gly Val Val Gln Ala Gly Gly Ser Leu Thr
        35                  40                  45

Val Ser Cys Thr Ala Ser Gly Phe Thr Phe Asp Arg Ala Val Ile Val
```

```
                    50                  55                  60
Trp Phe Arg Gln Ala Pro Gly Lys Gly Arg Glu Gly Val Ser Phe Ile
 65                  70                  75                  80

Lys Pro Ser Asp Gly Thr Ile Tyr Tyr Ile Asp Ser Leu Lys Gly Arg
                 85                  90                  95

Phe Thr Ile Ser Ser Asp Ile Ala Lys Asn Thr Val Tyr Leu Gln Met
            100                 105                 110

Lys Ser Leu Glu Ser Glu Asp Ser Ala Val Tyr Tyr Cys Ala Ala Ser
        115                 120                 125

Pro Glu Asp Trp Tyr Thr Asp Trp Ile Asp Trp Ser Ile Tyr Arg Trp
    130                 135                 140

Gln His Trp Gly Gln Gly Thr Gln Val Thr Val Ser Ser Thr Ser Thr
145                 150                 155                 160

Thr Thr Pro Ala Pro Arg Pro Pro Thr Pro Ala Pro Thr Ile Ala Ser
                165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Phe Trp Val Leu
        195                 200                 205

Val Val Val Gly Gly Val Leu Ala Cys Tyr Ser Leu Leu Val Thr Val
    210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
                245                 250                 255

His Tyr Gln Pro Tyr Ala Pro Pro Arg Asp Phe Ala Ala Tyr Arg Ser
            260                 265                 270

Lys Arg Gly Arg Lys Lys Leu Leu Tyr Ile Phe Lys Gln Pro Phe Met
        275                 280                 285

Arg Pro Val Gln Thr Thr Gln Glu Glu Asp Gly Cys Ser Cys Arg Phe
    290                 295                 300

Pro Glu Glu Glu Glu Gly Gly Cys Glu Leu Arg Val Lys Phe Ser Arg
305                 310                 315                 320

Ser Ala Asp Ala Pro Ala Tyr Lys Gln Gly Gln Asn Gln Leu Tyr Asn
                325                 330                 335

Glu Leu Asn Leu Gly Arg Arg Glu Glu Tyr Asp Val Leu Asp Lys Arg
            340                 345                 350

Arg Gly Arg Asp Pro Glu Met Gly Gly Lys Pro Arg Arg Lys Asn Pro
        355                 360                 365

Gln Glu Gly Leu Tyr Asn Glu Leu Gln Lys Asp Lys Met Ala Glu Ala
    370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                405                 410                 415

Ala Leu His Met Gln Ala Leu Pro Pro Arg
            420                 425

<210> SEQ ID NO 222
<211> LENGTH: 417
<212> TYPE: PRT
<213> ORGANISM: Artificial Sequence
<220> FEATURE:
<223> OTHER INFORMATION: Synthetic Construct
```

<400> SEQUENCE: 222

```
Met Ala Leu Pro Val Thr Ala Leu Leu Leu Pro Leu Ala Leu Leu Leu
1               5                   10                  15

His Ala Ala Arg Pro Val Asn Arg Thr Arg Met His Glu Val Gln
            20                  25                  30

Leu Val Glu Ser Gly Gly Gly Met Val Gln Ala Gly Asp Ser Leu Arg
        35                  40                  45

Leu Ser Cys Val Gln Ser Thr Tyr Thr Val Asn Ser Asp Val Met Gly
50                  55                  60

Trp Phe Arg Gln Ala Pro Gly Lys Glu Arg Glu Phe Val Gly Ala Ile
65                  70                  75                  80

Met Trp Asn Asp Gly Ile Thr Tyr Leu Gln Asp Ser Val Lys Gly Arg
                85                  90                  95

Phe Thr Ile Phe Arg Asp Asn Ala Lys Asn Thr Val Tyr Leu Gln Met
            100                 105                 110

Asn Ser Leu Lys Leu Glu Asp Thr Ala Val Tyr Tyr Cys Ala Ala Ser
        115                 120                 125

Lys Gly Arg Tyr Ser Glu Tyr Glu Tyr Trp Gly Gln Gly Thr Gln Val
130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Val Gly Gly Val Leu Ala Cys
        195                 200                 205

Tyr Ser Leu Leu Val Thr Val Ala Phe Ile Ile Phe Trp Val Arg Ser
210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415
```

Arg

<210> SEQ ID NO 223
<211> LENGTH: 418
<212> TYPE: PRT
<213> ORGANISM: Artificial Sequence
<220> FEATURE:
<223> OTHER INFORMATION: Synthetic Construct

<400> SEQUENCE: 223

```
Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
            20                  25                  30

Leu Val Glu Ser Gly Gly Gly Leu Val Gln Ala Gly Asp Ser Leu Arg
        35                  40                  45

Leu Ser Cys Thr Ala Ser Gly Ala Thr Leu Thr Asn Asp His Met Ala
    50                  55                  60

Trp Phe Arg Gln Ala Pro Gly Lys Gly Arg Glu Phe Val Ala Ala Ile
65                  70                  75                  80

Asp Trp Ser Gly Arg Thr Thr Asn Tyr Ala Asp Pro Val Glu Gly Arg
                85                  90                  95

Phe Thr Ile Ser Arg Asn Asn Ala Lys Asn Thr Val Tyr Leu Glu Met
            100                 105                 110

Asn Ser Leu Lys Leu Glu Asp Thr Ala Val Tyr Tyr Cys Ala Val Leu
        115                 120                 125

Arg Ala Trp Ile Ser Tyr Asp Asn Asp Tyr Trp Gly Gln Gly Thr Gln
    130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Gly Gly Val Leu Ala
        195                 200                 205

Cys Tyr Ser Leu Leu Val Thr Val Ala Phe Ile Ile Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Glu Gly Gly Cys
    290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350
```

```
Gly Lys Pro Arg Arg Lys Asn Pro Gln Glu Gly Leu Tyr Asn Glu Leu
            355                 360                 365

Gln Lys Asp Lys Met Ala Glu Ala Tyr Ser Glu Ile Gly Met Lys Gly
    370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 224
<211> LENGTH: 418
<212> TYPE: PRT
<213> ORGANISM: Artificial Sequence
<220> FEATURE:
<223> OTHER INFORMATION: Synthetic Construct

<400> SEQUENCE: 224

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
            20                  25                  30

Leu Val Glu Ser Gly Gly Gly Leu Val Gln Ala Gly Gly Ser Leu Arg
        35                  40                  45

Leu Ser Cys Ala Ala Ser Gly Thr Leu Ser Lys Asn Thr Val Ala
    50                  55                  60

Trp Phe Arg Gln Ala Pro Gly Lys Glu Arg Gly Phe Val Ala Ser Ile
65                  70                  75                  80

Thr Trp Asp Gly Arg Thr Thr Tyr Tyr Ala Asp Ser Val Lys Gly Arg
                85                  90                  95

Phe Thr Ile Ser Arg Asp Asn Ala Lys Asn Thr Val Tyr Leu Gln Met
            100                 105                 110

Asn Ser Leu Lys Pro Glu Asp Thr Ala Val Tyr Val Cys Ala Asp Leu
        115                 120                 125

Gly Lys Trp Pro Ala Gly Pro Ala Asp Tyr Trp Gly Gln Gly Thr Gln
    130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Val Gly Gly Val Leu Ala
        195                 200                 205

Cys Tyr Ser Leu Leu Val Thr Val Ala Phe Ile Ile Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Glu Gly Gly Cys
```

```
                290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
                340                 345                 350

Gly Lys Pro Arg Arg Lys Asn Pro Gln Glu Gly Leu Tyr Asn Glu Leu
            355                 360                 365

Gln Lys Asp Lys Met Ala Glu Ala Tyr Ser Glu Ile Gly Met Lys Gly
            370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 225
<211> LENGTH: 417
<212> TYPE: PRT
<213> ORGANISM: Artificial Sequence
<220> FEATURE:
<223> OTHER INFORMATION: Synthetic Construct

<400> SEQUENCE: 225

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
                20                  25                  30

Leu Glu Glu Ser Gly Gly Gly Leu Val Gln Ala Gly Arg Ser Leu Arg
            35                  40                  45

Leu Ser Cys Ala Ala Ser Glu His Thr Phe Ser Ser His Val Met Gly
50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                85                  90                  95

Phe Thr Ile Ser Arg Asp Asn Ala Lys Lys Thr Leu Tyr Leu Gln Met
                100                 105                 110

Asn Ser Leu Lys Pro Glu Asp Thr Ala Val Tyr Tyr Cys Ala Ala Arg
            115                 120                 125

Arg Ile Asp Ala Ala Asp Phe Asp Ser Trp Gly Gln Gly Thr Gln Val
130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Val Gly Gly Val Leu Ala Cys
            195                 200                 205

Tyr Ser Leu Leu Val Thr Val Ala Phe Ile Ile Phe Trp Val Arg Ser
            210                 215                 220

Lys Arg Ser Arg Leu Leu His Ser Asp Tyr Met Asn Met Thr Pro Arg
225                 230                 235                 240
```

```
Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 226
<211> LENGTH: 417
<212> TYPE: PRT
<213> ORGANISM: Artificial Sequence
<220> FEATURE:
<223> OTHER INFORMATION: Synthetic Construct

<400> SEQUENCE: 226

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
                20                  25                  30

Leu Val Glu Ser Gly Gly Gly Leu Val Gln Ala Gly Asp Ser Leu Arg
            35                  40                  45

Leu Thr Cys Thr Ala Ser Gly Arg Ala Phe Ser Thr Tyr Phe Met Ala
        50                  55                  60

Trp Phe Arg Gln Ala Pro Gly Lys Glu Arg Glu Phe Val Ala Gly Ile
65                  70                  75                  80

Ala Trp Ser Gly Gly Ser Thr Ala Tyr Ala Asp Ser Val Lys Gly Arg
                85                  90                  95

Phe Thr Ile Ser Arg Asp Asn Ala Lys Asn Thr Val Tyr Leu Gln Met
            100                 105                 110

Asn Ser Leu Lys Ser Glu Asp Thr Ala Val Tyr Tyr Cys Ala Ser Arg
        115                 120                 125

Gly Ile Glu Val Glu Gly Phe Gly Ala Trp Gly Gln Gly Thr Gln Val
    130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175
```

```
Cys Arg Pro Ala Ala Gly Gly Ala Val His Thr Arg Gly Leu Asp Phe
                180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 227
<211> LENGTH: 376
<212> TYPE: PRT
<213> ORGANISM: Artificial Sequence
<220> FEATURE:
<223> OTHER INFORMATION: Synthetic Construct

<400> SEQUENCE: 227

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
            20                  25                  30

Leu Val Glu Ser Gly Gly Gly Leu Val Gln Pro Gly Gly Ser Leu Arg
        35                  40                  45

Leu Ser Cys Glu Ala Ser Gly Phe Thr Leu Asp Tyr Tyr Ala Ile Gly
    50                  55                  60

Trp Phe Arg Gln Ala Pro Gly Lys Glu Arg Glu Gly Val Ile Cys Ile
65                  70                  75                  80

Ser Arg Ser Asp Gly Ser Thr Tyr Tyr Ala Asp Ser Val Lys Gly Arg
                85                  90                  95

Phe Thr Ile Ser Arg Asp Asn Ala Lys Lys Thr Val Tyr Leu Gln Met
            100                 105                 110

Ile Ser Leu Lys Pro Glu Asp Thr Ala Ala Tyr Tyr Cys Ala Ala Gly
```

115                 120                 125
Ala Asp Cys Ser Gly Tyr Leu Arg Asp Tyr Glu Phe Arg Gly Gln Gly
    130                 135                 140

Thr Gln Val Thr Val Ser Ser Thr Ser Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Gln Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375

<210> SEQ ID NO 228
<211> LENGTH: 373
<212> TYPE: PRT
<213> ORGANISM: Artificial Sequence
<220> FEATURE:
<223> OTHER INFORMATION: Synthetic Construct

<400> SEQUENCE: 228

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
                20                  25                  30

Leu Glu Glu Ser Gly Gly Gly Leu Val Gln Ala Gly Arg Ser Leu Arg
            35                  40                  45

Leu Ser Cys Ala Ala Ser Glu His Thr Phe Ser Ser His Val Met Gly
        50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                85                  90                  95

Phe Thr Ile Ser Arg Asp Asn Ala Lys Lys Thr Leu Tyr Leu Gln Met

```
                100             105             110
Asn Ser Leu Lys Pro Glu Asp Thr Ala Val Tyr Tyr Cys Ala Ala Arg
        115                 120                 125

Arg Ile Asp Ala Ala Asp Phe Asp Ser Trp Gly Gln Gly Thr Gln Val
130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
            195                 200                 205

Leu Leu Leu Ser Leu Val Ile Thr Leu Tyr Cys Lys Arg Gly Arg Lys
        210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu
                245                 250                 255

Gly Gly Cys Glu Leu Arg Val Lys Phe Ser Arg Ser Ala Asp Ala Pro
            260                 265                 270

Ala Tyr Gln Gln Gly Gln Asn Gln Leu Tyr Asn Glu Leu Asn Leu Gly
            275                 280                 285

Arg Arg Glu Glu Tyr Asp Val Leu Asp Lys Arg Arg Gly Arg Asp Pro
        290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
            355                 360                 365

Ala Leu Pro Pro Arg
    370

<210> SEQ ID NO 229
<211> LENGTH: 372
<212> TYPE: PRT
<213> ORGANISM: Artificial Sequence
<220> FEATURE:
<223> OTHER INFORMATION: Synthetic Construct

<400> SEQUENCE: 229

Met Ala Leu Pro Val Thr Ala Leu Leu Leu Pro Leu Ala Leu Leu Leu
1               5                   10                  15

His Ala Ala Arg Pro Val Asn Arg Thr Arg Met His Glu Val Gln
            20                  25                  30

Leu Val Glu Ser Gly Gly Gly Leu Val Gln Ala Gly Gly Ser Leu Arg
        35                  40                  45

Leu Ser Cys Ala Ala Ser Gly Arg Thr Phe Thr Met Gly Trp Phe Arg
    50                  55                  60

Gln Ala Pro Gly Lys Glu Arg Glu Phe Val Ala Ala Ile Ser Leu Ser
65                  70                  75                  80

Pro Thr Leu Ala Tyr Tyr Ala Glu Ser Val Lys Gly Arg Phe Thr Ile
```

```
                    85                  90                  95
Ser Arg Asp Asn Ala Lys Asn Thr Val Val Leu Gln Met Asn Ser Leu
                100                 105                 110

Lys Pro Glu Asp Thr Ala Leu Tyr Tyr Cys Ala Ala Asp Arg Lys Ser
                115                 120                 125

Val Met Ser Ile Arg Pro Asp Tyr Trp Gly Gln Gly Thr Gln Val Thr
                130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
                180                 185                 190

Cys Asp Ile Tyr Ile Trp Ala Pro Leu Ala Gly Thr Cys Gly Val Leu
                195                 200                 205

Leu Leu Ser Leu Val Ile Thr Leu Tyr Cys Lys Arg Gly Arg Lys Lys
                210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
                260                 265                 270

Tyr Gln Gln Gly Gln Asn Gln Leu Tyr Asn Glu Leu Asn Leu Gly Arg
                275                 280                 285

Arg Glu Glu Tyr Asp Val Leu Asp Lys Arg Arg Gly Arg Asp Pro Glu
                290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
                340                 345                 350

Leu Ser Thr Ala Thr Lys Asp Thr Tyr Asp Ala Leu His Met Gln Ala
                355                 360                 365

Leu Pro Pro Arg
    370

<210> SEQ ID NO 230
<211> LENGTH: 372
<212> TYPE: PRT
<213> ORGANISM: Artificial Sequence
<220> FEATURE:
<223> OTHER INFORMATION: Synthetic Construct

<400> SEQUENCE: 230

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Pro Pro Gly Gly Ser Leu Arg Leu Ser Cys Thr Ala Ser Gly Ser
                35                  40                  45

Thr Val Ser Ile Asn Val Met Ala Trp Tyr Arg Gln Val Ser Gly Lys
            50                  55                  60

Gln Arg Glu Leu Val Ala Ala Val Thr Arg Asp Gly Arg Lys Ser Cys
```

```
                65                  70                  75                  80
        Gly Asp Ser Val Lys Gly Arg Phe Thr Ile Ser Arg Asp Gly Ala Lys
                            85                  90                  95

Asn Ala Val Tyr Leu Gln Met Asn Ser Leu Lys Pro Glu Asp Thr Ala
                        100                 105                 110

Val Tyr Leu Cys Gly Ala Asp Gly Trp Gly Ala Thr Thr Leu Asp Tyr
                        115                 120                 125

Thr Tyr Gly Met Asp Tyr Trp Gly Lys Gly Thr Gln Val Thr Val Ser
                    130                 135                 140

Ser Ala Ala Thr Ser Thr Thr Pro Ala Pro Arg Pro Pro Thr Pro
        145                 150                 155                 160

Ala Pro Thr Ile Ala Ser Gln Pro Leu Ser Leu Arg Pro Glu Ala Cys
                            165                 170                 175

Arg Pro Ala Ala Gly Gly Ala Val His Thr Arg Gly Leu Asp Phe Ala
                        180                 185                 190

Cys Asp Ile Tyr Ile Trp Ala Pro Leu Ala Gly Thr Cys Gly Val Leu
                        195                 200                 205

Leu Leu Ser Leu Val Ile Thr Leu Tyr Cys Lys Arg Gly Arg Lys Lys
                    210                 215                 220

Leu Leu Tyr Ile Phe Lys Gln Pro Phe Met Arg Pro Val Gln Thr Thr
        225                 230                 235                 240

Gln Glu Glu Asp Gly Cys Ser Cys Arg Phe Pro Glu Glu Glu Glu Gly
                            245                 250                 255

Gly Cys Glu Leu Arg Val Lys Phe Ser Arg Ser Ala Asp Ala Pro Ala
                        260                 265                 270

Tyr Gln Gln Gly Gln Asn Gln Leu Tyr Asn Glu Leu Asn Leu Gly Arg
                        275                 280                 285

Arg Glu Glu Tyr Asp Val Leu Asp Lys Arg Arg Gly Arg Asp Pro Glu
                    290                 295                 300

Met Gly Gly Lys Pro Arg Arg Lys Asn Pro Gln Glu Gly Leu Tyr Asn
        305                 310                 315                 320

Glu Leu Gln Lys Asp Lys Met Ala Glu Ala Tyr Ser Glu Ile Gly Met
                            325                 330                 335

Lys Gly Glu Arg Arg Arg Gly Lys Gly His Asp Gly Leu Tyr Gln Gly
                        340                 345                 350

Leu Ser Thr Ala Thr Lys Asp Thr Tyr Asp Ala Leu His Met Gln Ala
                        355                 360                 365

Leu Pro Pro Arg
            370

<210> SEQ ID NO 231
<211> LENGTH: 364
<212> TYPE: PRT
<213> ORGANISM: Artificial Sequence
<220> FEATURE:
<223> OTHER INFORMATION: Synthetic Construct

<400> SEQUENCE: 231

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Gly
```

```
            50                  55                  60
Phe Val Ala Ser Ile Thr Trp Asp Gly Arg Ser Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
            115                 120                 125

Trp Gly Gln Gly Thr Gln Val Thr Val Ser Ser Thr Ser Thr Thr Thr
130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360

<210> SEQ ID NO 232
<211> LENGTH: 368
<212> TYPE: PRT
<213> ORGANISM: Artificial Sequence
<220> FEATURE:
<223> OTHER INFORMATION: Synthetic Construct

<400> SEQUENCE: 232

Met Ala Leu Pro Val Thr Ala Leu Leu Leu Pro Leu Ala Leu Leu Leu
 1               5                  10                  15

His Ala Ala Arg Pro Gln Val Gln Leu Val Glu Ser Gly Gly Gly Leu
                20                  25                  30

Val Gln Pro Gly Gly Ser Leu Arg Leu Ala Cys Glu Ala Pro Gly Ser
            35                  40                  45

Gly Asn Ser Ile Asn Ala Met Gly Trp Tyr Arg Gln Thr Pro Gly Lys
```

```
                50                  55                  60
Arg Arg Glu Leu Val Ala Thr Ile Thr Arg Gly Gly Ser Thr Asn Tyr
 65                  70                  75                  80

Gly Pro Ser Val Lys Gly Arg Phe Thr Ile Thr Arg Asp Asn Val Lys
                 85                  90                  95

Asn Thr Val His Leu Gln Met Asn Ser Leu Lys Pro Asp Asp Thr Ala
            100                 105                 110

Val Tyr Tyr Cys Asn Ala Glu Arg Leu Asp Gly Ser Gly Tyr Gly Tyr
        115                 120                 125

Glu Tyr Asp Tyr Trp Gly Gln Gly Thr Gln Val Thr Val Ser Ser Thr
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Gln Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365

<210> SEQ ID NO 233
<211> LENGTH: 367
<212> TYPE: PRT
<213> ORGANISM: Artificial Sequence
<220> FEATURE:
<223> OTHER INFORMATION: Synthetic Construct

<400> SEQUENCE: 233

Met Ala Leu Pro Val Thr Ala Leu Leu Leu Pro Leu Ala Leu Leu Leu
 1               5                  10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
```

```
            50                  55                  60
Glu Arg Gly Phe Val Thr Ser Ile Thr Cys Asp Gly Arg Thr Thr Tyr
 65                  70                  75                  80

Tyr Ala Asn Ser Val Asn Gly Arg Phe Pro Ile Asn Arg Asn Asn Ala
                 85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
                180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 234
<211> LENGTH: 367
<212> TYPE: PRT
<213> ORGANISM: Artificial Sequence
<220> FEATURE:
<223> OTHER INFORMATION: Synthetic Construct

<400> SEQUENCE: 234

Met Ala Leu Pro Val Thr Ala Leu Leu Leu Pro Leu Ala Leu Leu Leu
 1               5                  10                  15

His Ala Ala Arg Pro Asp Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Ser Ser Ile Val Met Gly Trp Phe Arg Gln Ala Pro Gly Lys
```

```
            50                  55                  60
Glu Arg Glu Phe Val Gly Ala Ile Met Trp Asn Asp Gly Leu Thr Tyr
 65                  70                  75                  80

Leu Gln Gly Ser Val Lys Gly Arg Phe Thr Ile Ser Arg Asp Asn Ala
                     85                  90                  95

Lys Asn Thr Val Val Leu Gln Met Asn Ser Leu Lys Pro Glu Asp Thr
                    100                 105                 110

Ala Leu Tyr Tyr Cys Ala Ala Asp Arg Lys Ser Val Met Ser Ile Arg
                    115                 120                 125

Pro Asp Tyr Trp Gly Gln Gly Thr Gln Val Thr Val Ser Ser Thr Ser
                130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                    165                 170                 175

Gly Ala Val His Thr Arg Gly Leu Asp Phe Ala Cys Asp Ile Tyr Ile
                180                 185                 190

Trp Ala Pro Leu Ala Gly Thr Cys Gly Val Leu Leu Leu Ser Leu Val
                195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
                275                 280                 285

Val Leu Asp Lys Arg Arg Gly Arg Asp Pro Glu Met Gly Gly Lys Pro
                290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                    325                 330                 335

Arg Gly Lys Gly His Asp Gly Leu Tyr Gln Gly Leu Ser Thr Ala Thr
                340                 345                 350

Lys Asp Thr Tyr Asp Ala Leu His Met Gln Ala Leu Pro Pro Arg
                355                 360                 365

<210> SEQ ID NO 235
<211> LENGTH: 362
<212> TYPE: PRT
<213> ORGANISM: Artificial Sequence
<220> FEATURE:
<223> OTHER INFORMATION: Synthetic Construct

<400> SEQUENCE: 235

Met Ala Leu Pro Val Thr Ala Leu Leu Leu Pro Leu Ala Leu Leu Leu
 1               5                  10                  15

His Ala Ala Arg Pro Gln Val Gln Leu Val Glu Ser Gly Gly Gly Leu
                 20                  25                  30

Val Gln Ala Gly Gly Ser Leu Arg Leu Ser Cys Ala Ala Ser Gly Arg
             35                  40                  45

Thr Phe Thr Met Gly Trp Phe Arg Gln Ala Pro Gly Lys Glu Arg Glu
```

```
            50                  55                  60
Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Val Tyr
            100                 105                 110

Tyr Cys Ala Ala Arg Arg Ile Asp Ala Ala Asp Phe Asp Ser Trp Gly
            115                 120                 125

Gln Gly Thr Gln Val Thr Val Ser Ser Thr Thr Thr Pro Ala
130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
            195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
            290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
            355                 360

<210> SEQ ID NO 236
<211> LENGTH: 366
<212> TYPE: PRT
<213> ORGANISM: Artificial Sequence
<220> FEATURE:
<223> OTHER INFORMATION: Synthetic Construct

<400> SEQUENCE: 236

Met Ala Leu Pro Val Thr Ala Leu Leu Leu Pro Leu Ala Leu Leu Leu
  1               5                  10                  15

His Ala Ala Arg Pro Gln Val Gln Leu Val Glu Ser Gly Gly Gly Leu
                 20                  25                  30

Val Gln Ala Gly Gly Ser Leu Arg Leu Ser Cys Ala Ala Ser Gly Gly
             35                  40                  45

Thr Leu Ser Lys Asn Thr Val Ala Trp Phe Arg Gln Ala Pro Gly Lys
```

```
            50                  55                  60
Glu Arg Gly Phe Val Ala Ser Ile Thr Trp Asp Gly Arg Thr Thr Tyr
 65                  70                  75                  80

Tyr Ala Asp Ser Val Lys Gly Arg Phe Thr Ile Ser Arg Asp Asn Ala
                 85                  90                  95

Lys Asn Thr Val Tyr Leu Gln Met Asn Ser Leu Lys Pro Glu Asp Thr
                100                 105                 110

Ala Val Tyr Val Cys Ala Asp Leu Gly Lys Trp Pro Ala Gly Pro Ala
                115                 120                 125

Asp Tyr Trp Gly Gln Gly Thr Gln Val Thr Val Ser Ser Thr Ser Thr
                130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
                180                 185                 190

Ala Pro Leu Ala Gly Thr Cys Gly Val Leu Leu Leu Ser Leu Val Ile
                195                 200                 205

Thr Leu Tyr Cys Lys Arg Gly Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Gly Gly Cys Glu Leu Arg Val
                245                 250                 255

Lys Phe Ser Arg Ser Ala Asp Ala Pro Ala Tyr Gln Gln Gly Gln Asn
                260                 265                 270

Gln Leu Tyr Asn Glu Leu Asn Leu Gly Arg Arg Glu Glu Tyr Asp Val
                275                 280                 285

Leu Asp Lys Arg Arg Gly Arg Asp Pro Glu Met Gly Gly Lys Pro Arg
                290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
                340                 345                 350

Asp Thr Tyr Asp Ala Leu His Met Gln Ala Leu Pro Pro Arg
                355                 360                 365

<210> SEQ ID NO 237
<211> LENGTH: 367
<212> TYPE: PRT
<213> ORGANISM: Artificial Sequence
<220> FEATURE:
<223> OTHER INFORMATION: Synthetic Construct

<400> SEQUENCE: 237

Met Ala Leu Pro Val Thr Ala Leu Leu Leu Pro Leu Ala Leu Leu Leu
 1               5                  10                  15

His Ala Ala Arg Pro Gln Val Gln Leu Val Glu Ser Gly Gly Gly Leu
                20                  25                  30

Val Gln Pro Gly Gly Ser Leu Thr Leu Ser Cys Ala Ala Ser Gly Ser
                35                  40                  45

Ile Asp Ser Ile Asn Thr Met Asp Trp Phe Arg Gln Ala Pro Gly Lys
```

```
            50                  55                  60
Glu Arg Glu Phe Val Ala Ala Ile Ser Leu Ser Pro Thr Leu Ala Tyr
 65                  70                  75                  80

Tyr Ala Glu Ser Val Lys Gly Arg Phe Thr Ile Ser Arg Asp Asn Ala
                 85                  90                  95

Lys Asn Thr Val Val Leu Gln Met Asn Ser Leu Lys Pro Glu Asp Thr
                100                 105                 110

Ala Leu Tyr Tyr Cys Ala Ala Asp Arg Lys Ser Val Met Ser Ile Arg
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 238
<211> LENGTH: 366
<212> TYPE: PRT
<213> ORGANISM: Artificial Sequence
<220> FEATURE:
<223> OTHER INFORMATION: Synthetic Construct

<400> SEQUENCE: 238

Met Ala Leu Pro Val Thr Ala Leu Leu Leu Pro Leu Ala Leu Leu Leu
 1               5                  10                  15

His Ala Ala Arg Pro Asp Val Gln Leu Val Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
```

```
            50                  55                  60
Glu Arg Gly Phe Val Thr Ser Ile Thr Cys Asp Gly Arg Thr Thr Tyr
 65                  70                  75                  80

Tyr Ala Asn Ser Val Lys Gly Arg Phe Pro Ile Ser Arg Asp Asn Ala
                 85                  90                  95

Glu Asn Thr Val Tyr Leu Gln Met Asn Ser Leu Lys Pro Glu Asp Thr
                100                 105                 110

Ala Gly Tyr Val Cys Ala Asp Leu Gly Lys Trp Pro Ala Gly Ser Ala
                115                 120                 125

Asp Tyr Trp Gly Gln Gly Thr His Val Thr Val Ser Ser Thr Ser Thr
            130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
                180                 185                 190

Ala Pro Leu Ala Gly Thr Cys Gly Val Leu Leu Leu Ser Leu Val Ile
                195                 200                 205

Thr Leu Tyr Cys Lys Arg Gly Arg Lys Lys Leu Leu Tyr Ile Phe Lys
            210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255

Lys Phe Ser Arg Ser Ala Asp Ala Pro Ala Tyr Gln Gln Gly Gln Asn
                260                 265                 270

Gln Leu Tyr Asn Glu Leu Asn Leu Gly Arg Arg Glu Glu Tyr Asp Val
            275                 280                 285

Leu Asp Lys Arg Arg Gly Arg Asp Pro Glu Met Gly Gly Lys Pro Arg
290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
            355                 360                 365

<210> SEQ ID NO 239
<211> LENGTH: 367
<212> TYPE: PRT
<213> ORGANISM: Artificial Sequence
<220> FEATURE:
<223> OTHER INFORMATION: Synthetic Construct

<400> SEQUENCE: 239

Met Ala Leu Pro Val Thr Ala Leu Leu Leu Pro Leu Ala Leu Leu Leu
 1               5                  10                  15

His Ala Ala Arg Pro Gln Val Lys Leu Glu Glu Ser Gly Gly Gly Leu
                20                  25                  30

Val Gln Pro Gly Gly Ser Leu Arg Leu Ser Cys Thr Ala Ser Glu Phe
                35                  40                  45

Thr Phe Ser Asp Tyr Trp Met His Trp Val Arg Gln Ala Pro Gly Lys
```

```
              50                  55                  60
Gly Leu Glu Trp Val Ala Ser Ile Asp Thr Ser Gly Gln Thr Thr Tyr
 65                  70                  75                  80

Tyr Ala Asp Ser Leu Lys Gly Arg Phe Thr Ile Ser Arg Asp Asn Ala
                 85                  90                  95

Lys Ser Thr Leu Tyr Leu Gln Met Asn Ser Leu Lys Ser Glu Asp Thr
                100                 105                 110

Gly Val Tyr Phe Cys Ala Lys Arg Tyr Arg Gly Gly Thr Trp Tyr Gly
                115                 120                 125

Met Ala Asn Trp Gly Lys Gly Thr Gln Val Thr Val Ser Ser Thr Ser
            130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
                180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
            290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
            355                 360                 365

<210> SEQ ID NO 240
<211> LENGTH: 366
<212> TYPE: PRT
<213> ORGANISM: Artificial Sequence
<220> FEATURE:
<223> OTHER INFORMATION: Synthetic Construct

<400> SEQUENCE: 240

Met Ala Leu Pro Val Thr Ala Leu Leu Leu Pro Leu Ala Leu Leu Leu
 1               5                  10                  15

His Ala Ala Arg Pro Gln Val Gln Leu Val Glu Ser Gly Gly Gly Leu
                 20                  25                  30

Val Gln Ala Gly Gly Ser Leu Arg Leu Ser Cys Ala Ala Ser Gly Arg
             35                  40                  45

Thr Leu Ser Ser Asn Thr Met Ala Trp Phe Arg Gln Ala Pro Gly Lys
```

```
            50                  55                  60
Glu Arg Glu Phe Val Ala Ser Thr Thr Trp Asn Gly Arg Ser Thr Tyr
 65                  70                  75                  80

Tyr Ala Asp Ser Val Lys Gly Arg Phe Thr Ile Ser Arg Asp Asn Ala
                 85                  90                  95

Lys Asn Thr Met Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
            115                 120                 125

Asp Tyr Trp Gly Gln Gly Thr Gln Val Thr Val Ser Ser Thr Ser Thr
            130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
            180                 185                 190

Ala Pro Leu Ala Gly Thr Cys Gly Val Leu Leu Leu Ser Leu Val Ile
            195                 200                 205

Thr Leu Tyr Cys Lys Arg Gly Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255

Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
            275                 280                 285

Leu Asp Lys Arg Arg Gly Arg Asp Pro Glu Met Gly Gly Lys Pro Arg
290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
            355                 360                 365

<210> SEQ ID NO 241
<211> LENGTH: 362
<212> TYPE: PRT
<213> ORGANISM: Artificial Sequence
<220> FEATURE:
<223> OTHER INFORMATION: Synthetic Construct

<400> SEQUENCE: 241

Met Ala Leu Pro Val Thr Ala Leu Leu Leu Pro Leu Ala Leu Leu Leu
 1               5                  10                  15

His Ala Ala Arg Pro Gln Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Gln Arg Glu
```

```
                50              55                  60
Leu Val Ala Asp Ile Ser Gly Gly Arg Thr Asn Tyr Ala Asp Ser Val
 65                  70                  75                  80

Lys Gly Arg Phe Thr Ile Ser Arg Asp Asn Ala Lys Asn Thr Val Tyr
                     85                  90                  95

Leu Gln Met Asn Ser Leu Lys Pro Glu Asp Thr Ala Val Tyr Tyr Cys
                100                 105                 110

Ala Ala Asp Arg Lys Ser Val Met Ser Ile Arg Pro Asp Tyr Trp Gly
                115                 120                 125

Gln Gly Thr Gln Val Thr Val Ser Ser Thr Thr Thr Thr Pro Ala
                130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
                180                 185                 190

Gly Thr Cys Gly Val Leu Leu Leu Ser Leu Val Ile Thr Leu Tyr Cys
                195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
                260                 265                 270

Glu Leu Asn Leu Gly Arg Arg Glu Glu Tyr Asp Val Leu Asp Lys Arg
                275                 280                 285

Arg Gly Arg Asp Pro Glu Met Gly Gly Lys Pro Arg Arg Lys Asn Pro
                290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
                340                 345                 350

Ala Leu His Met Gln Ala Leu Pro Pro Arg
                355                 360

<210> SEQ ID NO 242
<211> LENGTH: 350
<212> TYPE: PRT
<213> ORGANISM: Artificial Sequence
<220> FEATURE:
<223> OTHER INFORMATION: Synthetic Construct

<400> SEQUENCE: 242

Met Ala Leu Pro Val Thr Ala Leu Leu Leu Pro Leu Ala Leu Leu Leu
 1                   5                  10                  15

His Ala Ala Arg Pro Gln Val Gln Leu Val Glu Ser Gly Gly Gly Leu
                 20                  25                  30

Val Gln Ala Gly Ala Ser Leu Arg Leu Ser Cys Ala Ala Ser Gly Arg
                 35                  40                  45

Thr Phe Thr Val Ala Ala Ile Ser Leu Ser Pro Thr Leu Ala Tyr Tyr
```

```
            50                  55                  60
Ala Glu Ser Val Lys Gly Arg Phe Thr Ile Ser Arg Asp Asn Ala Lys
 65                  70                  75                  80

Asn Thr Val Val Leu Gln Met Asn Ser Leu Lys Pro Glu Asp Thr Ala
                 85                  90                  95

Leu Tyr Tyr Cys Ala Ala Asp Arg Lys Ser Val Met Ser Ile Arg Pro
            100                 105                 110

Asp Tyr Trp Gly Gln Gly Thr Gln Val Thr Val Ser Ser Thr Ser Thr
            115                 120                 125

Thr Thr Pro Ala Pro Arg Pro Pro Thr Pro Ala Pro Thr Ile Ala Ser
        130                 135                 140

Gln Pro Leu Ser Leu Arg Pro Glu Ala Cys Arg Pro Ala Ala Gly Gly
145                 150                 155                 160

Ala Val His Thr Arg Gly Leu Asp Phe Ala Cys Asp Ile Tyr Ile Trp
                165                 170                 175

Ala Pro Leu Ala Gly Thr Cys Gly Val Leu Leu Leu Ser Leu Val Ile
            180                 185                 190

Thr Leu Tyr Cys Lys Arg Gly Arg Lys Lys Leu Leu Tyr Ile Phe Lys
        195                 200                 205

Gln Pro Phe Met Arg Pro Val Gln Thr Thr Gln Glu Glu Asp Gly Cys
    210                 215                 220

Ser Cys Arg Phe Pro Glu Glu Glu Glu Gly Gly Cys Glu Leu Arg Val
225                 230                 235                 240

Lys Phe Ser Arg Ser Ala Asp Ala Pro Ala Tyr Gln Gln Gly Gln Asn
                245                 250                 255

Gln Leu Tyr Asn Glu Leu Asn Leu Gly Arg Arg Glu Glu Tyr Asp Val
            260                 265                 270

Leu Asp Lys Arg Arg Gly Arg Asp Pro Glu Met Gly Gly Lys Pro Arg
        275                 280                 285

Arg Lys Asn Pro Gln Glu Gly Leu Tyr Asn Glu Leu Gln Lys Asp Lys
    290                 295                 300

Met Ala Glu Ala Tyr Ser Glu Ile Gly Met Lys Gly Glu Arg Arg Arg
305                 310                 315                 320

Gly Lys Gly His Asp Gly Leu Tyr Gln Gly Leu Ser Thr Ala Thr Lys
                325                 330                 335

Asp Thr Tyr Asp Ala Leu His Met Gln Ala Leu Pro Pro Arg
            340                 345                 350

<210> SEQ ID NO 243
<211> LENGTH: 371
<212> TYPE: PRT
<213> ORGANISM: Artificial Sequence
<220> FEATURE:
<223> OTHER INFORMATION: Synthetic Construct

<400> SEQUENCE: 243

Met Ala Leu Pro Val Thr Ala Leu Leu Leu Pro Leu Ala Leu Leu Leu
  1               5                  10                  15

His Ala Ala Arg Pro Asp Val Gln Leu Val Glu Ser Gly Gly Gly Leu
                 20                  25                  30

Glu Gln Ala Gly Gly Ser Leu Arg Leu Ser Cys Ala Ala Ser Gly Gly
             35                  40                  45

Thr Leu Ser Lys Asn Thr Val Ala Trp Phe Arg Gln Ala Pro Gly Lys
         50                  55                  60

Glu Arg Gly Phe Val Ala Ser Ile Thr Trp Asp Gly Arg Thr Thr Tyr
```

```
            65                  70                  75                  80
        Tyr Ala Asp Ser Val Lys Gly Arg Phe Thr Ile Ser Arg Asp Asn Ala
                        85                  90                  95

Lys Asn Thr Val Tyr Leu Gln Met Asn Ser Leu Lys Pro Glu Asp Thr
                        100                 105                 110

Ala Val Tyr Tyr Cys Ala Ser Thr Ala Ser Cys His Leu Phe Gly Leu
                        115                 120                 125

Gly Ser Gly Ala Phe Val Ser Trp Gly Arg Gly Thr Gln Val Thr Val
                130                 135                 140

Ser Ser Thr Ser Thr Thr Pro Ala Pro Arg Pro Pro Thr Pro Ala
        145                 150                 155                 160

Pro Thr Ile Ala Ser Gln Pro Leu Ser Leu Arg Pro Glu Ala Cys Arg
                        165                 170                 175

Pro Ala Ala Gly Gly Ala Val His Thr Arg Gly Leu Asp Phe Ala Cys
                        180                 185                 190

Asp Ile Tyr Ile Trp Ala Pro Leu Ala Gly Thr Cys Gly Val Leu Leu
                        195                 200                 205

Leu Ser Leu Val Ile Thr Leu Tyr Cys Lys Arg Gly Arg Lys Lys Leu
                210                 215                 220

Leu Tyr Ile Phe Lys Gln Pro Phe Met Arg Pro Val Gln Thr Thr Gln
        225                 230                 235                 240

Glu Glu Asp Gly Cys Ser Cys Arg Phe Pro Glu Glu Glu Glu Gly Gly
                        245                 250                 255

Cys Glu Leu Arg Val Lys Phe Ser Arg Ser Ala Asp Ala Pro Ala Tyr
                        260                 265                 270

Gln Gln Gly Gln Asn Gln Leu Tyr Asn Glu Leu Asn Leu Gly Arg Arg
                        275                 280                 285

Glu Glu Tyr Asp Val Leu Asp Lys Arg Arg Gly Arg Asp Pro Glu Met
                        290                 295                 300

Gly Gly Lys Pro Arg Arg Lys Asn Pro Gln Glu Gly Leu Tyr Asn Glu
        305                 310                 315                 320

Leu Gln Lys Asp Lys Met Ala Glu Ala Tyr Ser Glu Ile Gly Met Lys
                        325                 330                 335

Gly Glu Arg Arg Arg Gly Lys Gly His Asp Gly Leu Tyr Gln Gly Leu
                        340                 345                 350

Ser Thr Ala Thr Lys Asp Thr Tyr Asp Ala Leu His Met Gln Ala Leu
                        355                 360                 365

Pro Pro Arg
            370

<210> SEQ ID NO 244
<211> LENGTH: 362
<212> TYPE: PRT
<213> ORGANISM: Artificial Sequence
<220> FEATURE:
<223> OTHER INFORMATION: Synthetic Construct

<400> SEQUENCE: 244

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe His Gln Ala Pro Gly Lys Glu Arg Glu
```

```
            50                  55                  60
Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Leu Tyr
            100                 105                 110

Tyr Cys Ala Ala Ser Lys Asp Arg Tyr Ser Glu Tyr Glu Tyr Trp Gly
            115                 120                 125

Gln Gly Thr Gln Val Thr Val Ser Ser Thr Thr Thr Pro Ala
        130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
            355                 360

<210> SEQ ID NO 245
<211> LENGTH: 360
<212> TYPE: PRT
<213> ORGANISM: Artificial Sequence
<220> FEATURE:
<223> OTHER INFORMATION: Synthetic Construct

<400> SEQUENCE: 245

Met Ala Leu Pro Val Thr Ala Leu Leu Leu Pro Leu Ala Leu Leu Leu
  1               5                  10                  15

His Ala Ala Arg Pro Gln Val Lys Leu Glu Glu Ser Gly Gly Gly Leu
                 20                  25                  30

Val Gln Ala Gly Gly Ser Leu Arg Leu Ser Cys Ala Ala Ser Gly Arg
             35                  40                  45

Thr Phe Thr Met Gly Trp Phe Arg Gln Ala Pro Gly Lys Glu Arg Glu
```

-continued

```
                50                  55                  60
Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Leu Tyr
                100                 105                 110

Tyr Cys Ala Lys Lys Asn Gly Gly Pro Val Asp Tyr Trp Gly Lys Gly
                115                 120                 125

Thr Gln Val Thr Val Ser Ser Thr Ser Thr Thr Pro Ala Pro Arg
                130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Lys Arg
                195                 200                 205

Gly Arg Lys Lys Leu Leu Tyr Ile Phe Lys Gln Pro Phe Met Arg Pro
                210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Arg Val Lys Phe Ser Arg Ser Ala
                245                 250                 255

Asp Ala Pro Ala Tyr Gln Gln Gly Gln Asn Gln Leu Tyr Asn Glu Leu
                260                 265                 270

Asn Leu Gly Arg Arg Glu Glu Tyr Asp Val Leu Asp Lys Arg Arg Gly
                275                 280                 285

Arg Asp Pro Glu Met Gly Gly Lys Pro Arg Arg Lys Asn Pro Gln Glu
                290                 295                 300

Gly Leu Tyr Asn Glu Leu Gln Lys Asp Lys Met Ala Glu Ala Tyr Ser
305                 310                 315                 320

Glu Ile Gly Met Lys Gly Glu Arg Arg Arg Gly Lys Gly His Asp Gly
                325                 330                 335

Leu Tyr Gln Gly Leu Ser Thr Ala Thr Lys Asp Thr Tyr Asp Ala Leu
                340                 345                 350

His Met Gln Ala Leu Pro Pro Arg
                355                 360
```

<210> SEQ ID NO 246
<211> LENGTH: 365
<212> TYPE: PRT
<213> ORGANISM: Artificial Sequence
<220> FEATURE:
<223> OTHER INFORMATION: Synthetic Construct

<400> SEQUENCE: 246

```
Met Ala Leu Pro Val Thr Ala Leu Leu Leu Pro Leu Ala Leu Leu Leu
 1               5                  10                  15

His Ala Ala Arg Pro Asp Val Gln Leu Val Glu Ser Gly Gly Gly Leu
                20                  25                  30

Val Gln Pro Gly Gly Ser Leu Arg Leu Ser Cys Ala Ala Ser Gly Arg
                35                  40                  45

Thr Phe Ser Ser Ile Val Met Gly Trp Phe Arg Gln Ala Pro Gly Lys
```

```
                50                  55                  60
Glu Arg Glu Phe Val Gly Ala Ile Met Trp Asn Asp Gly Ile Thr Tyr
 65                  70                  75                  80

Leu Gln Asp Ser Val Lys Gly Arg Phe Thr Ile Phe Arg Asp Asn Ala
                 85                  90                  95

Lys Asn Thr Val Tyr Leu Gln Met Asn Ser Leu Lys Leu Glu Asp Thr
                100                 105                 110

Ala Val Tyr Tyr Cys Ala Ala Ser Lys Gly Arg Tyr Ser Glu Tyr Glu
            115                 120                 125

Tyr Trp Gly Gln Gly Thr Gln Val Thr Val Ser Ser Thr Ser Thr Thr
        130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
                180                 185                 190

Pro Leu Ala Gly Thr Cys Gly Val Leu Leu Leu Ser Leu Val Ile Thr
            195                 200                 205

Leu Tyr Cys Lys Arg Gly Arg Lys Lys Leu Leu Tyr Ile Phe Lys Gln
        210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Gln Gln Gly Gln Asn Gln
                260                 265                 270

Leu Tyr Asn Glu Leu Asn Leu Gly Arg Arg Glu Glu Tyr Asp Val Leu
            275                 280                 285

Asp Lys Arg Arg Gly Arg Asp Pro Glu Met Gly Gly Lys Pro Arg Arg
        290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
        355                 360                 365

<210> SEQ ID NO 247
<211> LENGTH: 364
<212> TYPE: PRT
<213> ORGANISM: Artificial Sequence
<220> FEATURE:
<223> OTHER INFORMATION: Synthetic Construct

<400> SEQUENCE: 247

Met Ala Leu Pro Val Thr Ala Leu Leu Leu Pro Leu Ala Leu Leu Leu
 1               5                  10                  15

His Ala Ala Arg Pro Gln Val Lys Leu Glu Glu Ser Gly Gly Arg Leu
                20                  25                  30

Val Gln Ala Gly Gly Ser Leu Lys Leu Ser Trp Ala Ala Ser Gly Arg
            35                  40                  45

Thr Phe Thr Met Gly Trp Phe Arg Gln Ala Pro Gly Lys Glu Arg Glu
```

```
                50                  55                  60
Phe Val Thr Ala Ile Asn Leu Ser Pro Thr Leu Thr Tyr Tyr Ala Glu
 65                  70                  75                  80

Ser Val Lys Gly Arg Phe Pro Ile Ser Arg Asn Asn Ala Gln Asn Thr
                 85                  90                  95

Val Val Leu Gln Met Asn Ser Leu Lys Pro Glu Asp Thr Ala Leu Tyr
                100                 105                 110

Tyr Cys Ala Ala Glu Arg Lys Ser Val Met Ala Ile Pro Pro Asp Tyr
                115                 120                 125

Trp Gly Gln Gly Thr Gln Val Thr Val Ser Ser Thr Ser Thr Thr Thr
                130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
                180                 185                 190

Leu Ala Gly Thr Cys Gly Val Leu Leu Leu Ser Leu Val Ile Thr Leu
                195                 200                 205

Tyr Cys Lys Arg Gly Arg Lys Lys Leu Leu Tyr Ile Phe Lys Gln Pro
                210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
                260                 265                 270

Tyr Asn Glu Leu Asn Leu Gly Arg Arg Glu Glu Tyr Asp Val Leu Asp
                275                 280                 285

Lys Arg Arg Gly Arg Asp Pro Glu Met Gly Gly Lys Pro Arg Arg Lys
                290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
                340                 345                 350

Tyr Asp Ala Leu His Met Gln Ala Leu Pro Pro Arg
                355                 360

<210> SEQ ID NO 248
<211> LENGTH: 364
<212> TYPE: PRT
<213> ORGANISM: Artificial Sequence
<220> FEATURE:
<223> OTHER INFORMATION: Synthetic Construct

<400> SEQUENCE: 248

Met Ala Leu Pro Val Thr Ala Leu Leu Leu Pro Leu Ala Leu Leu Leu
 1               5                  10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
                35                  40                  45

Thr Phe Thr Met Gly Gly Phe Arg Arg Val Pro Arg Asp Glu Arg Glu
```

```
                50                  55                  60
Phe Val Ala Ser Ile Thr Leu Ile Pro Thr Phe Pro Tyr Tyr Ala Tyr
 65                  70                  75                  80

Ser Val Lys Gly Arg Phe Ala Leu Phe Arg Asp Asn Pro Asn Asn Thr
                 85                  90                  95

Val Ile Leu Leu Met Ile Ser Leu Lys Pro Glu Asp Pro Asp Leu Tyr
                100                 105                 110

Tyr Cys Ala Ser Tyr Arg Lys Tyr Leu Met Ser Ile Leu Pro Asp Tyr
                115                 120                 125

Trp Gly Gln Gly Thr Gln Gly Thr Val Ser Ser Thr Ser Thr Thr Thr
                130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
                180                 185                 190

Leu Ala Gly Thr Cys Gly Val Leu Leu Leu Ser Leu Val Ile Thr Leu
                195                 200                 205

Tyr Cys Lys Arg Gly Arg Lys Lys Leu Leu Tyr Ile Phe Lys Gln Pro
                210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
                260                 265                 270

Tyr Asn Glu Leu Asn Leu Gly Arg Arg Glu Glu Tyr Asp Val Leu Asp
                275                 280                 285

Lys Arg Arg Gly Arg Asp Pro Glu Met Gly Gly Lys Pro Arg Arg Lys
                290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
                340                 345                 350

Tyr Asp Ala Leu His Met Gln Ala Leu Pro Pro Arg
                355                 360

<210> SEQ ID NO 249
<211> LENGTH: 370
<212> TYPE: PRT
<213> ORGANISM: Artificial Sequence
<220> FEATURE:
<223> OTHER INFORMATION: Synthetic Construct

<400> SEQUENCE: 249

Met Ala Leu Pro Val Thr Ala Leu Leu Leu Pro Leu Ala Leu Leu Leu
 1               5                  10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Arg
                35                  40                  45

Thr Phe Thr Met Gly Trp Phe Arg Gln Ala Pro Gly Lys Glu Arg Glu
```

```
                 50                  55                  60
Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Asp Leu Gln Met Asn Ser Leu Lys Pro Glu Asp Thr Ala Val Tyr
            100                 105                 110

Phe Cys Ala Ala Asn Arg Asn Ser Gln Arg Val Ile Ala Ala Leu Ser
            115                 120                 125

Trp Ile Gly Met Asn Tyr Trp Gly Glu Trp Thr Gln Val Thr Val Ser
        130                 135                 140

Ser Thr Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Gln
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370

<210> SEQ ID NO 250
<211> LENGTH: 362
<212> TYPE: PRT
<213> ORGANISM: Artificial Sequence
<220> FEATURE:
<223> OTHER INFORMATION: Synthetic Construct

<400> SEQUENCE: 250

Met Ala Leu Pro Val Thr Ala Leu Leu Leu Pro Leu Ala Leu Leu Leu
  1               5                  10                  15

His Ala Ala Arg Pro Gln Val Gln Leu Val Glu Ser Gly Gly Gly Leu
                 20                  25                  30

Val Gln Ala Gly Gly Ser Leu Arg Leu Ser Cys Ala Ala Ser Gly Arg
```

```
            35                  40                  45
Thr Phe Thr Met Gly Trp Phe Arg Gln Ala Pro Gly Lys Glu Arg Glu
 50                  55                  60

Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Lys Thr
                 85                  90                  95

Leu Tyr Leu Arg Met Asn Ser Leu Lys Pro Glu Asp Thr Ala Val Tyr
                100                 105                 110

Tyr Cys Ala Ala Arg Arg Ile Asp Ala Ala Asp Phe Asp Ser Trp Gly
                115                 120                 125

Gln Gly Thr Gln Val Thr Val Ser Ser Thr Ser Thr Thr Thr Pro Ala
130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
                180                 185                 190

Gly Thr Cys Gly Val Leu Leu Leu Ser Leu Val Ile Thr Leu Tyr Cys
                195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
                260                 265                 270

Glu Leu Asn Leu Gly Arg Arg Glu Glu Tyr Asp Val Leu Asp Lys Arg
                275                 280                 285

Arg Gly Arg Asp Pro Glu Met Gly Gly Lys Pro Arg Arg Lys Asn Pro
                290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
                340                 345                 350

Ala Leu His Met Gln Ala Leu Pro Pro Arg
                355                 360

<210> SEQ ID NO 251
<211> LENGTH: 362
<212> TYPE: PRT
<213> ORGANISM: Artificial Sequence
<220> FEATURE:
<223> OTHER INFORMATION: Synthetic Construct

<400> SEQUENCE: 251

Met Ala Leu Pro Val Thr Ala Leu Leu Leu Pro Leu Ala Leu Leu Leu
 1               5                  10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Arg
```

```
            35                  40                  45
Thr Phe Thr Met Gly Trp Phe Arg Arg Ala Pro Gly Lys Glu Arg Glu
 50                  55                  60

Ser Val Ala Val Ile Gly Trp Arg Asp Ile Asn Ala Ser Tyr Ala Asp
 65                  70                  75                  80

Ser Val Lys Gly Arg Phe Ala Ile Ser Arg Asp Asn Ala Lys Lys Thr
                 85                  90                  95

Leu Tyr Leu Gln Met Asn Ser Leu Lys Pro Glu Asp Thr Ala Val Tyr
            100                 105                 110

Tyr Cys Ala Ala Arg Arg Ile Asp Ala Thr Asp Phe Asp Ser Trp Gly
            115                 120                 125

Gln Gly Thr Gln Val Thr Val Ser Ser Thr Ser Thr Thr Thr Pro Ala
130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
            195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
            355                 360

<210> SEQ ID NO 252
<211> LENGTH: 365
<212> TYPE: PRT
<213> ORGANISM: Artificial Sequence
<220> FEATURE:
<223> OTHER INFORMATION: Synthetic Construct

<400> SEQUENCE: 252

Met Ala Leu Pro Val Thr Ala Leu Leu Leu Pro Leu Ala Leu Leu Leu
 1                   5                  10                  15

His Ala Ala Arg Pro Gln Val Lys Leu Glu Glu Ser Gly Gly Gly Leu
                 20                  25                  30

Val Gln Thr Gly Gly Ser Leu Arg Leu Ser Cys Ala Ala Ser Glu His
```

```
                35                  40                  45
Thr Phe Ser Asn His Val Met Gly Trp Phe Arg Gln Ala Pro Gly Lys
 50                  55                  60
Glu Arg Glu Ser Val Ala Val Ile Gly Trp Arg Asp Ile Ser Thr Ser
 65                  70                  75                  80
Tyr Ala Asp Ser Val Lys Gly Arg Phe Thr Ile Ser Arg Asp Asn Ala
                 85                  90                  95
Lys Lys Thr Leu Tyr Leu Gln Met Asn Ser Leu Lys Pro Glu Asp Thr
            100                 105                 110
Ala Val Tyr Tyr Cys Ala Ala Arg Arg Ile Asp Ala Ala Asp Phe Asp
        115                 120                 125
Ser Arg Gly Gln Gly Thr Gln Val Thr Val Ser Ser Thr Ser Thr Thr
130                 135                 140
Thr Pro Ala Pro Arg Pro Pro Thr Pro Ala Pro Thr Ile Ala Ser Gln
145                 150                 155                 160
Pro Leu Ser Leu Arg Pro Glu Ala Cys Arg Pro Ala Ala Gly Gly Ala
                165                 170                 175
Val His Thr Arg Gly Leu Asp Phe Ala Cys Asp Ile Tyr Ile Trp Ala
            180                 185                 190
Pro Leu Ala Gly Thr Cys Gly Val Leu Leu Leu Ser Leu Val Ile Thr
        195                 200                 205
Leu Tyr Cys Lys Arg Gly Arg Lys Lys Leu Leu Tyr Ile Phe Lys Gln
210                 215                 220
Pro Phe Met Arg Pro Val Gln Thr Thr Gln Glu Glu Asp Gly Cys Ser
225                 230                 235                 240
Cys Arg Phe Pro Glu Glu Glu Glu Gly Gly Cys Glu Leu Arg Val Lys
                245                 250                 255
Phe Ser Arg Ser Ala Asp Ala Pro Ala Tyr Gln Gln Gly Gln Asn Gln
            260                 265                 270
Leu Tyr Asn Glu Leu Asn Leu Gly Arg Arg Glu Glu Tyr Asp Val Leu
        275                 280                 285
Asp Lys Arg Arg Gly Arg Asp Pro Glu Met Gly Gly Lys Pro Arg Arg
290                 295                 300
Lys Asn Pro Gln Glu Gly Leu Tyr Asn Glu Leu Gln Lys Asp Lys Met
305                 310                 315                 320
Ala Glu Ala Tyr Ser Glu Ile Gly Met Lys Gly Glu Arg Arg Arg Gly
                325                 330                 335
Lys Gly His Asp Gly Leu Tyr Gln Gly Leu Ser Thr Ala Thr Lys Asp
            340                 345                 350
Thr Tyr Asp Ala Leu His Met Gln Ala Leu Pro Pro Arg
        355                 360                 365

<210> SEQ ID NO 253
<211> LENGTH: 369
<212> TYPE: PRT
<213> ORGANISM: Artificial Sequence
<220> FEATURE:
<223> OTHER INFORMATION: Synthetic Construct

<400> SEQUENCE: 253

Met Ala Leu Pro Val Thr Ala Leu Leu Leu Pro Leu Ala Leu Leu Leu
 1               5                  10                  15
His Ala Ala Arg Pro Ala Val Gln Leu Val Asp Ser Gly Gly Gly Leu
                20                  25                  30
Val Gln Ala Gly Gly Ser Leu Arg Ile Ser Cys Ala Val Ser Gly Arg
```

```
                35                  40                  45
Thr Ser Ser Asn Tyr Ile Leu Ala Trp Phe Arg Gln Ala Pro Gly Lys
 50                  55                  60

Glu Arg Asp Phe Val Ala His Ile Ser Arg Ser Gly Gly Lys Ser Gly
 65                  70                  75                  80

Tyr Gly Asp Ser Val Lys Gly Arg Phe Thr Ile Ser Arg Asp Asn Ala
                 85                  90                  95

Glu Asn Thr Val Arg Val Tyr Leu Gln Met Asn Ser Leu Lys Pro Gly
                100                 105                 110

Asp Thr Ala Val Tyr Tyr Cys Asn Arg Pro Leu Trp Tyr Gly Ser Pro
                115                 120                 125

Thr Leu Ile Asp Tyr Trp Gly Gln Gly Thr Gln Val Thr Val Ser Ser
                130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
                195                 200                 205

Leu Val Ile Thr Leu Tyr Cys Lys Arg Gly Arg Lys Lys Leu Leu Tyr
210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Gln Gln
                260                 265                 270

Gly Gln Asn Gln Leu Tyr Asn Glu Leu Asn Leu Gly Arg Arg Glu Glu
                275                 280                 285

Tyr Asp Val Leu Asp Lys Arg Arg Gly Arg Asp Pro Glu Met Gly Gly
                290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
                340                 345                 350

Ala Thr Lys Asp Thr Tyr Asp Ala Leu His Met Gln Ala Leu Pro Pro
                355                 360                 365

Arg

<210> SEQ ID NO 254
<211> LENGTH: 364
<212> TYPE: PRT
<213> ORGANISM: Artificial Sequence
<220> FEATURE:
<223> OTHER INFORMATION: Synthetic Construct

<400> SEQUENCE: 254

Met Ala Leu Pro Val Thr Ala Leu Leu Leu Pro Leu Ala Leu Leu Leu
1               5                  10                  15

His Ala Ala Arg Pro Gln Val Gln Leu Val Glu Ser Gly Gly Gly Leu
                20                  25                  30
```

Val Gln Ala Gly Gly Ser Leu Arg Leu Ser Cys Ala Ala Ser Gly Arg
         35                  40                  45

Thr Phe Thr Met Gly Trp Phe Arg Gln Ala Pro Gly Lys Glu Arg Glu
 50                  55                  60

Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Leu Tyr
                100                 105                 110

Tyr Cys Ala Ala Asp Arg Lys Ser Val Met Ser Ile Arg Pro Asp Tyr
            115                 120                 125

Trp Gly Gln Gly Thr Gln Val Thr Val Ser Ser Thr Ser Thr Thr Thr
        130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
        195                 200                 205

Tyr Cys Lys Arg Gly Arg Lys Lys Leu Leu Tyr Ile Phe Lys Gln Pro
    210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360

<210> SEQ ID NO 255
<211> LENGTH: 364
<212> TYPE: PRT
<213> ORGANISM: Artificial Sequence
<220> FEATURE:
<223> OTHER INFORMATION: Synthetic Construct

<400> SEQUENCE: 255

Met Ala Leu Pro Val Thr Ala Leu Leu Leu Pro Leu Ala Leu Leu Leu
 1               5                  10                  15

His Ala Ala Arg Pro Ala Val Gln Leu Val Asp Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Pro Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Thr Ser Thr Thr Thr
    130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
        195                 200                 205

Tyr Cys Lys Arg Gly Arg Lys Lys Leu Leu Tyr Ile Phe Lys Gln Pro
    210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360

<210> SEQ ID NO 256
<211> LENGTH: 367
<212> TYPE: PRT
<213> ORGANISM: Artificial Sequence
<220> FEATURE:
<223> OTHER INFORMATION: Synthetic Construct

<400> SEQUENCE: 256

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Ser
            20                  25                  30

Val Gln Thr Gly Gly Ser Leu Arg Leu Ser Cys Thr Ala Ser Gly Arg
            35                  40                  45

Thr Leu Asn Asn Phe Val Met Gly Trp Phe Arg Gln Ala Pro Gly Lys
 50                  55                  60

Glu Arg Glu Phe Val Ala Ala Ile Ser Leu Ser Pro Thr Leu Ala Tyr
 65                  70                  75                  80

Tyr Val Glu Ser Val Lys Gly Arg Phe Thr Ile Ser Arg Asp Asn Ala
                 85                  90                  95

Lys Asn Thr Val Val Leu Gln Met Asn Ser Leu Lys Pro Glu Asp Thr
                100                 105                 110

Ala Leu Tyr Tyr Cys Ala Ala Asp Arg Lys Ser Val Met Ser Ile Arg
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 257
<211> LENGTH: 1263
<212> TYPE: DNA
<213> ORGANISM: Artificial Sequence
<220> FEATURE:
<223> OTHER INFORMATION: Synthetic Construct

<400> SEQUENCE: 257
atggccttac cagtgaccgc cttgctcctg ccgctggcct tgctgctcca cgccgccagg     60
ccggttaacc gcacgcgtcg catgcatcag gtgcagctgg tggagtctgg gggaggcttg    120
gtgcagcctg ggggttctct gaggctctcc tgtgaagcct ctggattcac tttggattat    180

```
tatgccatag gctggttccg ccaggcccca gggaaggagc gcgagggggt catatgtatt    240
agtagaagtg atggtagcac atactatgca gactccgtga agggccgatt caccatctcc    300
agagacaacg ccaagaaaac ggtgtatctg caaatgatca gcctgaaacc tgaggacacg    360
gccgcttatt actgtgcagc aggggccgat tgttcgggt acctacgaga ttatgagttc    420
cgggggcagg ggacccaggt caccgtctcc tcaactagta ccacgacgcc agcgccgcga    480
ccaccaacac cggcgcccac catcgcgtcg cagcccctgt ccctgcgccc agaggcgtgc    540
cggccagcgg cggggggcgc agtgcacacg aggggctgg acttcgcctg tgattttgg    600 gtgctggtg tggttggtgg agtcctggct tgctatagct tgctagtaac agtggccttt    660
attattttct gggtgaggag taagaggagc aggctcctgc acagtgacta catgaacatg    720
actccccgcc gccccgggcc cacccgcaag cattaccagc cctatgcccc accacgcgac    780
ttcgcagcct atcgctccaa acggggcaga agaaactcc tgtatatatt caaacaacca    840
tttatgagac cagtacaaac tactcaagag gaagatggct gtagctgccg atttccagaa    900
gaagaagaag gaggatgtga actgagagtg aagttcagca ggagcgcaga cgccccgcg    960 tacaagcagg gccagaacca gctctataac gagctcaatc taggacgaag agaggagtac   1020
gatgttttgg acaagagacg tggccgggac cctgagatgg ggggaaagcc gagaaggaag   1080
aaccctcagg aaggcctgta caatgaactg cagaaagata gatggcgga ggcctacagt   1140 gagattggga tgaaggcga cgccggagg ggcaaggggc acgatggcct ttaccagggt   1200
ctcagtacag ccaccaagga cacctacgac gcccttcaca tgcaggccct gccccctcgc   1260
tga                                                                 1263

<210> SEQ ID NO 258
<211> LENGTH: 1281
<212> TYPE: DNA
<213> ORGANISM: Artificial Sequence
<220> FEATURE:
<223> OTHER INFORMATION: Synthetic Construct

<400> SEQUENCE: 258
atggccttac cagtgaccgc cttgctcctg ccgctggcct tgctgctcca cgccgccagg     60
ccggttaacc gcacgcgtcg catgcatcag gtaaagctgg aggagtctgg gggacgattg    120
gtgcagccaa gggctctct gagactctcc tgtgcaggct ctggacgcac tttcagtacc    180
tatggtatgg cctggttccg ccaggctcca gggaaggagc gtgagttcgt agcgtctaaa    240
gcatcgatga attacagcgg tagaacatac tatgcagact ccgtgaaggg ccgattcacc    300
atcgccagag acaacgccaa gaacatggtg tttctgcaaa tgaacaacct gaagcctgag    360
gacacggccg tttattactg tgcagcgggc actggatgct caacatatgg tgtttttgac    420
gcccagataa tagactactg gggcaaaggg accctggtca ccgtctcctc aactagtacc    480
acgacgccag ccgcgcgacc accaacaccg gcgcccacca tcgcgtcgca gcccctgtcc    540
ctgcgcccag aggcgtgccg gccagcggcg ggggcgcag tgcacacgag ggggctggac    600
ttcgcctgtg attttggggt gctggtggtg gttggtggag tcctggcttg ctatagcttg    660
ctagtaacag tggcctttat tattttctgg gtgaggagta gaggagcag gctcctgcac    720 agtgactaca tgaacatgac tccccgccgc cccgggccca ccgcaagca ttaccagccc    780 tatgccccac cacgcgactt cgcagcctat cgctccaaac ggggcagaaa gaaactcctg    840
tatatattca acaaccatt tatgagacca gtacaaacta ctcaagagga agatggctgt    900
```

```
agctgccgat ttccagaaga agaagaagga ggatgtgaac tgagagtgaa gttcagcagg    960
agcgcagacg cccccgcgta caagcagggc cagaaccagc tctataacga gctcaatcta   1020
ggacgaagag aggagtacga tgttttggac aagagacgtg gccgggaccc tgagatgggg   1080
ggaaagccga gaaggaagaa ccctcaggaa ggcctgtaca atgaactgca gaaagataag   1140
atggcggagg cctacagtga gattgggatg aaaggcgagc gccggagggg caaggggcac   1200
gatggccttt accagggtct cagtacagcc accaaggaca cctacgacgc ccttcacatg   1260
caggccctgc cccctcgctg a                                             1281
```

<210> SEQ ID NO 259
<211> LENGTH: 1251
<212> TYPE: DNA
<213> ORGANISM: Artificial Sequence
<220> FEATURE:
<223> OTHER INFORMATION: Synthetic Construct

<400> SEQUENCE: 259

```
atggccttac cagtgaccgc cttgctcctg ccgctggcct tgctgctcca cgccgccagg     60
ccggttaacc gcacgcgtcg catgcatgag gtgcagctgg tggagtctgg gggaggcttg    120
gtgcaggctg gggggtctct gagactctcc tgtgcagcct ctggacgcac cttcaccatg    180 ggtggttcc gtcaggctcc agggaaggag cgtgagtttg tagcagctat tagtttgagt    240 cctacttag catattatgc agagtccgtg aagggccgat tcaccatcag ccgagacaac    300
gccaagaaca cggtggtttt tcaaatgaac agcctgaaac ctgaggacac ggcccttat    360 tactgtgcag cagaccggaa atcagtaatg tctattcggc ccgactactg gggccagggg    420
acccaggtca ccgtctcctc aactagtacc acgacgccag cgccgcgacc accaacaccg    480
gcgcccacca tcgcgtcgca gccctgtcc ctgcgcccag aggcgtgccg gccagcggcg    540
gggggcgcag tgcacacgag ggggctggac ttcgcctgtg atttttgggt gctggtggtg    600
gttggtggag tcctggcttg ctatagcttg ctagtaacag tggcctttat tattttctgg    660
gtgaggagta agaggagcag gctcctgcac agtgactaca tgaacatgac tccccgccgc    720
cccgggccca cccgcaagca ttaccagccc tatgccccac cacgcgactt cgcagcctat    780
cgctccaaac ggggcagaaa gaaactcctg tatatattca acaaccatt tatgagacca    840 gtacaaacta ctcaagagga agatggctgt agctgccgat ttccagaaga agaagaagga    900
ggatgtgaac tgagagtgaa gttcagcagg agcgcagacg cccccgcgta caagcagggc    960
cagaaccagc tctataacga gctcaatcta ggacgaagag aggagtacga tgttttggac   1020
aagagacgtg gccgggaccc tgagatgggg ggaaagccga gaaggaagaa ccctcaggaa   1080
ggcctgtaca atgaactgca gaaagataag atggcggagg cctacagtga gattgggatg   1140
aaaggcgagc gccggagggg caaggggcac gatggccttt accagggtct cagtacagcc   1200
accaaggaca cctacgacgc ccttcacatg caggccctgc cccctcgctg a            1251
```

<210> SEQ ID NO 260
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 260

```
atggccttac cagtgaccgc cttgctcctg ccgctggcct tgctgctcca cgccgccagg     60
ccggttaacc gcacgcgtcg catgcatgcc gtgcagctgg tggattctgg gggaggcttg    120
```

```
gtgcagcctg gggggtctct gagactctcc tgtgtagcct ctggaggtat cttcgtcatc      180
aatgccatgg gctggtaccg ccaggctcca ggaaagcagc gcgagttggt cgcatctatt      240
cgtggactag gcagaacaaa ctatgacgac tccgtgaagg gccgattcac catctccaga      300
gacaacgcca acaacacggt gtatctgcag atgaacagcc tggaacctga ggacacggcc      360
gtctactact gtacagtcta cgttacacta cttggtgggg ttaataggga ctactggggc      420
caggggaccc aggtcaccgt ctcctcaact agtaccacga cgccagcgcc gcgaccacca      480
acaccggcgc ccaccatcgc gtcgcagccc ctgtccctgc gcccagaggc gtgccggcca      540
gcggcggggg gcgcagtgca cacgagggggg ctggacttcg cctgtgattt ttgggtgctg      600
```

```
gtgcagcctg gggggtctct gagactctcc tgtgtagcct ctggaggtat cttcgtcatc      180
aatgccatgg gctggtaccg ccaggctcca ggaaagcagc gcgagttggt cgcatctatt      240
cgtggactag gcagaacaaa ctatgacgac tccgtgaagg gccgattcac catctccaga      300
gacaacgcca acaacacggt gtatctgcag atgaacagcc tggaacctga ggacacggcc      360
gtctactact gtacagtcta cgttacacta cttggtgggg ttaataggga ctactggggc      420
caggggaccc aggtcaccgt ctcctcaact agtaccacga cgccagcgcc gcgaccacca      480
acaccggcgc ccaccatcgc gtcgcagccc ctgtccctgc gcccagaggc gtgccggcca      540
gcggcggggg gcgcagtgca cacgaggggg ctggacttcg cctgtgattt ttgggtgctg      600
gtggtggttg gtggagtcct ggcttgctat agcttgctag taacagtggc ctttattatt      660
ttctgggtga ggagtaagag gagcaggctc ctgcacagtg actacatgaa catgactccc      720
cgccgccccg ggcccacccg caagcattac cagccctatg ccccaccacg cgacttcgca      780
gcctatcgct ccaaacgggg cagaaagaaa ctcctgtata tattcaaaca accatttatg      840
agaccagtac aaactactca gaggaagatg gctgtagct gccgatttcc agaagaagaa       900
gaaggaggat gtgaactgag agtgaagttc agcaggagcg cagacgcccc cgcgtacaag      960
cagggccaga accagctcta taacgagctc aatctaggac gaagagagga gtacgatgtt     1020
ttggacaaga gacgtggccg ggaccctgag atggggggaa agccgagaag gaagaaccct     1080
caggaaggcc tgtacaatga actgcagaaa gataagatgg cggaggccta cagtgagatt     1140
gggatgaaag cgagcgccg gaggggcaag gggcacgatg gcctttacca gggtctcagt     1200
acagccacca aggacaccta cgacgccctt cacatgcagg ccctgccccc tcgctga       1257

<210> SEQ ID NO 261
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 261
atggccttac cagtgaccgc cttgctcctg ccgctggcct tgctgctcca cgccgccagg       60
ccggttaacc gcacgcgtcg catgcatgag gtgcagctgg tggagtctgg gggaggattg      120
gtgcaggctg gggctctct gagactctcc tgtgcagcct ctggacggac cttcagtagc      180
attgtcatgg gctggttccg ccaggctcca gggaaggagc gtgagtttgt aggagcgatt      240
atgtggaatg atggtattac atacttgcaa gactccgtga agggccgatt taccatcttc      300
agagacaatg ccaagaacac ggtgtatctg caaatgaaca gcctgaaact tgaggatacg      360
gccgtttatt actgtgcagc atccaagggt agatactcgg aatatgagta ctggggccag      420
gggacccagg tcaccgtctc ctcaactagt accacgacgc cagcgccgcg accaccaaca      480
ccggcgccca ccatcgcgtc gcagcccctg tccctgcgcc cagaggcgtg ccggccagcg      540
gcggggggcg cagtgcacac gagggggctg gacttcgcct gtgattttg ggtgctggtg      600 gtggttggtg gagtcctggc ttgctatagc ttgctagtaa cagtggcctt tattattttc      660
tgggtgagga gtaagaggag caggctcctg cacagtgact acatgaacat gactccccgc      720
cgccccgggc ccacccgcaa gcattaccag ccctatgccc caccacgcga cttcgcagcc      780
tatcgctcca aacggggcag aaagaaactc ctgtatatat tcaaacaacc atttatgaga      840
ccagtacaaa ctactcaaga ggaagatggc tgtagctgcc gatttccaga agaagaa        900
```

```
ggaggatgtg aactgagagt gaagttcagc aggagcgcag acgcccccgc gtacaagcag    960
ggccagaacc agctctataa cgagctcaat ctaggacgaa gagaggagta cgatgttttg   1020
gacaagagac gtggccggga ccctgagatg gggggaaagc cgagaaggaa gaaccctcag   1080
gaaggcctgt acaatgaact gcagaaagat aagatggcgg aggcctacag tgagattggg   1140
atgaaaggcg agcgccggag gggcaagggg cacgatggcc tttaccaggg tctcagtaca   1200
gccaccaagg acacctacga cgcccttcac atgcaggccc tgccccctcg ctga         1254
```

<210> SEQ ID NO 262
<211> LENGTH: 1281
<212> TYPE: DNA
<213> ORGANISM: Artificial Sequence
<220> FEATURE:
<223> OTHER INFORMATION: Synthetic Construct

<400> SEQUENCE: 262

```
atggccttac cagtgaccgc cttgctcctg ccgctggcct tgctgctcca cgccgccagg     60
ccggttaacc gcacgcgtcg catgcatgag gtgcagctgg tggagtctgg ggaggcgtg    120 gtgcaggctg gggggtctct gacagtctcc tgtacagcct ctggattcac tttcgaccgt    180
gctgtcatag tctggttccg ccaggccccc gggaagggcc gtgaggggt ctcatttatt     240 aaacctagtg atggcaccat atactacatt gactccctga agggccgatt cacgatctcc    300
agtgacatcg ccaagaatac ggtatatctg caaatgaaaa gtctggaatc ggaggactcg    360
gccgtttatt actgtgcggc ctcgcctgag gactggtaca cggattggat cgactggagt    420
atatatcggt ggcagcactg gggccagggg acccaggtca ctgtctcctc aactagtacc    480
acgacgccag cgccgcgacc accaacaccg gcgcccacca tcgcgtcgca gcccctgtcc    540
ctgcgcccag aggcgtgccg gccagcggcg ggggcgcag tgcacacgag ggggctggac    600
ttcgcctgtg attttttgggt gctggtggtg gttggtggag tcctggcttg ctatagcttg    660
ctagtaacag tggcctttat tattttctgg gtgaggagta agaggagcag gctcctgcac    720
agtgactaca tgaacatgac tccccgccgc cccgggccca cccgcaagca ttaccagccc    780
tatgccccac cacgcgactt cgcagcctat cgctccaaac ggggcagaaa gaaactcctg    840
tatatattca acaaccatt tatgagacca gtacaaacta ctcaagagga gatggctgt     900 agctgccgat ttccagaaga agaagaagga ggatgtgaac tgagagtgaa gttcagcagg   960
agcgcagacg cccccgcgta caagcagggc agaaccagc tctataacga gctcaatcta   1020
ggacgaagag aggagtacga tgttttggac aagagacgtg gccgggaccc tgagatgggg   1080
ggaaagccga aggaagaa ccctcaggaa ggcctgtaca atgaactgca gaaagataag   1140
atggcggagg cctacagtga gattgggatg aaaggcgagc gccggagggg caaggggcac   1200
gatggccttt accagggtct cagtacagcc accaaggaca cctacgacgc ccttcacatg   1260
caggccctgc cccctcgctg a                                            1281
```

<210> SEQ ID NO 263
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 263

```
atggccttac cagtgaccgc cttgctcctg ccgctggcct tgctgctcca cgccgccagg     60
ccggttaacc gcacgcgtcg catgcatgag gtgcagctgg tggagtctgg ggaggaatg    120
```

```
gtgcaggctg gggactctct gagactatcc tgtgtgcagt ctacttacac cgtcaatagc      180
gatgtcatgg gctggttccg ccaggctcca gggaaggagc gtgagtttgt aggagcgatt      240
atgtggaatg atggtattac atacttgcaa gactccgtga agggccgatt taccatcttc      300
agagacaacg ccaagaacac ggtgtatctg caaatgaaca gcctgaaact tgaggatacg      360
gccgtttatt actgtgcagc atccaagggt agatactcgg aatatgagta ctggggccag      420
gggacccagg tcaccgtctc ctcaactagt accacgacgc cagcgccgcg accaccaaca      480
ccggcgccca ccatcgcgtc gcagcccctg tccctgcgcc cagaggcgtg ccggccagcg      540
gcggggggcg cagtgcacac gagggggctg gacttcgcct gtgattttg ggtgctggtg       600 gtggttggtg gagtcctggc ttgctatagc ttgctagtaa cagtggcctt tattattttc      660
tgggtgagga gtaagaggag caggctcctg cacagtgact acatgaacat gactccccgc      720
cgccccgggc ccacccgcaa gcattaccag ccctatgccc caccacgcga cttcgcagcc      780
tatcgctcca acggggcag aaagaaactc ctgtatatat tcaaacaacc atttatgaga       840
ccagtacaaa ctactcaaga ggaagatggc tgtagctgcc gatttccaga agaagaagaa      900
ggaggatgtg aactgagagt gaagttcagc aggagcgcag acgccccgc gtacaagcag       960 ggccagaacc agctctataa cgagctcaat ctaggacgaa gagaggagta cgatgttttg      1020
gacaagagac gtggccggga ccctgagatg ggggaaagc cgagaaggaa gaaccctcag       1080
gaaggcctgt acaatgaact gcagaaagat aagatggcgg aggcctacag tgagattggg      1140
atgaaaggcg agcgccggag gggcaagggg acgatggcc tttaccaggg tctcagtaca       1200
gccaccaagg acacctacga cgcccttcac atgcaggccc tgcccctcg ctga             1254

<210> SEQ ID NO 264
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 264
atggccttac cagtgaccgc cttgctcctg ccgctggcct tgctgctcca cgccgccagg       60
ccggttaacc gcacgcgtcg catgcatgcg gtgcagctgg tggagtctgg gggaggattg      120
gtgcaggctg gggactctct gagactctcc tgtacagcct tggtgcaac cttgactaac      180 gatcacatgg catggttccg ccaggctcca gggaagggc gtgaatttgt agcagctatt      240
gactggagtg gtcgtaccac aaattacgca gacccgtag agggccgatt caccatctcc      300
agaaacaacg ccaagaacac ggtgtatctg gaaatgaaca gcctgaaact tgaggacacg      360
gccgtttatt actgtgcggt cctccgcgct tggatctcat atgacaatga ctactggggc      420
caggggaccc aggtcaccgt ctcctcaact agtaccacga cgccagcgcc gcgaccacca      480
acaccggcgc ccaccatcgc gtcgcagccc ctgtccctgc gcccagaggc gtgccggcca      540
gcggcggggg gcgcagtgca cacgaggggg ctggacttcg cctgtgattt tgggtgctg       600 gtggtggttg gtggagtcct ggcttgctat agcttgctag taacagtggc ctttattatt      660
ttctgggtga ggagtaagag gagcaggctc ctgcacagtg actacatgaa catgactccc      720
cgccgccccg ggcccacccg caagcattac cagccctatg ccccaccacg cgacttcgca      780
gcctatcgct ccaaacgggg cagaaagaaa ctcctgtata tattcaaaca accatttatg      840
agaccagtac aaactactca agaggaagat ggctgtagct gccgatttcc agaagaagaa      900
```

| | |
|---|---|
| gaaggaggat gtgaactgag agtgaagttc agcaggagcg cagacgcccc cgcgtacaag | 960 |
| cagggccaga accagctcta taacgagctc aatctaggac gaagagagga gtacgatgtt | 1020 |
| ttggacaaga gacgtggccg ggaccctgag atgggggaa agccgagaag gaagaaccct | 1080 |
| caggaaggcc tgtacaatga actgcagaaa gataagatgg cggaggccta cagtgagatt | 1140 |
| gggatgaaag gcgagcgccg gagggggcaag gggcacgatg gcctttacca gggtctcagt | 1200 |
| acagccacca aggacaccta cgacgccctt cacatgcagg ccctgccccc tcgctga | 1257 |

<210> SEQ ID NO 265
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 265

| | |
|---|---|
| atggccttac cagtgaccgc cttgctcctg ccgctggcct tgctgctcca cgccgccagg | 60 |
| ccggttaacc gcacgcgtcg catgcatcag gtgcagctgg tggagtctgg gggaggattg | 120 |
| gtgcaggctg ggggctctct gagactctcc tgtgcagcct ctggaggcac cttaagtaaa | 180 |
| aataccgtgg cttggttccg ccaggctcca gggaaggagc gtgggtttgt agcgtctatt | 240 |
| acctgggatg gtcgtacgac atactatgca gactccgtga agggccgatt caccatctcc | 300 |
| agagacaacg ccaagaacac agtgtatctg caaatgaaca gcctgaaacc tgaggatacg | 360 |
| gccgtttatg tctgtgcaga cttagggaaa tggcctgcgg gccggcgga ctactggggc | 420 |
| caggggaccc aggtcaccgt ctcctcaact agtaccacga cgccagcgcc gcgaccacca | 480 |
| acaccggcgc ccaccatcgc gtcgcagccc ctgtccctgc gcccagaggc gtgccggcca | 540 |
| gcggcggggg gcgcagtgca cacgagggggg ctggacttcg cctgtgattt ttgggtgctg | 600 |
| gtggtggttg gtggagtcct ggcttgctat agcttgctag taacagtggc ctttattatt | 660 |
| ttctgggtga ggagtaagag gagcaggctc ctgcacagtg actacatgaa catgactccc | 720 |
| cgccgccccg ggcccacccg caagcattac cagccctatg ccccaccacg cgacttcgca | 780 |
| gcctatcgct ccaaacgggg cagaaagaaa ctcctgtata tattcaaaca accatttatg | 840 |
| agaccagtac aaactactca agaggaagat ggctgtagct gccgatttcc agaagaagaa | 900 |
| gaaggaggat gtgaactgag agtgaagttc agcaggagcg cagacgcccc cgcgtacaag | 960 |
| cagggccaga accagctcta taacgagctc aatctaggac gaagagagga gtacgatgtt | 1020 |
| ttggacaaga gacgtggccg ggaccctgag atgggggaa agccgagaag gaagaaccct | 1080 |
| caggaaggcc tgtacaatga actgcagaaa gataagatgg cggaggccta cagtgagatt | 1140 |
| gggatgaaag gcgagcgccg gagggggcaag gggcacgatg gcctttacca gggtctcagt | 1200 |
| acagccacca aggacaccta cgacgccctt cacatgcagg ccctgccccc tcgctga | 1257 |

<210> SEQ ID NO 266
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 266

| | |
|---|---|
| atggccttac cagtgaccgc cttgctcctg ccgctggcct tgctgctcca cgccgccagg | 60 |
| ccggttaacc gcacgcgtcg catgcatcag gtaaagctgg aggagtctgg gggaggcttg | 120 |
| gtgcaggctg ggcggtctct gagactctcc tgtgcagcct ctgaacacac cttcagtagc | 180 |

| | |
|---|---|
| catgtcatgg gctggttccg ccaggctcca gggaaggagc gtgagtctgt tgcagttatt | 240 |
| ggctggagag atattagcac aagctatgca gactccgtga agggccgatt caccatctcc | 300 |
| agagacaacg ccaagaagac gctgtatctg caaatgaata gcctgaaacc tgaggacacg | 360 |
| gccgtttact actgtgcagc acgtcggatc gacgcagctg actttgattc ctggggcag | 420 |
| gggacccagg tcaccgtctc ctcgactagt accacgacgc cagcgccgcg accaccaaca | 480 |
| ccggcgccca ccatcgcgtc gcagcccctg tccctgcgcc cagaggcgtg ccggccagcg | 540 |
| gcggggggcg cagtgcacac gagggggctg gacttcgcct gtgatttttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag ccctatgccc caccacgcga cttcgcagcc | 780 |
| tatcgctcca aacggggcag aaagaaactc ctgtatatat tcaaacaacc atttatgaga | 840 |
| ccagtacaaa ctactcaaga ggaagatggc tgtagctgcc gatttccaga agaagaagaa | 900 |
| ggaggatgtg aactgagagt gaagttcagc aggagcgcag acgcccccgc gtacaagcag | 960 |
| ggccagaacc agctctataa cgagctcaat ctaggacgaa gagaggagta cgatgttttg | 1020 |
| gacaagagac gtggccggga ccctgagatg ggggaaagc cgagaaggaa gaaccctcag | 1080 |
| gaaggcctgt acaatgaact gcagaaagat aagatggcgg aggcctacag tgagattggg | 1140 |
| atgaaaggcg agcgccggag gggcaagggg cacgatggcc tttaccaggg tctcagtaca | 1200 |
| gccaccaagg acacctacga cgcccttcac atgcaggccc tgccccctcg ctga | 1254 |

<210> SEQ ID NO 267
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 267

| | |
|---|---|
| atggccttac cagtgaccgc cttgctcctg ccgctggcct tgctgctcca cgccgccagg | 60 |
| ccggttaacc gcacgcgtcg catgcatgcg gtgcagctgg tggagtctgg gggaggattg | 120 |
| gtgcaggctg ggactctct gagactcacc tgtacagcct ctggacgcgc cttcagtacc | 180 |
| tatttcatgg cctggttccg ccaggctcca gggaaggagc gtgagtttgt agcaggaatt | 240 |
| gcatggagtg gtggtagcac ggcgtatgca gactccgtga agggccgatt caccatctcc | 300 |
| agagacaacg ccaagaacac ggtgtatctg caaatgaaca gcctgaaatc tgaggacacg | 360 |
| gccgtttatt actgtgccag cagggggatt gaggtcgaag agtttggtgc ctggggccag | 420 |
| gggacccagg tcaccgtctc gtcgactagt accacgacgc cagcgccgcg accaccaaca | 480 |
| ccggcgccca ccatcgcgtc gcagcccctg tccctgcgcc cagaggcgtg ccggccagcg | 540 |
| gcggggggcg cagtgcacac gagggggctg gacttcgcct gtgatttttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag ccctatgccc caccacgcga cttcgcagcc | 780 |
| tatcgctcca aacggggcag aaagaaactc ctgtatatat tcaaacaacc atttatgaga | 840 |
| ccagtacaaa ctactcaaga ggaagatggc tgtagctgcc gatttccaga agaagaagaa | 900 |
| ggaggatgtg aactgagagt gaagttcagc aggagcgcag acgcccccgc gtacaagcag | 960 |

| | |
|---|---|
| ggccagaacc agctctataa cgagctcaat ctaggacgaa gagaggagta cgatgttttg | 1020 |
| gacaagagac gtggccggga ccctgagatg ggggaaagc cgagaaggaa gaaccctcag | 1080 |
| gaaggcctgt acaatgaact gcagaaagat aagatggcgg aggcctacag tgagattggg | 1140 |
| atgaaaggcg agcgccggag gggcaagggg cacgatggcc tttaccaggg tctcagtaca | 1200 |
| gccaccaagg acacctacga cgcccttcac atgcaggccc tgcccctcg ctga | 1254 |

<210> SEQ ID NO 268
<211> LENGTH: 1131
<212> TYPE: DNA
<213> ORGANISM: Artificial Sequence
<220> FEATURE:
<223> OTHER INFORMATION: Synthetic Construct

<400> SEQUENCE: 268

| | |
|---|---|
| atggccttac cagtgaccgc cttgctcctg ccgctggcct tgctgctcca cgccgccagg | 60 |
| ccggttaacc gcacgcgtcg catgcatcag gtgcagctgg tggagtctgg ggaggcttg | 120 |
| gtgcagcctg ggggttctct gaggctctcc tgtgaagcct ctggattcac tttggattat | 180 |
| tatgccatag gctggttccg ccaggcccca gggaaggagc gcgaggggt catatgtatt | 240 |
| agtagaagtg atggtagcac atactatgca gactccgtga agggccgatt caccatctcc | 300 |
| agagacaacg ccaagaaaac ggtgtatctg caaatgatca gcctgaaacc tgaggacacg | 360 |
| gccgcttatt actgtgcagc aggggccgat tgttcgggt acctacgaga ttatgagttc | 420 |
| cggggggcagg ggaccaggt caccgtctcc tcaactagta ccacgacgcc agcgccgcga | 480 |
| ccaccaacac cggcgcccac catcgcgtcg cagcccctgt ccctgcgccc agaggcgtgc | 540 |
| cggccagcgg cggggggcgc agtgcacacg aggggctgg acttcgcctg tgatatctac | 600 |
| atctgggcgc ccttggccgg gacttgtggg gtccttctcc tgtcactggt tatcaccctt | 660 |
| tactgcaaac ggggcagaaa gaaactcctg tatatattca acaaccatt tatgagacca | 720 |
| gtacaaacta ctcaagagga agatggctgt agctgccgat ttccagaaga agaagaagga | 780 |
| ggatgtgaac tgagagtgaa gttcagcagg agcgcagacg cccccgcgta ccagcagggc | 840 |
| cagaaccagc tctataacga gctcaatcta ggacgaagag aggagtacga tgttttggac | 900 |
| aagagacgtg gccgggaccc tgagatgggg ggaaagccga aggaagaa ccctcaggaa | 960 |
| ggcctgtaca tgaactgca gaaagataag atggcgagg cctacagtga gattgggatg | 1020 |
| aaaggcgagc gccggagggg caaggggcac gatggccttt accagggtct cagtacagcc | 1080 |
| accaaggaca cctacgacgc ccttcacatg caggccctgc ccctcgcta a | 1131 |

<210> SEQ ID NO 269
<211> LENGTH: 1122
<212> TYPE: DNA
<213> ORGANISM: Artificial Sequence
<220> FEATURE:
<223> OTHER INFORMATION: Synthetic Construct

<400> SEQUENCE: 269

| | |
|---|---|
| atggccttac cagtgaccgc cttgctcctg ccgctggcct tgctgctcca cgccgccagg | 60 |
| ccggttaacc gcacgcgtcg catgcatcag gtaaagctgg aggagtctgg gggaggcttg | 120 |
| gtgcaggctg gcggtctct gagactctcc tgtgcagcct ctgaacacac cttcagtagc | 180 |
| catgtcatgg gctggttccg ccaggctcca gggaaggagc gtgagtctgt tgcagttatt | 240 |
| ggctggagag atattagcac aagctatgca gactccgtga agggccgatt caccatctcc | 300 |
| agagacaacg ccaagaagac gctgtatctg caaatgaata gcctgaaacc tgaggacacg | 360 |

```
gccgtttact actgtgcagc acgtcggatc gacgcagctg actttgattc ctgggggcag      420
gggacccagg tcaccgtctc ctcgactagt accacgacgc cagcgccgcg accaccaaca      480
ccggcgccca ccatcgcgtc gcagcccctg tccctgcgcc cagaggcgtg ccggccagcg      540 gcgggggggcg cagtgcacac gagggggctg gacttcgcct gtgatatcta catctgggcg     600
cccttggccg ggacttgtgg ggtccttctc ctgtcactgg ttatcaccct ttactgcaaa      660
cggggcagaa agaaactcct gtatatattc aaacaaccat ttatgagacc agtacaaact      720
actcaagagg aagatggctg tagctgccga tttccagaag aagaagaagg aggatgtgaa      780
ctgagagtga agttcagcag gagcgcagac gccccgcgt accagcaggg ccagaaccag       840
ctctataacg agctcaatct aggacgaaga gaggagtacg atgttttgga caagagacgt      900
ggccgggacc ctgagatggg gggaaagccg agaaggaaga accctcagga aggcctgtac      960
aatgaactgc agaaagataa gatggcggag cctacagtg agattgggat gaaaggcgag      1020
cgccggaggg gcaaggggca cgatggcctt taccagggtc tcagtacagc caccaaggac     1080
acctacgacg cccttcacat gcaggccctg cccctcgct aa                         1122

<210> SEQ ID NO 270
<211> LENGTH: 1119
<212> TYPE: DNA
<213> ORGANISM: Artificial Sequence
<220> FEATURE:
<223> OTHER INFORMATION: Synthetic Construct

<400> SEQUENCE: 270
atggccttac cagtgaccgc cttgctcctg ccgctggcct tgctgctcca cgccgccagg       60
ccggttaacc gcacgcgtcg catgcatgag gtgcagctgg tggagtctgg ggaggcttg       120 gtgcaggctg gggggtctct gagactctcc tgtgcagcct ctggacgcac cttcaccatg      180
gggtggttcc gtcaggctcc agggaaggag cgtgagtttg tagcagctat tagtttgagt      240
cctactttag catattatgc agagtccgtg aagggccgat tcaccatcag ccgagacaac      300
gccaagaaca cggtggtttt gcaaatgaac agcctgaaac ctgaggacac ggccctttat      360
tactgtgcag cagaccggaa atcagtaatg tctattcggc ccgactactg gggccagggg      420
acccaggtca ccgtctcctc aactagtacc acgacgccag cgccgcgacc accaacaccg      480
gcgcccacca tcgcgtcgca gcccctgtcc ctgcgcccag gcgtgccg gccagcggcg       540 gggggcgcag tgcacacgag ggggctggac ttcgcctgtg atatctacat ctgggcgccc     600
ttggccggga cttgtggggt ccttctcctg tcactggtta tcaccccttta ctgcaaacgg    660 ggcagaaaga aactcctgta tatattcaaa caaccattta tgagaccagt acaaactact     720
caagaggaag atggctgtag ctgccgattt ccagaagaag aagaaggagg atgtgaactg     780
agagtgaagt tcagcaggag cgcagacgcc cccgcgtacc agcagggcca gaaccagctc     840
tataacgagc tcaatctagg acgaagagag gagtacgatg ttttggacaa gagacgtggc     900
cgggaccctg agatgggggg aaagccgaga aggaagaacc ctcaggaagg cctgtacaat     960
gaactgcaga aagataagat ggcggaggcc tacagtgaga ttgggatgaa aggcgagcgc    1020
cggaggggca aggggcacga tggcctttac cagggtctca gtacagccac caaggacacc    1080
tacgacgccc ttcacatgca ggccctgccc ctcgctaa                            1119

<210> SEQ ID NO 271
<211> LENGTH: 1113
<212> TYPE: DNA
```

<213> ORGANISM: Artificial Sequence
<220> FEATURE:
<223> OTHER INFORMATION: Synthetic Construct

<400> SEQUENCE: 271

```
atggctctgc cgtcaccgc tctgctgctg cctctggctc tgctgctgca cgctgctcgc      60
cctgaggtgc agctggtgga gtctggggga ggcttggtgc cgcctggggg gtctctgaga     120
ctctcctgta cagcctctgg aagcacagtc agcatcaatg tcatggcctg gtaccgccag     180
gtttcaggga agcagcgcga gttggtcgcg gccgttacta gggatggtag gaaaagttgt     240
ggagactccg tgaagggccg attcaccatt tccagagacg cgccaagaa tgcggtatat      300
ttgcaaatga acagtctgaa acctgaggac acagcggtct atttatgtgg agccgatggt     360
tggggtgcta taccttaga ttatacctac ggcatggact attggggcaa agggacccag     420
gtcaccgtct cctcaactag taccacgacg ccagcgccgc gaccaccaac accggcgccc     480
accatcgcgt cgcagcccct gtccctgcgc ccagaggcgt gccggccagc ggcgggggc      540
gcagtgcaca cgagggggct ggacttcgcc tgtgatatct acatctgggc gcccttggcc     600
gggacttgtg gggtccttct cctgtcactg gttatcaccc tttactgcaa cggggcaga     660
aagaaactcc tgtatatatt caaacaacca tttatgagac cagtacaaac tactcaagag     720
gaagatggct gtagctgccg atttccagaa gaagaagaag gaggatgtga actgagagtg     780
aagttcagca ggagcgcaga cgcccccgcg taccagcagg gccagaacca gctctataac     840
gagctcaatc taggacgaag agaggagtac gatgttttgg acaagagacg tggccgggac     900
cctgagatgg ggggaaagcc gagaaggaag aaccctcagg aaggcctgta caatgaactg     960
cagaaagata gatggcgga ggcctacagt gagattggga tgaaaggcga gcgccggagg      1020
ggcaaggggc acgatggcct ttaccagggt ctcagtacag ccaccaagga cacctacgac     1080
gcccttcaca tgcaggccct gccccctcgc taa                                  1113
```

<210> SEQ ID NO 272
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 272

```
atggctctgc ccgtcaccgc tctgctgctg cctctggctc tgctgctgca cgctgctcgc      60
cctgcggtgc agctggtgga gtctggggga ggattggtgc aggctggggg ctctctgaga     120
ctctcctgtg cagcctctgg acgcaccttc accatggggt ggttccgtca ggctccaggg     180
aaggagcgtg ggtttgtagc gtctattacc tgggatggtc gttcggcata ctatgcagag     240
tccgtgaagg gccgattcac catcagccga gacaacgcca agaacacggt ggttttgcaa     300
atgaacagcc tgaaacctga ggacacggcc ctttattact gtgcagcaga ccggaaatca     360
gtaatgtcta ttcggcccga ctactggggc caggggaccc aggtcaccgt ctcctcaact     420
agtaccacga cgccagcgcc gcgaccacca acaccggcgc ccaccatcgc gtcgcagccc     480
ctgtccctgc gcccagaggc gtgccggcca gcggcggggg gcgcagtgca cacgaggggg     540
ctggacttcg cctgtgatat ctacatctgg gcgcccttgg ccgggacttg tggggtcctt     600
ctcctgtcac tggttatcac cctttactgc aaacgggca gaaagaaact cctgtatata     660
ttcaaacaac catttatgag accagtacaa actactcaag aggaagatgg ctgtagctgc     720
cgatttccag aagaagaaga aggaggatgt gaactgagag tgaagttcag caggagcgca     780
```

```
gacgccccg  cgtaccagca  gggccagaac  cagctctata  acgagctcaa  tctaggacga    840
agagaggagt  acgatgtttt  ggacaagaga  cgtggccggg  accctgagat  gggggggaaag   900 ccgagaagga  agaaccctca  ggaaggcctg  tacaatgaac  tgcagaaaga  taagatggcg    960
gaggcctaca  gtgagattgg  gatgaaaggc  gagcgccgga  ggggcaaggg  gcacgatggc   1020
ctttaccagg  gtctcagtac  agccaccaag  acacctacg   acgcccttca  catgcaggcc   1080
ctgccccctc  gctaa                                                        1095
```

<210> SEQ ID NO 273
<211> LENGTH: 1107
<212> TYPE: DNA
<213> ORGANISM: Artificial Sequence
<220> FEATURE:
<223> OTHER INFORMATION: Synthetic Construct

<400> SEQUENCE: 273

```
atggctctgc  ccgtcaccgc  tctgctgctg  cctctggctc  tgctgctgca  cgctgctcgc    60
cctcaggtac  agctggtgga  gtctggggga  ggattggtgc  agcctggggg  gtctctaaga   120
ctcgcatgtg  aagcgcctgg  aagcggcaat  agtatcaatg  ccatgggctg  gtaccggcag   180
actccgggga  gcggcgcga   gttggtcgca  actattactc  ggggtggtag  cacgaactat   240
ggaccctccg  tgaagggccg  attcacgatc  accagagaca  atgtcaagaa  tacggtgcat   300
ctgcagatga  acagcctgaa  acctgacgac  acggccgtct  attattgcaa  tgcggagagg   360
ctggacggct  cggggtacgg  atatgagtat  gattactggg  gccaggggac  ccaggtcacc   420
gtctcctcaa  ctagtaccac  gacgccagcg  ccgcgaccac  caacaccggc  gcccaccatc   480
gcgtcgcagc  ccctgtccct  gcgcccagag  gcgtgccggc  cagcggcggg  gggcgcagtg   540
cacacgaggg  ggctggactt  cgcctgtgat  atctacatct  gggcgccctt  ggccgggact   600
tgtggggtcc  ttctcctgtc  actggttatc  acccttact   gcaaacgggg  cagaaagaaa   660
ctcctgtata  tattcaaaca  accatttatg  agaccagtac  aaactactca  agaggaagat   720
ggctgtagct  gccgatttcc  agaagaagaa  gaaggaggat  gtgaactgag  agtgaagttc   780
agcaggagcg  cagacgcccc  cgcgtaccag  cagggccaga  accagctcta  taacgagctc   840
aatctaggac  gaagagagga  gtacgatgtt  ttggacaaga  gacgtggccg  ggaccctgag   900
atggggggaa  agccgagaag  gaagaaccct  caggaaggcc  tgtacaatga  actgcagaaa   960
gataagatgg  cggaggccta  cagtgagatt  gggatgaaag  gcgagcgccg  gaggggcaag  1020
gggcacgatg  gcctttacca  gggtctcagt  acagccacca  aggacaccta  cgacgccctt  1080
cacatgcagg  ccctgccccc  tcgctaa                                         1107
```

<210> SEQ ID NO 274
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 274

```
atggctctgc  ccgtcaccgc  tctgctgctg  cctctggctc  tgctgctgca  cgctgctcgc    60
cctcaggtaa  agctggagga  gtctggggga  ggattggtgc  aggctggggg  ctctctgaga   120
ctctcctgtg  cagcctctgg  aggcacctta  agtaagaata  ccgtggcttg  gtccgccag    180 gctccaggga  aggagcgtgg  gtttgtaacg  tctattacct  gtgatggtcg  tacgacatac   240
```

```
tatgcgaact ccgtaaacgg ccgattcccc atcaaccgaa acaacgccga gaatttggtg    300
gttttgcaaa tgaacagcct gaaacctgac gacacggccc tttattactg tgcagcatac    360
cggaagtcaa taatgtctat tcagcccgac tactggggcc aggggaccca ggtcaccgtc    420
tcctcaacta gtaccacgac gccagcgccg cgaccaccaa caccggcgcc caccatcgcg    480
tcgcagcccc tgtccctgcg cccagaggcg tgccggccag cggcgggggg cgcagtgcac    540 acgaggggc tggacttcgc ctgtgatatc tacatctggg cgcccttggc cgggacttgt     600
ggggtccttc tcctgtcact ggttatcacc ctttactgca acggggcag aaagaaactc     660 ctgtatatat tcaaacaacc atttatgaga ccagtacaaa ctactcaaga ggaagatggc    720
tgtagctgcc gatttccaga agaagaagaa ggaggatgtg aactgagagt gaagttcagc    780
aggagcgcag acgcccccgc gtaccagcag ggccagaacc agctctataa cgagctcaat    840
ctaggacgaa gagaggagta cgatgttttg gacaagagac gtggccggga ccctgagatg    900
gggggaaagc cgagaaggaa gaaccctcag gaaggcctgt acaatgaact gcagaaagat    960
aagatggcgg aggcctacag tgagattggg atgaaaggcg agcgccggag gggcaagggg   1020
cacgatggcc tttaccaggg tctcagtaca gccaccaagg acacctacga cgcccttcac   1080
atgcaggccc tgccccctcg ctaa                                          1104

<210> SEQ ID NO 275
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 275
atggctctgc ccgtcaccgc tctgctgctg cctctggctc tgctgctgca cgctgctcgc     60
cctgatgtgc agctggtgga gtctggggga ggattggtgc aggctggggg ctctctgaga    120
ctctcctgtg cagcctctgg acggaccttc agtagcattg tcatgggctg gttccgccag    180
gctccaggga aggagcgtga gtttgtagga gcgattatgt ggaatgatgg tctgacatac    240
ttgcaagggt ccgtgaaggg ccgattcacc atttccagag acaacgccaa gaacacggtg    300
gttttgcaaa tgaacagcct gaaacctgag gacacggccc tttattactg tgcagcagac    360
cggaaatcag taatgtctat tcggcccgac tactggggcc aggggaccca ggtcaccgtc    420
tcctcaacta gtaccacgac gccagcgccg cgaccaccaa caccggcgcc caccatcgcg    480
tcgcagcccc tgtccctgcg cccagaggcg tgccggccag cggcgggggg cgcagtgcac    540 acgaggggc tggacttcgc ctgtgatatc tacatctggg cgcccttggc cgggacttgt     600
ggggtccttc tcctgtcact ggttatcacc ctttactgca acggggcag aaagaaactc     660 ctgtatatat tcaaacaacc atttatgaga ccagtacaaa ctactcaaga ggaagatggc    720
tgtagctgcc gatttccaga agaagaagaa ggaggatgtg aactgagagt gaagttcagc    780
aggagcgcag acgcccccgc gtaccagcag ggccagaacc agctctataa cgagctcaat    840
ctaggacgaa gagaggagta cgatgttttg gacaagagac gtggccggga ccctgagatg    900
gggggaaagc cgagaaggaa gaaccctcag gaaggcctgt acaatgaact gcagaaagat    960
aagatggcgg aggcctacag tgagattggg atgaaaggcg agcgccggag gggcaagggg   1020
cacgatggcc tttaccaggg tctcagtaca gccaccaagg acacctacga cgcccttcac   1080
atgcaggccc tgccccctcg ctaa                                          1104
```

```
<210> SEQ ID NO 276
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 276
atggctctgc ccgtcaccgc tctgctgctg cctctggctc tgctgctgca cgctgctcgc      60
cctcaggtac agctggtgga gtctggggga ggattggtgc aggctggggg ctctctgaga     120
ctctcctgtg cagcctctgg acgcaccttc accatggggt ggttccgtca ggctccaggg     180
aaggagcgtg agtttgtagc agctattagt ttgagtccta ctttagcata ttatgcagag     240
tccgtgaagg gccgattcac catcagccga acaacgcca agaacacggt ggttttgcaa      300
atgaacagcc tgaaacctga ggacacggcc gtttactact gtgcagcacg tcggatcgac     360
gcagctgact ttgattcctg ggggcagggg acccaggtca ccgtctcctc aactagtacc     420
acgacgccag cgccgcgacc accaacaccg gcgcccacca tcgcgtcgca gccctgtcc      480 ctgcgcccag aggcgtgccg gccagcggcg gggggcgcag tgcacacgag ggggctggac     540
ttcgcctgtg atatctacat ctgggcgccc ttggccggga cttgtggggt ccttctcctg     600
tcactggtta tcacccttta ctgcaaacgg ggcagaaaga aactcctgta tatattcaaa     660
caaccattta tgagaccagt acaaactact caagaggaag atggctgtag ctgccgattt     720
ccagaagaag aagaaggagg atgtgaactg agagtgaagt tcagcaggag cgcagacgcc     780
cccgcgtacc agcagggcca gaaccagctc tataacgagc tcaatctagg acgaagagag     840
gagtacgatg tttttggaca agagacgtggc cgggaccctg atgggggg aaagccgaga     900 aggaagaacc ctcaggaagg cctgtacaat gaactgcaga agataagat ggcggaggcc     960 tacagtgaga ttgggatgaa aggcgagcgc cggaggggca aggggcacga tggcctttac    1020
cagggtctca gtacagccac caaggacacc tacgacgccc ttcacatgca ggccctgccc    1080
cctcgctaa                                                            1089

<210> SEQ ID NO 277
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 277
atggctctgc ccgtcaccgc tctgctgctg cctctggctc tgctgctgca cgctgctcgc      60
cctcaggtac agctggtgga gtctggggga ggattggtgc aggctggggg ctctctgaga     120
ctctcctgtg cagcctctgg aggcacctta agtaaaaata ccgtggcttg gttccgccag     180
gctccaggga aggagcgtgg gtttgtagcg tctattacct gggatggtcg tacgacatac     240
tatgcagact ccgtgaaggg ccgattcacc atctccagag acaacgccaa gaacacagtg     300
tatctgcaaa tgaacagcct gaaacctgag gatacggccg tttatgtctg tgcagactta     360
gggaaatggc ctgcgggccc ggcggactac tgggggccagg ggacccaggt caccgtctcc     420
tcaactagta ccacgacgcc agcgccgcga ccaccaacac cggcgcccac catcgcgtcg     480
cagcccctgt ccctgcgccc agaggcgtgc cggccagcgg cgggggcgc agtgcacacg      540 aggggctgg acttcgcctg tgatatctac atctgggcgc ccttggccgg gacttgtggg     600
gtccttctcc tgtcactggt tatcaccctt tactgcaaac ggggcagaaa gaaactcctg     660
```

| tatatattca aacaaccatt tatgagacca gtacaaacta ctcaagagga agatggctgt | 720 |
| agctgccgat ttccagaaga agaagaagga ggatgtgaac tgagagtgaa gttcagcagg | 780 |
| agcgcagacg cccccgcgta ccagcagggc cagaaccagc tctataacga gctcaatcta | 840 |
| ggacgaagag aggagtacga tgttttggac aagagacgtg gccgggaccc tgagatgggg | 900 |
| ggaaagccga aaggaagaa ccctcaggaa ggcctgtaca atgaactgca gaaagataag | 960 |
| atggcggagg cctacagtga gattgggatg aaaggcgagc gccggagggg caaggggcac | 1020 |
| gatggccttt accagggtct cagtacagcc accaaggaca cctacgacgc ccttcacatg | 1080 |
| caggccctgc cccctcgcta a | 1101 |

<210> SEQ ID NO 278
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 278

| atggctctgc ccgtcaccgc tctgctgctg cctctggctc tgctgctgca cgctgctcgc | 60 |
| cctcaggtgc agctggtgga gtctggggga ggcttggtgc agcctggggg gtctctgaca | 120 |
| ctctcctgtg cagcctctgg aagcatcgac agtatcaata ccatggactg gttccgtcag | 180 |
| gctccaggga aggagcgtga gtttgtagca gctattagtt tgagtcccac tttagcatat | 240 |
| tatgcagagt ccgtgaaggg ccgattcacc atcagccgag acaacgccaa gaacacggtg | 300 |
| gttttgcaaa tgaacagcct gaaacctgag gacacggccc tttattactg tgcagcagac | 360 |
| cggaaatcag taatgtctat tcggcccgac tactggggcc aggggaccca ggtcaccgtc | 420 |
| tcctcaacta gtaccacgac gccagcgccg cgaccaccaa caccggcgcc caccatcgcg | 480 |
| tcgcagcccc tgtccctgcg cccagaggcg tgccggccag gcggcggggg cgcagtgcac | 540 |
| acgaggggggg tggacttcgc ctgtgatatc tacatctggg cgcccttggc cgggacttgt | 600 |
| ggggtccttc tcctgtcact ggttatcacc ctttactgca acggggcag aaagaaactc | 660 |
| ctgtatatat tcaaacaacc atttatgaga ccagtacaaa ctactcaaga ggaagatggc | 720 |
| tgtagctgcc gatttccaga agaagaagaa ggaggatgtg aactgagagt gaagttcagc | 780 |
| aggagcgcag acgcccccgc gtaccagcag ggccagaacc agctctataa cgagctcaat | 840 |
| ctaggacgaa gagaggagta cgatgttttg gacaagagac gtggccggga ccctgagatg | 900 |
| gggggaaagc cgagaaggaa gaaccctcag gaaggcctgt acaatgaact gcagaaagat | 960 |
| aagatggcgg aggcctacag tgagattggg atgaaaggcg agcgccggag gggcaagggg | 1020 |
| cacgatggcc tttaccaggg tctcagtaca gccaccaagg acacctacga cgcccttcac | 1080 |
| atgcaggccc tgcccctcg ctaa | 1104 |

<210> SEQ ID NO 279
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 279

| atggctctgc ccgtcaccgc tctgctgctg cctctggctc tgctgctgca cgctgctcgc | 60 |
| cctgatgtgc agctggtgga gtctggggga ggattggtgc aggctggggg ctctctgaga | 120 |
| ctctcctgtg cagcctctgg aggcacctta agtaagaata ccgtggcttg ggtccgccag | 180 |

```
gctccaggga aggagcgtgg gtttgtaacg tctattacct gtgatggtcg tacgacatac    240
tatgcgaact ccgtgaaggg ccgattcccc atctccagag acaacgccga gaacacagtg    300
tatctgcaaa tgaacagcct gaaacctgag gatacggccg ttatgtctg tgcagactta     360 gggaagtggc ctgcgggttc ggcggactac tggggccagg ggacccacgt caccgtctcc    420
tccactagta ccacgacgcc agcgccgcga ccaccaacac cggcgcccac catcgcgtcg    480
cagcccctgt ccctgcgccc agaggcgtgc cggccagcgg cggggggcgc agtgcacacg    540
agggggctgg acttcgcctg tgatatctac atctgggcgc ccttggccgg acttgtggg     600 gtccttctcc tgtcactggt tatcacccct tactgcaaac ggggcagaaa gaaactcctg    660
tatatattca acaaccatt tatgagacca gtacaaacta ctcaagagga gatggctgt     720 agctgccgat ttccagaaga agaaggga ggatgtgaac tgagagtgaa gttcagcagg     780
agcgcagacg ccccgcgta ccagcagggc cagaaccagc tctataacga gctcaatcta     840
ggacgaagag aggagtacga tgttttggac aagagacgtg gccgggaccc tgagatgggg    900
ggaaagccga aggaagaa ccctcaggaa ggcctgtaca atgaactgca gaaagataag      960
atggcggagg cctacagtga gattgggatg aaaggcgagc gccggagggg caaggggcac   1020
gatggccttt accagggtct cagtacagcc accaaggaca cctacgacgc ccttcacatg   1080
caggccctgc cccctcgcta a                                             1101

<210> SEQ ID NO 280
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 280
atggctctgc ccgtcaccgc tctgctgctg cctctggctc tgctgctgca cgctgctcgc     60
cctcaggtaa agctggagga gtctggggga ggcttggtgc agcctggggg gtctctgaga    120
ctctcctgta cagcctcgga attcacattc agtgactact ggatgcattg ggtccgtcag    180
gctccgggga aggggctcga gtgggtcgca tctatagata ctagtggaca gaccacatac    240
tatgcagact ccctgaaggg ccgattcacc atctccagag acaacgccaa gagcacgttg    300
tatctgcaaa tgaacagtct gaaatctgaa gacacggggc tgtatttctg tgcaaaacga    360
tataggggtg gtacctggta tggcatggcc aactggggca aagggaccca ggtcaccgtc    420
tcctcaacta gtaccacgac gccagcgccg cgaccaccaa caccggcgcc caccatcgcg    480
tcgcagcccc tgtccctgcg cccagaggcg tgccggccag gcggggggg cgcagtgcac    540 acgagggggg tggacttcgc ctgtgatatc tacatctggg cgcccttggc cgggacttgt    600
ggggtccttc tcctgtcact ggttatcacc ctttactgca acggggcag aaagaaactc     660 ctgtatatat tcaaacaacc atttatgaga ccagtacaaa ctactcaaga ggaagatggc    720
tgtagctgcc gatttccaga agaagaagaa ggaggatgtg aactgagagt gaagttcagc    780
aggagcgcag acgccccgcg gtaccagcag ggccagaacc agctctataa cgagctcaat    840
ctaggacgaa gagaggagta cgatgttttg gacaagagac gtggccggga ccctgagatg    900 ggggaaagc cgagaaggaa gaaccctcag gaaggcctgt acaatgaact gcagaaagat    960
aagatggcgg aggcctacag tgagattggg atgaaaggcg agcgccggag gggcaagggg   1020
cacgatggcc tttaccaggg tctcagtaca gccaccaagg acacctacga cgcccttcac   1080
```

| | |
|---|---|
| atgcaggccc tgccccctcg ctaa | 1104 |

<210> SEQ ID NO 281
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 281

| | |
|---|---|
| atggctctgc ccgtcaccgc tctgctgctg cctctggctc tgctgctgca cgctgctcgc | 60 |
| cctcaggtgc agctggtgga gtctggggga ggattggtgc aggctggggg ctctctgaga | 120 |
| ctctcctgtg cagcctctgg acgcacctta agtagtaata ccatggcttg gttccgccag | 180 |
| gctccaggga aggagcgtga gtttgtagcg tctactacct ggaatggtcg tagcacatac | 240 |
| tatgcagact ccgtgaaggg ccgattcacc atctccagag acaacgccaa gaacacgatg | 300 |
| tatctgcaaa tgaacagcct gaaacctgag gatacggccg tttatgtctg tgcagactta | 360 |
| gggaaatggc ctgcgggccc ggcggactac tggggccagg ggacccaggt caccgtctcc | 420 |
| tcaactagta ccacgacgcc agcgccgcga ccaccaacac cggcgcccac catcgcgtcg | 480 |
| cagcccctgt ccctgcgccc agaggcgtgc cggccagcgg cggggggcgc agtgcacacg | 540 |
| aggggggctgg acttcgcctg tgatatctac atctgggcgc ccttggccgg gacttgtggg | 600 |
| gtccttctcc tgtcactggt tatcacccttt tactgcaaac ggggcagaaa gaaactcctg | 660 |
| tatatattca acaaccatt tatgagacca gtacaaacta ctcaagagga gatggctgt | 720 |
| agctgccgat ttccagaaga agaagaagga ggatgtgaac tgagagtgaa gttcagcagg | 780 |
| agcgcagacg cccccgcgta ccagcagggc cagaaccagc tctataacga gctcaatcta | 840 |
| ggacgaagag aggagtacga tgttttggac aagagacgtg gccgggaccc tgagatgggg | 900 |
| ggaaagccga aggaagaa ccctcaggaa ggcctgtaca tgaactgca gaaagataag | 960 |
| atggcggagg cctacagtga gattgggatg aaaggcgagc gccggagggg caaggggcac | 1020 |
| gatggccttt accagggtct cagtacagcc accaaggaca cctacgacgc ccttcacatg | 1080 |
| caggccctgc cccctcgcta a | 1101 |

<210> SEQ ID NO 282
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 282

| | |
|---|---|
| atggctctgc ccgtcaccgc tctgctgctg cctctggctc tgctgctgca cgctgctcgc | 60 |
| cctcaggtgc agctggtgga gtctggggga ggattggtgc aggctggggg ctctctgaga | 120 |
| ctctcctgtg cagcctctgg acgcacctta ccatgggt ggttccgtca ggctccaggg | 180 |
| aagcagcgcg aattggtcgc agatattagt ggtggtcgca caaactatgc agattccgtg | 240 |
| aagggacgat tcaccatctc cagagacaac gccaagaaca cggtatatct gcaaatgaac | 300 |
| agcctgaaac ctgaggacac ggccgtttat tactgtgcag cagaccggaa atcagtaatg | 360 |
| tctattcggc ccgactactg ggggccaggg acccaggtca ccgtctcctc aactagtacc | 420 |
| acgacgccag cgccgcgacc accaacaccg gcgcccacca tcgcgtcgca gcccctgtcc | 480 |
| ctgcgcccag aggcgtgccg gccagcgcg ggggcgca tgcacacgag ggggctggac | 540 |
| ttcgcctgtg atatctacat ctgggcgccc ttggccggga cttgtggggt ccttctcctg | 600 |

```
tcactggtta tcacccttta ctgcaaacgg ggcagaaaga aactcctgta tatattcaaa    660
caaccattta tgagaccagt acaaactact caagaggaag atggctgtag ctgccgattt    720
ccagaagaag aagaaggagg atgtgaactg agagtgaagt tcagcaggag cgcagacgcc    780
cccgcgtacc agcagggcca gaaccagctc tataacgagc tcaatctagg acgaagagag    840
gagtacgatg ttttggacaa gagacgtggc cgggaccctg agatgggggg aaagccgaga    900
aggaagaacc ctcaggaagg cctgtacaat gaactgcaga agataagat ggcggaggcc     960 tacagtgaga ttgggatgaa aggcgagcgc cggaggggca aggggcacga tggcctttac    1020
cagggtctca gtacagccac caaggacacc tacgacgccc ttcacatgca ggccctgccc    1080
cctcgctaa                                                            1089

<210> SEQ ID NO 283
<211> LENGTH: 1053
<212> TYPE: DNA
<213> ORGANISM: Artificial Sequence
<220> FEATURE:
<223> OTHER INFORMATION: Synthetic Construct

<400> SEQUENCE: 283
atggctctgc ccgtcaccgc tctgctgctg cctctggctc tgctgctgca cgctgctcgc     60
cctcaggtgc agctggtgga gtctggggga ggcttggtgc aggctggggc ctctctgaga    120
ctctcctgtg cagcctctgg acgcaccttc accgtggcag ctattagttt gagtcctact    180
ttagcatatt atgcagagtc cgtgaagggc cgattcacca tcagccgaga caacgccaag    240
aacacggtgg ttttgcaaat gaacagcctg aaacctgagg acacggccct ttattactgt    300
gcagcagacc ggaaatcagt aatgtctatt cggcccgact actggggcca ggggacccag    360
gtcaccgtct cctcaactag taccacgacg ccagcgccgc gaccaccaac accggcgccc    420
accatcgcgt cgcagcccct gtccctgcgc ccagaggcgt gccggccagc ggcggggggc    480
gcagtgcaca cgagggggct ggacttcgcc tgtgatatct acatctgggc gcccttggcc    540
gggacttgtg gggtccttct cctgtcactg gttatcaccc tttactgcaa cgggcagaa    600 aagaaactcc tgtatatatt caaacaacca tttatgagac cagtacaaac tactcaagag    660
gaagatggct gtagctgccg atttccagaa gaagaagaag aggatgtgaa actgagagtg    720
aagttcagca ggagcgcaga cgcccccgcg taccagcagg gccagaacca gctctataac    780
gagctcaatc taggacgaag agaggagtac gatgttttgg acaagagacg tggccgggac    840
cctgagatgg ggggaaagcc gagaaggaag aaccctcagg aaggcctgta caatgaactg    900
cagaaagata gatggcgga ggcctacagt gagattggga tgaaaggcga gcgccggagg    960 ggcaagggc acgatggcct ttaccagggt ctcagtacag ccaccaagga cacctacgac    1020
gcccttcaca tgcaggccct gcccctcgc taa                                  1053

<210> SEQ ID NO 284
<211> LENGTH: 1116
<212> TYPE: DNA
<213> ORGANISM: Artificial Sequence
<220> FEATURE:
<223> OTHER INFORMATION: Synthetic Construct

<400> SEQUENCE: 284
atggctctgc ccgtcaccgc tctgctgctg cctctggctc tgctgctgca cgctgctcgc     60
cctgatgtgc agctggtgga gtctggggga ggattggagc aggctggggg ctctctgaga    120
```

| | |
|---|---|
| ctctcctgtg cagcctctgg aggcacctta agtaaaaata ccgtggcttg gttccgccag | 180 |
| gctccaggga aggagcgtgg gtttgtagcg tctattacct gggatggtcg tacgacatac | 240 |
| tatgcagact ccgtgaaggg ccgattcacc atctccagag acaacgccaa gaacacagtg | 300 |
| tatctgcaaa tgaacagcct gaaacctgag gatacggccg tttattactg tgcgtcgacg | 360 |
| gcatcgtgcc acctcttcgg attggggtcc ggggcctttg tgtcctgggg ccggggacc | 420 |
| caggtcaccg tctcctcaac tagtaccacg acgccagcgc cgcgaccacc aacaccggcg | 480 |
| cccaccatcg cgtcgcagcc cctgtccctg cgcccagagg cgtgccggcc agcggcgggg | 540 |
| ggcgcagtgc acacgagggg gctggacttc gcctgtgata tctacatctg gcgcccttg | 600 |
| gccgggactt gtggggtcct tctcctgtca ctggttatca ccctttactg caaacggggc | 660 |
| agaaagaaac tcctgtatat attcaaacaa ccatttatga ccagtaca aactactcaa | 720 |
| gaggaagatg gctgtagctg ccgatttcca gaagaagaag aaggaggatg tgaactgaga | 780 |
| gtgaagttca gcaggagcgc agacgccccc gcgtaccagc agggccagaa ccagctctat | 840 |
| aacgagctca atctaggacg aagagaggag tacgatgttt tggacaagag acgtggccgg | 900 |
| gaccctgaga tgggggaaa gccgagaagg aagaaccctc aggaaggcct gtacaatgaa | 960 |
| ctgcagaaag ataagatggc ggaggcctac agtgagattg ggatgaaagg cgagcgccgg | 1020 |
| aggggcaagg ggcacgatgg cctttaccag ggtctcagta cagccaccaa ggacacctac | 1080 |
| gacgccttc acatgcaggc cctgcccct cgctaa | 1116 |

<210> SEQ ID NO 285
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 285

| | |
|---|---|
| atggctctgc ccgtcaccgc tctgctgctg cctctggctc tgctgctgca cgctgctcgc | 60 |
| cctgcggtgc agctggtgga gtctggggga ggattggtgc aggctggggg ctctctgaga | 120 |
| ctctcctgtg cagcctctgg acgcaccttc accatgggt ggttccatca ggctccaggg | 180 |
| aaggagcgtg agtttgtagc agctattagt ttgagtccta ctttagcata ttatgcagag | 240 |
| tccgtgaagg gccgattcac catcagccga gacaacgcca gaacacggt ggttttgcaa | 300 |
| atgaacagcc tgaaacctga ggacacggcc ctttattact gtgcagcatc caaggataga | 360 |
| tattcggaat atgagtactg gggccagggg acccaggtca ccgtctcctc aactagtacc | 420 |
| acgacgccag cgccgcgacc accaacaccg gcgcccacca tcgcgtcgca gcccctgtcc | 480 |
| ctgcgcccag aggcgtgccg gccagcggcg ggggcgcag tgcacacgag ggggctggac | 540 |
| ttcgcctgtg atatctacat ctgggcgccc ttggccggga cttgtggggt ccttctcctg | 600 |
| tcactggtta tcacccttta ctgcaaacgg ggcagaaaga aactcctgta tatattcaaa | 660 |
| caaccatttta tgagaccagt acaaactact caagaggaag atggctgtag ctgccgattt | 720 |
| ccagaagaag aagaaggagg atgtgaactg agagtgaagt tcagcaggag cgcagacgcc | 780 |
| cccgcgtacc agcagggcca gaaccagctc tataacgagc tcaatctagg acgaagagag | 840 |
| gagtacgatg tttggacaa gagacgtggc cgggaccctg atgggggg aaagccgaga | 900 |
| aggaagaacc tcaggaagg cctgtacaat gaactgcaga agataagat ggcggaggcc | 960 |
| tacagtgaga ttgggatgaa aggcgagcgc cggaggggca aggggcacga tggcctttac | 1020 |
| cagggtctca gtacagccac caaggacacc tacgacgccc ttcacatgca ggccctgccc | 1080 | cctcgctaa                                                                        1089

<210> SEQ ID NO 286
<211> LENGTH: 1083
<212> TYPE: DNA
<213> ORGANISM: Artificial Sequence
<220> FEATURE:
<223> OTHER INFORMATION: Synthetic Construct

<400> SEQUENCE: 286
atggctctgc ccgtcaccgc tctgctgctg cctctggctc tgctgctgca cgctgctcgc      60
cctcaggtaa agctggagga gtctggggga ggattggtgc aggctggggg ctctctgaga     120
ctctcctgtg cagcctctgg acgcaccttc accatggggt ggttccgtca ggctccaggg     180
aaggagcgtg agtttgtagc agctattagt ttgagtccta ctttagcata ttatgcagag     240
tccgtgaagg gccgattcac catcagccga gacaacgcca agaacacggt ggttttgcaa     300
atgaacagcc tgaaacctga ggacacggcc ctttattact gtgcaaaaaa aaacggggga     360
cctgtggact actggggcaa agggacccag gtcaccgtct cctcaactag taccacgacg     420
ccagcgccgc gaccaccaac accggcgccc accatcgcgt cgcagcccct gtccctgcgc     480
ccagaggcgt gccggccagc ggcggggggc gcagtgcaca cgagggggct ggacttcgcc     540
tgtgatatct acatctgggc gcccttggcc gggacttgtg gggtccttct cctgtcactg     600
gttatcaccc tttactgcaa cgggcagaa agaaactcc tgtatatatt caaacaacca     660
tttatgagac cagtacaaac tactcaagag gaagatggct gtagctgccg atttccagaa     720
gaagaagaag gaggatgtga actgagagtg aagttcagca ggagcgcaga cgcccccgcg     780
taccagcagg gccagaacca gctctataac gagctcaatc taggacgaag agaggagtac     840
gatgttttgg acaagagacg tggccgggac cctgagatgg ggggaaagcc gagaaggaag     900
aaccctcagg aaggcctgta caatgaactg cagaaagata gatggcggga ggcctacagt     960
gagattggga tgaaaggcga gcgccggagg ggcaaggggc acgatggcct ttaccagggt    1020
ctcagtacag ccaccaagga cacctacgac gcccttcaca tgcaggccct gccccctcgc    1080
taa                                                                   1083

<210> SEQ ID NO 287
<211> LENGTH: 1098
<212> TYPE: DNA
<213> ORGANISM: Artificial Sequence
<220> FEATURE:
<223> OTHER INFORMATION: Synthetic Construct

<400> SEQUENCE: 287
atggctctgc ccgtcaccgc tctgctgctg cctctggctc tgctgctgca cgctgctcgc      60
cctgatgtgc agctggtgga gtctggggga ggcttggtgc agcctggggg gtctctgaga     120
ctctcctgtg cagcctctgg acggaccttc agtagcattg tcatgggctg gttccgccag     180
gctccaggga aggagcgtga gtttgtagga gcgattatgt ggaatgatgg tattacatac     240
ttgcaagact ccgtgaaggg ccgatttacc atcttcagag acaacgccaa gaacacggtg     300
tatctgcaaa tgaacagcct gaaacttgag gatacgcccg tttattactg tgcagcatcc     360
aagggtagat actcggaata tgagtactgg ggccagggga cccaggtcac cgtctcctca     420
actagtacca cgacgccagc gccgcgacca ccaacaccgg cgccaccat cgcgtcgcag     480
cccctgtccc tgcgcccaga ggcgtgccgg ccagcggcgg ggggcgcagt gcacacgagg     540

| | |
|---|---|
| gggctggact tcgcctgtga tatctacatc tgggcgccct tggccgggac ttgtggggtc | 600 |
| cttctcctgt cactggttat cacccttta c tgcaaacggg gcagaaagaa actcctgtat | 660 |
| atattcaaac aaccatttat gagaccagta caaactactc aagaggaaga tggctgtagc | 720 |
| tgccgatttc cagaagaaga agaaggagga tgtgaactga gagtgaagtt cagcaggagc | 780 |
| gcagacgccc ccgcgtacca gcagggccag aaccagctct ataacgagct caatctagga | 840 |
| cgaagagagg agtacgatgt tttggacaag agacgtggcc gggaccctga tgggggga | 900 |
| aagccgagaa ggaagaaccc tcaggaaggc ctgtacaatg aactgcagaa agataagatg | 960 |
| gcggaggcct acagtgagat tgggatgaaa ggcgagcgcc ggaggggcaa ggggcacgat | 1020 |
| ggcctttacc agggtctcag tacagccacc aaggacacct cgacgccct tcacatgcag | 1080 |
| gccctgcccc ctcgctaa | 1098 |

<210> SEQ ID NO 288
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 288

| | |
|---|---|
| atggctctgc ccgtcaccgc tctgctgctg cctctggctc tgctgctgca cgctgctcgc | 60 |
| cctcaggtaa agctggagga atctggggga agattggtgc aggctggggg ctctctgaaa | 120 |
| ctctcctggg cagcctctgg acgcaccttc accatggggt ggttccgtca ggctccaggg | 180 |
| aaggaacgtg agtttgtaac agctattaat ttgagtccta cttaacata ttatgcagaa | 240 |
| tccgtgaagg gccgattccc catcagccga acaacgccc agaacacggt ggttttgcaa | 300 |
| atgaacagcc tgaaacctga ggacacggcc ctttattact gtgcagcaga acggaaatca | 360 |
| gtaatggcta ttccgcccga ctactggggc caggggaccc aggtcaccgt ctcctcaact | 420 |
| agtaccacga cgccagcgcc gcgaccacca acaccggcgc ccaccatcgc gtcgcagccc | 480 |
| ctgtccctgc gcccagaggc gtgccggcca gcggcggggg gcgcagtgca cacgaggggg | 540 |
| ctggacttcg cctgtgatat ctacatctgg gcgcccttgg ccgggacttg tggggtcctt | 600 |
| ctcctgtcac tggttatcac cctttactgc aaacggggca gaaagaaact cctgtatata | 660 |
| ttcaaacaac catttatgag accagtacaa actactcaag aggaagatgg ctgtagctgc | 720 |
| cgatttccag aagaagaaga aggaggatgt gaactgagag tgaagttcag caggagcgca | 780 |
| gacgccccg cgtaccagca gggccagaac cagctctata cgagctcaa tctaggacga | 840 |
| agagaggagt acgatgtttt ggacaagaga cgtggccggg accctgagat gggggaaag | 900 |
| ccgagaagga agaaccctca ggaaggcctg tacaatgaac tgcagaaaga taagatggcg | 960 |
| gaggcctaca gtgagattgg gatgaaaggc gagcgccgga ggggcaaggg gcacgatggc | 1020 |
| ctttaccagg gtctcagtac agccaccaag gacacctacg acgcccttca catgcaggcc | 1080 |
| ctgccccctc gctaa | 1095 |

<210> SEQ ID NO 289
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 289

| | |
|---|---|
| atggctctgc ccgtcaccgc tctgctgctg cctctggctc tgctgctgca cgctgctcgc | 60 |

```
cctgaggtgc agctggtgga gtctgggggga ggattggtgc aggctggggg ctctctgaga    120
ctctcctgtg cagcctctgg acgcaccttc accatggggg ggttccgtcg ggttcctcgg    180
gatgagcggg agtttgtagc atctattact ttgattccta cttttcctta ttatgcatat    240
tccgtgaagg gccgattcgc cctcttccga dacaacccca acaacaccgt gattttgctg    300
atgatcagcc tgaaacctga ggacccggac ctttattact gtgcttcata ccggaaatac    360
ctaatgtcta ttctgcccga ctactgggc caggggaccc agggcaccgt ctcctccact    420
agtaccacga cgccagcgcc gcgaccacca acaccggcgc caccatcgc gtcgcagccc    480
ctgtccctgc gcccagaggc gtgccggcca cggcggggg gcgcagtgca cacgagggggg    540
ctggacttcg cctgtgatat ctacatctgg gcgcccttgg ccgggacttg tggggtcctt    600
ctcctgtcac tggttatcac cctttactgc aaacggggca gaagaaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780
gacgcccccg cgtaccagca gggccagaac cagctctata cgagctcaa tctaggacga    840
agagaggagt acgatgtttt ggacaagaga cgtggccggg accctgagat gggggggaaag    900
ccgagaagga agaaccctca ggaaggcctg tacaatgaac tgcagaaaga taagatggcg    960
gaggcctaca gtgagattgg gatgaaaggc gagcgccgga ggggcaaggg gcacgatggc   1020
ctttaccagg gtctcagtac agccaccaag gacacctacg acgcccttca catgcaggcc   1080
ctgcccctc gctaa                                                     1095

<210> SEQ ID NO 290
<211> LENGTH: 1113
<212> TYPE: DNA
<213> ORGANISM: Artificial Sequence
<220> FEATURE:
<223> OTHER INFORMATION: Synthetic Construct

<400> SEQUENCE: 290
atggctctgc ccgtcaccgc tctgctgctg cctctggctc tgctgctgca cgctgctcgc     60
cctcaggtaa agctggagga gtctgggggga ggattggtgc aggctggggg ctctctgaga    120
ctctcctgtg cagcctctgg acgcaccttc accatggggt ggttccgtca ggctccaggg    180
aaggagcgtg agtttgtagc agctattagt ttgagtccta ctttagcata ttatgcagag    240
tccgtgaagg gccgattcac catcagccga dacaacgcca agaacacggt ggatctgcaa    300
atgaacagcc tgaaacctga ggacacggcc gtctatttct gtgcagcaaa tcggaactcc    360
caacgggtaa ttgcggcact gtcctggatt ggcatgaact actggggcga atggacccag    420
gtcaccgtct cctccactag taccacgacg ccagcgccgc gaccaccaac accggcgccc    480
accatcgcgt cgcagcccct gtccctgcgc ccagaggcgt gccggccagc ggcgggggc    540
gcagtgcaca cgagggggct ggacttcgcc tgtgatatct acatctgggc gcccttggcc    600
gggacttgtg ggtccttct cctgtcactg gttatcaccc tttactgcaa acggggcaga    660
aagaaactcc tgtatatatt caaacaacca tttatgagac cagtacaaac tactcaagag    720
gaagatggct gtagctgccg atttccagaa gaagaagaag aggatgtga actgagagtg    780
aagttcagca ggagcgcaga cgcccccgcg taccagcagg gccagaacca gctctataac    840
gagctcaatc taggacgaag agaggagtac gatgttttgg acaagagacg tggccgggac    900
cctgagatgg ggggaaagcc gagaaggaag aaccctcagg aaggcctgta caatgaactg    960
```

| | |
|---|---|
| cagaaagata agatggcgga ggcctacagt gagattggga tgaaaggcga gcgccggagg | 1020 |
| ggcaagggc acgatggcct ttaccagggt ctcagtacag ccaccaagga cacctacgac | 1080 |
| gcccttcaca tgcaggccct gccccctcgc taa | 1113 |

<210> SEQ ID NO 291
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 291

| | |
|---|---|
| atggctctgc ccgtcaccgc tctgctgctg cctctggctc tgctgctgca cgctgctcgc | 60 |
| cctcaggtgc agctggtgga gtctggggga ggattggtgc aggctggggg ctctctgaga | 120 |
| ctctcctgtg cagcctctgg acgcaccttc accatgggt ggttccgtca ggctccaggg | 180 |
| aaggagcgtg agtttgtagc agctattagt ttgagtccta ctttagcata ttatgcagag | 240 |
| tccgtgaagg gccgattcac catctccaga gacaacgcca agaagacgct gtatctgcga | 300 |
| atgaatagcc tgaaacctga ggacacggcc gtttactact gtgcagcacg tcggatcgac | 360 |
| gcagctgact tgattcctg ggggcagggg acccaggtca ccgtctcctc aactagtacc | 420 |
| acgacgccag cgccgcgacc accaacaccg gcgcccacca tcgcgtcgca gcccctgtcc | 480 |
| ctgcgcccag aggcgtgccg gccagcgcg ggggcgcag tgcacacgag ggggctggac | 540 |
| ttcgcctgtg atatctacat ctgggcgccc ttggccggga cttgtgggt ccttctcctg | 600 |
| tcactggtta tcacccttta ctgcaaacgg gcagaaaga aactcctgta tatattcaaa | 660 |
| caaccattta tgagaccagt acaaactact caagaggaag atggctgtag ctgccgattt | 720 |
| ccagaagaag aagaaggagg atgtgaactg agagtgaagt tcagcaggag cgcagacgcc | 780 |
| cccgcgtacc agcagggcca gaaccagctc tataacgagc tcaatctagg acgaagagag | 840 |
| gagtacgatg ttttggacaa gagacgtggc cgggaccctg agatgggggg aaagccgaga | 900 |
| aggaagaacc ctcaggaagg cctgtacaat gaactgcaga agataagat ggcggaggcc | 960 |
| tacagtgaga ttgggatgaa aggcgagcgc cggaggggca aggggcacga tggcctttac | 1020 |
| cagggtctca gtacagccac caaggacacc tacgacgccc ttcacatgca ggccctgccc | 1080 |
| cctcgctaa | 1089 |

<210> SEQ ID NO 292
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 292

| | |
|---|---|
| atggctctgc ccgtcaccgc tctgctgctg cctctggctc tgctgctgca cgctgctcgc | 60 |
| cctcaggtaa agctggagga gtctggggga ggattggtgc aggctggggg ctctctgaga | 120 |
| ctctcctgtg cagcctctgg acgcaccttc accatgggt ggttccgtcg ggctccaggg | 180 |
| aaggagcgtg agtctgttgc agttattggc tggagagata ttaacgcaag ctatgcagac | 240 |
| tccgtgaagg gccgattcgc catctccaga gacaacgcca agaagacgct gtatctgcag | 300 |
| atgaatagcc tgaaacctga ggacacggcc gtttactact gtgcagcacg tcggatcgac | 360 |
| gcaactgact tgattcctg ggggcagggg acccaggtca ccgtctcctc aactagtacc | 420 |
| acgacgccag cgccgcgacc accaacaccg gcgcccacca tcgcgtcgca gcccctgtcc | 480 |

```
ctgcgcccag aggcgtgccg gccagcggcg gggggcgcag tgcacacgag ggggctggac    540
ttcgcctgtg atatctacat ctgggcgccc ttggccggga cttgtggggt ccttctcctg    600
tcactggtta tcacccttta ctgcaaacgg ggcagaaaga aactcctgta tatattcaaa    660
caaccattta tgagaccagt acaaactact caagaggaag atggctgtag ctgccgattt    720
ccagaagaag aagaaggagg atgtgaactg agagtgaagt tcagcaggag cgcagacgcc    780
cccgcgtacc agcagggcca gaaccagctc tataacgagc tcaatctagg acgaagagag    840
gagtacgatg ttttggacaa gagacgtggc cgggaccctg atgggggga aaagccgaga    900 aggaagaacc ctcaggaagg cctgtacaat gaactgcaga agataagat ggcggaggcc     960 tacagtgaga ttgggatgaa aggcgagcgc cggaggggca aggggcacga tggcctttac   1020
cagggtctca gtacagccac caaggacacc tacgacgccc ttcacatgca ggccctgccc   1080
cctcgctaa                                                           1089

<210> SEQ ID NO 293
<211> LENGTH: 1098
<212> TYPE: DNA
<213> ORGANISM: Artificial Sequence
<220> FEATURE:
<223> OTHER INFORMATION: Synthetic Construct

<400> SEQUENCE: 293
atggctctgc ccgtcaccgc tctgctgctg cctctggctc tgctgctgca cgctgctcgc     60
cctcaggtaa agctggagga gtctgggggga ggattggtgc agactggggg ctctctgaga   120
ctctcctgtg cagcctctga acacaccttc agtaaccatg tcatgggctg gttccgccag   180
gctccaggga aggagcgtga gtctgttgca gttattggct ggagagatat tagcacaagc   240
tatgcagact ccgtgaaggg ccgattcacc atctccagag acaacgccaa gaagacgctg   300
tatctgcaaa tgaatagcct gaaacctgag gacacggccg tttactactg tgcagcacgt   360
cggatcgacg cagctgactt tgattcccgg gggcagggga cccaggtcac cgtctcctca   420
actagtacca cgacgccagc gccgcgacca ccaacaccgg cgcccaccat cgcgtcgcag   480 ccccctgtccc tgcgcccaga ggcgtgccgg ccagcggcgg ggggcgcagt gcacacgag   540 gggctggact cgcctgtga tatctacatc tgggcgccct tggccgggac ttgtggggtc    600
cttctcctgt cactggttat cacccttta ctgcaaacggg gcagaaagaa actcctgtat   660
atattcaaac aaccatttat gagaccagta caaactactc aagaggaaga tggctgtagc   720
tgccgatttc cagaagaaga agaaggagga tgtgaactga gagtgaagtt cagcaggagc   780
gcagacgccc ccgcgtacca gcagggccag aaccagctct ataacgagct caatctagga   840
cgaagagagg agtacgatgt tttggacaag agacgtggcc gggaccctga tgggggga     900 aagccgagaa ggaagaaccc tcaggaaggc ctgtacaatg aactgcagaa agataagatg   960
gcggaggcct acagtgagat tgggatgaaa ggcgagcgcc ggaggggcaa ggggcacgat   1020
ggcctttacc agggtctcag tacagccacc aaggacacct acgacgccct tcacatgcag   1080
gccctgcccc ctcgctaa                                                 1098

<210> SEQ ID NO 294
<211> LENGTH: 1110
<212> TYPE: DNA
<213> ORGANISM: Artificial Sequence
<220> FEATURE:
<223> OTHER INFORMATION: Synthetic Construct
```

<400> SEQUENCE: 294

```
atggctctgc ccgtcaccgc tctgctgctg cctctggctc tgctgctgca cgctgctcgc      60
cctgccgtgc agctggtgga ttctggggga ggattggtgc aggctggggg ctctctgaga     120
atttcctgtg cagtctctgg acgcacctcc agtaactata tattggcctg gttccgtcag     180
gctccaggaa aagagcgtga ctttgtagca catattagcc ggagtggtgg taagtccggc     240
tatgagact ccgtgaaggg ccgattcacc atctccagag acaacgccga gaacacggtc      300
agggtgtatc tgcaaatgaa cagtctgaaa cctggggaca cggccgtcta ttactgtaat     360
cgcccctct ggtacggaag tcccacgttg attgactact ggggccaggg gacccaggtc      420
accgtctcct caactagtac cacgacgcca gcgccgcgac caccaacacc ggcgcccacc     480
atcgcgtcgc agcccctgtc cctgcgccca gaggcgtgcc ggccagcggc gggggcgca     540
gtgcacacga gggggctgga cttcgcctgt gatatctaca tctgggcgcc cttggccggg     600
acttgtgggg tccttctcct gtcactggtt atcacccttt actgcaaacg ggcagaaag     660
aaactcctgt atatattcaa acaaccttt atgagaccag tacaaactac tcaagaggaa     720
gatggctgta gctgccgatt ccagaagaa aagaaggag gatgtgaact gagagtgaag     780
ttcagcagga gcgcagacgc ccccgcgtac cagcaggggcc agaaccagct ctataacgag     840
ctcaatctag gacgaagaga ggagtacgat gttttggaca agagacgtgg ccgggaccct     900
gagatggggg gaaagccgag aaggaagaac cctcaggaag gcctgtacaa tgaactgcag     960
aaagataaga tggcggaggc ctacagtgag attgggatga aggcgagcg ccggagggc     1020
aaggggcacg atgcctttta ccagggtctc agtacagcca ccaaggacac ctacgacgcc    1080
cttcacatgc aggccctgcc ccctcgctaa                                     1110
```

<210> SEQ ID NO 295
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 295

```
atggctctgc ccgtcaccgc tctgctgctg cctctggctc tgctgctgca cgctgctcgc      60
cctgcggtgc agctggtgga gtctggggga ggcttggtgc agcctggggg gtctctgaga     120
ctctcctgtg cagcctctgg acgcaccttc accatggggt ggttccgtca ggctccaggg     180
aaggagcgtg agtttgtagc agctattagt ttgagtccta cttttagcata ttatgcagag     240
tccgtgaagg gccgattcac catcagccga acaacgcca agaacacggt ggttttgcaa     300
atgaacagcc tgaaacctga ggacacggcc ctttattact gtgcagcaga ccggaaatca     360
gtaatgtcta ttcggcccga ctactgggc caggggaccc aggtcaccgt ctcctcaact     420
agtaccacga cgccagcgcc gcgaccacca caccggcgc ccaccatcgc gtcgcagccc     480
ctgtccctgc gcccagaggc gtgccggcca gcggcggggg cgcagtgca cacgagggg     540
ctggacttcg cctgtgatat ctacatctgg gcgcccttgg ccgggacttg tggggtcctt     600
ctcctgtcac tggttatcac ccttactgc aaacggggca gaagaaaact cctgtatata     660
ttcaaacaac catttatgag accagtacaa actactcaag aggaagatgg ctgtagctgc     720
cgatttccag aagaagaaga aggaggatgt gaactgagag tgaagttcag caggagcgca     780
gacgccccccg cgtaccagca gggccagaac cagctctata cgagctcaa tctaggacga    840
agagaggagt acgatgtttt ggacaagaga cgtggccggg accctgagat ggggggaaag    900
```

```
ccgagaagga agaaccctca ggaaggcctg tacaatgaac tgcagaaaga taagatggcg    960
gaggcctaca gtgagattgg gatgaaaggc gagcgccgga ggggcaaggg gcacgatggc   1020
ctttaccagg gtctcagtac agccaccaag gacacctacg acgcccttca catgcaggcc   1080
ctgcccccct gctaa                                                   1095
```

<210> SEQ ID NO 296
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 296

```
atggctctgc ccgtcaccgc tctgctgctg cctctggctc tgctgctgca cgctgctcgc     60
cctgcggtgc agctggtgga gtctggggga ggattggtgc aggctggggg ctctctgaga    120
ctctcctgtg cagcctctgg acgcaccttc accatgggt ggttccgtca ggctccaggg    180
aaggagcgtg agtttgtagc agctattagt ttgagtccta ctttagcata ttatgcagag    240
tccgtgaagg gccgattcac catcagccga gacaacgcca agaacacggt ggttttgcaa    300
atgaacagcc tgaaacctga ggacacggcc ctttattact gtgcagcaga ccggaaatca    360
gtaatgtcta ttcggcccga ctactgggc caggggaccc aggtcaccgt ctcctcaact    420
agtaccacga cgccagcgcc gcgaccacca acaccggcgc ccaccatcgc gtcgcagccc    480
ctgtccctgc gcccagaggc gtgccggcca cggcggggg gcgcagtgca cacgagggg    540 ctggacttcg cctgtgatat ctacatctgg gcgcccttgg ccgggacttg tggggtcctt    600
ctcctgtcac tggttatcac cctttactgc aaacggggca gaagaaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780
gacgcccccg cgtaccagca gggccagaac cagctctata acgagctcaa tctaggacga    840
agagaggagt acgatgtttt ggacaagaga cgtggccggg accctgagat gggggaaag    900 ccgagaagga agaaccctca ggaaggcctg tacaatgaac tgcagaaaga taagatggcg    960
gaggcctaca gtgagattgg gatgaaaggc gagcgccgga ggggcaaggg gcacgatggc   1020
ctttaccagg gtctcagtac agccaccaag gacacctacg acgcccttca catgcaggcc   1080
ctgcccccct gctaa                                                   1095
```

<210> SEQ ID NO 297
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 297

```
atggctctgc ccgtcaccgc tctgctgctg cctctggctc tgctgctgca cgctgctcgc     60
cctgatgtgc agctggtgga gtctggggga ggatcggtgc agactggggg ctctctgaga    120
ctctcctgta cagcctctgg acgcaccctc aataactttg tcatgggctg gttccgtcag    180
gctccaggga aggagcgtga gtttgtagca gctattagtt tgagtcctac tttagcatat    240
tatgtagagt ccgtgaaggg ccgattcacc atcagccgag acaacgccaa gaacacggtg    300
gttttgcaaa tgaacagcct gaaacctgag gacacggccc tttattactg tgcagcagac    360
```

```
cggaaatcag taatgtctat tcggcccgac tactggggcc aggggaccca ggtcaccgtc    420
tcctcaacta gtaccacgac gccagcgccg cgaccaccaa caccggcgcc caccatcgcg    480
tcgcagcccc tgtccctgcg cccagaggcg tgccggccag cggcgggggg cgcagtgcac    540 acgaggggc tggacttcgc ctgtgatatc tacatctggg cgcccttggc cgggacttgt     600
ggggtccttc tcctgtcact ggttatcacc ctttactgca aacggggcag aaagaaactc    660
ctgtatatat tcaaacaacc atttatgaga ccagtacaaa ctactcaaga ggaagatggc    720
tgtagctgcc gatttccaga agaagaagaa ggaggatgtg aactgagagt gaagttcagc    780
aggagcgcag acgccccccgc gtaccagcag ggccagaacc agctctataa cgagctcaat    840
ctaggacgaa gagaggagta cgatgttttg gacaagagac gtggccggga ccctgagatg    900 ggggaaagc cgagaaggaa gaaccctcag gaaggcctgt acaatgaact gcagaaagat     960
aagatggcgg aggcctacag tgagattggg atgaaggcg agcgccggag gggcaagggg    1020
cacgatggcc tttaccaggg tctcagtaca gccaccaagg acacctacga cgcccttcac    1080
atgcaggccc tgccccctcg ctaa                                          1104
```

<210> SEQ ID NO 298
<211> LENGTH: 495
<212> TYPE: PRT
<213> ORGANISM: Artificial Sequence
<220> FEATURE:
<223> OTHER INFORMATION: Synthetic Construct

<400> SEQUENCE: 298

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gln Val Gln Leu Val Glu Ser Gly Gly Gly Leu Val
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala

-continued

```
                225                 230                 235                 240
Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Thr Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 299
<211> LENGTH: 622
<212> TYPE: PRT
<213> ORGANISM: Artificial Sequence
<220> FEATURE:
<223> OTHER INFORMATION: Synthetic Construct

<400> SEQUENCE: 299

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Pro Gly Gly Ser Leu Arg Leu Ser Cys Glu Ala Ser Gly Phe
            35                  40                  45

Thr Leu Asp Tyr Tyr Ala Ile Gly Trp Phe Arg Gln Ala Pro Gly Lys
        50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
```

```
                100             105             110
Ala Ala Tyr Tyr Cys Ala Ala Gly Ala Asp Cys Ser Gly Tyr Leu Arg
            115             120             125

Asp Tyr Glu Phe Arg Gly Gln Gly Thr Gln Val Thr Val Ser Ser Gly
            130             135             140

Gly Gly Gly Ser Gln Val Gln Leu Val Glu Ser Gly Gly Gly Leu Val
145             150             155             160

Gln Pro Gly Gly Ser Leu Arg Leu Ser Cys Glu Ala Ser Gly Phe Thr
                165             170             175

Leu Asp Tyr Tyr Ala Ile Gly Trp Phe Arg Gln Ala Pro Gly Lys Glu
            180             185             190

Arg Glu Gly Val Ile Cys Ile Ser Arg Ser Asp Gly Ser Thr Tyr Tyr
            195             200             205

Ala Asp Ser Val Lys Gly Arg Phe Thr Ile Ser Arg Asp Asn Ala Lys
            210             215             220

Lys Thr Val Tyr Leu Gln Met Ile Ser Leu Lys Pro Glu Asp Thr Ala
225             230             235             240

Ala Tyr Tyr Cys Ala Ala Gly Ala Asp Cys Ser Gly Tyr Leu Arg Asp
            245             250             255

Tyr Glu Phe Arg Gly Gln Gly Thr Gln Val Thr Val Ser Ser Gly Gly
            260             265             270

Gly Gly Ser Gln Val Gln Leu Val Glu Ser Gly Gly Gly Leu Val Gln
            275             280             285

Pro Gly Gly Ser Leu Arg Leu Ser Cys Glu Ala Ser Gly Phe Thr Leu
            290             295             300

Asp Tyr Tyr Ala Ile Gly Trp Phe Arg Gln Ala Pro Gly Lys Glu Arg
305             310             315             320

Glu Gly Val Ile Cys Ile Ser Arg Ser Asp Gly Ser Thr Tyr Tyr Ala
            325             330             335

Asp Ser Val Lys Gly Arg Phe Thr Ile Ser Arg Asp Asn Ala Lys Lys
            340             345             350

Thr Val Tyr Leu Gln Met Ile Ser Leu Lys Pro Glu Asp Thr Ala Ala
            355             360             365

Tyr Tyr Cys Ala Ala Gly Ala Asp Cys Ser Gly Tyr Leu Arg Asp Tyr
            370             375             380

Glu Phe Arg Gly Gln Gly Thr Gln Val Thr Val Ser Ser Thr Ser Thr
385             390             395             400

Thr Thr Pro Ala Pro Arg Pro Thr Pro Ala Pro Thr Ile Ala Ser
                405             410             415

Gln Pro Leu Ser Leu Arg Pro Glu Ala Cys Arg Pro Ala Ala Gly Gly
            420             425             430

Ala Val His Thr Arg Gly Leu Asp Phe Ala Cys Asp Ile Tyr Ile Trp
            435             440             445

Ala Pro Leu Ala Gly Thr Cys Gly Val Leu Leu Leu Ser Leu Val Ile
            450             455             460

Thr Leu Tyr Cys Lys Arg Gly Arg Lys Lys Leu Leu Tyr Ile Phe Lys
465             470             475             480

Gln Pro Phe Met Arg Pro Val Gln Thr Thr Gln Glu Glu Asp Gly Cys
            485             490             495

Ser Cys Arg Phe Pro Glu Glu Glu Glu Gly Gly Cys Glu Leu Arg Val
            500             505             510

Lys Phe Ser Arg Ser Ala Asp Ala Pro Ala Tyr Gln Gln Gly Gln Asn
            515             520             525
```

```
Gln Leu Tyr Asn Glu Leu Asn Leu Gly Arg Arg Glu Tyr Asp Val
        530                 535                 540

Leu Asp Lys Arg Arg Gly Arg Asp Pro Glu Met Gly Gly Lys Pro Arg
545                 550                 555                 560

Arg Lys Asn Pro Gln Glu Gly Leu Tyr Asn Glu Leu Gln Lys Asp Lys
                565                 570                 575

Met Ala Glu Ala Tyr Ser Glu Ile Gly Met Lys Gly Glu Arg Arg Arg
            580                 585                 590

Gly Lys Gly His Asp Gly Leu Tyr Gln Gly Leu Ser Thr Ala Thr Lys
        595                 600                 605

Asp Thr Tyr Asp Ala Leu His Met Gln Ala Leu Pro Pro Arg
    610                 615                 620

<210> SEQ ID NO 300
<211> LENGTH: 488
<212> TYPE: PRT
<213> ORGANISM: Artificial Sequence
<220> FEATURE:
<223> OTHER INFORMATION: Synthetic Construct

<400> SEQUENCE: 300

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Arg Thr Phe Thr Met
                165                 170                 175

Gly Trp Phe Arg Gln Ala Pro Gly Lys Glu Arg Glu Phe Val Ala Ala
            180                 185                 190

Ile Ser Leu Ser Pro Thr Leu Ala Tyr Tyr Ala Glu Ser Val Lys Gly
        195                 200                 205

Arg Phe Thr Ile Ser Arg Asp Asn Ala Lys Asn Thr Val Val Leu Gln
    210                 215                 220

Met Asn Ser Leu Lys Pro Glu Asp Thr Ala Leu Tyr Tyr Cys Ala Ala
225                 230                 235                 240

Asp Arg Lys Ser Val Met Ser Ile Arg Pro Asp Tyr Trp Gly Gln Gly
                245                 250                 255

Thr Gln Val Thr Val Ser Ser Thr Ser Thr Thr Pro Ala Pro Arg
            260                 265                 270
```

-continued

```
Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
        370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 301
<211> LENGTH: 498
<212> TYPE: PRT
<213> ORGANISM: Artificial Sequence
<220> FEATURE:
<223> OTHER INFORMATION: Synthetic Construct

<400> SEQUENCE: 301

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
                100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140
```

Ser Gly Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
            165                 170                 175

Cys Ala Ala Ser Gly Arg Thr Phe Thr Met Gly Trp Phe Arg Gln Ala
            180                 185                 190

Pro Gly Lys Glu Arg Glu Phe Val Ala Ala Ile Ser Leu Ser Pro Thr
            195                 200                 205

Leu Ala Tyr Tyr Ala Glu Ser Val Lys Gly Arg Phe Thr Ile Ser Arg
210                 215                 220

Asp Asn Ala Lys Asn Thr Val Val Leu Gln Met Asn Ser Leu Lys Pro
225                 230                 235                 240

Glu Asp Thr Ala Leu Tyr Tyr Cys Ala Ala Asp Arg Lys Ser Val Met
            245                 250                 255

Ser Ile Arg Pro Asp Tyr Trp Gly Gln Gly Thr Gln Val Thr Val Ser
            260                 265                 270

Ser Thr Ser Thr Thr Thr Pro Ala Pro Arg Pro Pro Thr Pro Ala Pro
            275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
            325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
            355                 360                 365

Glu Asp Gly Cys Ser Cys Arg Phe Pro Glu Glu Glu Glu Gly Gly Cys
370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
            405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
            450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
            485                 490                 495

Pro Arg

<210> SEQ ID NO 302
<211> LENGTH: 508
<212> TYPE: PRT
<213> ORGANISM: Artificial Sequence
<220> FEATURE:
<223> OTHER INFORMATION: Synthetic Construct

<400> SEQUENCE: 302

-continued

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Ala Ala Ser Gly Arg
            180                 185                 190

Thr Phe Thr Met Gly Trp Phe Arg Gln Ala Pro Gly Lys Glu Arg Glu
        195                 200                 205

Phe Val Ala Ala Ile Ser Leu Ser Pro Thr Leu Ala Tyr Tyr Ala Glu
    210                 215                 220

Ser Val Lys Gly Arg Phe Thr Ile Ser Arg Asp Asn Ala Lys Asn Thr
225                 230                 235                 240

Val Val Leu Gln Met Asn Ser Leu Lys Pro Glu Asp Thr Ala Leu Tyr
                245                 250                 255

Tyr Cys Ala Ala Asp Arg Lys Ser Val Met Ser Ile Arg Pro Asp Tyr
            260                 265                 270

Trp Gly Gln Gly Thr Gln Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
```

```
                420             425             430
Lys Arg Arg Gly Arg Asp Pro Glu Met Gly Gly Lys Pro Arg Arg Lys
            435                 440                 445

Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
                500                 505

<210> SEQ ID NO 303
<211> LENGTH: 493
<212> TYPE: PRT
<213> ORGANISM: Artificial Sequence
<220> FEATURE:
<223> OTHER INFORMATION: Synthetic Construct

<400> SEQUENCE: 303

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gln Val Lys Leu Glu Glu Ser Gly Gly Gly Leu
145                 150                 155                 160

Val Gln Ala Gly Arg Ser Leu Arg Leu Ser Cys Ala Ala Ser Glu His
                165                 170                 175

Thr Phe Ser Ser His Val Met Gly Trp Phe Arg Gln Ala Pro Gly Lys
            180                 185                 190

Glu Arg Glu Ser Val Ala Val Ile Gly Trp Arg Asp Ile Ser Thr Ser
        195                 200                 205

Tyr Ala Asp Ser Val Lys Gly Arg Phe Thr Ile Ser Arg Asp Asn Ala
    210                 215                 220

Lys Lys Thr Leu Tyr Leu Gln Met Asn Ser Leu Lys Pro Glu Asp Thr
225                 230                 235                 240

Ala Val Tyr Tyr Cys Ala Ala Arg Arg Ile Asp Ala Ala Asp Phe Asp
                245                 250                 255

Ser Trp Gly Gln Gly Thr Gln Val Thr Val Ser Ser Thr Ser Thr Thr
            260                 265                 270

Thr Pro Ala Pro Arg Pro Pro Thr Pro Ala Pro Thr Ile Ala Ser Gln
```

-continued

```
                275                 280                 285
Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 304
<211> LENGTH: 498
<212> TYPE: PRT
<213> ORGANISM: Artificial Sequence
<220> FEATURE:
<223> OTHER INFORMATION: Synthetic Construct

<400> SEQUENCE: 304

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gly Gly Gly Gly Ser Gln Val Lys Leu Glu Glu
```

```
            145                 150                 155                 160
        Ser Gly Gly Gly Leu Val Gln Ala Gly Arg Ser Leu Arg Leu Ser Cys
                        165                 170                 175

Ala Ala Ser Glu His Thr Phe Ser Ser His Val Met Gly Trp Phe Arg
                        180                 185                 190

Gln Ala Pro Gly Lys Glu Arg Glu Ser Val Ala Val Ile Gly Trp Arg
                        195                 200                 205

Asp Ile Ser Thr Ser Tyr Ala Asp Ser Val Lys Gly Arg Phe Thr Ile
                        210                 215                 220

Ser Arg Asp Asn Ala Lys Lys Thr Leu Tyr Leu Gln Met Asn Ser Leu
        225                 230                 235                 240

Lys Pro Glu Asp Thr Ala Val Tyr Tyr Cys Ala Ala Arg Arg Ile Asp
                        245                 250                 255

Ala Ala Asp Phe Asp Ser Trp Gly Gln Gly Thr Gln Val Thr Val Ser
                        260                 265                 270

Ser Thr Ser Thr Thr Thr Pro Ala Pro Arg Pro Pro Thr Pro Ala Pro
                        275                 280                 285

Thr Ile Ala Ser Gln Pro Leu Ser Leu Arg Pro Glu Ala Cys Arg Pro
                        290                 295                 300

Ala Ala Gly Gly Ala Val His Thr Arg Gly Leu Asp Phe Ala Cys Asp
        305                 310                 315                 320

Ile Tyr Ile Trp Ala Pro Leu Ala Gly Thr Cys Gly Val Leu Leu Leu
                        325                 330                 335

Ser Leu Val Ile Thr Leu Tyr Cys Lys Arg Gly Arg Lys Lys Leu Leu
                        340                 345                 350

Tyr Ile Phe Lys Gln Pro Phe Met Arg Pro Val Gln Thr Thr Gln Glu
                        355                 360                 365

Glu Asp Gly Cys Ser Cys Arg Phe Pro Glu Glu Glu Glu Gly Gly Cys
                        370                 375                 380

Glu Leu Arg Val Lys Phe Ser Arg Ser Ala Asp Ala Pro Ala Tyr Gln
        385                 390                 395                 400

Gln Gly Gln Asn Gln Leu Tyr Asn Glu Leu Asn Leu Gly Arg Arg Glu
                        405                 410                 415

Glu Tyr Asp Val Leu Asp Lys Arg Arg Gly Arg Asp Pro Glu Met Gly
                        420                 425                 430

Gly Lys Pro Arg Arg Lys Asn Pro Gln Glu Gly Leu Tyr Asn Glu Leu
                        435                 440                 445

Gln Lys Asp Lys Met Ala Glu Ala Tyr Ser Glu Ile Gly Met Lys Gly
                        450                 455                 460

Glu Arg Arg Arg Gly Lys Gly His Asp Gly Leu Tyr Gln Gly Leu Ser
        465                 470                 475                 480

Thr Ala Thr Lys Asp Thr Tyr Asp Ala Leu His Met Gln Ala Leu Pro
                        485                 490                 495

Pro Arg

<210> SEQ ID NO 305
<211> LENGTH: 503
<212> TYPE: PRT
<213> ORGANISM: Artificial Sequence
<220> FEATURE:
<223> OTHER INFORMATION: Synthetic Construct

<400> SEQUENCE: 305

Met Ala Leu Pro Val Thr Ala Leu Leu Leu Pro Leu Ala Leu Leu Leu
1               5                   10                  15
```

-continued

```
His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
 50                  55                  60

Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                    85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
130                 135                 140

Gly Gly Gly Gly Ser Gly Gly Gly Ser Gly Gly Gly Gly Ser Gln
145                 150                 155                 160

Val Lys Leu Glu Glu Ser Gly Gly Leu Val Gln Ala Gly Arg Ser
                165                 170                 175

Leu Arg Leu Ser Cys Ala Ala Ser Glu His Thr Phe Ser Ser His Val
            180                 185                 190

Met Gly Trp Phe Arg Gln Ala Pro Gly Lys Glu Arg Glu Ser Val Ala
        195                 200                 205

Val Ile Gly Trp Arg Asp Ile Ser Thr Ser Tyr Ala Asp Ser Val Lys
    210                 215                 220

Gly Arg Phe Thr Ile Ser Arg Asp Asn Ala Lys Lys Thr Leu Tyr Leu
225                 230                 235                 240

Gln Met Asn Ser Leu Lys Pro Glu Asp Thr Ala Val Tyr Tyr Cys Ala
                245                 250                 255

Ala Arg Arg Ile Asp Ala Ala Asp Phe Asp Ser Trp Gly Gln Gly Thr
            260                 265                 270

Gln Val Thr Val Ser Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430
```

```
Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
                500

<210> SEQ ID NO 306
<211> LENGTH: 489
<212> TYPE: PRT
<213> ORGANISM: Artificial Sequence
<220> FEATURE:
<223> OTHER INFORMATION: Synthetic Construct

<400> SEQUENCE: 306

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Ala Val Gln Leu Val Glu Ser Gly Gly Gly Leu Val Gln Ala Gly
145                 150                 155                 160

Asp Ser Leu Arg Leu Thr Cys Thr Ala Ser Gly Arg Ala Phe Ser Thr
                165                 170                 175

Tyr Phe Met Ala Trp Phe Arg Gln Ala Pro Gly Lys Glu Arg Glu Phe
            180                 185                 190

Val Ala Gly Ile Ala Trp Ser Gly Gly Ser Thr Ala Tyr Ala Asp Ser
        195                 200                 205

Val Lys Gly Arg Phe Thr Ile Ser Arg Asp Asn Ala Lys Asn Thr Val
    210                 215                 220

Tyr Leu Gln Met Asn Ser Leu Lys Ser Glu Asp Thr Ala Val Tyr Tyr
225                 230                 235                 240

Cys Ala Ser Arg Gly Ile Glu Val Glu Glu Phe Gly Ala Trp Gly Gln
                245                 250                 255

Gly Thr Gln Val Thr Val Ser Ser Thr Thr Thr Pro Ala Pro
            260                 265                 270

Arg Pro Pro Thr Pro Ala Pro Thr Ile Ala Ser Gln Pro Leu Ser Leu
        275                 280                 285
```

```
Arg Pro Glu Ala Cys Arg Pro Ala Ala Gly Gly Ala Val His Thr Arg
    290                 295                 300
Gly Leu Asp Phe Ala Cys Asp Ile Tyr Ile Trp Ala Pro Leu Ala Gly
305                 310                 315                 320
Thr Cys Gly Val Leu Leu Leu Ser Leu Val Ile Thr Leu Tyr Cys Lys
                325                 330                 335
Arg Gly Arg Lys Lys Leu Leu Tyr Ile Phe Lys Gln Pro Phe Met Arg
                340                 345                 350
Pro Val Gln Thr Thr Gln Glu Glu Asp Gly Cys Ser Cys Arg Phe Pro
                355                 360                 365
Glu Glu Glu Glu Gly Gly Cys Glu Leu Arg Val Lys Phe Ser Arg Ser
370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
                420                 425                 430
Glu Gly Leu Tyr Asn Glu Leu Gln Lys Asp Lys Met Ala Glu Ala Tyr
                435                 440                 445
Ser Glu Ile Gly Met Lys Gly Glu Arg Arg Arg Gly Lys Gly His Asp
450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 307
<211> LENGTH: 499
<212> TYPE: PRT
<213> ORGANISM: Artificial Sequence
<220> FEATURE:
<223> OTHER INFORMATION: Synthetic Construct

<400> SEQUENCE: 307

Met Ala Leu Pro Val Thr Ala Leu Leu Leu Pro Leu Ala Leu Leu Leu
1               5                   10                  15
His Ala Ala Arg Pro Gln Val Lys Leu Glu Glu Ser Gly Gly Gly Leu
                20                  25                  30
Val Gln Ala Gly Arg Ser Leu Arg Leu Ser Cys Ala Ala Ser Glu His
            35                  40                  45
Thr Phe Ser Ser His Val Met Gly Trp Phe Arg Gln Ala Pro Gly Lys
        50                  55                  60
Glu Arg Glu Ser Val Ala Val Ile Gly Trp Arg Asp Ile Ser Thr Ser
65                  70                  75                  80
Tyr Ala Asp Ser Val Lys Gly Arg Phe Thr Ile Ser Arg Asp Asn Ala
                85                  90                  95
Lys Lys Thr Leu Tyr Leu Gln Met Asn Ser Leu Lys Pro Glu Asp Thr
                100                 105                 110
Ala Val Tyr Tyr Cys Ala Ala Arg Arg Ile Asp Ala Ala Asp Phe Asp
                115                 120                 125
Ser Trp Gly Gln Gly Thr Gln Val Thr Val Ser Ser Gly Gly Gly Gly
            130                 135                 140
Ser Gly Gly Gly Gly Ser Gly Gly Gly Gly Ser Ala Val Gln Leu Val
145                 150                 155                 160
```

```
Glu Ser Gly Gly Gly Leu Val Gln Ala Gly Asp Ser Leu Arg Leu Thr
            165                 170                 175

Cys Thr Ala Ser Gly Arg Ala Phe Ser Thr Tyr Phe Met Ala Trp Phe
        180                 185                 190

Arg Gln Ala Pro Gly Lys Glu Arg Glu Phe Val Ala Gly Ile Ala Trp
    195                 200                 205

Ser Gly Gly Ser Thr Ala Tyr Ala Asp Ser Val Lys Gly Arg Phe Thr
210                 215                 220

Ile Ser Arg Asp Asn Ala Lys Asn Thr Val Tyr Leu Gln Met Asn Ser
225                 230                 235                 240

Leu Lys Ser Glu Asp Thr Ala Val Tyr Tyr Cys Ala Ser Arg Gly Ile
                245                 250                 255

Glu Val Glu Glu Phe Gly Ala Trp Gly Gln Gly Thr Gln Val Thr Val
            260                 265                 270

Ser Ser Thr Ser Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 308
<211> LENGTH: 509
<212> TYPE: PRT
<213> ORGANISM: Artificial Sequence
<220> FEATURE:
<223> OTHER INFORMATION: Synthetic Construct

<400> SEQUENCE: 308

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
```

```
                20                  25                  30
Val Gln Ala Gly Arg Ser Leu Arg Leu Ser Cys Ala Ala Ser Glu His
            35                  40                  45
Thr Phe Ser Ser His Val Met Gly Trp Phe Arg Gln Ala Pro Gly Lys
        50                  55                  60
Glu Arg Glu Ser Val Ala Val Ile Gly Trp Arg Asp Ile Ser Thr Ser
65                  70                  75                  80
Tyr Ala Asp Ser Val Lys Gly Arg Phe Thr Ile Ser Arg Asp Asn Ala
                85                  90                  95
Lys Lys Thr Leu Tyr Leu Gln Met Asn Ser Leu Lys Pro Glu Asp Thr
            100                 105                 110
Ala Val Tyr Tyr Cys Ala Ala Arg Ile Asp Ala Ala Asp Phe Asp
        115                 120                 125
Ser Trp Gly Gln Gly Thr Gln Val Thr Val Ser Gly Gly Gly Gly
    130                 135                 140
Ser Gly Gly Gly Gly Ser Gly Gly Gly Ser Gly Gly Gly Gly Ser
145                 150                 155                 160
Gly Gly Gly Gly Ser Ala Val Gln Leu Val Glu Ser Gly Gly Leu
                165                 170                 175
Val Gln Ala Gly Asp Ser Leu Arg Leu Thr Cys Thr Ala Ser Gly Arg
            180                 185                 190
Ala Phe Ser Thr Tyr Phe Met Ala Trp Phe Arg Gln Ala Pro Gly Lys
        195                 200                 205
Glu Arg Glu Phe Val Ala Gly Ile Ala Trp Ser Gly Gly Ser Thr Ala
    210                 215                 220
Tyr Ala Asp Ser Val Lys Gly Arg Phe Thr Ile Ser Arg Asp Asn Ala
225                 230                 235                 240
Lys Asn Thr Val Tyr Leu Gln Met Asn Ser Leu Lys Ser Glu Asp Thr
                245                 250                 255
Ala Val Tyr Tyr Cys Ala Ser Arg Gly Ile Glu Val Glu Glu Phe Gly
            260                 265                 270
Ala Trp Gly Gln Gly Thr Gln Val Thr Val Ser Ser Thr Ser Thr Thr
        275                 280                 285
Thr Pro Ala Pro Arg Pro Pro Thr Pro Ala Pro Thr Ile Ala Ser Gln
    290                 295                 300
Pro Leu Ser Leu Arg Pro Glu Ala Cys Arg Pro Ala Ala Gly Gly Ala
305                 310                 315                 320
Val His Thr Arg Gly Leu Asp Phe Ala Cys Asp Ile Tyr Ile Trp Ala
                325                 330                 335
Pro Leu Ala Gly Thr Cys Gly Val Leu Leu Leu Ser Leu Val Ile Thr
            340                 345                 350
Leu Tyr Cys Lys Arg Gly Arg Lys Lys Leu Leu Tyr Ile Phe Lys Gln
        355                 360                 365
Pro Phe Met Arg Pro Val Gln Thr Thr Gln Glu Glu Asp Gly Cys Ser
    370                 375                 380
Cys Arg Phe Pro Glu Glu Glu Glu Gly Gly Cys Glu Leu Arg Val Lys
385                 390                 395                 400
Phe Ser Arg Ser Ala Asp Ala Pro Ala Tyr Gln Gln Gly Gln Asn Gln
                405                 410                 415
Leu Tyr Asn Glu Leu Asn Leu Gly Arg Arg Glu Glu Tyr Asp Val Leu
            420                 425                 430
Asp Lys Arg Arg Gly Arg Asp Pro Glu Met Gly Gly Lys Pro Arg Arg
        435                 440                 445
```

```
Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 309
<211> LENGTH: 494
<212> TYPE: PRT
<213> ORGANISM: Artificial Sequence
<220> FEATURE:
<223> OTHER INFORMATION: Synthetic Construct

<400> SEQUENCE: 309

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
                20                  25                  30

Val Gln Ala Gly Asp Ser Leu Arg Leu Thr Cys Thr Ala Ser Gly Arg
            35                  40                  45

Ala Phe Ser Thr Tyr Phe Met Ala Trp Phe Arg Gln Ala Pro Gly Lys
        50                  55                  60

Glu Arg Glu Phe Val Ala Gly Ile Ala Trp Ser Gly Gly Ser Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Ser Glu Asp Thr
            100                 105                 110

Ala Val Tyr Tyr Cys Ala Ser Arg Gly Ile Glu Val Glu Glu Phe Gly
        115                 120                 125

Ala Trp Gly Gln Gly Thr Gln Val Thr Val Ser Ser Gly Gly Gly Gly
    130                 135                 140

Ser Gly Gly Gly Gly Ser Gln Val Lys Leu Glu Glu Ser Gly Gly Gly
145                 150                 155                 160

Leu Val Gln Ala Gly Arg Ser Leu Arg Leu Ser Cys Ala Ala Ser Glu
                165                 170                 175

His Thr Phe Ser Ser His Val Met Gly Trp Phe Arg Gln Ala Pro Gly
            180                 185                 190

Lys Glu Arg Glu Ser Val Ala Val Ile Gly Trp Arg Asp Ile Ser Thr
        195                 200                 205

Ser Tyr Ala Asp Ser Val Lys Gly Arg Phe Thr Ile Ser Arg Asp Asn
    210                 215                 220

Ala Lys Lys Thr Leu Tyr Leu Gln Met Asn Ser Leu Lys Pro Glu Asp
225                 230                 235                 240

Thr Ala Val Tyr Tyr Cys Ala Ala Arg Arg Ile Asp Ala Ala Asp Phe
                245                 250                 255

Asp Ser Trp Gly Gln Gly Thr Gln Val Thr Val Ser Ser Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
            325                 330                 335

Thr Leu Tyr Cys Lys Arg Gly Arg Lys Leu Leu Tyr Ile Phe Lys
        340                 345                 350

Gln Pro Phe Met Arg Pro Val Gln Thr Thr Gln Glu Glu Asp Gly Cys
    355                 360                 365

Ser Cys Arg Phe Pro Glu Glu Glu Gly Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
            450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 310
<211> LENGTH: 499
<212> TYPE: PRT
<213> ORGANISM: Artificial Sequence
<220> FEATURE:
<223> OTHER INFORMATION: Synthetic Construct

<400> SEQUENCE: 310

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Ala Gly Asp Ser Leu Arg Leu Thr Cys Thr Ala Ser Gly Arg
        35                  40                  45

Ala Phe Ser Thr Tyr Phe Met Ala Trp Phe Arg Gln Ala Pro Gly Lys
    50                  55                  60

Glu Arg Glu Phe Val Ala Gly Ile Ala Trp Ser Gly Gly Ser Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Ser Glu Asp Thr
            100                 105                 110

Ala Val Tyr Tyr Cys Ala Ser Arg Gly Ile Glu Val Glu Glu Phe Gly
        115                 120                 125

Ala Trp Gly Gln Gly Thr Gln Val Thr Val Ser Ser Gly Gly Gly Gly
    130                 135                 140

Ser Gly Gly Gly Gly Ser Gly Gly Gly Ser Gln Val Lys Leu Glu
145                 150                 155                 160

Glu Ser Gly Gly Gly Leu Val Gln Ala Gly Arg Ser Leu Arg Leu Ser
                165                 170                 175
```

Cys Ala Ala Ser Glu His Thr Phe Ser Ser His Val Met Gly Trp Phe
            180                 185                 190

Arg Gln Ala Pro Gly Lys Glu Arg Glu Ser Val Ala Val Ile Gly Trp
        195                 200                 205

Arg Asp Ile Ser Thr Ser Tyr Ala Asp Ser Val Lys Gly Arg Phe Thr
210                 215                 220

Ile Ser Arg Asp Asn Ala Lys Lys Thr Leu Tyr Leu Gln Met Asn Ser
225                 230                 235                 240

Leu Lys Pro Glu Asp Thr Ala Val Tyr Tyr Cys Ala Ala Arg Ile
                245                 250                 255

Asp Ala Ala Asp Phe Asp Ser Trp Gly Gln Gly Thr Gln Val Thr Val
                260                 265                 270

Ser Ser Thr Ser Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
                355                 360                 365

Glu Glu Asp Gly Cys Ser Cys Arg Phe Pro Glu Glu Glu Gly Gly
        370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
                420                 425                 430

Gly Gly Lys Pro Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 311
<211> LENGTH: 504
<212> TYPE: PRT
<213> ORGANISM: Artificial Sequence
<220> FEATURE:
<223> OTHER INFORMATION: Synthetic Construct

<400> SEQUENCE: 311

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

-continued

Val Gln Ala Gly Asp Ser Leu Arg Leu Thr Cys Thr Ala Ser Gly Arg
                35                  40                  45

Ala Phe Ser Thr Tyr Phe Met Ala Trp Phe Arg Gln Ala Pro Gly Lys
 50                  55                  60

Glu Arg Glu Phe Val Ala Gly Ile Ala Trp Ser Gly Ser Thr Ala
 65                  70                  75                  80

Tyr Ala Asp Ser Val Lys Gly Arg Phe Thr Ile Ser Arg Asp Asn Ala
                 85                  90                  95

Lys Asn Thr Val Tyr Leu Gln Met Asn Ser Leu Lys Ser Glu Asp Thr
                100                 105                 110

Ala Val Tyr Tyr Cys Ala Ser Arg Gly Ile Glu Val Glu Glu Phe Gly
                115                 120                 125

Ala Trp Gly Gln Gly Thr Gln Val Thr Val Ser Ser Gly Gly Gly Gly
130                 135                 140

Ser Gly Gly Gly Gly Ser Gly Gly Gly Gly Ser Gly Gly Gly Gly Ser
145                 150                 155                 160

Gln Val Lys Leu Glu Glu Ser Gly Gly Leu Val Gln Ala Gly Arg
                165                 170                 175

Ser Leu Arg Leu Ser Cys Ala Ala Ser Glu His Thr Phe Ser Ser His
                180                 185                 190

Val Met Gly Trp Phe Arg Gln Ala Pro Gly Lys Glu Arg Glu Ser Val
                195                 200                 205

Ala Val Ile Gly Trp Arg Asp Ile Ser Thr Ser Tyr Ala Asp Ser Val
                210                 215                 220

Lys Gly Arg Phe Thr Ile Ser Arg Asp Asn Ala Lys Lys Thr Leu Tyr
225                 230                 235                 240

Leu Gln Met Asn Ser Leu Lys Pro Glu Asp Thr Ala Val Tyr Tyr Cys
                245                 250                 255

Ala Ala Arg Arg Ile Asp Ala Ala Asp Phe Asp Ser Trp Gly Gln Gly
                260                 265                 270

Thr Gln Val Thr Val Ser Ser Thr Thr Thr Pro Ala Pro Arg
                275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
                340                 345                 350

Gly Arg Lys Lys Leu Leu Tyr Ile Phe Lys Gln Pro Phe Met Arg Pro
                355                 360                 365

Val Gln Thr Thr Gln Glu Glu Asp Gly Cys Ser Cys Arg Phe Pro Glu
                370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
                420                 425                 430

Arg Asp Pro Glu Met Gly Gly Lys Pro Arg Arg Lys Asn Pro Gln Glu
                435                 440                 445

Gly Leu Tyr Asn Glu Leu Gln Lys Asp Lys Met Ala Glu Ala Tyr Ser

```
            450                 455                 460
Glu Ile Gly Met Lys Gly Glu Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 312
<211> LENGTH: 498
<212> TYPE: PRT
<213> ORGANISM: Artificial Sequence
<220> FEATURE:
<223> OTHER INFORMATION: Synthetic Construct

<400> SEQUENCE: 312

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Gly Gly Gly Gly
    130                 135                 140

Ser Gln Val Lys Leu Glu Glu Ser Gly Gly Arg Leu Val Gln Pro Arg
145                 150                 155                 160

Gly Ser Leu Arg Leu Ser Cys Ala Gly Ser Gly Arg Thr Phe Ser Thr
                165                 170                 175

Tyr Gly Met Ala Trp Phe Arg Gln Ala Pro Gly Lys Glu Arg Glu Phe
            180                 185                 190

Val Ala Ser Lys Ala Ser Met Asn Tyr Ser Gly Arg Thr Tyr Tyr Ala
        195                 200                 205

Asp Ser Val Lys Gly Arg Phe Thr Ile Ala Arg Asp Asn Ala Lys Asn
    210                 215                 220

Met Val Phe Leu Gln Met Asn Asn Leu Lys Pro Glu Asp Thr Ala Val
225                 230                 235                 240

Tyr Tyr Cys Ala Ala Gly Thr Gly Cys Ser Thr Tyr Gly Cys Phe Asp
                245                 250                 255

Ala Gln Ile Ile Asp Tyr Trp Gly Lys Gly Thr Leu Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
```

-continued

```
305                 310                 315                 320
Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
                340                 345                 350

Tyr Ile Phe Lys Gln Pro Phe Met Arg Pro Val Gln Thr Thr Gln Glu
                355                 360                 365

Glu Asp Gly Cys Ser Cys Arg Phe Pro Glu Glu Glu Gly Gly Cys
370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
                420                 425                 430

Gly Lys Pro Arg Arg Lys Asn Pro Gln Glu Gly Leu Tyr Asn Glu Leu
                435                 440                 445

Gln Lys Asp Lys Met Ala Glu Ala Tyr Ser Glu Ile Gly Met Lys Gly
                450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 313
<211> LENGTH: 508
<212> TYPE: PRT
<213> ORGANISM: Artificial Sequence
<220> FEATURE:
<223> OTHER INFORMATION: Synthetic Construct

<400> SEQUENCE: 313

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
                20                  25                  30

Val Gln Ala Gly Asp Ser Leu Arg Leu Ser Cys Val Gln Ser Thr Tyr
                35                  40                  45

Thr Val Asn Ser Asp Val Met Gly Trp Phe Arg Gln Ala Pro Gly Lys
                50                  55                  60

Glu Arg Glu Phe Val Gly Ala Ile Met Trp Asn Asp Gly Ile Thr Tyr
65              70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
                100                 105                 110

Ala Val Tyr Tyr Cys Ala Ala Ser Lys Gly Arg Tyr Ser Glu Tyr Glu
                115                 120                 125

Tyr Trp Gly Gln Gly Thr Gln Val Thr Val Ser Ser Gly Gly Gly Gly
                130                 135                 140

Ser Gly Gly Gly Gly Ser Gly Gly Gly Ser Gln Val Lys Leu Glu
145             150                 155                 160

Glu Ser Gly Gly Arg Leu Val Gln Pro Arg Gly Ser Leu Arg Leu Ser
                165                 170                 175
```

```
Cys Ala Gly Ser Gly Arg Thr Phe Ser Thr Tyr Gly Met Ala Trp Phe
            180                 185                 190

Arg Gln Ala Pro Gly Lys Glu Arg Glu Phe Val Ala Ser Lys Ala Ser
        195                 200                 205

Met Asn Tyr Ser Gly Arg Thr Tyr Tyr Ala Asp Ser Val Lys Gly Arg
    210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
                245                 250                 255

Thr Gly Cys Ser Thr Tyr Gly Cys Phe Asp Ala Gln Ile Ile Asp Tyr
            260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 314
<211> LENGTH: 518
<212> TYPE: PRT
<213> ORGANISM: Artificial Sequence
<220> FEATURE:
<223> OTHER INFORMATION: Synthetic Construct

<400> SEQUENCE: 314

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30
```

```
Val Gln Ala Gly Asp Ser Leu Arg Leu Ser Cys Val Gln Ser Thr Tyr
        35                  40                  45
Thr Val Asn Ser Asp Val Met Gly Trp Phe Arg Gln Ala Pro Gly Lys
 50                  55                  60
Glu Arg Glu Phe Val Gly Ala Ile Met Trp Asn Asp Gly Ile Thr Tyr
 65                  70                  75                  80
Leu Gln Asp Ser Val Lys Gly Arg Phe Thr Ile Phe Arg Asp Asn Ala
                 85                  90                  95
Lys Asn Thr Val Tyr Leu Gln Met Asn Ser Leu Lys Leu Glu Asp Thr
                100                 105                 110
Ala Val Tyr Tyr Cys Ala Ala Ser Lys Gly Arg Tyr Ser Glu Tyr Glu
            115                 120                 125
Tyr Trp Gly Gln Gly Thr Gln Val Thr Val Ser Ser Gly Gly Gly Gly
    130                 135                 140
Ser Gly Gly Gly Gly Ser Gly Gly Gly Ser Gly Gly Gly Gly Ser
145                 150                 155                 160
Gly Gly Gly Gly Ser Gln Val Lys Leu Glu Glu Ser Gly Gly Arg Leu
                165                 170                 175
Val Gln Pro Arg Gly Ser Leu Arg Leu Ser Cys Ala Gly Ser Gly Arg
            180                 185                 190
Thr Phe Ser Thr Tyr Gly Met Ala Trp Phe Arg Gln Ala Pro Gly Lys
        195                 200                 205
Glu Arg Glu Phe Val Ala Ser Lys Ala Ser Met Asn Tyr Ser Gly Arg
        210                 215                 220
Thr Tyr Tyr Ala Asp Ser Val Lys Gly Arg Phe Thr Ile Ala Arg Asp
225                 230                 235                 240
Asn Ala Lys Asn Met Val Phe Leu Gln Met Asn Asn Leu Lys Pro Glu
                245                 250                 255
Asp Thr Ala Val Tyr Tyr Cys Ala Ala Gly Thr Gly Cys Ser Thr Tyr
            260                 265                 270
Gly Cys Phe Asp Ala Gln Ile Ile Asp Tyr Trp Gly Lys Gly Thr Leu
        275                 280                 285
Val Thr Val Ser Ser Thr Ser Thr Thr Thr Pro Ala Pro Arg Pro Pro
        290                 295                 300
Thr Pro Ala Pro Thr Ile Ala Ser Gln Pro Leu Ser Leu Arg Pro Glu
305                 310                 315                 320
Ala Cys Arg Pro Ala Ala Gly Gly Ala Val His Thr Arg Gly Leu Asp
                325                 330                 335
Phe Ala Cys Asp Ile Tyr Ile Trp Ala Pro Leu Ala Gly Thr Cys Gly
            340                 345                 350
Val Leu Leu Leu Ser Leu Val Ile Thr Leu Tyr Cys Lys Arg Gly Arg
        355                 360                 365
Lys Lys Leu Leu Tyr Ile Phe Lys Gln Pro Phe Met Arg Pro Val Gln
        370                 375                 380
Thr Thr Gln Glu Glu Asp Gly Cys Ser Cys Arg Phe Pro Glu Glu Glu
385                 390                 395                 400
Glu Gly Gly Cys Glu Leu Arg Val Lys Phe Ser Arg Ser Ala Asp Ala
                405                 410                 415
Pro Ala Tyr Gln Gln Gly Gln Asn Gln Leu Tyr Asn Glu Leu Asn Leu
            420                 425                 430
Gly Arg Arg Glu Glu Tyr Asp Val Leu Asp Lys Arg Arg Gly Arg Asp
        435                 440                 445
```

```
Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
                485                 490                 495

Gln Gly Leu Ser Thr Ala Thr Lys Asp Thr Tyr Asp Ala Leu His Met
            500                 505                 510

Gln Ala Leu Pro Pro Arg
            515

<210> SEQ ID NO 315
<211> LENGTH: 503
<212> TYPE: PRT
<213> ORGANISM: Artificial Sequence
<220> FEATURE:
<223> OTHER INFORMATION: Synthetic Construct

<400> SEQUENCE: 315

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gln Val Lys Leu Glu Glu Ser Gly Gly Arg
145                 150                 155                 160

Leu Val Gln Pro Arg Gly Ser Leu Arg Leu Ser Cys Ala Gly Ser Gly
                165                 170                 175

Arg Thr Phe Ser Thr Tyr Gly Met Ala Trp Phe Arg Gln Ala Pro Gly
            180                 185                 190

Lys Glu Arg Glu Phe Val Ala Ser Lys Ala Ser Met Asn Tyr Ser Gly
        195                 200                 205

Arg Thr Tyr Tyr Ala Asp Ser Val Lys Gly Arg Phe Thr Ile Ala Arg
    210                 215                 220

Asp Asn Ala Lys Asn Met Val Phe Leu Gln Met Asn Asn Leu Lys Pro
225                 230                 235                 240

Glu Asp Thr Ala Val Tyr Tyr Cys Ala Ala Gly Thr Gly Cys Ser Thr
                245                 250                 255

Tyr Gly Cys Phe Asp Ala Gln Ile Ile Asp Tyr Trp Gly Lys Gly Thr
            260                 265                 270

Leu Val Thr Val Ser Ser Thr Thr Thr Pro Ala Pro Arg Pro
        275                 280                 285
```

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                    325                 330                 335

Gly Val Leu Leu Leu Ser Leu Val Ile Thr Leu Tyr Cys Lys Arg Gly
                340                 345                 350

Arg Lys Lys Leu Leu Tyr Ile Phe Lys Gln Pro Phe Met Arg Pro Val
            355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                    405                 410                 415

Leu Gly Arg Arg Glu Glu Tyr Asp Val Leu Asp Lys Arg Arg Gly Arg
                420                 425                 430

Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                    485                 490                 495

Met Gln Ala Leu Pro Pro Arg
            500

<210> SEQ ID NO 316
<211> LENGTH: 508
<212> TYPE: PRT
<213> ORGANISM: Artificial Sequence
<220> FEATURE:
<223> OTHER INFORMATION: Synthetic Construct

<400> SEQUENCE: 316

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Ser Gln Val Lys Leu Glu
145                 150                 155                 160

Glu Ser Gly Gly Arg Leu Val Gln Pro Arg Gly Ser Leu Arg Leu Ser
            165                 170                 175

Cys Ala Gly Ser Gly Arg Thr Phe Ser Thr Tyr Gly Met Ala Trp Phe
        180                 185                 190

Arg Gln Ala Pro Gly Lys Glu Arg Glu Phe Val Ala Ser Lys Ala Ser
        195                 200                 205

Met Asn Tyr Ser Gly Arg Thr Tyr Tyr Ala Asp Ser Val Lys Gly Arg
        210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
            245                 250                 255

Thr Gly Cys Ser Thr Tyr Gly Cys Phe Asp Ala Gln Ile Ile Asp Tyr
        260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
            325                 330                 335

Leu Ala Gly Thr Cys Gly Val Leu Leu Leu Ser Leu Val Ile Thr Leu
        340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
            405                 410                 415

Tyr Asn Glu Leu Asn Leu Gly Arg Arg Glu Glu Tyr Asp Val Leu Asp
        420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
            485                 490                 495

Tyr Asp Ala Leu His Met Gln Ala Leu Pro Pro Arg
        500                 505

<210> SEQ ID NO 317
<211> LENGTH: 513
<212> TYPE: PRT
<213> ORGANISM: Artificial Sequence
<220> FEATURE:
<223> OTHER INFORMATION: Synthetic Construct

<400> SEQUENCE: 317

-continued

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Ser Gly Gly Gly Ser Gly Gly Gly Ser
145                 150                 155                 160

Gln Val Lys Leu Glu Glu Ser Gly Gly Arg Leu Val Gln Pro Arg Gly
            165                 170                 175

Ser Leu Arg Leu Ser Cys Ala Gly Ser Gly Arg Thr Phe Ser Thr Tyr
        180                 185                 190

Gly Met Ala Trp Phe Arg Gln Ala Pro Gly Lys Glu Arg Glu Phe Val
    195                 200                 205

Ala Ser Lys Ala Ser Met Asn Tyr Ser Gly Arg Thr Tyr Tyr Ala Asp
    210                 215                 220

Ser Val Lys Gly Arg Phe Thr Ile Ala Arg Asp Asn Ala Lys Asn Met
225                 230                 235                 240

Val Phe Leu Gln Met Asn Asn Leu Lys Pro Glu Asp Thr Ala Val Tyr
                245                 250                 255

Tyr Cys Ala Ala Gly Thr Gly Cys Ser Thr Tyr Gly Cys Phe Asp Ala
        260                 265                 270

Gln Ile Ile Asp Tyr Trp Gly Lys Gly Thr Leu Val Thr Val Ser Ser
    275                 280                 285

Thr Ser Thr Thr Thr Pro Ala Pro Arg Pro Pro Thr Pro Ala Pro Thr
    290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Tyr Ile Trp Ala Pro Leu Ala Gly Thr Cys Gly Val Leu Leu Leu Ser
        340                 345                 350

Leu Val Ile Thr Leu Tyr Cys Lys Arg Gly Arg Lys Lys Leu Leu Tyr
    355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
```

```
                420                 425                 430
Tyr Asp Val Leu Asp Lys Arg Arg Gly Arg Asp Pro Glu Met Gly Gly
                435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
                500                 505                 510

Arg

<210> SEQ ID NO 318
<211> LENGTH: 500
<212> TYPE: PRT
<213> ORGANISM: Artificial Sequence
<220> FEATURE:
<223> OTHER INFORMATION: Synthetic Construct

<400> SEQUENCE: 318

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
                20                  25                  30

Val Gln Pro Arg Gly Ser Leu Arg Leu Ser Cys Ala Gly Ser Gly Arg
                35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
                100                 105                 110

Asp Thr Ala Val Tyr Tyr Cys Ala Ala Gly Thr Gly Cys Ser Thr Tyr
            115                 120                 125

Gly Cys Phe Asp Ala Gln Ile Ile Asp Tyr Trp Gly Lys Gly Thr Leu
        130                 135                 140

Val Thr Val Ser Ser Gly Gly Gly Ser Gln Val Lys Leu Glu Glu
145                 150                 155                 160

Ser Gly Gly Gly Leu Val Gln Ala Gly Ser Leu Arg Leu Ser Cys
                165                 170                 175

Ala Ala Ser Gly Gly Thr Leu Ser Lys Asn Thr Val Ala Trp Val Arg
            180                 185                 190

Gln Ala Pro Gly Lys Glu Arg Gly Phe Val Thr Ser Ile Thr Cys Asp
        195                 200                 205

Gly Arg Thr Thr Tyr Ala Asn Ser Val Asn Gly Arg Phe Pro Ile
        210                 215                 220

Asn Arg Asn Asn Ala Glu Asn Leu Val Val Leu Gln Met Asn Ser Leu
225                 230                 235                 240

Lys Pro Asp Asp Thr Ala Leu Tyr Tyr Cys Ala Ala Tyr Arg Lys Ser
                245                 250                 255

Ile Met Ser Ile Gln Pro Asp Tyr Trp Gly Gln Gly Thr Gln Val Thr
                260                 265                 270
```

-continued

```
Val Ser Ser Thr Ser Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
            500

<210> SEQ ID NO 319
<211> LENGTH: 510
<212> TYPE: PRT
<213> ORGANISM: Artificial Sequence
<220> FEATURE:
<223> OTHER INFORMATION: Synthetic Construct

<400> SEQUENCE: 319

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125
```

```
Gly Cys Phe Asp Ala Gln Ile Ile Asp Tyr Trp Gly Lys Gly Thr Leu
    130                 135                 140

Val Thr Val Ser Ser Gly Gly Gly Ser Gly Gly Gly Ser Gly
145                 150                 155                 160

Gly Gly Gly Ser Gln Val Lys Leu Glu Glu Ser Gly Gly Gly Leu Val
                165                 170                 175

Gln Ala Gly Gly Ser Leu Arg Leu Ser Cys Ala Ala Ser Gly Gly Thr
            180                 185                 190

Leu Ser Lys Asn Thr Val Ala Trp Val Arg Gln Ala Pro Gly Lys Glu
        195                 200                 205

Arg Gly Phe Val Thr Ser Ile Thr Cys Asp Gly Arg Thr Thr Tyr Tyr
    210                 215                 220

Ala Asn Ser Val Asn Gly Arg Phe Pro Ile Asn Arg Asn Asn Ala Glu
225                 230                 235                 240

Asn Leu Val Val Leu Gln Met Asn Ser Leu Lys Pro Asp Asp Thr Ala
                245                 250                 255

Leu Tyr Tyr Cys Ala Ala Tyr Arg Lys Ser Ile Met Ser Ile Gln Pro
            260                 265                 270

Asp Tyr Trp Gly Gln Gly Thr Gln Val Thr Val Ser Ser Thr Ser Thr
        275                 280                 285

Thr Thr Pro Ala Pro Arg Pro Pro Thr Pro Ala Pro Thr Ile Ala Ser
290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 320
<211> LENGTH: 520
<212> TYPE: PRT
<213> ORGANISM: Artificial Sequence
<220> FEATURE:
```

<223> OTHER INFORMATION: Synthetic Construct

<400> SEQUENCE: 320

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Ser Gly Gly Gly Gly Ser Gly
145                 150                 155                 160

Gly Gly Ser Gly Gly Gly Gly Ser Gly Gly Gly Gly Ser Gln Val
                165                 170                 175

Lys Leu Glu Glu Ser Gly Gly Gly Leu Val Gln Ala Gly Gly Ser Leu
            180                 185                 190

Arg Leu Ser Cys Ala Ala Ser Gly Gly Thr Leu Ser Lys Asn Thr Val
        195                 200                 205

Ala Trp Val Arg Gln Ala Pro Gly Lys Glu Arg Gly Phe Val Thr Ser
    210                 215                 220

Ile Thr Cys Asp Gly Arg Thr Thr Tyr Tyr Ala Asn Ser Val Asn Gly
225                 230                 235                 240

Arg Phe Pro Ile Asn Arg Asn Asn Ala Glu Asn Leu Val Val Leu Gln
                245                 250                 255

Met Asn Ser Leu Lys Pro Asp Asp Thr Ala Leu Tyr Tyr Cys Ala Ala
            260                 265                 270

Tyr Arg Lys Ser Ile Met Ser Ile Gln Pro Asp Tyr Trp Gly Gln Gly
        275                 280                 285

Thr Gln Val Thr Val Ser Ser Thr Thr Thr Pro Ala Pro Arg
    290                 295                 300

Pro Pro Thr Pro Ala Pro Thr Ile Ala Ser Gln Pro Leu Ser Leu Arg
305                 310                 315                 320

Pro Glu Ala Cys Arg Pro Ala Ala Gly Gly Ala Val His Thr Arg Gly
                325                 330                 335

Leu Asp Phe Ala Cys Asp Ile Tyr Ile Trp Ala Pro Leu Ala Gly Thr
            340                 345                 350

Cys Gly Val Leu Leu Leu Ser Leu Val Ile Thr Leu Tyr Cys Lys Arg
        355                 360                 365

Gly Arg Lys Lys Leu Leu Tyr Ile Phe Lys Gln Pro Phe Met Arg Pro
    370                 375                 380

Val Gln Thr Thr Gln Glu Glu Asp Gly Cys Ser Cys Arg Phe Pro Glu
385                 390                 395                 400
```

```
Glu Glu Glu Gly Gly Cys Glu Leu Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly
        435                 440                 445

Arg Asp Pro Glu Met Gly Gly Lys Pro Arg Arg Lys Asn Pro Gln Glu
    450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
                500                 505                 510

His Met Gln Ala Leu Pro Pro Arg
                515                 520

<210> SEQ ID NO 321
<211> LENGTH: 505
<212> TYPE: PRT
<213> ORGANISM: Artificial Sequence
<220> FEATURE:
<223> OTHER INFORMATION: Synthetic Construct

<400> SEQUENCE: 321

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
                20                  25                  30

Val Gln Pro Arg Gly Ser Leu Arg Leu Ser Cys Ala Gly Ser Gly Arg
            35                  40                  45

Thr Phe Ser Thr Tyr Gly Met Ala Trp Phe Arg Gln Ala Pro Gly Lys
        50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gly Gly Gly Gly Ser Gln
145                 150                 155                 160

Val Lys Leu Glu Glu Ser Gly Gly Gly Leu Val Gln Ala Gly Gly Ser
                165                 170                 175

Leu Arg Leu Ser Cys Ala Ala Ser Gly Gly Thr Leu Ser Lys Asn Thr
            180                 185                 190

Val Ala Trp Val Arg Gln Ala Pro Gly Lys Glu Arg Gly Phe Val Thr
        195                 200                 205

Ser Ile Thr Cys Asp Gly Arg Thr Thr Tyr Tyr Ala Asn Ser Val Asn
    210                 215                 220

Gly Arg Phe Pro Ile Asn Arg Asn Asn Ala Glu Asn Leu Val Val Leu
225                 230                 235                 240
```

```
Gln Met Asn Ser Leu Lys Pro Asp Asp Thr Ala Leu Tyr Tyr Cys Ala
            245                 250                 255

Ala Tyr Arg Lys Ser Ile Met Ser Ile Gln Pro Asp Tyr Trp Gly Gln
        260                 265                 270

Gly Thr Gln Val Thr Val Ser Ser Thr Ser Thr Thr Pro Ala Pro
        275                 280                 285

Arg Pro Pro Thr Pro Ala Pro Thr Ile Ala Ser Gln Pro Leu Ser Leu
290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Lys
            340                 345                 350

Arg Gly Arg Lys Lys Leu Leu Tyr Ile Phe Lys Gln Pro Phe Met Arg
        355                 360                 365

Pro Val Gln Thr Thr Gln Glu Glu Asp Gly Cys Ser Cys Arg Phe Pro
370                 375                 380

Glu Glu Glu Glu Gly Gly Cys Glu Leu Arg Val Lys Phe Ser Arg Ser
385                 390                 395                 400

Ala Asp Ala Pro Ala Tyr Gln Gln Gly Gln Asn Gln Leu Tyr Asn Glu
                405                 410                 415

Leu Asn Leu Gly Arg Arg Glu Glu Tyr Asp Val Leu Asp Lys Arg Arg
            420                 425                 430

Gly Arg Asp Pro Glu Met Gly Gly Lys Pro Arg Arg Lys Asn Pro Gln
        435                 440                 445

Glu Gly Leu Tyr Asn Glu Leu Gln Lys Asp Lys Met Ala Glu Ala Tyr
450                 455                 460

Ser Glu Ile Gly Met Lys Gly Glu Arg Arg Arg Gly Lys Gly His Asp
465                 470                 475                 480

Gly Leu Tyr Gln Gly Leu Ser Thr Ala Thr Lys Asp Thr Tyr Asp Ala
                485                 490                 495

Leu His Met Gln Ala Leu Pro Pro Arg
            500                 505

<210> SEQ ID NO 322
<211> LENGTH: 510
<212> TYPE: PRT
<213> ORGANISM: Artificial Sequence
<220> FEATURE:
<223> OTHER INFORMATION: Synthetic Construct

<400> SEQUENCE: 322

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95
```

-continued

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Ser Gly Gly Gly Ser Gly
145                 150                 155                 160

Gly Gly Gly Ser Gln Val Lys Leu Glu Glu Ser Gly Gly Gly Leu Val
                165                 170                 175

Gln Ala Gly Gly Ser Leu Arg Leu Ser Cys Ala Ala Ser Gly Gly Thr
            180                 185                 190

Leu Ser Lys Asn Thr Val Ala Trp Val Arg Gln Ala Pro Gly Lys Glu
        195                 200                 205

Arg Gly Phe Val Thr Ser Ile Thr Cys Asp Gly Arg Thr Thr Tyr Tyr
    210                 215                 220

Ala Asn Ser Val Asn Gly Arg Phe Pro Ile Asn Arg Asn Asn Ala Glu
225                 230                 235                 240

Asn Leu Val Val Leu Gln Met Asn Ser Leu Lys Pro Asp Asp Thr Ala
                245                 250                 255

Leu Tyr Tyr Cys Ala Ala Tyr Arg Lys Ser Ile Met Ser Ile Gln Pro
            260                 265                 270

Asp Tyr Trp Gly Gln Gly Thr Gln Val Thr Val Ser Ser Thr Ser Thr
        275                 280                 285

Thr Thr Pro Ala Pro Arg Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

```
<210> SEQ ID NO 323
<211> LENGTH: 515
<212> TYPE: PRT
<213> ORGANISM: Artificial Sequence
<220> FEATURE:
<223> OTHER INFORMATION: Synthetic Construct

<400> SEQUENCE: 323

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Gly Gly Gly Gly Ser Gln Val Lys Leu Glu Glu Ser
                165                 170                 175

Gly Gly Gly Leu Val Gln Ala Gly Gly Ser Leu Arg Leu Ser Cys Ala
            180                 185                 190

Ala Ser Gly Gly Thr Leu Ser Lys Asn Thr Val Ala Trp Val Arg Gln
        195                 200                 205

Ala Pro Gly Lys Glu Arg Gly Phe Val Thr Ser Ile Thr Cys Asp Gly
    210                 215                 220

Arg Thr Thr Tyr Tyr Ala Asn Ser Val Asn Gly Arg Phe Pro Ile Asn
225                 230                 235                 240

Arg Asn Asn Ala Glu Asn Leu Val Val Leu Gln Met Asn Ser Leu Lys
                245                 250                 255

Pro Asp Asp Thr Ala Leu Tyr Tyr Cys Ala Ala Tyr Arg Lys Ser Ile
            260                 265                 270

Met Ser Ile Gln Pro Asp Tyr Trp Gly Gln Gly Thr Gln Val Thr Val
        275                 280                 285

Ser Ser Thr Ser Thr Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Asp Ile Tyr Ile Trp Ala Pro Leu Ala Gly Thr Cys Gly Val Leu Leu
            340                 345                 350

Leu Ser Leu Val Ile Thr Leu Tyr Cys Lys Arg Gly Arg Lys Lys Leu
        355                 360                 365

Leu Tyr Ile Phe Lys Gln Pro Phe Met Arg Pro Val Gln Thr Thr Gln
```

```
                    370                 375                 380
Glu Asp Gly Cys Ser Cys Arg Phe Pro Glu Glu Glu Gly
385                 390                 395             400

Cys Glu Leu Arg Val Lys Phe Ser Arg Ser Ala Asp Ala Pro Ala Tyr
                405                 410                 415

Gln Gln Gly Gln Asn Gln Leu Tyr Asn Glu Leu Asn Leu Gly Arg Arg
                420                 425                 430

Glu Glu Tyr Asp Val Leu Asp Lys Arg Gly Arg Asp Pro Glu Met
                435                 440                 445

Gly Gly Lys Pro Arg Arg Lys Asn Pro Gln Glu Gly Leu Tyr Asn Glu
                450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
                500                 505                 510

Pro Pro Arg
        515

<210> SEQ ID NO 324
<211> LENGTH: 492
<212> TYPE: PRT
<213> ORGANISM: Artificial Sequence
<220> FEATURE:
<223> OTHER INFORMATION: Synthetic Construct

<400> SEQUENCE: 324

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
                100                 105                 110

Ala Leu Tyr Tyr Cys Ala Ala Tyr Arg Lys Ser Ile Met Ser Ile Gln
                115                 120                 125

Pro Asp Tyr Trp Gly Gln Gly Thr Gln Val Thr Val Ser Ser Gly Gly
                130                 135                 140

Gly Gly Ser Gln Val Gln Leu Val Glu Ser Gly Gly Gly Leu Val Gln
145                 150                 155                 160

Ala Gly Gly Ser Leu Arg Leu Ser Cys Ala Ala Ser Gly Gly Thr Leu
                165                 170                 175

Ser Lys Asn Thr Val Ala Trp Phe Arg Gln Ala Pro Gly Lys Glu Arg
                180                 185                 190

Gly Phe Val Ala Ser Ile Thr Trp Asp Gly Arg Thr Thr Tyr Tyr Ala
                195                 200                 205

Asp Ser Val Lys Gly Arg Phe Thr Ile Ser Arg Asp Asn Ala Lys Asn
```

```
            210                 215                 220
Thr Val Tyr Leu Gln Met Asn Ser Leu Lys Pro Glu Asp Thr Ala Val
225                 230                 235                 240

Tyr Val Cys Ala Asp Leu Gly Lys Trp Pro Ala Gly Pro Ala Asp Tyr
                245                 250                 255

Trp Gly Gln Gly Thr Gln Val Thr Val Ser Ser Thr Ser Thr Thr Thr
                260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 325
<211> LENGTH: 502
<212> TYPE: PRT
<213> ORGANISM: Artificial Sequence
<220> FEATURE:
<223> OTHER INFORMATION: Synthetic Construct

<400> SEQUENCE: 325

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
        50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
```

```
                    85                  90                  95
Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
            115                 120                 125

Pro Asp Tyr Trp Gly Gln Gly Thr Gln Val Thr Val Ser Ser Gly Gly
        130                 135                 140

Gly Gly Ser Gly Gly Gly Ser Gly Gly Gly Ser Gln Val Gln
145                 150                 155                 160

Leu Val Glu Ser Gly Gly Gly Leu Val Gln Ala Gly Gly Ser Leu Arg
                165                 170                 175

Leu Ser Cys Ala Ala Ser Gly Gly Thr Leu Ser Lys Asn Thr Val Ala
            180                 185                 190

Trp Phe Arg Gln Ala Pro Gly Lys Glu Arg Gly Phe Val Ala Ser Ile
        195                 200                 205

Thr Trp Asp Gly Arg Thr Thr Tyr Tyr Ala Asp Ser Val Lys Gly Arg
    210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
            260                 265                 270

Val Thr Val Ser Ser Thr Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```

<210> SEQ ID NO 326
<211> LENGTH: 512
<212> TYPE: PRT
<213> ORGANISM: Artificial Sequence
<220> FEATURE:
<223> OTHER INFORMATION: Synthetic Construct

<400> SEQUENCE: 326

```
Met Ala Leu Pro Val Thr Ala Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
                100                 105                 110

Ala Leu Tyr Tyr Cys Ala Ala Tyr Arg Lys Ser Ile Met Ser Ile Gln
            115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gly Gly Gly Ser Gly Gly Gly
145                 150                 155                 160

Gly Ser Gly Gly Gly Gly Ser Gln Val Gln Leu Val Glu Ser Gly Gly
                165                 170                 175

Gly Leu Val Gln Ala Gly Gly Ser Leu Arg Leu Ser Cys Ala Ala Ser
                180                 185                 190

Gly Gly Thr Leu Ser Lys Asn Thr Val Ala Trp Phe Arg Gln Ala Pro
            195                 200                 205

Gly Lys Glu Arg Gly Phe Val Ala Ser Ile Thr Trp Asp Gly Arg Thr
    210                 215                 220

Thr Tyr Tyr Ala Asp Ser Val Lys Gly Arg Phe Thr Ile Ser Arg Asp
225                 230                 235                 240

Asn Ala Lys Asn Thr Val Tyr Leu Gln Met Asn Ser Leu Lys Pro Glu
                245                 250                 255

Asp Thr Ala Val Tyr Val Cys Ala Asp Leu Gly Lys Trp Pro Ala Gly
            260                 265                 270

Pro Ala Asp Tyr Trp Gly Gln Gly Thr Gln Val Thr Val Ser Ser Thr
    275                 280                 285

Ser Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Cys Lys Arg Gly Arg Lys Lys Leu Leu Tyr Ile
        355                 360                 365
```

```
Phe Lys Gln Pro Phe Met Arg Pro Val Gln Thr Thr Gln Glu Glu Asp
        370                 375                 380

Gly Cys Ser Cys Arg Phe Pro Glu Glu Glu Gly Gly Cys Glu Leu
385                 390                 395                 400

Arg Val Lys Phe Ser Arg Ser Ala Asp Ala Pro Ala Tyr Gln Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
            435                 440                 445

Pro Arg Arg Lys Asn Pro Gln Glu Gly Leu Tyr Asn Glu Leu Gln Lys
        450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510

<210> SEQ ID NO 327
<211> LENGTH: 497
<212> TYPE: PRT
<213> ORGANISM: Artificial Sequence
<220> FEATURE:
<223> OTHER INFORMATION: Synthetic Construct

<400> SEQUENCE: 327

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gln Val Gln Leu Val Glu Ser Gly
145                 150                 155                 160

Gly Gly Leu Val Gln Ala Gly Gly Ser Leu Arg Leu Ser Cys Ala Ala
                165                 170                 175

Ser Gly Gly Thr Leu Ser Lys Asn Thr Val Ala Trp Phe Arg Gln Ala
            180                 185                 190

Pro Gly Lys Glu Arg Gly Phe Val Ala Ser Ile Thr Trp Asp Gly Arg
        195                 200                 205

Thr Thr Tyr Tyr Ala Asp Ser Val Lys Gly Arg Phe Thr Ile Ser Arg
    210                 215                 220
```

```
Asp Asn Ala Lys Asn Thr Val Tyr Leu Gln Met Asn Ser Leu Lys Pro
225                 230                 235                 240

Glu Asp Thr Ala Val Tyr Val Cys Ala Asp Leu Gly Lys Trp Pro Ala
            245                 250                 255

Gly Pro Ala Asp Tyr Trp Gly Gln Gly Thr Gln Val Thr Val Ser Ser
        260                 265                 270

Thr Ser Thr Thr Thr Pro Ala Pro Arg Pro Pro Thr Pro Ala Pro Thr
    275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
            325                 330                 335

Leu Val Ile Thr Leu Tyr Cys Lys Arg Gly Arg Lys Lys Leu Leu Tyr
        340                 345                 350

Ile Phe Lys Gln Pro Phe Met Arg Pro Val Gln Thr Thr Gln Glu Glu
    355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
            405                 410                 415

Tyr Asp Val Leu Asp Lys Arg Arg Gly Arg Asp Pro Glu Met Gly Gly
        420                 425                 430

Lys Pro Arg Arg Lys Asn Pro Gln Glu Gly Leu Tyr Asn Glu Leu Gln
    435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

Arg

<210> SEQ ID NO 328
<211> LENGTH: 502
<212> TYPE: PRT
<213> ORGANISM: Artificial Sequence
<220> FEATURE:
<223> OTHER INFORMATION: Synthetic Construct

<400> SEQUENCE: 328

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80
```

```
Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gly Gly Gly Gly Ser Gln Val Gln
145                 150                 155                 160

Leu Val Glu Ser Gly Gly Gly Leu Val Gln Ala Gly Gly Ser Leu Arg
                165                 170                 175

Leu Ser Cys Ala Ala Ser Gly Gly Thr Leu Ser Lys Asn Thr Val Ala
            180                 185                 190

Trp Phe Arg Gln Ala Pro Gly Lys Glu Arg Gly Phe Val Ala Ser Ile
        195                 200                 205

Thr Trp Asp Gly Arg Thr Thr Tyr Tyr Ala Asp Ser Val Lys Gly Arg
    210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
            260                 265                 270

Val Thr Val Ser Ser Thr Ser Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
```

<210> SEQ ID NO 329
<211> LENGTH: 507
<212> TYPE: PRT
<213> ORGANISM: Artificial Sequence
<220> FEATURE:
<223> OTHER INFORMATION: Synthetic Construct

<400> SEQUENCE: 329

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Ser Gly Gly Gly Ser Gly Gly Gly
145                 150                 155                 160

Gly Ser Gln Val Gln Leu Val Glu Ser Gly Gly Gly Leu Val Gln Ala
                165                 170                 175

Gly Gly Ser Leu Arg Leu Ser Cys Ala Ala Ser Gly Gly Thr Leu Ser
            180                 185                 190

Lys Asn Thr Val Ala Trp Phe Arg Gln Ala Pro Gly Lys Glu Arg Gly
        195                 200                 205

Phe Val Ala Ser Ile Thr Trp Asp Gly Arg Thr Thr Tyr Tyr Ala Asp
    210                 215                 220

Ser Val Lys Gly Arg Phe Thr Ile Ser Arg Asp Asn Ala Lys Asn Thr
225                 230                 235                 240

Val Tyr Leu Gln Met Asn Ser Leu Lys Pro Glu Asp Thr Ala Val Tyr
                245                 250                 255

Val Cys Ala Asp Leu Gly Lys Trp Pro Ala Gly Pro Ala Asp Tyr Trp
            260                 265                 270

Gly Gln Gly Thr Gln Val Thr Val Ser Ser Thr Ser Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Lys Arg Gly Arg Lys Lys Leu Leu Tyr Ile Phe Lys Gln Pro Phe
```

-continued

```
                355                 360                 365
Met Arg Pro Val Gln Thr Thr Gln Glu Glu Asp Gly Cys Ser Cys Arg
        370                 375                 380
Phe Pro Glu Glu Glu Gly Gly Cys Glu Leu Arg Val Lys Phe Ser
385                 390                 395                 400
Arg Ser Ala Asp Ala Pro Ala Tyr Gln Gln Gly Gln Asn Gln Leu Tyr
                405                 410                 415
Asn Glu Leu Asn Leu Gly Arg Arg Glu Glu Tyr Asp Val Leu Asp Lys
            420                 425                 430
Arg Arg Gly Arg Asp Pro Glu Met Gly Gly Lys Pro Arg Arg Lys Asn
        435                 440                 445
Pro Gln Glu Gly Leu Tyr Asn Glu Leu Gln Lys Asp Lys Met Ala Glu
    450                 455                 460
Ala Tyr Ser Glu Ile Gly Met Lys Gly Glu Arg Arg Arg Gly Lys Gly
465                 470                 475                 480
His Asp Gly Leu Tyr Gln Gly Leu Ser Thr Ala Thr Lys Asp Thr Tyr
                485                 490                 495
Asp Ala Leu His Met Gln Ala Leu Pro Pro Arg
            500                 505

<210> SEQ ID NO 330
<211> LENGTH: 491
<212> TYPE: PRT
<213> ORGANISM: Artificial Sequence
<220> FEATURE:
<223> OTHER INFORMATION: Synthetic Construct

<400> SEQUENCE: 330

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Leu
            20                  25                  30
Val Gln Ala Gly Gly Ser Leu Arg Leu Ser Cys Ala Ala Ser Gly Gly
        35                  40                  45
Thr Leu Ser Lys Asn Thr Val Ala Trp Phe Arg Gln Ala Pro Gly Lys
    50                  55                  60
Glu Arg Gly Phe Val Ala Ser Ile Thr Trp Asp Gly Arg Thr Thr Tyr
65                  70                  75                  80
Tyr Ala Asp Ser Val Lys Gly Arg Phe Thr Ile Ser Arg Asp Asn Ala
                85                  90                  95
Lys Asn Thr Val Tyr Leu Gln Met Asn Ser Leu Lys Pro Glu Asp Thr
            100                 105                 110
Ala Val Tyr Val Cys Ala Asp Leu Gly Lys Trp Pro Ala Gly Pro Ala
        115                 120                 125
Asp Tyr Trp Gly Gln Gly Thr Gln Val Thr Val Ser Ser Gly Gly Gly
    130                 135                 140
Gly Ser Asp Val Gln Leu Val Glu Ser Gly Gly Gly Leu Val Gln Ala
145                 150                 155                 160
Gly Gly Ser Leu Arg Leu Ser Cys Ala Ala Ser Gly Gly Thr Leu Ser
                165                 170                 175
Lys Asn Thr Val Ala Trp Val Arg Gln Ala Pro Gly Lys Glu Arg Gly
            180                 185                 190
Phe Val Thr Ser Ile Thr Cys Asp Gly Arg Thr Thr Tyr Tyr Ala Asn
        195                 200                 205
Ser Val Lys Gly Arg Phe Pro Ile Ser Arg Asp Asn Ala Glu Asn Thr
```

```
            210                 215                 220
Val Tyr Leu Gln Met Asn Ser Leu Lys Pro Glu Asp Thr Ala Gly Tyr
225                 230                 235                 240

Val Cys Ala Asp Leu Gly Lys Trp Pro Ala Gly Ser Ala Asp Tyr Trp
                245                 250                 255

Gly Gln Gly Thr His Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 331
<211> LENGTH: 501
<212> TYPE: PRT
<213> ORGANISM: Artificial Sequence
<220> FEATURE:
<223> OTHER INFORMATION: Synthetic Construct

<400> SEQUENCE: 331

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
```

```
            85                  90                  95
Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
            115                 120                 125

Asp Tyr Trp Gly Gln Gly Thr Gln Val Thr Val Ser Ser Gly Gly Gly
            130                 135                 140

Gly Ser Gly Gly Gly Ser Gly Gly Gly Ser Asp Val Gln Leu
145                 150                 155                 160

Val Glu Ser Gly Gly Gly Leu Val Gln Ala Gly Gly Ser Leu Arg Leu
            165                 170                 175

Ser Cys Ala Ala Ser Gly Gly Thr Leu Ser Lys Asn Thr Val Ala Trp
            180                 185                 190

Val Arg Gln Ala Pro Gly Lys Glu Arg Gly Phe Val Thr Ser Ile Thr
            195                 200                 205

Cys Asp Gly Arg Thr Thr Tyr Tyr Ala Asn Ser Val Lys Gly Arg Phe
            210                 215                 220

Pro Ile Ser Arg Asp Asn Ala Glu Asn Thr Val Tyr Leu Gln Met Asn
225                 230                 235                 240

Ser Leu Lys Pro Glu Asp Thr Ala Gly Tyr Val Cys Ala Asp Leu Gly
            245                 250                 255

Lys Trp Pro Ala Gly Ser Ala Asp Tyr Trp Gly Gln Gly Thr His Val
            260                 265                 270

Thr Val Ser Ser Thr Ser Thr Thr Thr Pro Ala Pro Arg Pro Pro Thr
            275                 280                 285

Pro Ala Pro Thr Ile Ala Ser Gln Pro Leu Ser Leu Arg Pro Glu Ala
            290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
            325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
            355                 360                 365

Thr Gln Glu Glu Asp Gly Cys Ser Cys Arg Phe Pro Glu Glu Glu Glu
            370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500
```

<210> SEQ ID NO 332
<211> LENGTH: 511
<212> TYPE: PRT
<213> ORGANISM: Artificial Sequence
<220> FEATURE:
<223> OTHER INFORMATION: Synthetic Construct

<400> SEQUENCE: 332

```
Met Ala Leu Pro Val Thr Ala Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Asp Val Gln Leu Val Glu Ser Gly Gly Gly
                165                 170                 175

Leu Val Gln Ala Gly Gly Ser Leu Arg Leu Ser Cys Ala Ala Ser Gly
            180                 185                 190

Gly Thr Leu Ser Lys Asn Thr Val Ala Trp Val Arg Gln Ala Pro Gly
        195                 200                 205

Lys Glu Arg Gly Phe Val Thr Ser Ile Thr Cys Asp Gly Arg Thr Thr
    210                 215                 220

Tyr Tyr Ala Asn Ser Val Lys Gly Arg Phe Pro Ile Ser Arg Asp Asn
225                 230                 235                 240

Ala Glu Asn Thr Val Tyr Leu Gln Met Asn Ser Leu Lys Pro Glu Asp
                245                 250                 255

Thr Ala Gly Tyr Val Cys Ala Asp Leu Gly Lys Trp Pro Ala Gly Ser
            260                 265                 270

Ala Asp Tyr Trp Gly Gln Gly Thr His Val Thr Val Ser Ser Thr Ser
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Lys Arg Gly Arg Lys Lys Leu Leu Tyr Ile Phe
        355                 360                 365
```

```
Lys Gln Pro Phe Met Arg Pro Val Gln Thr Thr Gln Glu Glu Asp Gly
    370                 375                 380

Cys Ser Cys Arg Phe Pro Glu Glu Glu Gly Gly Cys Glu Leu Arg
385                 390                 395                 400

Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
            435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 333
<211> LENGTH: 496
<212> TYPE: PRT
<213> ORGANISM: Artificial Sequence
<220> FEATURE:
<223> OTHER INFORMATION: Synthetic Construct

<400> SEQUENCE: 333

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Asp Val Gln Leu Val Glu Ser Gly Gly
145                 150                 155                 160

Gly Leu Val Gln Ala Gly Gly Ser Leu Arg Leu Ser Cys Ala Ala Ser
                165                 170                 175

Gly Gly Thr Leu Ser Lys Asn Thr Val Ala Trp Val Arg Gln Ala Pro
            180                 185                 190

Gly Lys Glu Arg Gly Phe Val Thr Ser Ile Thr Cys Asp Gly Arg Thr
        195                 200                 205

Thr Tyr Tyr Ala Asn Ser Val Lys Gly Arg Phe Pro Ile Ser Arg Asp
    210                 215                 220
```

Asn Ala Glu Asn Thr Val Tyr Leu Gln Met Asn Ser Leu Lys Pro Glu
225                 230                 235                 240

Asp Thr Ala Gly Tyr Val Cys Ala Asp Leu Gly Lys Trp Pro Ala Gly
            245                 250                 255

Ser Ala Asp Tyr Trp Gly Gln Gly Thr His Val Thr Val Ser Ser Thr
        260                 265                 270

Ser Thr Thr Thr Pro Ala Pro Arg Pro Thr Pro Ala Pro Thr Ile
    275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
                340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Glu Gly Gly Cys Glu Leu
370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 334
<211> LENGTH: 501
<212> TYPE: PRT
<213> ORGANISM: Artificial Sequence
<220> FEATURE:
<223> OTHER INFORMATION: Synthetic Construct

<400> SEQUENCE: 334

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Phe Arg Gln Ala Pro Gly Lys
        50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

-continued

```
Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
            115                 120                 125

Asp Tyr Trp Gly Gln Gly Thr Gln Val Thr Val Ser Ser Gly Gly Gly
130             135                 140

Gly Ser Gly Gly Gly Ser Gly Gly Gly Ser Asp Val Gln Leu
145             150                 155                 160

Val Glu Ser Gly Gly Gly Leu Val Gln Ala Gly Gly Ser Leu Arg Leu
            165                 170                 175

Ser Cys Ala Ala Ser Gly Gly Thr Leu Ser Lys Asn Thr Val Ala Trp
            180                 185                 190

Val Arg Gln Ala Pro Gly Lys Glu Arg Gly Phe Val Thr Ser Ile Thr
            195                 200                 205

Cys Asp Gly Arg Thr Thr Tyr Tyr Ala Asn Ser Val Lys Gly Arg Phe
210             215                 220

Pro Ile Ser Arg Asp Asn Ala Glu Asn Thr Val Tyr Leu Gln Met Asn
225             230                 235                 240

Ser Leu Lys Pro Glu Asp Thr Ala Gly Tyr Val Cys Ala Asp Leu Gly
            245                 250                 255

Lys Trp Pro Ala Gly Ser Ala Asp Tyr Trp Gly Gln Gly Thr His Val
            260                 265                 270

Thr Val Ser Ser Thr Ser Thr Thr Thr Pro Ala Pro Arg Pro Pro Thr
            275                 280                 285

Pro Ala Pro Thr Ile Ala Ser Gln Pro Leu Ser Leu Arg Pro Glu Ala
            290                 295                 300

Cys Arg Pro Ala Ala Gly Gly Ala Val His Thr Arg Gly Leu Asp Phe
305             310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
            355                 360                 365

Thr Gln Glu Glu Asp Gly Cys Ser Cys Arg Phe Pro Glu Glu Glu Glu
370             375                 380

Gly Gly Cys Glu Leu Arg Val Lys Phe Ser Arg Ser Ala Asp Ala Pro
385             390                 395                 400

Ala Tyr Gln Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465             470                 475                 480

Gly Leu Ser Thr Ala Thr Lys Asp Thr Tyr Asp Ala Leu His Met Gln
                485                 490                 495

Ala Leu Pro Pro Arg
            500
```

<210> SEQ ID NO 335
<211> LENGTH: 506
<212> TYPE: PRT
<213> ORGANISM: Artificial Sequence
<220> FEATURE:
<223> OTHER INFORMATION: Synthetic Construct

<400> SEQUENCE: 335

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Val Gln Leu Val Glu Ser Gly Gly Gly Leu Val Gln Ala Gly
                165                 170                 175

Gly Ser Leu Arg Leu Ser Cys Ala Ala Ser Gly Gly Thr Leu Ser Lys
            180                 185                 190

Asn Thr Val Ala Trp Val Arg Gln Ala Pro Gly Lys Glu Arg Gly Phe
        195                 200                 205

Val Thr Ser Ile Thr Cys Asp Gly Arg Thr Thr Tyr Tyr Ala Asn Ser
    210                 215                 220

Val Lys Gly Arg Phe Pro Ile Ser Arg Asp Asn Ala Glu Asn Thr Val
225                 230                 235                 240

Tyr Leu Gln Met Asn Ser Leu Lys Pro Glu Asp Thr Ala Gly Tyr Val
                245                 250                 255

Cys Ala Asp Leu Gly Lys Trp Pro Ala Gly Ser Ala Asp Tyr Trp Gly
            260                 265                 270

Gln Gly Thr His Val Thr Val Ser Ser Thr Ser Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Lys Arg Gly Arg Lys Lys Leu Leu Tyr Ile Phe Lys Gln Pro Phe Met
        355                 360                 365
```

Arg Pro Val Gln Thr Thr Gln Glu Glu Asp Gly Cys Ser Cys Arg Phe
    370                 375                 380
Pro Glu Glu Glu Gly Gly Cys Glu Leu Arg Val Lys Phe Ser Arg
385                 390                 395                 400
Ser Ala Asp Ala Pro Ala Tyr Gln Gln Gly Gln Asn Gln Leu Tyr Asn
                405                 410                 415
Glu Leu Asn Leu Gly Arg Arg Glu Glu Tyr Asp Val Leu Asp Lys Arg
            420                 425                 430
Arg Gly Arg Asp Pro Glu Met Gly Gly Lys Pro Arg Arg Lys Asn Pro
        435                 440                 445
Gln Glu Gly Leu Tyr Asn Glu Leu Gln Lys Asp Lys Met Ala Glu Ala
    450                 455                 460
Tyr Ser Glu Ile Gly Met Lys Gly Glu Arg Arg Arg Gly Lys Gly His
465                 470                 475                 480
Asp Gly Leu Tyr Gln Gly Leu Ser Thr Ala Thr Lys Asp Thr Tyr Asp
                485                 490                 495
Ala Leu His Met Gln Ala Leu Pro Pro Arg
            500                 505

<210> SEQ ID NO 336
<211> LENGTH: 1488
<212> TYPE: DNA
<213> ORGANISM: Artificial Sequence
<220> FEATURE:
<223> OTHER INFORMATION: Synthetic Construct

<400> SEQUENCE: 336

```
atggctctgc ccgtcactgc tctgctgctg cccctggctc tgctgctgca cgctgctcgc    60
cctcaggtcc agctggtgga aagcggagga ggcctggtgc agccaggagg cagcctgagg   120
ctgtcctgcg aggcctctgg cttcaccctg gactactatg ccatcggctg gtttaggcag   180
gcacctggaa aggagaggga gggagtgatc tgtatctctc gcagcgacgg cagcacatac   240
tatgccgatt ccgtgaaggg ccggttcacc atcagcagag acaacgccaa gaagacagtg   300
tacctgcaga tgatctccct gaagcctgag gataccgcag catactattg cgcagcagga   360
gcagactgta gcggataccct gagggattat gagtttaggg gacagggaac ccaggtgaca   420
gtgagctccg gaggaggagg ctcccaggtg cagctggtgg agtctggagg cggcctggtg   480
cagcctggag gcagcctgag actgagctgt gaagcttccg gatttaccct ggactactat   540
gcaatcggat ggtttaggca ggcaccagga aggagagag aaggcgtgat ctgtatctcc   600
agatctgacg gctctacata ctatgccgat agtgtcaaag acggttcac catctctaga   660
gataatgcca agaagacagt ctatctgcag atgattagcc tgaagcccga ggacacagcc   720
gcctattact gcgcagcagg agcagattgt agtgggtatc tgagggacta tgagtttcgg   780
ggcagggga cacaggtgac agtgagttct actagtacca cgacgccagc gccgcgacca   840
ccaacaccgg cgcccaccat cgcgtcgcag ccctgtccc tgcgccaga ggcgtgccgg   900
ccagcggcgg ggggcgcagt gcacacgagg gggctggact tcgcctgtga tatctacatc   960
tgggcgccct tggccgggac ttgtggggtc cttctcctgt cactggttat cacccttac   1020
tgcaaacggg gcagaaagaa actcctgtat atattcaaac aaccattat gagaccagta   1080
caaactactc aagaggaaga tggctgtagc tgccgatttc cagaagaaga agaggagga   1140
tgtgaactga gagtgaagtt cagcaggagc gcagacgccc ccgcgtacca gcagggccag   1200
aaccagctct ataacgagct caatctagga cgaagagagg agtacgatgt tttggacaag   1260
```

| | |
|---|---|
| agacgtggcc gggaccctga gatgggggga aagccgagaa ggaagaaccc tcaggaaggc | 1320 |
| ctgtacaatg aactgcagaa agataagatg gcggaggcct acagtgagat tgggatgaaa | 1380 |
| ggcgagcgcc ggaggggcaa ggggcacgat ggcctttacc agggtctcag tacagccacc | 1440 |
| aaggacacct acgacgccct tcacatgcag gccctgcccc ctcgctaa | 1488 |

<210> SEQ ID NO 337
<211> LENGTH: 1869
<212> TYPE: DNA
<213> ORGANISM: Artificial Sequence
<220> FEATURE:
<223> OTHER INFORMATION: Synthetic Construct

<400> SEQUENCE: 337

| | |
|---|---|
| atggctctgc ccgtcactgc tctgctgctg cctctggccc tgctgctgca cgccgcacgc | 60 |
| cctcaggtcc agctggtcga gtcaggagga ggcctggtgc agccaggagg ctccctgcgg | 120 |
| ctgtcttgcg aggccagcgg cttcaccctg gactactatg ccatcggctg gtttaggcag | 180 |
| gcacctggaa aggagaggga gggagtgatc tgtatctcca gatctgacgg ctccacatac | 240 |
| tatgccgatt ctgtgaaggg ccggttcacc atctctagag acaacgccaa gaagacagtg | 300 |
| tacctgcaga tgatcagcct gaagcccgag gataccgcag catactattg cgcagcagga | 360 |
| gcagactgtt ccggatacct gagggattat gagtttaggg gacagggaac ccaggtgaca | 420 |
| gtgagctccg gaggaggagg ctcccaggtg cagctggtgg agtctggagg cggcctggtg | 480 |
| cagcctggag gctccctgag gctgtcttgc gaggcaagcg gcttcaccct ggattactat | 540 |
| gcaatcggat ggtttaggca ggcaccagga aaggagagag aaggcgtgat ctgtatcagc | 600 |
| cgctccgacg gcagtaccta ctatgccgat tccgtcaaag gccggttcac catctccaga | 660 |
| gacaatgcca agaagacagt ctatctgcag atgatctctc tgaagcctga ggatacagcc | 720 |
| gcctattact gtgccgcagg agcagactgt agtggctatc tgagagatta tgagtttcgc | 780 |
| ggccagggca cccaggtgac agtgtctagc ggaggaggag gcagccaggt ccagctggtg | 840 |
| gaatccggcg gaggcctggt gcagcccggc ggctccctga actgtcctg tgaagcctcc | 900 |
| ggatttactc tggattatta cgctattgga tggttcagac aggcccctgg caaagaaaga | 960 |
| gaaggggtga tctgtatctc tcggagcgac ggctctacat actatgccga tagcgtcaag | 1020 |
| ggaagattta ccatctccag agataatgcc aagaagacag tgtatctgca gatgatttcc | 1080 |
| ctgaagcccg aggacactgc cgcctattac tgtgcagcag gagcagattg tagcgggtat | 1140 |
| ctgcgggatt atgaatttag aggacagggc actcaggtga cagtctcaag cactagtacc | 1200 |
| acgacgccag cgccgcgacc accaacaccg gcgcccacca tcgcgtcgca gcccctgtcc | 1260 |
| ctgcgcccag aggcgtgccg gccagcggcg gggggcgcag tgcacacgag ggggctggac | 1320 |
| ttcgcctgtg atatctacat ctgggcgccc ttggccggga cttgtggggt ccttctcctg | 1380 |
| tcactggtta tcaccctta ctgcaaacgg ggcagaaaga aactcctgta tatattcaaa | 1440 |
| caaccattta tgagaccagt acaaactact caagaggaag atggctgtag ctgccgattt | 1500 |
| ccagaagaag aagaaggagg atgtgaactg agagtgaagt tcagcaggag cgcagacgcc | 1560 |
| cccgcgtacc agcagggcca gaaccagctc tataacgagc tcaatctagg acgaagagag | 1620 |
| gagtacgatg ttttggacaa gagacgtggc cgggaccctg agatgggggg aaagccgaga | 1680 |
| aggaagaacc ctcaggaagg cctgtacaat gaactgcaga agataagat ggcggaggcc | 1740 |
| tacagtgaga ttgggatgaa aggcgagcgc cggaggggca aggggcacga tggcctttac | 1800 |
| cagggtctca gtacagccac caaggacacc tacgacgccc ttcacatgca ggccctgccc | 1860 |

-continued cctcgctaa                                                        1869

<210> SEQ ID NO 338
<211> LENGTH: 1467
<212> TYPE: DNA
<213> ORGANISM: Artificial Sequence
<220> FEATURE:
<223> OTHER INFORMATION: Synthetic Construct

<400> SEQUENCE: 338
atggctctgc ccgtcaccgc tctgctgctg cctctggctc tgctgctgca cgctgctcgc    60
cctcaggtca aactggaaga atctggcgga ggcctggtgc aggcaggacg gagcctgcgc   120
ctgagctgcg cagcatccga gcacaccttc agctcccacg tgatgggctg gtttcggcag   180
gccccaggca aggagagaga gagcgtggcc gtgatcggct ggagggacat ctccacatct   240
tacgccgatt ccgtgaaggg ccggttcacc atcagccggg acaacgccaa gagacactg   300
tatctgcaga tgaacagcct gaagcccgag gacaccgccg tgtactattg cgcagcaagg   360
agaatcgacg cagcagactt tgattcctgg ggccagggca cccaggtgac agtgtctagc   420
ggaggaggag gatctgaggt gcagctggtg gagagcggag gcggcctggt gcaggccgga   480
ggctctctga ggctgagctg tgcagcatcc ggaagaacct cacaatgggc tggtttagg   540
caggcaccag gaaaggagag ggagttcgtg gcagcaatca gcctgtcccc taccctggcc   600
tactatgccg agagcgtgaa gggcaggttt accatctccc gcgataacgc caagaataca   660
gtggtgctgc agatgaactc cctgaaacct gaggacacag ccctgtacta ttgtgccgcc   720
gatcggaaga gcgtgatgag cattagacca gactattggg gcagggaac acaggtgacc   780
gtgagcagca ctagtaccac gacgccagcg ccgcgaccac caacaccggc gccaccatc   840
gcgtcgcagc cctgtccct cgcccagag gcgtgccggc cagcggcggg gggcgcagtg   900
cacacgaggg ggctggactt cgcctgtgat atctacatct gggcgccctt ggccgggact   960
tgtggggtcc ttctcctgtc actggttatc acccttact gcaaacgggg cagaaagaaa  1020
ctcctgtata tattcaaaca accattatg agaccagtac aaactactca agaggaagat  1080
ggctgtagct gccgatttcc agaagaagaa gaaggaggat gtgaactgag agtgaagttc  1140
agcaggagcg cagacgcccc cgcgtaccag cagggccaga accagctcta taacgagctc  1200
aatctaggac gaagagagga gtacgatgtt ttggacaaga cgtggccg ggaccctgag    1260
atggggggaa agccgagaag gaagaaccct caggaaggcc tgtacaatga actgcagaaa  1320
gataagatgg cggaggccta cagtgagatt gggatgaaag cgagcgccg gaggggcaag   1380
gggcacgatg gcctttacca gggtctcagt acagccacca aggacaccta cgacgccctt  1440
cacatgcagg ccctgccccc tcgctaa                                    1467

<210> SEQ ID NO 339
<211> LENGTH: 1497
<212> TYPE: DNA
<213> ORGANISM: Artificial Sequence
<220> FEATURE:
<223> OTHER INFORMATION: Synthetic Construct

<400> SEQUENCE: 339
atggctctgc ctgtcaccgc tctgctgctg cctctggctc tgctgctgca cgctgctcgc    60
cctcaggtca aactggaaga aagtggggga ggcctggtgc aggcaggacg gagcctgcgc   120
ctgagctgcg cagcatccga gcacaccttc agctcccacg tgatgggctg gtttcggcag   180

```
gccccaggca aggagagaga gtccgtggcc gtgatcggct ggagggacat ctccacatct    240
tacgccgatt ctgtgaaggg ccggttcacc atcagcagag acaacgccaa gaagacactg    300
tatctgcaga tgaatagcct gaagcccgag acaccgccg tgtactattg cgcagcaagg     360
agaatcgacg cagcagactt tgattcctgg ggccagggca cccaggtgac agtgtctagc    420
ggaggaggag gatctggagg aggaggaagc ggaggaggag gatccgaggt gcagctggtg    480
gagtctggag cgggcctggt gcaggccgga ggctctctga ggctgagctg tgcagcatcc    540
ggaagaacct tcacaatggg ctggtttagg caggcaccag gaaaggagag ggagttcgtg    600
gcagcaatca gcctgtcccc taccctggcc tactatgccg agtccgtgaa gggcaggttt    660
accatctctc gcgataacgc caagaataca gtggtgctgc agatgaacag cctgaaacct    720
gaggacacag ccctgtacta ttgtgccgcc gatcggaaga gcgtgatgag cattagaccc    780
gattattggg gacagggcac acaggtgaca gtgagtagca ctagtaccac gacgccagcg    840
ccgcgaccac caacaccggc gcccaccatc gcgtcgcagc ccctgtccct gcgcccagag    900
gcgtgccggc cagcggcggg gggcgcagtg cacacgaggg gctgaacttt cgcctgtgat    960
atctacatct gggcgccctt ggccgggact tgtgggggtcc ttctcctgtc actggttatc   1020 acccttacttgcaaacgggg cagaaagaaa ctcctgtata tattcaaaca accatttatg    1080
agaccagtac aaactactca agaggaagat ggctgtagct gccgatttcc agaagaagaa    1140
gaaggaggat gtgaactgag agtgaagttc agcaggagcg cagacgcccc cgcgtaccag    1200
cagggccaga accagctcta taacgagctc aatctaggac aagagagga gtacgatgtt    1260 ttggacaaga cgtggccg ggaccctgag atgggggaa agccgagaag gaagaaccct      1320
caggaaggcc tgtacaatga actgcagaaa gataagatgg cggaggccta cagtgagatt    1380
gggatgaaag cgagcgccg gaggggcaag ggcacgatg gcctttacca gggtctcagt    1440
acagccacca aggacaccta cgacgccctt cacatgcagg ccctgccccc tcgctaa        1497
```

<210> SEQ ID NO 340
<211> LENGTH: 1527
<212> TYPE: DNA
<213> ORGANISM: Artificial Sequence
<220> FEATURE:
<223> OTHER INFORMATION: Synthetic Construct

<400> SEQUENCE: 340

```
atggctctgc ccgtcaccgc actgctgctg cctctggctc tgctgctgca cgccgcaaga    60
ccacaggtca aactggaaga atcaggagga ggcctggtgc aggcaggacg gagcctgcgc   120
ctgagctgcg cagcatccga gcacaccttc agctcccacg tgatgggctg gtttcggcag   180
gccccaggca aggagagaga gtccgtggcc gtgatcggct ggagggacat ctccacatct    240
tacgccgatt ccgtgaaggg ccggttcacc atcagccggg acaacgccaa gaagacactg    300
tatctgcaga tgaacagcct gaagcccgag acaccgccg tgtactattg cgcagcaagg     360
agaatcgacg cagcagactt tgatagctgg ggccaggca cccaggtgac agtgtctagc     420
ggaggaggag gatctggagg aggaggaagc ggaggaggag gaagcggcgg cggcggctct    480
ggcggcggcg cagcgaggt gcagctggtg gagagcggcg cgggcctggt gcaggccggc    540
ggctctctga ggctgagctg tgcagcatcc ggaagaacct tcacaatggg ctggtttagg    600
caggcaccag gaaaggagag ggagttcgtg gcagcaatca gcctgtcccc taccctggcc    660
tactatgccg agagcgtgaa gggcaggttt accatctccc gcgataacgc caagaataca    720
gtggtgttac aaatgaacag cctgaaacct gaggacacag ccctgtacta ttgtgccgcc    780
```

```
gatcggaaga gcgtgatgag cattagaccc gattattggg ggcaggggac acaggtgacc    840
gtgagcagca ctagtaccac gacgccagcg ccgcgaccac caacaccggc gcccaccatc    900
gcgtcgcagc ccctgtccct gcgcccagag gcgtgccggc cagcggcggg gggcgcagtg    960
cacacgaggg ggctggactt cgcctgtgat atctacatct gggcgccctt ggccgggact   1020
tgtggggtcc ttctcctgtc actggttatc acccttact gcaaacgggg cagaaagaaa   1080
ctcctgtata tattcaaaca accatttatg agaccagtac aaactactca agaggaagat   1140
ggctgtagct gccgatttcc agaagaagaa gaaggaggat gtgaactgag agtgaagttc   1200
agcaggagcg cagacgcccc cgcgtaccag cagggccaga accagctcta taacgagctc   1260
aatctaggac gaagagagga gtacgatgtt ttggacaaga cgtggccg ggaccctgag    1320 atgggggaa agccgagaag gaagaaccct caggaaggcc tgtacaatga actgcagaaa   1380
gataagatgg cggaggccta cagtgagatt gggatgaaag gcgagcgccg gaggggcaag   1440
gggcacgatg gcctttacca gggtctcagt acagccacca aggacaccta cgacgccctt   1500
cacatgcagg ccctgccccc tcgctaa                                     1527

<210> SEQ ID NO 341
<211> LENGTH: 1482
<212> TYPE: DNA
<213> ORGANISM: Artificial Sequence
<220> FEATURE:
<223> OTHER INFORMATION: Synthetic Construct

<400> SEQUENCE: 341
atggctctgc ctgtgaccgc actgctgctg cctctggctc tgctgctgca cgccgcacga     60
cctgaagtcc agctggtgga atccggggga ggcctggtgc aggcaggagg ctccctgagg    120
ctgtcttgcg cagcaagcgg aagaaccttc acaatgggct ggtttaggca ggcaccagga    180
aaggagaggg agttcgtggc cgccatctcc ctgtctccta ccctggccta ctatgccgag    240
agcgtgaagg gcaggtttac catctcccgc gacaacgcca agaatacagt ggtgctgcag    300
atgaacagcc tgaagccaga ggacacagcc ctgtactatt gcgccgccga tcggaagtct    360
gtgatgagca tcagacccga ttactggggc cagggcaccc aggtgacagt gagctccgga    420
ggaggaggat ccggcggagg aggctctcag gtgaagctgg aggagtccgg aggcggcctg    480
gtgcaggccg acggtccct gagactgtct tgtgccgcca gcgagcacac cttctctagc    540
cacgtgatgg gatggttcag gcaggcacct ggaaaggaga gggagtccgt ggcagtgatc    600
ggatggaggg acatcagcac atcctacgcc gattctgtga agggccggtt caccatcagc    660
agagacaacg ccaagaagac actgtattta caaatgaaca gcctgaagcc gaggatacc    720 gccgtgtact attgtgccgc ccggcggatt gacgccgcag actttgactc atggggggcag   780 ggaactcagg tgaccgtgtc ctcaactagt accacgacgc cagcgccgcg accaccaaca    840
ccggcgccca ccatcgcgtc gcagcccctg tccctgcgcc cagaggcgtg ccggccagcg    900
gcggggggcg cagtgcacac gagggggctg acttcgcct gtgatatcta catctgggcg    960 ccccttggccg gacttgtgg ggtccttctc ctgtcactgg ttatcaccct ttactgcaaa   1020
cggggcagaa agaaactcct gtatatattc aaacaaccat ttatgagacc agtacaaact   1080
actcaagagg aagatggctg tagctgccga tttccagaag aagaagaagg aggatgtgaa   1140
ctgagagtga agttcagcag gagcgcagac gcccccgcgt accagcaggg ccagaaccag   1200
ctctataacg agctcaatct aggacgaaga gaggagtacg atgttttgga caagagacgt   1260
```

```
ggccgggacc ctgagatggg gggaaagccg agaaggaaga accctcagga aggcctgtac    1320
aatgaactgc agaaagataa gatggcggag gcctacagtg agattgggat gaaaggcgag    1380
cgccggaggg gcaaggggca cgatggcctt taccagggtc tcagtacagc caccaaggac    1440
acctacgacg cccttcacat gcaggccctg cccctcgct aa                       1482

<210> SEQ ID NO 342
<211> LENGTH: 1497
<212> TYPE: DNA
<213> ORGANISM: Artificial Sequence
<220> FEATURE:
<223> OTHER INFORMATION: Synthetic Construct

<400> SEQUENCE: 342
atggccctgc ctgtcaccgc tctgctgctg cccctggccc tgctgctgca cgccgcacgc      60
cctgaggtcc agctggtcga gtccggggga ggcctggtgc aggcaggagg ctccctgagg    120
ctgtcttgcg cagcaagcgg aagaaccttc acaatgggct ggtttaggca ggcaccagga    180
aaggagaggg agttcgtggc cgccatctcc ctgtctccta ccctggccta ctatgccgag    240
tccgtgaagg gcaggtttac catctctcgc gacaacgcca agaatacagt ggtgctgcag    300
atgaactccc tgaagccaga ggacacagcc ctgtactatt gcgccgccga tcggaagtct    360
gtgatgagca tcagacccga ttactggggc cagggcaccc aggtgacagt gagctccgga    420
ggaggaggat ccggcggagg aggctctggc ggcggcggca gccaggtgaa gctggaggag    480
agcggaggcg gcctggtgca ggccggacgg tccctgagac tgtcttgtgc cgccagcgag    540
cacaccttct ctagccacgt gatgggatgg ttcaggcagg cacctggaaa ggagagggag    600
tctgtggccg tgatcggctg gagggacatc agcacatcct acgccgatag cgtgaagggc    660
cggttcacca tctccagaga caacgccaag aagacactgt atctgcagat gaatagcctg    720
aagcccgagg ataccgccgt gtactattgt gccgcccggc ggattgacgc cgcagatttt    780
gattcttggg gcagggaac tcaggtgacc gtgtcctcaa ctagtaccac gacgccagcg    840
ccgcgaccac caacaccggc gcccaccatc gcgtcgcagc cctgtccct gcgcccagag    900 gcgtgccggc cagcggcggg gggcgcagtg cacacgaggg gctgactt cgcctgtgat    960 atctacatct gggcgccctt ggccgggact tgtggggtcc ttctcctgtc actggttatc   1020 acctttact gcaaacgggg cagaaagaaa ctcctgtata tattcaaaca accatttatg   1080
agaccagtac aaactactca agaggaagat ggctgtagct gccgatttcc agaagaagaa   1140
gaaggaggat gtgaactgag agtgaagttc agcaggagcg cagacgcccc cgcgtaccag   1200
cagggccaga accagctcta taacgagctc aatctaggac gaagagagga gtacgatgtt   1260
ttggacaaga cgtggccg ggaccctgag atggggggaa agccgagaag gaagaaccct   1320
caggaaggcc tgtacaatga actgcagaaa gataagatgg cggaggccta cagtgagatt   1380
gggatgaaag gcgagcgccg gaggggcaag gggcacgatg gcctttacca gggtctcagt   1440
acagccacca aggacaccta cgacgccctt cacatgcagg ccctgccccc tcgctaa      1497

<210> SEQ ID NO 343
<211> LENGTH: 1512
<212> TYPE: DNA
<213> ORGANISM: Artificial Sequence
<220> FEATURE:
<223> OTHER INFORMATION: Synthetic Construct

<400> SEQUENCE: 343
atggctctgc ctgtgaccgc cctgctgctg cccctggccc tgctgctgca cgccgcacga      60
```

```
cctgaagtcc agctggtgga atctggcgga ggcctggtgc aggcaggagg ctccctgagg     120
ctgtcttgcg cagcaagcgg aagaaccttc acaatgggct ggtttaggca ggcaccagga     180
aaggagaggg agttcgtggc cgccatctcc ctgtctccta ccctggccta ctatgccgag     240
tctgtgaagg gcaggtttac catcagccgc gacaacgcca agaatacagt ggtgctgcag     300
atgaacagcc tgaagccaga ggacacagcc ctgtactatt gcgccgccga tcggaagtct     360
gtgatgagca tcagacccga ttactggggc cagggcaccc aggtgacagt gagctccgga     420
ggaggaggat ccggcggagg aggctctggc ggcggcggct ccggcggcgg cggctcccag     480
gtgaagctgg aggagtccgg aggcggcctg gtgcaggccg acggtccct  gagactgtct     540 tgtgccgcca gcgagcacac cttctctagc acgtgatgg  gatggttcag gcaggcacct     600
ggaaaggaga gggagagcgt ggcagtgatc ggatggaggg acatcagcac atcctacgcc     660
gattccgtga agggccggtt caccatcagc cgggacaacg ccaagaagac actgtattta     720
caaatgaaca gcctgaagcc cgaggatacc gccgtgtact attgtgccgc ccggcggatt     780
gatgccgcag actttgatag ttggggacag gggactcagg tcaccgtcag cagcactagt     840
accacgacgc cagcgccgcg accaccaaca ccggcgccca ccatcgcgtc gcagcccctg     900
tccctgcgcc cagaggcgtg ccggccagcg cgggggggcg cagtgcacac gaggggggctg     960 gacttcgcct gtgatatcta catctgggcg cccttggccg ggacttgtgg ggtccttctc    1020
ctgtcactgg ttatcaccct ttactgcaaa cggggcagaa agaaactcct gtatatattc    1080
aaacaaccat ttatgagacc agtacaaact actcaagagg aagatggctg tagctgccga    1140
tttccagaag aagaagaagg aggatgtgaa ctgagagtga agttcagcag gagcgcagac    1200
gcccccgcgt accagcaggg ccagaaccag ctctataacg agctcaatct aggacgaaga    1260
gaggagtacg atgttttgga caagagacgt ggccgggacc ctgagatggg gggaaagccg    1320
agaaggaaga accctcagga aggcctgtac aatgaactgc agaaagataa gatggcggag    1380
gcctacagtg agattgggat gaaaggcgag cgccggaggg caaggggca  cgatggcctt    1440 taccagggtc tcagtacagc caccaaggac acctacgacg cccttcacat gcaggccctg    1500
ccccctcgct aa                                                         1512
```

<210> SEQ ID NO 344
<211> LENGTH: 1470
<212> TYPE: DNA
<213> ORGANISM: Artificial Sequence
<220> FEATURE:
<223> OTHER INFORMATION: Synthetic Construct

<400> SEQUENCE: 344

```
atggctctgc ccgtcaccgc actgctgctg cctctggctc tgctgctgca cgctgctcgc      60
cctcaggtca aactggaaga atctggcgga ggcctggtgc aggcaggcag gtccctgagg     120
ctgtcttgcg cagcaagcga gcacaccttt agctcccacg tgatgggatg gttcaggcag     180
gcaccaggca aggagagaga gtccgtggcc gtgatcggct ggagggacat ctccacatct     240
tacgccgatt ctgtgaaggg ccggtttacc atcagcagag acaacgccaa gaagacactg     300
tatctgcaga tgaatagcct gaagcctgag gacaccgccg tgtactattg cgcagcaagg     360
agaatcgatg cagcagactt cgattcctgg ggacagggaa cccaggtgac agtgtctagc     420
ggaggaggag gaagcgccgt gcagctggtg gagtccggcg gcggcctggt gcaggccggc     480
gattctctgc ggctgacctg tacagcctcc ggcagagcct tctctaccta ctttatggcc     540
```

| | |
|---|---|
| tggtttagac aggcccctgg caaggagagg gagtttgtgg caggaatcgc atggagcgga | 600 |
| ggatccacag catacgccga ctccgtgaag ggcaggttca ccatctctcg cgataacgcc | 660 |
| aagaatacag tgtatctgca gatgaactct ctgaagagcg aggacacagc cgtgtactat | 720 |
| tgtgccagcc ggggaatcga ggtggaggaa tttggggctt gggggcaggg aactcaggtg | 780 |
| accgtctcat caactagtac cacgacgcca gcgccgcgac caccaacacc ggcgcccacc | 840 |
| atcgcgtcgc agcccctgtc cctgcgccca gaggcgtgcc ggccagcggc gggggcgca | 900 |
| gtgcacacga gggggctgga cttcgcctgt gatatctaca tctgggcgcc cttggccggg | 960 |
| acttgtgggg tccttctcct gtcactggtt atcacccttt actgcaaacg gggcagaaag | 1020 |
| aaactcctgt atatattcaa acaaccattt atgagaccag tacaaactac tcaagaggaa | 1080 |
| gatggctgta gctgccgatt ccagaagaa gaagaaggag gatgtgaact gagagtgaag | 1140 |
| ttcagcagga gcgcagacgc ccccgcgtac cagcagggcc agaaccagct ctataacgag | 1200 |
| ctcaatctag gacgaagaga ggagtacgat gttttggaca agagacgtgg ccgggaccct | 1260 |
| gagatggggg gaaagccgag aaggaagaac cctcaggaag gcctgtacaa tgaactgcag | 1320 |
| aaagataaga tggcggaggc ctacagtgag attgggatga aggcgagcg ccggaggggc | 1380 |
| aagggggcacg atgccttta ccagggtctc agtacagcca ccaaggacac ctacgacgcc | 1440 |
| cttcacatgc aggccctgcc ccctcgctaa | 1470 |

<210> SEQ ID NO 345
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 345

| | |
|---|---|
| atggctctgc ccgtcaccgc tctgctgctg cctctggctc tgctgctgca cgctgctcgc | 60 |
| cctcaggtca aactggaaga atctggcgga ggcctggtgc aggcaggcag gtccctgagg | 120 |
| ctgtcttgcg cagcaagcga gcacaccttt agctcccacg tgatgggatg gttcaggcag | 180 |
| gcaccaggca aggagagaga gagcgtggcc gtgatcggct ggagggacat ctccacatct | 240 |
| tacgccgata gcgtgaaggg ccggtttacc atctccagag acaacgccaa gaagacactg | 300 |
| tatctgcaga tgaatagcct gaagcctgag gacaccgccg tgtactattg cgcagcaagg | 360 |
| agaatcgatg cagcagactt cgattcctgg ggacagggaa cccaggtgac agtgtctagc | 420 |
| ggaggaggag gatccggagg aggaggatct ggcggcggcg gcagcgccgt gcagctggtg | 480 |
| gagtccggcg gcggcctggt gcaggccggc gactctctga gctgacctg tacagcctcc | 540 |
| ggcagagcct tctctaccta ctttatggcc tggtttagac aggcccctgg caaggagagg | 600 |
| gagtttgtgg caggaatcgc atggagcgga ggatccacag catacgcaga ctctgtgaag | 660 |
| ggcaggttca ccatcagccg cgataacgcc aagaatacag tgtatctgca gatgaactct | 720 |
| ctgaagagcg aggatacagc cgtgtactat tgtgcctccc gggggattga agtcgaggaa | 780 |
| tttggggctt gggggcaggg cactcaggtc accgtctcat ctactagtac cacgacgcca | 840 |
| gcgccgcgac caccaacacc ggcgcccacc atcgcgtcgc agcccctgtc cctgcgccca | 900 |
| gaggcgtgcc ggccagcggc gggggcgca gtgcacacga gggggctgga cttcgcctgt | 960 |
| gatatctaca tctgggcgcc cttggccggg acttgtgggg tccttctcct gtcactggtt | 1020 |
| atcacccttt actgcaaacg gggcagaaag aaactcctgt atatattcaa acaaccattt | 1080 |
| atgagaccag tacaaactac tcaagaggaa gatggctgta gctgccgatt ccagaagaa | 1140 |

| | |
|---|---|
| gaagaaggag gatgtgaact gagagtgaag ttcagcagga gcgcagacgc ccccgcgtac | 1200 |
| cagcagggcc agaaccagct ctataacgag ctcaatctag gacgaagaga ggagtacgat | 1260 |
| gttttggaca agagacgtgg ccgggaccct gagatggggg gaaagccgag aaggaagaac | 1320 |
| cctcaggaag gcctgtacaa tgaactgcag aaagataaga tggcggaggc ctacagtgag | 1380 |
| attgggatga aggcgagcg ccggagggggc aaggggcacg atggccttta ccagggtctc | 1440 |
| agtacagcca ccaaggacac ctacgacgcc cttcacatgc aggccctgcc ccctcgctaa | 1500 |

<210> SEQ ID NO 346
<211> LENGTH: 1530
<212> TYPE: DNA
<213> ORGANISM: Artificial Sequence
<220> FEATURE:
<223> OTHER INFORMATION: Synthetic Construct

<400> SEQUENCE: 346

| | |
|---|---|
| atggctctgc ccgtcactgc tctgctgctg cctctggctc tgctgctgca cgctgctaga | 60 |
| ccacaggtca aactggagga gtcagggggga ggcctggtgc aggcaggcag gtccctgagg | 120 |
| ctgtcttgcg cagcaagcga gcacaccttt agctcccacg tgatgggatg gttcaggcag | 180 |
| gcaccaggca aggagagaga gagcgtggcc gtgatcggct ggagggacat ctccacatct | 240 |
| tacgccgatt ctgtgaaggg ccggtttacc atcagcagag acaacgccaa gaagacactg | 300 |
| tatctgcaga tgaacagcct gaagcctgag gacaccgccg tgtactattg cgcagcaagg | 360 |
| agaatcgatg cagcagactt cgattcctgg ggacagggaa cccaggtgac agtgtctagc | 420 |
| ggaggaggag gatccggagg aggaggatct ggcggcggcg gcagtggcgg cggcggctcc | 480 |
| ggcggcggcg gctctgccgt gcagctggtg gagtccggcg gcggcctggt gcaggccggc | 540 |
| gactccctga ggctgacctg tacagccagc ggcagagcct tctccaccta ctttatggcc | 600 |
| tggtttagac aggcccctgg caaggagagg gagtttgtgg caggaatcgc atggagcgga | 660 |
| ggatccacag catacgccga ctccgtgaag gcaggttca ccatctctcg cgataacgcc | 720 |
| aagaatacag tgtatctgca gatgaactct ctgaagagcg aggatacagc cgtgtactat | 780 |
| tgtgcctccc ggggcattga agtggaagaa tttgggcctt ggggacaggg gactcaggtc | 840 |
| accgtcagca gcactagtac cacgacgcca gcgccgcgac caccaacacc ggcgcccacc | 900 |
| atcgcgtcgc agccctgtc cctgcgccca gaggcgtgcc ggccagcggc ggggggcgca | 960 |
| gtgcacacga gggggctgga cttcgcctgt gatatctaca tctgggcgcc cttggccggg | 1020 |
| acttgtgggg tccttctcct gtcactggtt atcaccttt actgcaaacg gggcagaaag | 1080 |
| aaactcctgt atatattcaa acaaccattt atgagaccag tacaaactac tcaagaggaa | 1140 |
| gatggctgta gctgccgatt tccagaagaa gaagaaggag gatgtgaact gagagtgaag | 1200 |
| ttcagcagga gcgcagacgc ccccgcgtac cagcagggcc agaaccagct ctataacgag | 1260 |
| ctcaatctag gacgaagaga ggagtacgat gttttggaca agagacgtgg ccgggaccct | 1320 |
| gagatggggg gaaagccgag aaggaagaac cctcaggaag gcctgtacaa tgaactgcag | 1380 |
| aaagataaga tggcggaggc ctacagtgag attgggatga aggcgagcg ccggagggggc | 1440 |
| aagggggcacg atggccttta ccagggtctc agtacagcca ccaaggacac ctacgacgcc | 1500 |
| cttcacatgc aggccctgcc ccctcgctaa | 1530 |

<210> SEQ ID NO 347
<211> LENGTH: 1485
<212> TYPE: DNA

<213> ORGANISM: Artificial Sequence
<220> FEATURE:
<223> OTHER INFORMATION: Synthetic Construct

<400> SEQUENCE: 347

| | | | | | |
|---|---|---|---|---|---|
| atggctctgc | ccgtgaccgc | tctgctgctg | cctctggctc | tgctgctgca | tgctgctcgc | 60 |
| cctcaggtga | aactggaaga | atctggcgga | ggcctggtgc | aggcaggcag | gtccctgagg | 120 |
| ctgtcttgcg | cagcaagcga | gcacaccttt | agctcccacg | tgatgggatg | gttcaggcag | 180 |
| gcaccaggca | aggagagaga | gtccgtggcc | gtgatcggct | ggagggacat | ctccacatct | 240 |
| tacgccgatt | ctgtgaaggg | ccggtttacc | atcagcagag | acaacgccaa | gaagacactg | 300 |
| tatctgcaga | tgaacagcct | gaagcctgag | gacaccgccg | tgtactattg | cgcagcaagg | 360 |
| agaatcgatg | cagcagactt | cgatagctgg | ggacagggaa | cccaggtgac | agtgtctagc | 420 |
| ggaggaggag | gatccggagg | aggaggatct | gccgtgcagc | tggtggagag | cggcggcggc | 480 |
| ctggtgcagg | ccggcgattc | cctgaggctg | acctgtacag | ccagcggcag | agccttctcc | 540 |
| acctacttta | tggcctggtt | tagacaggcc | cctggcaagg | agagggagtt | tgtggcagga | 600 |
| atcgcatgga | gcggaggatc | cacagcatac | gccgactccg | tgaagggcag | gttcaccatc | 660 |
| tctcgcgata | acgccaagaa | tacagtgtat | ctgcagatga | actctctgaa | gagcgaggac | 720 |
| acagccgtgt | actattgtgc | cagccggggg | attgaagtgg | aagaatttgg | ggcttggggg | 780 |
| caggggactc | aggtcacagt | gtcatctact | agtaccacga | cgccagcgcc | gcgaccacca | 840 |
| acaccggcgc | ccaccatcgc | gtcgcagccc | ctgtccctgc | gcccagaggc | gtgccggcca | 900 |
| gcggcggggg | gcgcagtgca | cacgagggggg | ctggacttcg | cctgtgatat | ctacatctgg | 960 |
| gcgcccttgg | ccgggacttg | tgggtccttc | tcctgtcac | tggttatcac | cctttactgc | 1020 |
| aaacggggca | gaaagaaact | cctgtatata | ttcaaacaac | catttatgag | accagtacaa | 1080 |
| actactcaag | aggaagatgg | ctgtagctgc | cgatttccag | aagaagaaga | aggaggatgt | 1140 |
| gaactgagag | tgaagttcag | caggagcgca | gacgcccccg | cgtaccagca | gggccagaac | 1200 |
| cagctctata | acgagctcaa | tctaggacga | agagaggagt | acgatgtttt | ggacaagaga | 1260 |
| cgtggccggg | accctgagat | ggggggaaag | ccgagaagga | agaaccctca | ggaaggcctg | 1320 |
| tacaatgaac | tgcagaaaga | taagatggcg | gaggcctaca | gtgagattgg | gatgaaaggc | 1380 |
| gagcgccgga | ggggcaaggg | gcacgatggc | ctttaccagg | gtctcagtac | agccaccaag | 1440 |
| gacacctacg | acgcccttca | catgcaggcc | ctgccccctc | gctaa | | 1485 |

<210> SEQ ID NO 348
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 348

| | | | | | |
|---|---|---|---|---|---|
| atggctctgc | ccgtcaccgc | actgctgctg | cccctggctc | tgctgctgca | cgctgctcgc | 60 |
| cctcaggtca | aactggaaga | atctggagga | ggcctggtgc | aggcaggcag | gtccctgagg | 120 |
| ctgtcttgcg | cagcaagcga | gcacaccttt | agctcccacg | tgatgggatg | gttcaggcag | 180 |
| gcaccaggca | aggagagaga | gagcgtggcc | gtgatcggct | ggagggacat | ctccacatct | 240 |
| tacgccgata | gcgtgaaggg | ccggtttacc | atctccagag | acaacgccaa | gaagacactg | 300 |
| tatctgcaga | tgaatagcct | gaagcctgag | gacaccgccg | tgtactattg | cgcagcaagg | 360 |
| agaatcgatg | cagcagactt | cgattcctgg | ggacagggaa | cccaggtgac | agtgtctagc | 420 |

```
ggaggaggag gatccggagg aggaggatct ggcggcggcg gcagcgccgt gcagctggtg      480
gagtccggcg gcggcctggt gcaggccggc gactctctga ggctgacctg tacagcctcc      540
ggcagagcct tctctaccta ctttatggcc tggtttagac aggcccctgg caaggagagg      600
gagtttgtgg caggaatcgc atggagcgga ggatccacag catacgcaga ctctgtgaag      660
ggcaggttca ccatcagccg cgataacgcc aagaatacag tgtatctgca gatgaactct      720
ctgaagagcg aggatacagc cgtgtactat tgtgcctccc gggggattga agtggaagaa      780
tttggggctt gggggcaggg gactcaggtc accgtcagca gcactagtac cacgacgcca      840
gcgccgcgac caccaacacc ggcgcccacc atcgcgtcgc agcccctgtc cctgcgccca      900
gaggcgtgcc ggccagcggc ggggggcgca gtgcacacga ggggctgga cttcgcctgt       960 gatatctaca tctgggcgcc cttggccggg acttgtgggg tccttctcct gtcactggtt     1020
atcacccttt actgcaaacg gggcagaaag aaactcctgt atatattcaa acaaccattt     1080
atgagaccag tacaaactac tcaagaggaa gatggctgta gctgccgatt tccagaagaa     1140
gaagaaggag gatgtgaact gagagtgaag ttcagcagga gcgcagacgc ccccgcgtac     1200
cagcagggcc agaaccagct ctataacgag ctcaatctag gacgaagaga ggagtacgat     1260
gttttggaca gagacgtgg ccgggaccct gagatggggg gaaagccgag aaggaagaac      1320
cctcaggaag gcctgtacaa tgaactgcag aaagataaga tggcggaggc ctacagtgag     1380
attgggatga aggcgagcg ccggaggggc aagggggcacg atggccttta ccagggtctc     1440
agtacagcca ccaaggacac ctacgacgcc cttcacatgc aggccctgcc ccctcgctaa     1500
```

<210> SEQ ID NO 349  
<211> LENGTH: 1515  
<212> TYPE: DNA  
<213> ORGANISM: Artificial Sequence  
<220> FEATURE:  
<223> OTHER INFORMATION: Synthetic Construct

<400> SEQUENCE: 349

```
atggctctgc ctgtgaccgc tctgctgctg cctctggctc tgctgctgca cgccgctcgc       60
cctcaggtga aactggaaga atctggagga ggcctggtgc aggcaggcag gtccctgagg      120
ctgtcttgcg cagcaagcga gcacaccttt agctcccacg tgatgggatg gttcaggcag      180
gcaccaggca aggagagaga gtccgtggcc gtgatcggct ggagggacat ctccacatct      240
tacgccgatt ccgtgaaggg ccggtttacc atcagccggg acaacgccaa gaagacactg      300
tatctgcaga tgaacagcct gaagcctgag gacaccgccg tgtactattg cgcagcaagg      360
agaatcgatg cagcagactt cgattcttgg ggccagggca cccaggtgac agtgtctagc      420
ggaggaggag gatccggagg aggaggatct ggcggcggcg gctccggcgg cggcggctcc      480
gccgtgcagc tggtggagtc tggcggcggc ctggtgcagg ccggcgacag cctgaggctg      540
acctgtacag cctctggcag agccttcagc acctacttta tggcctggtt tagacaggcc      600
cctggcaagg agagggagtt tgtggcagga atcgcatgga gcggaggatc cacagcatac      660
gccgacagcg tgaagggcag gttcaccatc tcccgcgata cgccaagaa tacagtgtat      720 ctgcagatga actctctgaa gagcgaggat acagccgtgt actattgtgc cagccggggg     780
attgaagtgg aagaatttgg ggcatggggg caggggactc aggtcaccgt cagtagcact     840
agtaccacga cgccagcgcc gcgaccacca acaccggcgc ccaccatcgc gtcgcagccc     900
ctgtccctgc gcccagaggc gtgccggcca gcggcggggg gcgcagtgca cacgaggggg     960
```

```
ctggacttcg cctgtgatat ctacatctgg gcgcccttgg ccgggacttg tggggtcctt    1020
ctcctgtcac tggttatcac cctttactgc aaacggggca gaaagaaact cctgtatata    1080
ttcaaacaac catttatgag accagtacaa actactcaag aggaagatgg ctgtagctgc    1140
cgatttccag aagaagaaga aggaggatgt gaactgagag tgaagttcag caggagcgca    1200
gacgcccccg cgtaccagca gggccagaac cagctctata cgagctcaa tctaggacga     1260 agagaggagt acgatgtttt ggacaagaga cgtggccggg accctgagat gggggggaaag   1320 ccgagaagga agaaccctca ggaaggcctg tacaatgaac tgcagaaaga taagatggcg    1380
gaggcctaca gtgagattgg gatgaaaggc gagcgccgga ggggcaaggg gcacgatggc    1440
ctttaccagg gtctcagtac agccaccaag gacacctacg acgcccttca catgcaggcc    1500
ctgccccctc gctaa                                                     1515

<210> SEQ ID NO 350
<211> LENGTH: 1470
<212> TYPE: DNA
<213> ORGANISM: Artificial Sequence
<220> FEATURE:
<223> OTHER INFORMATION: Synthetic Construct

<400> SEQUENCE: 350
atggctctgc ccgtcaccgc tctgctgctg cctctggctc tgctgctgca cgctgctcgc     60
cctgaggtgc agctggtgga gtctggggga ggaatggtgc aggctgggga ctctctgaga    120
ctatcctgtg tgcagtctac ttacaccgtc aatagcgatg tcatgggctg gttccgccag    180
gctccaggga aggagcgtga gtttgtagga gcgattatgt ggaatgatgg tattacatac    240
ttgcaagact ccgtgaaggg ccgatttacc atcttcagag acaacgccaa gaacacggtg    300
tatctgcaaa tgaacagcct gaaacttgag gatacggccg tttattactg tgcagcatcc    360
aagggtagat actcggaata tgagtactgg ggccagggga cccaggtcac cgtctcctca    420
ggaggaggag gatctgcggt gcagctggtg gagtctgggg gaggattggt gcaggctggg    480
gactctctga gactcacctg tacagcctct ggacgcgcct tcagtaccta tttcatggcc    540
tggttccgcc aggctccagg gaaggagcgt gagtttgtag caggaattgc atggagtggt    600
ggtagcacgg cgtatgcaga ctccgtgaag gccgattca ccatctccag agacaacgcc     660
aagaacacgg tgtatctgca aatgaacagc ctgaaatctg aggacacggc cgtttattac    720
tgtgccagca gggggattga ggtcgaagag tttggtgcct ggggccaggg gacccaggtc    780
accgtctcgt cgactagtac cacgacgcca gcgccgcgac caccaacacc ggcgcccacc    840
atcgcgtcgc agcccctgtc cctgcgccca gaggcgtgcc ggccagcggc ggggggcgca    900
gtgcacacga ggggctgga cttcgcctgt gatatctaca tctgggcgcc cttggccggg     960
acttgtgggg tccttctcct gtcactggtt atcacccttt actgcaaacg gggcagaaag   1020
aaactcctgt atatattcaa acaaccattt atgagaccag tacaaactac tcaagaggaa   1080
gatggctgta gctgccgatt ccagaagaa gaagaaggag gatgtgaact gagagtgaag    1140
ttcagcagga gcgcagacgc ccccgcgtac cagcagggcc agaaccagct ctataacgag   1200
ctcaatctag gacgaagaga ggagtacgat gttttggaca agagacgtgg ccgggaccct   1260
gagatggggg gaaagccgag aaggaagaac cctcaggaag gcctgtacaa tgaactgcag   1320
aaagataaga tggcggaggc ctacagtgag attgggatga aggcgagcg ccggagggc    1380 aaggggcacg atggccttta ccagggtctc agtacagcca ccaaggacac ctacgacgcc   1440
cttcacatgc aggccctgcc cctcgctaa                                     1470
```

<210> SEQ ID NO 351
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 351

| | | | | | |
|---|---|---|---|---|---|
| atggctctgc | ccgtcaccgc | tctgctgctg | cctctggctc | tgctgctgca | cgctgctcgc | 60 |
| cctgaggtgc | agctggtgga | gtctggggga | ggaatggtgc | aggctgggga | ctctctgaga | 120 |
| ctatcctgtg | tgcagtctac | ttacaccgtc | aatagcgatg | tcatgggctg | gttccgccag | 180 |
| gctccaggga | aggagcgtga | gtttgtagga | gcgattatgt | ggaatgatgg | tattacatac | 240 |
| ttgcaagact | ccgtgaaggg | ccgatttacc | atcttcagag | acaacgccaa | gaacacggtg | 300 |
| tatctgcaaa | tgaacagcct | gaaacttgag | gatacggccg | tttattactg | tgcagcatcc | 360 |
| aagggtagat | actcggaata | tgagtactgg | ggccagggga | cccaggtcac | cgtctcctca | 420 |
| ggaggaggag | gatctggagg | aggaggaagc | ggaggaggag | gatccgcggt | gcagctggtg | 480 |
| gagtctgggg | gaggattggt | gcaggctggg | gactctctga | gactcacctg | tacagcctct | 540 |
| ggacgcgcct | tcagtaccta | tttcatggcc | tggttccgcc | aggctccagg | gaaggagcgt | 600 |
| gagtttgtag | caggaattgc | atggagtggt | ggtagcacgg | cgtatgcaga | ctccgtgaag | 660 |
| ggccgattca | ccatctccag | agacaacgcc | aagaacacgg | tgtatctgca | aatgaacagc | 720 |
| ctgaaatctg | aggacacggc | cgtttattac | tgtgccagca | gggggattga | ggtcgaagag | 780 |
| tttggtgcct | ggggccaggg | gacccaggtc | accgtctcgt | cgactagtac | cacgacgcca | 840 |
| gcgccgcgac | caccaacacc | ggcgcccacc | atcgcgtcgc | agccctgtc | cctgcgccca | 900 |
| gaggcgtgcc | ggccagcggc | ggggggcgca | gtgcacacga | ggggctgga | cttcgcctgt | 960 |
| gatatctaca | tctgggcgcc | cttggccggg | acttgtgggg | tccttctcct | gtcactggtt | 1020 |
| atcacccttt | actgcaaacg | gggcagaaag | aaactcctgt | atatattcaa | acaaccattt | 1080 |
| atgagaccag | tacaaactac | tcaagaggaa | gatggctgta | gctgccgatt | tccagaagaa | 1140 |
| gaagaaggag | gatgtgaact | gagagtgaag | ttcagcagga | gcgcagacgc | cccgcgtac | 1200 |
| cagcagggcc | agaaccagct | ctataacgag | ctcaatctag | gacgaagaga | ggagtacgat | 1260 |
| gttttggaca | agagacgtgg | ccgggaccct | gagatggggg | gaaagccgag | aaggaagaac | 1320 |
| cctcaggaag | gcctgtacaa | tgaactgcag | aaagataaga | tggcggaggc | ctacagtgag | 1380 |
| attgggatga | aaggcgagcg | ccggaggggc | aaggggcacg | atggccttta | ccagggtctc | 1440 |
| agtacagcca | ccaaggacac | ctacgacgcc | cttcacatgc | aggccctgcc | ccctcgctaa | 1500 |

<210> SEQ ID NO 352
<211> LENGTH: 1530
<212> TYPE: DNA
<213> ORGANISM: Artificial Sequence
<220> FEATURE:
<223> OTHER INFORMATION: Synthetic Construct

<400> SEQUENCE: 352

| | | | | | |
|---|---|---|---|---|---|
| atggctctgc | ccgtcaccgc | tctgctgctg | cctctggctc | tgctgctgca | cgctgctcgc | 60 |
| cctgaggtgc | agctggtgga | gtctggggga | ggaatggtgc | aggctgggga | ctctctgaga | 120 |
| ctatcctgtg | tgcagtctac | ttacaccgtc | aatagcgatg | tcatgggctg | gttccgccag | 180 |
| gctccaggga | aggagcgtga | gtttgtagga | gcgattatgt | ggaatgatgg | tattacatac | 240 |

| | |
|---|---|
| ttgcaagact ccgtgaaggg ccgatttacc atcttcagag acaacgccaa gaacacggtg | 300 |
| tatctgcaaa tgaacagcct gaaacttgag gatacggccg tttattactg tgcagcatcc | 360 |
| aagggtagat actcggaata tgagtactgg ggccagggga cccaggtcac cgtctcctca | 420 |
| ggaggaggag gatctggagg aggaggaagc ggaggaggag gaagcggcgg cggcggctct | 480 |
| ggcggcggcg gcagcgcggt gcagctggtg gagtctgggg gaggattggt gcaggctggg | 540 |
| gactctctga gactcacctg tacagcctct ggacgcgcct tcagtaccta tttcatggcc | 600 |
| tggttccgcc aggctccagg gaaggagcgt gagtttgtag caggaattgc atggagtggt | 660 |
| ggtagcacgg cgtatgcaga ctccgtgaag ggccgattca ccatctccag agacaacgcc | 720 |
| aagaacacgg tgtatctgca aatgaacagc ctgaaatctg aggacacggc cgtttattac | 780 |
| tgtgccagca gggggattga ggtcgaagag tttggtgcct ggggccaggg gacccaggtc | 840 |
| accgtctcgt cgactagtac cacgacgcca gcgccgcgac caccaacacc ggcgcccacc | 900 |
| atcgcgtcgc agcccctgtc cctgcgccca gaggcgtgcc ggccagcggc gggggggcgca | 960 |
| gtgcacacga gggggctgga cttcgcctgt gatatctaca tctgggcgcc cttggccggg | 1020 |
| acttgtgggg tccttctcct gtcactggtt atcacccttt actgcaaacg gggcagaaag | 1080 |
| aaactcctgt atatattcaa acaacctttt atgagaccag tacaaactac tcaagaggaa | 1140 |
| gatggctgta gctgccgatt ccagaagaa gaagaaggag gatgtgaact gagagtgaag | 1200 |
| ttcagcagga gcgcagacgc ccccgcgtac cagcagggcc agaaccagct ctataacgag | 1260 |
| ctcaatctag gacgaagaga ggagtacgat gttttggaca gagacgtggc cgggaccct | 1320 |
| gagatggggg gaaagccgag aaggaagaac cctcaggaag gcctgtacaa tgaactgcag | 1380 |
| aaagataaga tggcggaggc ctacagtgag attgggatga aggcgagcg ccggaggggc | 1440 |
| aaggggcacg atggccttta ccagggtctc agtacagcca ccaaggacac ctacgacgcc | 1500 |
| cttcacatgc aggccctgcc ccctcgctaa | 1530 |

<210> SEQ ID NO 353
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 353

| | |
|---|---|
| atggctctgc ccgtcaccgc tctgctgctg cctctggctc tgctgctgca cgctgctcgc | 60 |
| cctgaggtgc agctggtgga gtctggggga ggaatggtgc aggctgggga ctctctgaga | 120 |
| ctatcctgtg tgcagtctac ttacaccgtc aatagcgatg tcatgggctg gttccgccag | 180 |
| gctccaggga aggagcgtga gtttgtagga gcgattatgt ggaatgatgg tattacatac | 240 |
| ttgcaagact ccgtgaaggg ccgatttacc atcttcagag acaacgccaa gaacacggtg | 300 |
| tatctgcaaa tgaacagcct gaaacttgag gatacggccg tttattactg tgcagcatcc | 360 |
| aagggtagat actcggaata tgagtactgg ggccagggga cccaggtcac cgtctcctca | 420 |
| ggaggaggag gatccggcgg aggaggctct gcggtgcagc tggtggagtc tgggggagga | 480 |
| ttggtgcagg ctggggactc tctgagactc acctgtacag cctctggacg cgccttcagt | 540 |
| acctatttca tggcctggtt ccgccaggct ccagggaagg agcgtgagtt tgtagcagga | 600 |
| attgcatgga gtggtggtag cacggcgtat gcagactccg tgaagggccg attcaccatc | 660 |
| tccagagaca cgccaagaa cacggtgtat ctgcaaatga acagcctgaa atctgaggac | 720 |
| acggccgttt attactgtgc cagcaggggg attgaggtcg aagagtttgg tgcctggggc | 780 |

```
caggggaccc aggtcaccgt ctcgtcgact agtaccacga cgccagcgcc gcgaccacca    840
acaccggcgc ccaccatcgc gtcgcagccc ctgtccctgc gcccagaggc gtgccggcca    900
gcggcggggg gcgcagtgca cacgaggggg ctggacttcg cctgtgatat ctacatctgg    960
gcgcccttgg ccgggacttg tggggtcctt ctcctgtcac tggttatcac cctttactgc   1020
aaacggggca gaaagaaact cctgtatata ttcaaacaac catttatgag accagtacaa   1080
actactcaag aggaagatgg ctgtagctgc cgatttccag aagaagaaga aggaggatgt   1140
gaactgagag tgaagttcag caggagcgca gacgcccccg cgtaccagca gggccagaac   1200
cagctctata cgagctcaa tctaggacga agagaggagt acgatgtttt ggacaagaga    1260
cgtggccggg accctgagat gggggaaag ccgagaagga agaaccctca ggaaggcctg     1320
tacaatgaac tgcagaaaga taagatggcg gaggcctaca gtgagattgg gatgaaaggc   1380
gagcgccgga ggggcaaggg gcacgatggc ctttaccagg gtctcagtac agccaccaag   1440
gacacctacg acgcccttca catgcaggcc ctgcccctc gctaa                    1485
```

<210> SEQ ID NO 354
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 354

```
atggctctgc ccgtcaccgc tctgctgctg cctctggctc tgctgctgca cgctgctcgc     60
cctgaggtgc agctggtgga gtctggggga ggaatggtgc aggctgggga ctctctgaga    120
ctatcctgtg tgcagtctac ttacaccgtc aatagcgatg tcatgggctg gttccgccag    180
gctccaggga aggagcgtga gtttgtagga gcgattatgt ggaatgatgg tattacatac    240
ttgcaagact ccgtgaaggg ccgatttacc atcttcagag acaacgccaa gaacacggtg    300
tatctgcaaa tgaacagcct gaaacttgag gatacggccg tttattactg tgcagcatcc    360
aagggtagat actcggaata tgagtactgg ggccagggga cccaggtcac cgtctcctca    420
ggaggaggag gatccggcgg aggaggctct ggcggcggcg gcagcgcggt gcagctggtg    480
gagtctgggg gaggattggt gcaggctggg gactctctga gactcacctg tacagcctct    540
ggacgcgcct tcagtaccta tttcatggcc tggttccgcc aggctccagg gaaggagcgt    600
gagtttgtag caggaattgc atggagtggt ggtagcacgg cgtatgcaga ctccgtgaag    660
ggccgattca ccatctccag agacaacgcc aagaacacgt gtatctgca aatgaacagc     720 ctgaaatctg aggacacggc cgtttattac tgtgccagca ggggattga ggtcgaagag     780 tttggtgcct ggggccaggg gacccaggtc accgtctcgt cgactagtac cacgacgcca    840
gcgccgcgac caccaacacc ggcgcccacc atcgcgtcgc agcccctgtc cctgcgccca    900
gaggcgtgcc ggcagcggc gggggcgca gtgcacacga gggggctgga cttcgcctgt     960
gatatctaca tctgggcgcc cttggccggg acttgtgggg tccttctcct gtcactggtt   1020
atcacccttt actgcaaacg gggcagaaag aaactcctgt atatattcaa acaaccattt   1080
atgagaccag tacaaactac tcaagaggaa gatggctgta gctgccgatt tccagaagaa   1140
gaagaaggag gatgtgaact gagagtgaag ttcagcagga gcgcagacgc ccccgcgtac   1200
cagcagggcc agaaccagct ctataacgag ctcaatctag gacgaagaga ggagtacgat   1260
gttttggaca agagacgtgg ccgggaccct gagatggggg gaaagccgag aaggaagaac   1320
```

| | |
|---|---|
| cctcaggaag gcctgtacaa tgaactgcag aaagataaga tggcggaggc ctacagtgag | 1380 |
| attgggatga aaggcgagcg ccggaggggc aaggggcacg atggccttta ccagggtctc | 1440 |
| agtacagcca ccaaggacac ctacgacgcc cttcacatgc aggccctgcc ccctcgctaa | 1500 |

<210> SEQ ID NO 355
<211> LENGTH: 1515
<212> TYPE: DNA
<213> ORGANISM: Artificial Sequence
<220> FEATURE:
<223> OTHER INFORMATION: Synthetic Construct

<400> SEQUENCE: 355

| | |
|---|---|
| atggctctgc ccgtcaccgc tctgctgctg cctctggctc tgctgctgca cgctgctcgc | 60 |
| cctgaggtgc agctggtgga gtctggggga ggaatggtgc aggctgggga ctctctgaga | 120 |
| ctatcctgtg tgcagtctac ttacaccgtc aatagcgatg tcatgggctg gttccgccag | 180 |
| gctccaggga aggagcgtga gtttgtagga gcgattatgt ggaatgatgg tattacatac | 240 |
| ttgcaagact ccgtgaaggg ccgatttacc atcttcagac aacgccaa gaacacggtg | 300 |
| tatctgcaaa tgaacagcct gaaacttgag gatacggccg tttattactg tgcagcatcc | 360 |
| aagggtagat actcggaata tgagtactgg ggccagggga cccaggtcac cgtctcctca | 420 |
| ggaggaggag gatccggcgg aggaggctct ggcggcggcg gctccggcgg cggcggctcc | 480 |
| gcggtgcagc tggtggagtc tgggggagga ttggtgcagg ctggggactc tctgagactc | 540 |
| acctgtacag cctctggacg cgccttcagt acctatttca tggcctggtt ccgccaggct | 600 |
| ccagggaagg agcgtgagtt tgtagcagga attgcatgga gtggtggtag cacggcgtat | 660 |
| gcagactccg tgaagggccg attcaccatc tccagagaca acgccaagaa cacggtgtat | 720 |
| ctgcaaatga acagcctgaa atctgaggac acggccgttt attactgtgc cagcaggggg | 780 |
| attgaggtcg aagagtttgg tgcctggggc caggggaccc aggtcaccgt ctcgtcgact | 840 |
| agtaccacga cgccagcgcc gcgaccacca acaccggcgc ccaccatcgc gtcgcagccc | 900 |
| ctgtccctgc gcccagaggc gtgccggcca gcggcggggg gcgcagtgca cacgaggggg | 960 |
| ctggacttcg cctgtgatat ctacatctgg gcgcccttgg ccgggacttg tggggtcctt | 1020 |
| ctcctgtcac tggttatcac cctttactgc aaacgggca gaaagaaact cctgtatata | 1080 |
| ttcaaacaac catttatgag accagtacaa actactcaag aggaagatgg ctgtagctgc | 1140 |
| cgatttccag aagaagaaga aggaggatgt gaactgagag tgaagttcag caggagcgca | 1200 |
| gacgccccg cgtaccagca gggccagaac cagctctata cgagctcaa tctaggacga | 1260 |
| agagaggagt acgatgtttt ggacaagaga cgtggccggg accctgagat ggggggaaag | 1320 |
| ccgagaagga gaacccctca ggaaggcctg tacaatgaac tgcagaaaga taagatggcg | 1380 |
| gaggcctaca gtgagattgg gatgaaaggc gagcgccgga ggggcaaggg gcacgatggc | 1440 |
| ctttaccagg gtctcagtac agccaccaag gacacctacg acgcccttca catgcaggcc | 1500 |
| ctgcccctc gctaa | 1515 |

<210> SEQ ID NO 356
<211> LENGTH: 1479
<212> TYPE: DNA
<213> ORGANISM: Artificial Sequence
<220> FEATURE:
<223> OTHER INFORMATION: Synthetic Construct

<400> SEQUENCE: 356

| | |
|---|---|
| atggctctgc ccgtcaccgc tctgctgctg cctctggctc tgctgctgca cgctgctcgc | 60 |

```
cctcaggtaa agctggagga gtctgggga ggattggtgc aggctggggg ctctctgaga      120
ctctcctgtg cagcctctgg aggcacctta agtaagaata ccgtggcttg ggtccgccag      180
gctccaggga aggagcgtgg gtttgtaacg tctattacct gtgatggtcg tacgacatac      240
tatgcgaact ccgtaaacgg ccgattcccc atcaaccgaa acaacgccga gaatttggtg      300
gttttgcaaa tgaacagcct gaaacctgac gacacggccc tttattactg tgcagcatac      360
cggaagtcaa taatgtctat tcagcccgac tactggggcc aggggaccca ggtcaccgtc      420
tcctcaggag gaggaggatc tcaggtacag ctggtggagt ctgggggagg attggtgcag      480
gctgggggct ctctgagact ctcctgtgca gcctctggag gcaccttaag taaaaatacc      540
gtggcttggt ccgccaggc tccagggaag gagcgtgggt tgtagcgtc tattacctgg      600
gatggtcgta cgacatacta tgcagactcc gtgaagggcc gattcaccat ctccagagac      660
aacgccaaga acacagtgta tctgcaaatg aacagcctga acctgaggga tacggccgtt      720
tatgtctgtg cagacttagg gaatggcct gcgggcccgg cggactactg ggccagggg      780
acccaggtca ccgtctcctc aactagtacc acgacgccag cgccgcgacc accaacaccg      840
gcgcccacca tcgcgtcgca gcccctgtcc ctgcgcccag aggcgtgccg gccagcggcg      900
gggggcgcag tgcacacgag ggggctggac ttcgcctgtg atatctacat ctgggcgccc      960
ttggccggga cttgtggggt ccttctcctg tcactggtta tcaccttta ctgcaaacgg     1020
ggcagaaaga aactcctgta tatattcaaa caaccattta tgagaccagt acaaactact     1080
caagaggaag atggctgtag ctgccgattt ccagaagaag aagaaggagg atgtgaactg     1140
agagtgaagt tcagcaggag cgcagacgcc cccgcgtacc agcagggcca gaaccagctc     1200
tataacgagc tcaatctagg acgaagagag gagtacgatg ttttggacaa gagacgtggc     1260
cgggaccctg agatggggg aaagccgaga aggaagaacc ctcaggaagg cctgtacaat     1320
gaactgcaga agataagat ggcggaggcc tacagtgaga ttgggatgaa aggcgagcgc     1380
cggagggca aggggcacga tggcctttac cagggtctca gtacagccac caaggacacc     1440
tacgacgccc ttcacatgca ggccctgccc cctcgctaa                            1479
```

<210> SEQ ID NO 357
<211> LENGTH: 1509
<212> TYPE: DNA
<213> ORGANISM: Artificial Sequence
<220> FEATURE:
<223> OTHER INFORMATION: Synthetic Construct

<400> SEQUENCE: 357

```
atggctctgc ccgtcaccgc tctgctgctg cctctggctc tgctgctgca cgctgctcgc       60
cctcaggtaa agctggagga gtctgggga ggattggtgc aggctggggg ctctctgaga      120
ctctcctgtg cagcctctgg aggcacctta agtaagaata ccgtggcttg ggtccgccag      180
gctccaggga aggagcgtgg gtttgtaacg tctattacct gtgatggtcg tacgacatac      240
tatgcgaact ccgtaaacgg ccgattcccc atcaaccgaa acaacgccga gaatttggtg      300
gttttgcaaa tgaacagcct gaaacctgac gacacggccc tttattactg tgcagcatac      360
cggaagtcaa taatgtctat tcagcccgac tactggggcc aggggaccca ggtcaccgtc      420
tcctcaggag gaggaggatc tggaggagga ggaagcggag gaggaggatc ccaggtacag      480
ctggtggagt ctggggagg attggtgcag gctgggggct ctctgagact ctcctgtgca      540
gcctctggag gcaccttaag taaaaatacc gtggcttggt ccgccaggc tccagggaag      600
```

| | |
|---|---|
| gagcgtgggt tgtagcgtc tattacctgg gatggtcgta cgacatacta tgcagactcc | 660 |
| gtgaagggcc gattcaccat ctccagagac aacgccaaga acacagtgta tctgcaaatg | 720 |
| aacagcctga aacctgagga tacggccgtt tatgtctgtg cagacttagg gaaatggcct | 780 |
| gcgggcccgg cggactactg gggccagggg acccaggtca ccgtctcctc aactagtacc | 840 |
| acgacgccag cgccgcgacc accaacaccg gcgcccacca tcgcgtcgca gcccctgtcc | 900 |
| ctgcgcccag aggcgtgccg gccagcggcg ggggcgcag tgcacacgag ggggctggac | 960 |
| ttcgcctgtg atatctacat ctgggcgccc ttggccggga cttgtggggt ccttctcctg | 1020 |
| tcactggtta tcacccttta ctgcaaacgg ggcagaaaga aactcctgta tatattcaaa | 1080 |
| caaccattta tgagaccagt acaaactact caagaggaag atggctgtag ctgccgattt | 1140 |
| ccagaagaag aagaaggagg atgtgaactg agagtgaagt tcagcaggag cgcagacgcc | 1200 |
| cccgcgtacc agcagggcca gaaccagctc tataacgagc tcaatctagg acgaagagag | 1260 |
| gagtacgatg tttggacaa gagacgtggc cgggaccctg agatggggg aaagccgaga | 1320 |
| aggaagaacc tcaggaagg cctgtacaat gaactgcaga agataagat ggcggaggcc | 1380 |
| tacagtgaga ttgggatgaa aggcgagcgc cggaggggca aggggcacga tggcctttac | 1440 |
| cagggtctca gtacagccac caaggacacc tacgacgccc ttcacatgca ggccctgccc | 1500 |
| cctcgctaa | 1509 |

<210> SEQ ID NO 358
<211> LENGTH: 1539
<212> TYPE: DNA
<213> ORGANISM: Artificial Sequence
<220> FEATURE:
<223> OTHER INFORMATION: Synthetic Construct

<400> SEQUENCE: 358

| | |
|---|---|
| atggctctgc ccgtcaccgc tctgctgctg cctctggctc tgctgctgca cgctgctcgc | 60 |
| cctcaggtaa agctggagga gtctggggga ggattggtgc aggctggggg ctctctgaga | 120 |
| ctctcctgtg cagcctctgg aggcacctta agtaagaata ccgtggcttg ggtccgccag | 180 |
| gctccaggga aggagcgtgg gtttgtaacg tctattacct gtgatggtcg tacgacatac | 240 |
| tatgcgaact ccgtaaacgg ccgattcccc atcaaccgaa caacgccga gaatttggtg | 300 |
| gtttgcaaa tgaacagcct gaaacctgac gacacggccc tttattactg tgcagcatac | 360 |
| cggaagtcaa taatgtctat tcagcccgac tactggggcc aggggaccca ggtcaccgtc | 420 |
| tcctcaggag gaggaggatc tggaggagga ggaagcggag gaggaggaag cggcggcggc | 480 |
| ggctctggcg gcggcggcag ccaggtacag ctggtggagt ctgggggagg attggtgcag | 540 |
| gctgggggct ctctgagact ctcctgtgca gcctctggag gcaccttaag taaaaatacc | 600 |
| gtggcttggt tccgccaggc tccagggaag gagcgtgggt ttgtagcgtc tattacctgg | 660 |
| gatggtcgta cgacatacta tgcagactcc gtgaagggcc gattcaccat ctccagagac | 720 |
| aacgccaaga acacagtgta tctgcaaatg aacagcctga aacctgagga tacggccgtt | 780 |
| tatgtctgtg cagacttagg gaaatggcct gcgggcccgg cggactactg gggccagggg | 840 |
| acccaggtca ccgtctcctc aactagtacc acgacgccag cgccgcgacc accaacaccg | 900 |
| gcgcccacca tcgcgtcgca gcccctgtcc ctgcgcccag aggcgtgccg gccagcggcg | 960 |
| ggggcgcag tgcacacgag ggggctggac ttcgcctgtg atatctacat ctgggcgccc | 1020 |
| ttggccggga cttgtggggt ccttctcctg tcactggtta tcacccttta ctgcaaacgg | 1080 |
| ggcagaaaga aactcctgta tatattcaaa caaccattta tgagaccagt acaaactact | 1140 |

| | |
|---|---|
| caagaggaag atggctgtag ctgccgattt ccagaagaag aagaaggagg atgtgaactg | 1200 |
| agagtgaagt tcagcaggag cgcagacgcc cccgcgtacc agcagggcca gaaccagctc | 1260 |
| tataacgagc tcaatctagg acgaagagag gagtacgatg ttttggacaa gagacgtggc | 1320 |
| cgggaccctg agatggggg aaagccgaga aggaagaacc ctcaggaagg cctgtacaat | 1380 |
| gaactgcaga agataagat ggcggaggcc tacagtgaga ttgggatgaa aggcgagcgc | 1440 |
| cggaggggca aggggcacga tggcctttac cagggtctca gtacagccac caaggacacc | 1500 |
| tacgacgccc ttcacatgca ggccctgccc cctcgctaa | 1539 |

<210> SEQ ID NO 359
<211> LENGTH: 1494
<212> TYPE: DNA
<213> ORGANISM: Artificial Sequence
<220> FEATURE:
<223> OTHER INFORMATION: Synthetic Construct

<400> SEQUENCE: 359

| | |
|---|---|
| atggctctgc ccgtcaccgc tctgctgctg cctctggctc tgctgctgca cgctgctcgc | 60 |
| cctcaggtaa agctggagga gtctggggga ggattggtgc aggctggggg ctctctgaga | 120 |
| ctctcctgtg cagcctctgg aggcacctta agtaagaata ccgtggcttg ggtccgccag | 180 |
| gctccaggga aggagcgtgg gtttgtaacg tctattacct gtgatggtcg tacgacatac | 240 |
| tatgcgaact ccgtaaacgg ccgattcccc atcaaccgaa caacgccga gatttggtg | 300 |
| gttttgcaaa tgaacagcct gaaacctgac gacacggccc tttattactg tgcagcatac | 360 |
| cggaagtcaa taatgtctat tcagcccgac tactggggcc aggggaccca ggtcaccgtc | 420 |
| tcctcaggag gaggaggatc cggcggagga ggctctcagg tacagctggt ggagtctggg | 480 |
| ggaggattgg tgcaggctgg gggctctctg agactctcct gtgcagcctc tggaggcacc | 540 |
| ttaagtaaaa ataccgtggc ttggttccgc caggctccag gaaggagcg tgggtttgta | 600 |
| gcgtctatta cctgggatgg tcgtacgaca tactatgcag actccgtgaa gggccgattc | 660 |
| accatctcca gagacaacgc caagaacaca gtgtatctgc aaatgaacag cctgaaacct | 720 |
| gaggatacgg ccgtttatgt ctgtgcagac ttagggaaat ggcctgcggg cccggcggac | 780 |
| tactggggcc aggggaccca ggtcaccgtc tcctcaacta gtaccacgac gccagcgccg | 840 |
| cgaccaccaa caccggcgcc caccatcgcg tcgcagcccc tgtccctgcg cccagaggcg | 900 |
| tgccggccag cggcgggggg cgcagtgcac acgaggggc tggacttcgc ctgtgatatc | 960 |
| tacatctggg cgcccttggc cgggacttgt ggggtccttc tcctgtcact ggttatcacc | 1020 |
| ctttactgca acggggcag aaagaaactc ctgtatatat tcaaacaacc atttatgaga | 1080 |
| ccagtacaaa ctactcaaga ggaagatggc tgtagctgcc gatttccaga agaagaagaa | 1140 |
| ggaggatgtg aactgagagt gaagttcagc aggagcgcag acgccccgc gtaccagcag | 1200 |
| ggccagaacc agctctataa cgagctcaat ctaggacgaa gagaggagta cgatgttttg | 1260 |
| gacaagagac gtggccggga ccctgagatg ggggaaagc cgagaaggaa gaaccctcag | 1320 |
| gaaggcctgt acaatgaact gcagaaagat aagatggcgg aggcctacag tgagattggg | 1380 |
| atgaaaggcg agcgccggag gggcaagggg cacgatggcc tttaccaggg tctcagtaca | 1440 |
| gccaccaagg acacctacga cgcccttcac atgcaggccc tgcccctcg ctaa | 1494 |

<210> SEQ ID NO 360
<211> LENGTH: 1509
<212> TYPE: DNA

<213> ORGANISM: Artificial Sequence
<220> FEATURE:
<223> OTHER INFORMATION: Synthetic Construct

<400> SEQUENCE: 360

```
atggctctgc cgtcaccgc tctgctgctg cctctggctc tgctgctgca cgctgctcgc      60
cctcaggtaa agctggagga gtctggggga ggattggtgc aggctggggg ctctctgaga     120
ctctcctgtg cagcctctgg aggcacctta agtaagaata ccgtggcttg ggtccgccag     180
gctccaggga aggagcgtgg gtttgtaacg tctattacct gtgatggtcg tacgacatac     240
tatgcgaact ccgtaaacgg ccgattcccc atcaaccgaa acaacgccga gaatttggtg     300
gttttgcaaa tgaacagcct gaaacctgac gacacggccc tttattactg tgcagcatac     360
cggaagtcaa taatgtctat tcagcccgac tactggggcc aggggaccca ggtcaccgtc     420
tcctcaggag gaggaggatc cggcggagga ggctctggcg gcggcggcag ccaggtacag     480
ctggtggagt ctgggggagg attggtgcag gctgggggct ctctgagact ctcctgtgca     540
gcctctggag gcaccttaag taaaaatacc gtggcttggt ccgccaggc tccagggaag     600
gagcgtgggt ttgtagcgtc tattacctgg gatggtcgta cgacatacta tgcagactcc     660
gtgaagggcc gattcaccat ctccagagac aacgccaaga cacagtgta tctgcaaatg     720
aacagcctga acctgagga tacggccgtt tatgtctgtg cagacttagg gaaatggcct     780
gcgggccccg cggactactg gggccagggg acccaggtca ccgtctcctc aactagtacc     840
acgacgccag cgccgcgacc accaacaccg gcgcccacca tcgcgtcgca gcccctgtcc     900
ctgcgcccag aggcgtgccg gccagcggcg ggggcgcag tgcacacgag ggggctggac     960
ttcgcctgtg atatctacat ctgggcgccc ttggccggga cttgtggggt ccttctcctg    1020
tcactggtta tcacccttta ctgcaaacgg ggcagaaaga aactcctgta tatattcaaa    1080
caaccattta tgagaccagt acaaactact caagaggaag atggctgtag ctgccgattt    1140
ccagaagaag aagaaggagg atgtgaactg agagtgaagt tcagcaggag cgcagacgcc    1200
cccgcgtacc agcagggcca gaaccagctc tataacgagc tcaatctagg acgaagagag    1260
gagtacgatg ttttggacaa gagacgtggc cgggaccctg agatgggggg aaagccgaga    1320
aggaagaacc ctcaggaagg cctgtacaat gaactgcaga agataagat ggcggaggcc    1380
tacagtgaga ttgggatgaa aggcgagcgc cggaggggca aggggcacga tggcctttac    1440
cagggtctca gtacagccac caaggacacc tacgacgccc ttcacatgca ggccctgccc    1500
cctcgctaa                                                             1509
```

<210> SEQ ID NO 361
<211> LENGTH: 1524
<212> TYPE: DNA
<213> ORGANISM: Artificial Sequence
<220> FEATURE:
<223> OTHER INFORMATION: Synthetic Construct

<400> SEQUENCE: 361

```
atggctctgc cgtcaccgc tctgctgctg cctctggctc tgctgctgca cgctgctcgc      60
cctcaggtaa agctggagga gtctggggga ggattggtgc aggctggggg ctctctgaga     120
ctctcctgtg cagcctctgg aggcacctta agtaagaata ccgtggcttg ggtccgccag     180
gctccaggga aggagcgtgg gtttgtaacg tctattacct gtgatggtcg tacgacatac     240
tatgcgaact ccgtaaacgg ccgattcccc atcaaccgaa acaacgccga gaatttggtg     300
gttttgcaaa tgaacagcct gaaacctgac gacacggccc tttattactg tgcagcatac     360
```

```
cggaagtcaa taatgtctat tcagcccgac tactggggcc aggggaccca ggtcaccgtc    420
tcctcaggag gaggaggatc cggcggagga ggctctggcg gcggcggctc cggcggcggc    480
ggctcccagg tacagctggt ggagtctggg ggaggattgg tgcaggctgg gggctctctg    540
agactctcct gtgcagcctc tggaggcacc ttaagtaaaa ataccgtggc ttggttccgc    600
caggctccag ggaaggagcg tgggtttgta gcgtctatta cctgggatgg tcgtacgaca    660
tactatgcag actccgtgaa gggccgattc accatctcca gagacaacgc caagaacaca    720
gtgtatctgc aaatgaacag cctgaaacct gaggatacgg ccgtttatgt ctgtgcagac    780
ttagggaaat ggcctgcggg cccggcggac tactggggcc aggggaccca ggtcaccgtc    840
tcctcaacta gtaccacgac gccagcgccg cgaccaccaa caccggcgcc caccatcgcg    900
tcgcagcccc tgtccctgcg cccagaggcg tgccggccag cggcggggg cgcagtgcac     960 acgagggggc tggacttcgc ctgtgatatc tacatctggg cgcccttggc cgggacttgt   1020
ggggtccttc tcctgtcact ggttatcacc ctttactgca acggggcag aaagaaactc    1080 ctgtatatat tcaaacaacc atttatgaga ccagtacaaa ctactcaaga ggaagatggc   1140
tgtagctgcc gatttccaga agaagaagaa ggaggatgtg aactgagagt gaagttcagc   1200
aggagcgcag acgcccccgc gtaccagcag ggccagaacc agctctataa cgagctcaat   1260
ctaggacgaa gagaggagta cgatgttttg gacaagagac gtggccggga ccctgagatg   1320
gggggaaagc cgagaaggaa gaaccctcag gaaggcctgt acaatgaact gcagaaagat   1380
aagatggcgg aggcctacag tgagattggg atgaaaggcg agcgccggag gggcaagggg   1440
cacgatggcc tttaccaggg tctcagtaca gccaccaagg acacctacga cgcccttcac   1500
atgcaggccc tgccccctcg ctaa                                          1524
```

<210> SEQ ID NO 362
<211> LENGTH: 1476
<212> TYPE: DNA
<213> ORGANISM: Artificial Sequence
<220> FEATURE:
<223> OTHER INFORMATION: Synthetic Construct

<400> SEQUENCE: 362

```
atggctctgc ccgtcaccgc tctgctgctg cctctggctc tgctgctgca cgctgctcgc     60
cctcaggtac agctggtgga gtctgggga ggattggtgc aggctggggg ctctctgaga    120
ctctcctgtg cagcctctgg aggcacctta agtaaaaata ccgtggcttg gttccgccag    180
gctccaggga aggagcgtgg gtttgtagcg tctattacct gggatggtcg tacgacatac    240
tatgcagact ccgtgaaggg ccgattcacc atctccagag acaacgccaa gaacacagtg    300
tatctgcaaa tgaacagcct gaaacctgag gatacggcct ttatgtctg tgcagactta    360 gggaaatggc ctgcgggccc ggcggactac tggggccagg gacccaggt caccgtctcc     420 tcaggaggag gaggatctga tgtgcagctg gtggagtctg gggaggatt ggtgcaggct    480 ggggctctc tgagactctc ctgtgcagcc tctggaggca ccttaagtaa gataccgtg    540 gcttgggtcc gccaggctcc agggaaggag cgtgggtttg taacgtctat tacctgtgat    600
ggtcgtacga catactatgc gaactccgtg aagggccgat tccccatctc cagagacaac    660
gccgagaaca cagtgtatct gcaaatgaac agcctgaaac ctgaggatac ggccggttat    720
gtctgtgcag acttagggaa gtggcctgcg ggttcgcgg actactgggg ccaggggacc    780
cacgtcaccg tctcctccac tagtaccacg acgccagcgc cgcgaccacc aacaccggcg    840
```

| | |
|---|---|
| cccaccatcg cgtcgcagcc cctgtccctg cgcccagagg cgtgccggcc agcggcgggg | 900 |
| ggcgcagtgc acacgagggg gctggacttc gcctgtgata tctacatctg ggcgcccttg | 960 |
| gccgggactt gtggggtcct tctcctgtca ctggttatca cccttttactg caaacggggc | 1020 |
| agaaagaaac tcctgtatat attcaaacaa ccatttatga gaccagtaca aactactcaa | 1080 |
| gaggaagatg gctgtagctg ccgatttcca gaagaagaag aaggaggatg tgaactgaga | 1140 |
| gtgaagttca gcaggagcgc agacgccccc gcgtaccagc agggccagaa ccagctctat | 1200 |
| aacgagctca atctaggacg aagagaggag tacgatgttt tggacaagag acgtggccgg | 1260 |
| gacccctgaga tgggggggaaa gccgagaagg aagaaccctc aggaaggcct gtacaatgaa | 1320 |
| ctgcagaaag ataagatggc ggaggcctac agtgagattg gatgaaaagg cgagcgccgg | 1380 |
| aggggcaagg ggcacgatgg cctttaccag ggtctcagta cagccaccaa ggacacctac | 1440 |
| gacgcccttc acatgcaggc cctgcccct cgctaa | 1476 |

<210> SEQ ID NO 363
<211> LENGTH: 1506
<212> TYPE: DNA
<213> ORGANISM: Artificial Sequence
<220> FEATURE:
<223> OTHER INFORMATION: Synthetic Construct

<400> SEQUENCE: 363

| | |
|---|---|
| atggctctgc ccgtcaccgc tctgctgctg cctctggctc tgctgctgca cgctgctcgc | 60 |
| cctcaggtac agctggtgga gtctggggga ggattggtgc aggctggggg ctctctgaga | 120 |
| ctctcctgtg cagcctctgg aggcacctta agtaaaaata ccgtggcttg gttccgccag | 180 |
| gctccaggga aggagcgtgg gtttgtagcg tctattacct gggatggtcg tacgacatac | 240 |
| tatgcagact ccgtgaaggg ccgattcacc atctccagag acaacgccaa gaacacagtg | 300 |
| tatctgcaaa tgaacagcct gaaacctgag gatacggccg tttatgtctg tgcagactta | 360 |
| gggaaatggc ctgcgggccc ggcggactac tggggccagg ggacccaggt caccgtctcc | 420 |
| tcaggaggag gaggatctgg aggaggagga agcggaggag gaggatccga tgtgcagctg | 480 |
| gtggagtctg ggggaggatt ggtgcaggct ggggggctctc tgagactctc ctgtgcagcc | 540 |
| tctggaggca ccttaagtaa aataccgtg gcttgggtcc gccaggctcc agggaaggag | 600 |
| cgtgggtttg taacgtctat tacctgtgat ggtcgtacga catactatgc gaactccgtg | 660 |
| aagggccgat tccccatctc cagagacaac gccgagaaca cagtgtatct gcaaatgaac | 720 |
| agcctgaaac ctgaggatac ggccggttat gtctgtgcag acttagggaa gtggcctgcg | 780 |
| ggttcggcgg actactgggg ccaggggacc cacgtcaccg tctcctccac tagtaccacg | 840 |
| acgccagcgc cgccgaccac caacaccggcg cccaccatcg cgtcgcagcc cctgtccctg | 900 |
| cgcccagagg cgtgccggcc agcggcgggg ggcgcagtgc acacgagggg gctggacttc | 960 |
| gcctgtgata tctacatctg ggcgcccttg gccgggactt gtggggtcct tctcctgtca | 1020 |
| ctggttatca cccttttactg caaacggggc agaaagaaac tcctgtatat attcaaacaa | 1080 |
| ccatttatga gaccagtaca aactactcaa gaggaagatg gctgtagctg ccgatttcca | 1140 |
| gaagaagaag aaggaggatg tgaactgaga gtgaagttca gcaggagcgc agacgccccc | 1200 |
| gcgtaccagc agggccagaa ccagctctat aacgagctca atctaggacg aagagaggag | 1260 |
| tacgatgttt tggacaagag acgtggccgg gacccctgaga tgggggggaaa gccgagaagg | 1320 |
| aagaaccctc aggaaggcct gtacaatgaa ctgcagaaag ataagatggc ggaggcctac | 1380 |
| agtgagattg gatgaaaagg cgagcgccgg aggggcaagg ggcacgatgg cctttaccag | 1440 |

```
ggtctcagta cagccaccaa ggacacctac gacgcccttc acatgcaggc cctgcccect    1500 cgctaa                                                               1506
```

<210> SEQ ID NO 364
<211> LENGTH: 1536
<212> TYPE: DNA
<213> ORGANISM: Artificial Sequence
<220> FEATURE:
<223> OTHER INFORMATION: Synthetic Construct

<400> SEQUENCE: 364

```
atggctctgc cgtcaccgc tctgctgctg cctctggctc tgctgctgca cgctgctcgc      60
cctcaggtac agctggtgga gtctggggga ggattggtgc aggctggggg ctctctgaga    120
ctctcctgtg cagcctctgg aggcaccta agtaaaaata ccgtggcttg gttccgccag    180
gctccaggga aggagcgtgg gtttgtagcg tctattacct gggatggtcg tacgacatac    240
tatgcagact ccgtgaaggg ccgattcacc atctccagag acaacgccaa gaacacagtg    300
tatctgcaaa tgaacagcct gaaacctgag gatacggccg tttatgtctg tgcagactta    360
gggaaatggc ctgcgggccc ggcggactac tggggccagg ggacccaggt caccgtctcc    420
tcaggaggag gaggatctgg aggaggagga agcggaggag gaggaagcgg cggcggcggc    480
tctggcggcg gcggcagcga tgtgcagctg gtggagtctg ggggaggatt ggtgcaggct    540
gggggctctc tgagactctc ctgtgcagcc tctggaggca ccttaagtaa gaataccgtg    600
gcttgggtcc gccaggctcc agggaaggag cgtgggttg taacgtctat tacctgtgat    660
ggtcgtacga catactatgc gaactccgtg aagggccgat tccccatctc cagagacaac    720
gccgagaaca cagtgtatct gcaaatgaac agcctgaaac ctgaggatac ggccggttat    780
gtctgtgcag acttagggaa gtggcctgcg gttcggcgg actactgggg ccaggggacc    840
cacgtcaccg tctcctccac tagtaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg gcgcccctg    1020 gccgggactt gtgggtcct tctcctgtca ctggttatca ccctttactg caaacggggc    1080
agaaagaaac tcctgtatat attcaaacaa ccatttatga ccagtacaa actactcaa    1140 gaggaagatg gctgtagctg ccgatttcca gaagaagaag aaggaggatg tgaactgaga    1200
gtgaagttca gcaggagcgc agacgccccc gcgtaccagc agggccagaa ccagctctat    1260
aacgagctca atctaggacg aagagaggag tacgatgttt tggacaagag acgtggccgg    1320
gaccctgaga tgggggaaaa gccgagaagg aagaaccctc aggaaggcct gtacaatgaa    1380
ctgcagaaag ataagatggc ggaggcctac agtgagattg gatgaaagg cgagcgccgg    1440 aggggcaagg ggcacgatgg cctttaccag ggtctcagta cagccaccaa ggacacctac    1500
gacgcccttc acatgcaggc cctgcccect cgctaa                             1536
```

<210> SEQ ID NO 365
<211> LENGTH: 1491
<212> TYPE: DNA
<213> ORGANISM: Artificial Sequence
<220> FEATURE:
<223> OTHER INFORMATION: Synthetic Construct

<400> SEQUENCE: 365

```
atggctctgc cgtcaccgc tctgctgctg cctctggctc tgctgctgca cgctgctcgc      60
```

```
cctcaggtac agctggtgga gtctggggga ggattggtgc aggctggggg ctctctgaga    120
ctctcctgtg cagcctctgg aggcacctta agtaaaaata ccgtggcttg gttccgccag    180
gctccaggga aggagcgtgg gtttgtagcg tctattacct gggatggtcg tacgacatac    240
tatgcagact ccgtgaaggg ccgattcacc atctccagag acaacgccaa gaacacagtg    300
tatctgcaaa tgaacagcct gaaacctgag gatacggccg tttatgtctg tgcagactta    360
gggaaatggc ctgcgggccc ggcggactac tggggccagg gacccaggt caccgtctcc    420
tcaggaggag gaggatccgg cggaggaggc tctgatgtgc agctggtgga gtctggggga    480
ggattggtgc aggctggggg ctctctgaga ctctcctgtg cagcctctgg aggcacctta    540
agtaagaata ccgtggcttg gtccgccag gctccaggga aggagcgtgg gtttgtaacg    600
tctattacct gtgatggtcg tacgacatac tatgcgaact ccgtgaaggg ccgattcccc    660
atctccagag acaacgccga gaacacagtg tatctgcaaa tgaacagcct gaaacctgag    720
gatacggccg ttatgtctg tgcagactta gggaagtggc ctgcgggttc ggcggactac    780
tggggccagg gacccacgt caccgtctcc tccactagta ccacgacgcc agcgccgcga    840
ccaccaacac cggcgcccac catcgcgtcg cagcccctgt ccctgcgccc agaggcgtgc    900
cggccagcgc cggggggcgc agtgcacacg aggggctgg acttcgcctg tgatatctac    960
atctgggcgc ccttggccgg gacttgtggg gtccttctcc tgtcactggt tatcaccctt   1020
tactgcaaac ggggcagaaa gaaactcctg tatatattca acaaccatt tatgagacca   1080
gtacaaacta ctcaagagga agatggctgt agctgccgat tccagaaga agaagaagga   1140
ggatgtgaac tgagagtgaa gttcagcagg agcgcagacg cccccgcgta ccagcagggc   1200
cagaaccagc tctataacga gctcaatcta ggacgaagag aggagtacga tgttttggac   1260
aagagacgtg gccgggaccc tgagatgggg ggaaagccga aaggaagaa ccctcaggaa   1320
ggcctgtaca atgaactgca gaaagataag atggcggagg cctacagtga gattgggatg   1380
aaaggcgagc gccggagggg caaggggcac gatggccttt accagggtct cagtacagcc   1440
accaaggaca cctacgacgc ccttcacatg caggccctgc cccctcgcta a           1491
```

<210> SEQ ID NO 366
<211> LENGTH: 1506
<212> TYPE: DNA
<213> ORGANISM: Artificial Sequence
<220> FEATURE:
<223> OTHER INFORMATION: Synthetic Construct

<400> SEQUENCE: 366

```
atggctctgc ccgtcaccgc tctgctgctg cctctggctc tgctgctgca cgctgctcgc     60
cctcaggtac agctggtgga gtctggggga ggattggtgc aggctggggg ctctctgaga    120
ctctcctgtg cagcctctgg aggcacctta agtaaaaata ccgtggcttg gttccgccag    180
gctccaggga aggagcgtgg gtttgtagcg tctattacct gggatggtcg tacgacatac    240
tatgcagact ccgtgaaggg ccgattcacc atctccagag acaacgccaa gaacacagtg    300
tatctgcaaa tgaacagcct gaaacctgag gatacggccg tttatgtctg tgcagactta    360
gggaaatggc ctgcgggccc ggcggactac tggggccagg gacccaggt caccgtctcc    420
tcaggaggag gaggatccgg cggaggaggc tctgcggcg gcggcagcga tgtgcagctg    480
gtggagtctg ggggaggatt ggtgcaggct ggggctctc tgagactctc ctgtgcagcc    540
tctggaggca ccttaagtaa gaataccgtg gcttgggtcc gccaggctcc agggaaggag    600
cgtgggtttg taacgtctat tacctgtgat ggtcgtacga catactatgc gaactccgtg    660
```

```
aagggccgat tccccatctc cagagacaac gccgagaaca cagtgtatct gcaaatgaac      720
agcctgaaac ctgaggatac ggccggttat gtctgtgcag acttagggaa gtggcctgcg      780
ggttcggcgg actactgggg ccaggggacc cacgtcaccg tctcctccac tagtaccacg      840
acgccagcgc cgcgaccacc aacaccggcg cccaccatcg cgtcgcagcc cctgtccctg      900
cgcccagagg cgtgccggcc agcggcgggg ggcgcagtgc acacgagggg gctggacttc      960
gcctgtgata tctacatctg gcgcccttg gccgggactt gtggggtcct tctcctgtca     1020
ctggttatca ccctttactg caaacggggc agaagaaac tcctgtatat attcaaacaa     1080
ccatttatga gaccagtaca aactactcaa gaggaagatg gctgtagctg ccgatttcca     1140
gaagaagaag aaggaggatg tgaactgaga gtgaagttca gcaggagcgc agacgccccc     1200
gcgtaccagc agggccagaa ccagctctat aacgagctca atctaggacg aagagaggag     1260
tacgatgttt tggacaagag acgtggccgg gaccctgaga tgggggggaaa gccgagaagg     1320 aagaaccctc aggaaggcct gtacaatgaa ctgcagaaag ataagatggc ggaggcctac     1380
agtgagattg ggatgaaagg cgagcgccgg aggggcaagg ggcacgatgg cctttaccag     1440
ggtctcagta cagccaccaa ggacacctac gacgcccttc acatgcaggc cctgccccct     1500
cgctaa                                                                1506
```

<210> SEQ ID NO 367
<211> LENGTH: 1521
<212> TYPE: DNA
<213> ORGANISM: Artificial Sequence
<220> FEATURE:
<223> OTHER INFORMATION: Synthetic Construct

<400> SEQUENCE: 367

```
atggctctgc ccgtcaccgc tctgctgctg cctctggctc tgctgctgca cgctgctcgc       60
cctcaggtac agctggtgga gtctggggga ggattggtgc aggctggggg ctctctgaga      120
ctctcctgtg cagcctctgg aggcacctta agtaaaaata ccgtggcttg gttccgccag      180
gctccaggga aggagcgtgg gtttgtagcg tctattacct gggatggtcg tacgacatac      240
tatgcagact ccgtgaaggg ccgattcacc atctccagag acaacgccaa gaacacagtg      300
tatctgcaaa tgaacagcct gaaacctgag gatacggccg tttatgtctg tgcagactta      360
gggaaatggc ctgcgggccc ggcggactac tggggccagg ggacccaggt caccgtctcc      420
tcaggaggag aggatccggc ggaggaggc tctggcggcg cggctccgg cggcggcggc      480 tccgatgtgc agctggtgga gtctggggga ggattggtgc aggctggggg ctctctgaga      540
ctctcctgtg cagcctctgg aggcacctta agtaagaata ccgtggcttg ggtccgccag      600
gctccaggga aggagcgtgg gtttgtaacg tctattacct gtgatggtcg tacgacatac      660
tatgcgaact ccgtgaaggg ccgattcccc atctccagag acaacgccga gaacacagtg      720
tatctgcaaa tgaacagcct gaaacctgag gatacggccg ttatgtctg tgcagactta      780 gggaagtggc ctgcgggttc ggcggactac tggggccagg gaccacgt caccgtctcc      840 tccactagta ccacgacgcc agcgccgcga ccaccaacac cggcgcccac catcgcgtcg      900
cagcccctgt ccctgcgccc agaggcgtgc cggcagcgg cggggggcgc agtgcacacg      960
agggggctgg acttcgcctg tgatatctac atctgggcgc ccttggccgg gacttgtggg     1020
gtccttctcc tgtcactggt tatcaccctt tactgcaaac ggggcagaaa gaaactcctg     1080
tatatattca aacaaccatt tatgagacca gtacaaacta ctcaagagga agatggctgt     1140
```

| agctgccgat | ttccagaaga | agaagaagga | ggatgtgaac | tgagagtgaa | gttcagcagg | 1200 |
| agcgcagacg | cccccgcgta | ccagcagggc | cagaaccagc | tctataacga | gctcaatcta | 1260 |
| ggacgaagag | aggagtacga | tgttttggac | aagagacgtg | gccgggaccc | tgagatgggg | 1320 |
| ggaaagccga | gaaggaagaa | ccctcaggaa | ggcctgtaca | atgaactgca | gaaagataag | 1380 |
| atggcggagg | cctacagtga | gattgggatg | aaaggcgagc | gccggagggg | caaggggcac | 1440 |
| gatggccttt | accagggtct | cagtacagcc | accaaggaca | cctacgacgc | ccttcacatg | 1500 |
| caggccctgc | cccctcgcta | a | | | | 1521 |

<210> SEQ ID NO 368
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 368

| atggctctgc | ccgtcaccgc | tctgctgctg | cctctggctc | tgctgctgca | cgctgctcgc | 60 |
| cctgatgtgc | agctggtgga | gtctggggga | ggattggtgc | aggctggggg | ctctctgaga | 120 |
| ctctcctgtg | cagcctctgg | aggcacctta | agtaagaata | ccgtggcttg | ggtccgccag | 180 |
| gctccaggga | aggagcgtgg | gtttgtaacg | tctattacct | gtgatggtcg | tacgacatac | 240 |
| tatgcgaact | ccgtgaaggg | ccgattcccc | atctccagag | acaacgccga | gaacacagtg | 300 |
| tatctgcaaa | tgaacagcct | gaaacctgag | gatacggccg | ttatgtctg | tgcagactta | 360 |
| gggaagtggc | ctgcgggttc | ggcggactac | tggggccagg | ggacccacgt | caccgtctcc | 420 |
| tccggaggag | gaggatctga | tgtgcagctg | gtggagtctg | ggggaggctt | ggtgcagcct | 480 |
| ggggggtctc | tgagactctc | ctgtgcagcc | tctggacgga | ccttcagtag | cattgtcatg | 540 |
| ggctggttcc | gccaggctcc | agggaaggag | cgtgagtttg | taggagcgat | tatgtggaat | 600 |
| gatggtatta | catacttgca | agactccgtg | aagggccgat | ttaccatctt | cagagacaac | 660 |
| gccaagaaca | cggtgtatct | gcaaatgaac | agcctgaaac | ttgaggatac | ggccgtttat | 720 |
| tactgtgcag | catccaaggg | tagatactcg | gaatatgagt | actggggcca | ggggacccag | 780 |
| gtcaccgtct | cctcaactag | taccacgacg | ccagcgccgc | gaccaccaac | accggcgccc | 840 |
| accatcgcgt | cgcagcccct | gtccctgcgc | ccagaggcgt | gccggccagc | ggcgggggc | 900 |
| gcagtgcaca | cgagggggct | ggacttcgcc | tgtgatatct | acatctgggc | gcccttggcc | 960 |
| gggacttgtg | ggtccttct | cctgtcactg | gttatcaccc | tttactgcaa | cgggcagaa | 1020 |
| aagaaactcc | tgtatatatt | caaacaacca | tttatgagac | cagtacaaac | tactcaagag | 1080 |
| gaagatggct | gtagctgccg | atttccagaa | gaagaagaag | gaggatgtga | actgagagtg | 1140 |
| aagttcagca | ggagcgcaga | cgcccccgcg | taccagcagg | gccagaacca | gctctataac | 1200 |
| gagctcaatc | taggacgaag | agaggagtac | gatgttttgg | acaagagacg | tggccgggac | 1260 |
| cctgagatgg | ggggaaagcc | gagaaggaag | aaccctcagg | aaggcctgta | caatgaactg | 1320 |
| cagaaagata | agatggcgga | ggcctacagt | gagattggga | tgaaaggcga | gcgccggagg | 1380 |
| ggcaaggggc | acgatggcct | ttaccagggt | ctcagtacag | ccaccaagga | cacctacgac | 1440 |
| gcccttcaca | tgcaggccct | gccccctcgc | taa | | | 1473 |

<210> SEQ ID NO 369
<211> LENGTH: 1503
<212> TYPE: DNA
<213> ORGANISM: Artificial Sequence
<220> FEATURE:
<223> OTHER INFORMATION: Synthetic Construct

<400> SEQUENCE: 369

```
atggctctgc ccgtcaccgc tctgctgctg cctctggctc tgctgctgca cgctgctcgc    60
cctgatgtgc agctggtgga gtctggggga ggattggtgc aggctggggg ctctctgaga   120
ctctcctgtg cagcctctgg aggcacctta agtaagaata ccgtggcttg gtccgccag    180
gctccaggga aggagcgtgg gtttgtaacg tctattacct gtgatggtcg tacgacatac   240
tatgcgaact ccgtgaaggg ccgattcccc atctccagag acaacgccga gaacacagtg   300
tatctgcaaa tgaacagcct gaaacctgag gatacggccg ttatgtctg tgcagactta    360
gggaagtggc ctgcgggttc ggcggactac tggggccagg gacccacgt caccgtctcc    420
tccggaggag gaggatctgg aggaggagga gcggaggag gaggatccga tgtgcagctg    480
gtggagtctg ggggaggctt ggtgcagcct gggggtctc tgagactctc ctgtgcagcc   540
tctgacgga ccttcagtag cattgtcatg ggctggttcc gccaggctcc agggaaggag    600
cgtgagtttg taggagcgat tatgtggaat gatggtatta catacttgca agactccgtg   660
aagggccgat ttaccatctt cagagacaac gccaagaaca cggtgtatct gcaaatgaac   720
agcctgaaac ttgaggatac ggccgtttat tactgtgcag catccaaggg tagatactcg   780
gaatatgagt actggggcca ggggacccag gtcaccgtct cctcaactag taccacgacg   840
ccagcgccgc gaccaccaac accggcgccc accatcgcgt cgcagcccct gtccctgcgc   900
ccagaggcgt gccggccagc ggcggggggc gcagtgcaca cgaggggct ggacttcgcc    960
tgtgatatct acatctgggc gcccttggcc gggacttgtg gggtccttct cctgtcactg  1020
gttatcaccc tttactgcaa acggggcaga aagaaactcc tgtatatatt caaacaacca  1080
tttatgagac cagtacaaac tactcaagag gaagatggct gtagctgccg atttccagaa  1140
gaagaagaag aggatgtgaa actgagagtg aagttcagca ggagcgcaga cgcccccgcg  1200
taccagcagg gccagaacca gctctataac gagctcaatc taggacgaag agaggagtac  1260
gatgttttgg acaagagacg tggccgggac cctgagatgg ggggaaagcc gagaaggaag  1320
aaccctcagg aaggcctgta caatgaactg cagaaagata gatggcgga ggcctacagt   1380
gagattggga tgaaaggcga gcgccggagg ggcaagggc acgatggcct ttaccagggt  1440
ctcagtacag ccaccaagga cacctacgac gcccttcaca tgcaggccct gccccctcgc  1500
taa                                                                 1503
```

<210> SEQ ID NO 370
<211> LENGTH: 1533
<212> TYPE: DNA
<213> ORGANISM: Artificial Sequence
<220> FEATURE:
<223> OTHER INFORMATION: Synthetic Construct

<400> SEQUENCE: 370

```
atggctctgc ccgtcaccgc tctgctgctg cctctggctc tgctgctgca cgctgctcgc    60
cctgatgtgc agctggtgga gtctggggga ggattggtgc aggctggggg ctctctgaga   120
ctctcctgtg cagcctctgg aggcacctta agtaagaata ccgtggcttg gtccgccag    180
gctccaggga aggagcgtgg gtttgtaacg tctattacct gtgatggtcg tacgacatac   240
tatgcgaact ccgtgaaggg ccgattcccc atctccagag acaacgccga gaacacagtg   300
tatctgcaaa tgaacagcct gaaacctgag gatacggccg ttatgtctg tgcagactta    360
```

```
gggaagtggc ctgcgggttc ggcggactac tggggccagg ggacccacgt caccgtctcc    420
tccggaggag gaggatctgg aggaggagga agcggaggag gaggaagcgg cggcggcggc    480
tctggcggcg gcggcagcga tgtgcagctg gtggagtctg ggggaggctt ggtgcagcct    540
ggggggtctc tgagactctc ctgtgcagcc tctggacgga ccttcagtag cattgtcatg    600
ggctggttcc gccaggctcc agggaaggag cgtgagtttg taggagcgat tatgtggaat    660
gatggtatta catacttgca agactccgtg aagggccgat ttaccatctt cagagacaac    720
gccaagaaca cggtgtatct gcaaatgaac agcctgaaac ttgaggatac ggccgtttat    780
tactgtgcag catccaaggg tagatactcg gaatatgagt actggggcca ggggacccag    840
gtcaccgtct cctcaactag taccacgacg ccagcgccgc gaccaccaac accggcgccc    900
accatcgcgt cgcagcccct gtccctgcgc ccagaggcgt gccggccagc ggcgggggc     960
gcagtgcaca cgagggggct ggacttcgcc tgtgatatct acatctgggc gcccttggcc    1020
gggacttgtg gggtccttct cctgtcactg gttatcaccc tttactgcaa cggggcagaa    1080
aagaaactcc tgtatatatt caaacaacca tttatgagac agtacaaaac tactcaagag    1140
gaagatggct gtagctgccg atttccagaa gaagaagaag gaggatgtga actgagagtg    1200
aagttcagca ggagcgcaga cgcccccgcg taccagcagg gccagaacca gctctataac    1260
gagctcaatc taggacgaag agaggagtac gatgttttgg acaagagacg tggccgggac    1320
cctgagatgg ggggaaagcc gagaaggaag aaccctcagg aaggcctgta caatgaactg    1380
cagaaagata gatggcggag ggcctacagt gagattggga tgaaaggcga gcgccggagg    1440
ggcaaggggc acgatggcct ttaccagggt ctcagtacag ccaccaagga cacctacgac    1500
gcccttcaca tgcaggcccc gccccctcgc taa                                 1533
```

```
<210> SEQ ID NO 371
<211> LENGTH: 1488
<212> TYPE: DNA
<213> ORGANISM: Artificial Sequence
<220> FEATURE:
<223> OTHER INFORMATION: Synthetic Construct

<400> SEQUENCE: 371
```

```
atggctctgc ccgtcaccgc tctgctgctg cctctggctc tgctgctgca cgctgctcgc     60
cctgatgtgc agctggtgga gtctggggga ggattggtgc aggctggggg ctctctgaga    120
ctctcctgtg cagcctctgg aggcacctta agtaagaata ccgtggcttg ggtccgccag    180
gctccaggga aggagcgtgg gtttgtaacg tctattacct gtgatggtcg tacgacatac    240
tatgcgaact ccgtgaaggg ccgattcccc atctccagag acaacgccga gaacacagtg    300
tatctgcaaa tgaacagcct gaaacctgag gatacggccg ttatgtctg tgcagactta    360
gggaagtggc ctgcgggttc ggcggactac tggggccagg ggacccacgt caccgtctcc    420
tccggaggag gaggatccgg cggaggaggc tctgatgtgc agctggtgga gtctggggga    480
ggcttggtgc agcctggggg gtctctgaga ctctcctgtg cagcctctgg acggaccttc    540
agtagcattg tcatgggctg gttccgccag gctccaggga aggagcgtga gtttgtagga    600
gcgattatgt ggaatgatgg tattacatac ttgcaagact ccgtgaaggg ccgatttacc    660
atcttcagag acaacgccaa gaacacggtg tatctgcaaa tgaacagcct gaaacttgag    720
gatacggccg tttattactg tgcagcatcc aagggtagat actcggaata tgagtactgg    780
ggccagggga cccaggtcac cgtctcctca actagtacca cgacgccagc gccgcgacca    840
ccaacaccgg cgcccaccat cgcgtcgcag cccctgtccc tgcgcccaga ggcgtgccgg    900
```

```
ccagcggcgg ggggcgcagt gcacacgagg gggctggact tcgcctgtga tatctcacatc    960 tgggcgccct tggccgggac ttgtggggtc cttctcctgt cactggttat cacccttac    1020 tgcaaacggg gcagaaagaa actcctgtat atattcaaac aaccatttat gagaccagta   1080
caaactactc aagaggaaga tggctgtagc tgccgatttc agaagaaga agaaggagga    1140 tgtgaactga gagtgaagtt cagcaggagc gcagacgccc ccgcgtacca gcagggccag   1200
aaccagctct ataacgagct caatctagga cgaagagagg agtacgatgt tttggacaag   1260
agacgtggcc gggaccctga gatgggggga aagccgagaa ggaagaaccc tcaggaaggc   1320
ctgtacaatg aactgcagaa agataagatg cggaggcct acagtgagat tgggatgaaa    1380
ggcgagcgcc ggaggggcaa ggggcacgat ggcctttacc agggtctcag tacagccacc   1440
aaggacacct acgacgccct tcacatgcag gccctgcccc ctcgctaa                1488
```

<210> SEQ ID NO 372
<211> LENGTH: 1503
<212> TYPE: DNA
<213> ORGANISM: Artificial Sequence
<220> FEATURE:
<223> OTHER INFORMATION: Synthetic Construct

<400> SEQUENCE: 372

```
atggctctgc ccgtcaccgc tctgctgctg cctctggctc tgctgctgca cgctgctcgc     60
cctgatgtgc agctggtgga gtctggggga ggattggtgc aggctggggg ctctctgaga    120
ctctcctgtg cagcctctgg aggcacctta agtaagaata ccgtggcttg gtccgccag    180 gctccaggga aggagcgtgg gtttgtaacg tctattacct gtgatggtcg tacgacatac    240
tatgcgaact ccgtgaaggg ccgattcccc atctccagag acaacgccga gaacacagtg    300
tatctgcaaa tgaacagcct gaaacctgag gatacggccg ttatgtctg tgcagactta    360 gggaagtggc ctgcgggttc ggcggactac tggggccagg gaacccacgt caccgtctcc    420
tccggaggag gaggatccgg cggaggaggc tctggcggcg gcggcagcga tgtgcagctg    480
gtggagtctg ggggaggctt ggtgcagcct gggggtctc tgagactctc ctgtgcagcc    540
tctggacgga ccttcagtag cattgtcatg ggctggttcc gccaggctcc agggaaggag    600
cgtgagtttg taggagcgat tatgtggaat gatggtatta catacttgca agactccgtg    660
aagggccgat ttaccatctt cagagacaac gccaagaaca cggtgtatct gcaaatgaac    720
agcctgaaac ttgaggatac ggccgtttat tactgtgcag catccaaggg tagatactcg    780
gaatatgagt actggggcca ggggacccag gtcaccgtct cctcaactag taccacgacg    840
ccagcgccgc gaccaccaac accggcgccc accatcgcgt cgcagcccct gtccctgcgc    900
ccagaggcgt gccggccagc ggcgggggc gcagtgcaca cgagggggct ggacttcgcc    960
tgtgatatct acatctgggc gcccttggcc gggacttgtg ggtccttct cctgtcactg   1020 gttatcaccc tttactgcaa acggggcaga aagaaactcc tgtatatatt caaacaacca   1080
tttatgagac cagtacaaac tactcaagag gaagatggct gtagctgccg atttccagaa   1140
gaagaagaag aggatgtgaa ctgagagtg aagttcagca ggagcgcaga cgccccgcg    1200 taccagcagg gccagaacca gctctataac gagctcaatc taggacgaag agaggagtac   1260
gatgttttgg acaagagacg tggccgggac cctgagatgg ggggaaagcc gagaaggaag   1320
aaccctcagg aaggcctgta caatgaactg cagaaagata agatgcggga ggcctacagt   1380
gagattggga tgaaaggcga gcgccggagg ggcaaggggc acgatggcct ttaccagggt   1440
```

```
ctcagtacag ccaccaagga cacctacgac gcccttcaca tgcaggccct gcccctcgc     1500 taa                                                                  1503

<210> SEQ ID NO 373
<211> LENGTH: 1518
<212> TYPE: DNA
<213> ORGANISM: Artificial Sequence
<220> FEATURE:
<223> OTHER INFORMATION: Synthetic Construct

<400> SEQUENCE: 373
atggctctgc ccgtcaccgc tctgctgctg cctctggctc tgctgctgca cgctgctcgc     60
cctgatgtgc agctggtgga gtctggggga ggattggtgc aggctggggg ctctctgaga    120
ctctcctgtg cagcctctgg aggcacctta agtaagaata ccgtggcttg gtccgccag     180 gctccaggga aggagcgtgg gtttgtaacg tctattacct gtgatggtcg tacgacatac    240
tatgcgaact ccgtgaaggg ccgattcccc atctccagag acaacgccga gaacacagtg    300
tatctgcaaa tgaacagcct gaaacctgag gatacggccg ttatgtctg tgcagactta     360 gggaagtggc ctgcgggttc ggcggactac tggggccagg ggaccacgt caccgtctcc     420 tccgaggag gaggatccgg cggaggaggc tctggcggcg cggctccgg cggcggcggc     480 tccgatgtgc agctggtgga gtctggggga ggcttggtgc agcctggggg gtctctgaga    540
ctctcctgtg cagcctctgg acggaccttc agtagcattg tcatgggctg gttccgccag    600
gctccaggga aggagcgtga gtttgtagga gcgattatgt ggaatgatgg tattacatac    660
ttgcaagact ccgtgaaggg ccgatttacc atcttcagag acaacgccaa gaacacggtg    720
tatctgcaaa tgaacagcct gaaacttgag gatacggccg tttattactg tgcagcatcc    780
aagggtagat actcggaata tgagtactgg ggccagggga cccaggtcac cgtctcctca    840
actagtacca cgacgccagc gccgcgacca ccaacaccgg cgcccaccat cgcgtcgcag    900 ccccctgtccc tgcgcccaga ggcgtgccgg ccagcggcgg ggggcgcagt gcacacgagg    960
gggctggact tcgcctgtga tatctacatc tgggcgccct tggccgggac ttgtggggtc   1020
cttctcctgt cactggttat cacccttt ac tgcaaacggg gcagaaagaa actcctgtat   1080
atattcaaac aaccatttat gagaccagta caaactactc aagaggaaga tggctgtagc   1140
tgccgatttc cagaagaaga agaaggagga tgtgaactga gagtgaagtt cagcaggagc   1200
gcagacgccc ccgcgtacca gcagggccag aaccagctct ataacgagct caatctagga   1260
cgaagagagg agtacgatgt tttggacaag agacgtggcc gggaccctga tgggggga    1320 aagccgagaa ggaagaaccc tcaggaaggc ctgtacaatg aactgcagaa agataagatg   1380
gcggaggcct acagtgagat tgggatgaaa ggcgagcgcc ggagggcaa ggggcacgat    1440 ggcctttacc agggtctcag tacagccacc aaggacacct acgacgccct tcacatgcag   1500
gccctgcccc ctcgctaa                                                1518

<210> SEQ ID NO 374
<211> LENGTH: 23
<212> TYPE: DNA
<213> ORGANISM: Artificial Sequence
<220> FEATURE:
<223> OTHER INFORMATION: Synthetic Construct

<400> SEQUENCE: 374
gtcctggctg ctcttctaca agg                                            23
```

```
<210> SEQ ID NO 375
<211> LENGTH: 23
<212> TYPE: DNA
<213> ORGANISM: Artificial Sequence
<220> FEATURE:
<223> OTHER INFORMATION: Synthetic Construct

<400> SEQUENCE: 375
ggtacgtgct gttgaactgt tcc                                              23

<210> SEQ ID NO 376
<211> LENGTH: 29
<212> TYPE: DNA
<213> ORGANISM: Artificial Sequence
<220> FEATURE:
<223> OTHER INFORMATION: Synthetic Construct

<400> SEQUENCE: 376
gatgtgcagc tgcaggagtc tggaggagg                                        29

<210> SEQ ID NO 377
<211> LENGTH: 29
<212> TYPE: DNA
<213> ORGANISM: Artificial Sequence
<220> FEATURE:
<223> OTHER INFORMATION: Synthetic Construct

<400> SEQUENCE: 377
gatgtgcagc tgcaggagtc tggggagg                                         29

<210> SEQ ID NO 378
<211> LENGTH: 34
<212> TYPE: DNA
<213> ORGANISM: Artificial Sequence
<220> FEATURE:
<223> OTHER INFORMATION: Synthetic Construct

<400> SEQUENCE: 378
ctagtgcggc cgctgaggag acggtgacct gggt                                  34

<210> SEQ ID NO 379
<211> LENGTH: 9
<212> TYPE: DNA
<213> ORGANISM: Artificial Sequence
<220> FEATURE:
<223> OTHER INFORMATION: Synthetic Construct

<400> SEQUENCE: 379 gccgccacc                                                               9

<210> SEQ ID NO 380
<211> LENGTH: 6
<212> TYPE: DNA
<213> ORGANISM: Artificial Sequence
<220> FEATURE:
<223> OTHER INFORMATION: Synthetic Construct

<400> SEQUENCE: 380 gaattc                                                                  6

<210> SEQ ID NO 381
<211> LENGTH: 6
<212> TYPE: DNA
<213> ORGANISM: Artificial Sequence
<220> FEATURE:
<223> OTHER INFORMATION: Synthetic Construct
```

```
<400> SEQUENCE: 381 actagt                                                              6

<210> SEQ ID NO 382
<211> LENGTH: 6
<212> TYPE: DNA
<213> ORGANISM: Artificial Sequence
<220> FEATURE:
<223> OTHER INFORMATION: Synthetic Construct

<400> SEQUENCE: 382 gttaac                                                              6

<210> SEQ ID NO 383
<211> LENGTH: 6
<212> TYPE: DNA
<213> ORGANISM: Artificial Sequence
<220> FEATURE:
<223> OTHER INFORMATION: Synthetic Construct

<400> SEQUENCE: 383 acgcgt                                                              6

<210> SEQ ID NO 384
<211> LENGTH: 6
<212> TYPE: DNA
<213> ORGANISM: Artificial Sequence
<220> FEATURE:
<223> OTHER INFORMATION: Synthetic Construct

<400> SEQUENCE: 384 atgcat                                                              6

<210> SEQ ID NO 385
<211> LENGTH: 21
<212> TYPE: PRT
<213> ORGANISM: Artificial Sequence
<220> FEATURE:
<223> OTHER INFORMATION: Synthetic Construct

<400> SEQUENCE: 385

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 386
<211> LENGTH: 18
<212> TYPE: PRT
<213> ORGANISM: Homo sapiens

<400> SEQUENCE: 386

Met Lys Trp Val Thr Phe Ile Ser Leu Leu Phe Leu Phe Ser Ser Ala
1               5                   10                  15

Tyr Ser

<210> SEQ ID NO 387
<211> LENGTH: 9
<212> TYPE: PRT
<213> ORGANISM: Artificial Sequence
<220> FEATURE:
<223> OTHER INFORMATION: Synthetic Construct

<400> SEQUENCE: 387
```

```
Gly Ser Gly His His His His His His
1               5

<210> SEQ ID NO 388
<211> LENGTH: 10
<212> TYPE: PRT
<213> ORGANISM: Artificial Sequence
<220> FEATURE:
<223> OTHER INFORMATION: Synthetic Construct

<400> SEQUENCE: 388

Met Leu Gln Met Ala Gly Gln Cys Ser Gln
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Synthetic Construct

<400> SEQUENCE: 389

Cys Ser Gln Asn Glu Tyr Phe Asp Ser Leu Leu His Ala Cys
1               5                   10

<210> SEQ ID NO 390
<211> LENGTH: 13
<212> TYPE: PRT
<213> ORGANISM: Artificial Sequence
<220> FEATURE:
<223> OTHER INFORMATION: Synthetic Construct

<400> SEQUENCE: 390

Asn Glu Tyr Phe Asp Ser Leu Leu His Ala Cys Ile Pro
1               5                   10

<210> SEQ ID NO 391
<211> LENGTH: 11
<212> TYPE: PRT
<213> ORGANISM: Artificial Sequence
<220> FEATURE:
<223> OTHER INFORMATION: Synthetic Construct

<400> SEQUENCE: 391

Ala Cys Ile Pro Cys Gln Leu Arg Cys Ser Ser
1               5                   10

<210> SEQ ID NO 392
<211> LENGTH: 19
<212> TYPE: PRT
<213> ORGANISM: Artificial Sequence
<220> FEATURE:
<223> OTHER INFORMATION: Synthetic Construct

<400> SEQUENCE: 392

Cys Gln Leu Arg Cys Ser Ser Asn Thr Pro Pro Leu Thr Cys Gln Arg
1               5                   10                  15

Tyr Cys Asn

<210> SEQ ID NO 393
<211> LENGTH: 10
<212> TYPE: PRT
<213> ORGANISM: Artificial Sequence
<220> FEATURE:
<223> OTHER INFORMATION: Synthetic Construct

<400> SEQUENCE: 393
```

```
Leu Thr Cys Gln Arg Tyr Cys Asn Ala Ser
1               5                   10
```

<210> SEQ ID NO 394
<211> LENGTH: 12
<212> TYPE: PRT
<213> ORGANISM: Artificial Sequence
<220> FEATURE:
<223> OTHER INFORMATION: Synthetic Construct

<400> SEQUENCE: 394

```
Ala Ser Val Thr Asn Ser Val Lys Gly Thr Asn Ala
1               5                   10
```

<210> SEQ ID NO 395
<211> LENGTH: 54
<212> TYPE: PRT
<213> ORGANISM: Artificial Sequence
<220> FEATURE:
<223> OTHER INFORMATION: Synthetic Construct

<400> SEQUENCE: 395

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
        35                  40                  45

Val Lys Gly Thr Asn Ala
    50
```

<210> SEQ ID NO 396
<211> LENGTH: 23
<212> TYPE: PRT
<213> ORGANISM: Artificial Sequence
<220> FEATURE:
<223> OTHER INFORMATION: Synthetic Construct

<400> SEQUENCE: 396

```
Ile Leu Trp Thr Cys Leu Gly Leu Ser Leu Ile Ile Ser Leu Ala Val
1               5                   10                  15

Phe Val Leu Met Phe Leu Leu
                20
```

<210> SEQ ID NO 397
<211> LENGTH: 107
<212> TYPE: PRT
<213> ORGANISM: Artificial Sequence
<220> FEATURE:
<223> OTHER INFORMATION: Synthetic Construct

<400> SEQUENCE: 397

```
Arg Lys Ile Asn Ser Glu Pro Leu Lys Asp Glu Phe Lys Asn Thr Gly
1               5                   10                  15

Ser Gly Leu Leu Gly Met Ala Asn Ile Asp Leu Glu Lys Ser Arg Thr
                20                  25                  30

Gly Asp Glu Ile Ile Leu Pro Arg Gly Leu Glu Tyr Thr Val Glu Glu
        35                  40                  45

Cys Thr Cys Glu Asp Cys Ile Lys Ser Lys Pro Lys Val Asp Ser Asp
    50                  55                  60

His Cys Phe Pro Leu Pro Ala Met Glu Glu Gly Ala Thr Ile Leu Val
65                  70                  75                  80
```

```
Thr Thr Lys Thr Asn Asp Tyr Cys Lys Ser Leu Pro Ala Ala Leu Ser
                85                  90                  95

Ala Thr Glu Ile Glu Lys Ser Ile Ser Ala Arg
            100                 105

<210> SEQ ID NO 398
<211> LENGTH: 23
<212> TYPE: DNA
<213> ORGANISM: Artificial Sequence
<220> FEATURE:
<223> OTHER INFORMATION: Synthetic Construct

<400> SEQUENCE: 398
gtccttctcc tgtcactggt tat                                         23

<210> SEQ ID NO 399
<211> LENGTH: 23
<212> TYPE: DNA
<213> ORGANISM: Artificial Sequence
<220> FEATURE:
<223> OTHER INFORMATION: Synthetic Construct

<400> SEQUENCE: 399
tcttcttctt ctggaaatcg gca                                         23
```

CHIMERIC ANTIGEN RECEPTORS TARGETING BCMA AND METHODS OF USE THEREOF

CROSS REFERENCE TO RELATED APPLICATIONS

This application is a continuation of U.S. application Ser. No. 16/303,587, filed Nov. 20, 2018, which is a U.S. national stage of International Patent Application No. PCT/CN2017/096938, filed Aug. 10, 2017, which claims the priority to International Patent Application No. PCT/CN2016/094408, filed Aug. 10, 2016, the content of each of which is incorporated by reference herein in its entirety.

SUBMISSION OF SEQUENCE LISTING ON ASCII TEXT FILE

This application incorporates by reference in its entirety the Computer Readable Form (CRF) of a Sequence Listing in ASCII text format submitted via EFS-Web. The Sequence Listing text file submitted via EFS-Web is entitled 14651-018-999_SEQ_LISTING.txt, was created on Jan. 21, 2021 and is 532,554 bytes in size.

FIELD OF THE PRESENT APPLICATION

The present invention relates to single-domain antibodies, chimeric antigen receptors and engineered immune effector cells that target BCMA, and methods of use thereof.

BACKGROUND OF THE PRESENT APPLICATION

With the development of tumor immunotherapy and clinical technology, chimeric antigen receptor T cell (CAR-T) immunotherapy is now one of the most promising tumor immunotherapy approaches. Generally, a chimeric antigen receptor (CAR) comprises an extracellular antigen binding domain, a transmembrane domain and an intracellular signaling domain. The extracellular antigen binding domain may comprise a single chain variable fragment (scFv) targeting an identified tumor antigen. CARs can be expressed on the surface of T cells using gene transfection techniques. Upon binding to the target tumor antigen, the CARs can activate the T cells to launch specific anti-tumor response in an antigen-dependent manner without being limited by the availability of major histocompatibility complexes (MHC) specific to the target tumor antigen.

Single-domain antibodies (sdAbs) are different from conventional 4-chain antibodies by having a single monomeric antibody variable domain. For example, camelids and sharks produce sdAbs named heavy chain-only antibodies (HcAbs), which naturally lack light chains. The antigen-binding fragment in each arm of the camelid heavy-chain only antibodies has a single heavy chain variable domain ($V_HH$), which can have high affinity to an antigen without the aid of a light chain. Camelid $V_HH$ is known as the smallest functional antigen-binding fragment with a molecular weight of approximately 15 kD.

Multiple myeloma (MM) is an incurable aggressive plasma malignancy, which is categorized as a B-cell neoplasia and proliferates in uncontrollably method in the bone marrow, interfering with the normal metabolic production of blood cells and causing painful bone lesions (Garfall, A. L. et al., *Discovery Med.* 2014, 17, 37). Multiple myeloma can present clinically with hypercalcemia, renal insufficiency, anemia, bony lesions, bacterial infections, hyperviscosity, and amyloidosis (Robert Z. Orlowski, *Cancer Cell.* 2013, 24(3)). According to investigation and statistics, nearly 86,000 patients will be diagnosed each year with myeloma, and while about 63,000 patients die every year from the disease-related complications (Becker, 2011). Because of an aging populace, it is predicted that the number of cases of myeloma will increase year by year. Like many cancers, there is no known cause of multiple myeloma, and no cure. Some treatments for multiple myeloma are similar to treatments for other cancers, such as chemotherapy or radiation therapy, stem cell transplant or bone marrow transplant, targeted therapy or biological therapy (George, 2014). Antibody-based cell immunotherapies have demonstrated substantial clinical benefit for patients with hematological malignancies, particular in B cell Non-Hodgkin's lymphoma. Although current therapies for multiple myeloma often lead to remissions, nearly all patients eventually relapse. There is a need for effective immunotherapeutic agent for treating multiple myeloma.

The LCAR-B38M disclosed in the current invention is a bivalent BCMA targeting CAR-T which have already shown clinical advantages in terms of both safety and efficacy in treating refractory or relapsed multiple myeloma patients in a clinical trial. In an early clinical trial, 33 out of 35 (94%) patients had clinical remission of multiple myeloma upon receiving LCAR-B38M CAR-T cells. Most patients had only mild side effects. The study was presented by the major inventor at both the 2017 ASCO Annual Meeting (Abstract LBA3001) and the press briefing which recruited extensive media coverage (http://www.ascopost.com/News/55713).

Overall, the objective response rate was 100%, and 33 patients (94%) had an evident clinical remission of myeloma (complete response, very good partial response, or partial response) within 2 months of receiving CAR T cells. After following the group for a period of more than 4 months, of the 19 patients, 14 have reached stringent complete response criteria, 1 patient has reached partial response, and 4 patients have achieved very good partial remission criteria in efficacy.

Since the outstanding efficacy and safety profile obtained from LCAR-B38M clinical trial are significantly superior than a few other BCMA CAR-T trials reported at the same time in the ASCO, the works had been widely recognized as an "revolutionized breakthrough" in the immunotherapy field. It is notable that all these BCMA CAR design are conventional CAR in which BCMA antigen binding domain is composed of a monovalent ScFv antibody.

The disclosures of all publications, patents, patent applications and published patent applications referred to herein are hereby incorporated herein by reference in their entirety.

BRIEF SUMMARY OF THE PRESENT APPLICATION

The present application provides anti-BCMA single-domain antibodies (sdAb), chimeric antigen receptors (CARs) comprising one or more anti-BCMA sdAbs (such as $V_HH$ fragments), engineered immune effector cells, and methods of use thereof in cancer immunotherapy.

One aspect of the present application provides an anti-BCMA sdAb comprising the CDR regions of any one of SEQ ID NOs: 115-152. In some embodiments, the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb comprises a $V_HH$ domain comprising an amino acid sequence selected from the group consisting of SEQ ID NO: 115-152.

In some embodiments, there is provided an anti-BCMA heavy-chain only antibody (HCAB) or an antigen binding protein comprising any one of the anti-BCMA sdAbs described above. Also provided are BCMA epitopes that any one of the anti-BCMA sdAbs described above specifically bind to, and anti-BCMA antibodies (such as anti-BCMA sdAbs) that compete with any one of the anti-BCMA sdAbs described above.

In some embodiments according to any one of the anti-BCMA sdAbs described above, the anti-BCMA sdAb is a camelid antibody. In some embodiments, the anti-BCMA sdAb is a chimeric antibody. In some embodiments, the anti-BCMA sdAb is humanized. In some embodiments, the anti-BCMA sdAb is a $V_HH$ fragment.

One aspect of the present application provides a BCMA chimeric antigen receptor comprising a polypeptide comprising: (a) an extracellular antigen binding domain comprising an anti-BCMA sdAb (such as any one of the anti-BCMA sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific). In some embodiments, the extracellular antigen binding domain comprises at least two anti-BCMA sdAbs (such as any one or more of the anti-BCMA sdAbs described above).

One aspect of the present application provides a multivalent chimeric antigen receptor (CAR) comprising a polypeptide comprising: (a) an extracellular antigen binding domain comprising a first BCMA binding moiety and a second BCMA binding moiety; (b) a transmembrane domain; and (c) an intracellular signaling domain. In some embodiments, one or more of the first BCMA binding moiety and the second BCMA binding moiety is an anti-BCMA sdAb. In some embodiments, the first BCMA binding moiety is a first anti-BCMA sdAb and the second BCMA binding moiety is a second anti-BCMA sdAb. In some embodiments, the first BCMA binding moiety is an anti-BCMA sdAb and the second BCMA binding moiety is derived from a human antibody. In some embodiments, the first BCMA binding moiety is an anti-BCMA sdAb and the second BCMA binding moiety is a polypeptide ligand of BCMA. In some embodiments, the first BCMA binding moiety and the second BCMA binding moiety specifically bind to the same epitope on BCMA. In some embodiments, the first BCMA binding moiety and the second BCMA binding moiety specifically bind to the different epitopes on BCMA. In some embodiments, the first BCMA binding moiety and/or the second BCMA binding moiety specifically binds to an epitope on BCMA derived from an amino acid sequence selected from SEQ ID NOs: 388-394. In some embodiments, the first BCMA binding moiety specifically binds to an epitope derived from SEQ ID NO: 389 and/or 390. In some embodiments, the second BCMA binding moiety specifically binds to an epitope derived from SEQ ID NO: 391 and/or 392.

One aspect of the present application provides a multivalent (such as bivalent or trivalent) chimeric antigen receptor comprising a polypeptide comprising: (a) an extracellular antigen binding domain comprising a first anti-BCMA sdAb (such as any one of the anti-BCMA sdAbs described above) and a second anti-BCMA sdAb (such as any one of the anti-BCMA sdAbs described above); (b) a transmembrane domain; and (c) an intracellular signaling domain. In some embodiments, the first anti-BCMA sdAb and the second anti-BCMA sdAb specifically bind to the same epitope on BCMA. In some embodiments, the first anti-BCMA sdAb and the second anti-BCMA sdAb specifically bind to different epitopes on BCMA. In some embodiments, the first anti-BCMA sdAb and/or the second anti-BCMA sdAb specifically binds to an epitope on BCMA derived from an amino acid sequence selected from SEQ ID NOs: 388-394. In some embodiments, the first anti-BCMA sdAb specifically binds to an epitope derived from SEQ ID NO: 389 and/or 390. In some embodiments, the second anti-BCMA sdAb specifically binds to an epitope derived from SEQ ID NO: 391 and/or 392.

In some embodiments according to any one of the multivalent CARs provided above, the first BCMA binding moiety (e.g., the first anti-BCMA sdAb) is located at the N-terminus of the second BCMA binding moiety (e.g., the second anti-BCMA sdAb). In some embodiments, the first BCMA binding moiety (e.g., the first anti-BCMA sdAb) is located at the C-terminus of the second BCMA binding moiety (e.g., the second anti-BCMA sdAb). In some embodiments, the first BCMA binding moiety (e.g., the first anti-BCMA sdAb) and the second BCMA binding moiety (e.g., the second anti-BCMA sdAb) are directly fused to each other via a peptide bond. In some embodiments, the first BCMA binding moiety (e.g., the first anti-BCMA sdAb) and the second BCMA binding moiety (e.g., the second anti-BCMA sdAb) are fused to each other via a peptide linker. In some embodiments, the peptide linker is no more than about 50 (such as no more than about any one 35, 25, 20, 15, 10, or 5) amino acids long. In some embodiments, the peptide linker comprises an amino acid sequence selected from SEQ ID NOs: 208-215.

In some embodiments according to any one of the CARs (including multivalent CARs) described above, the transmembrane domain is derived from a molecule selected from the group consisting of CD8α, CD4, CD28, CD137, CD80, CD86, CD152 and PD1. In some embodiments, the transmembrane domain is derived from CD8α or CD28. In some embodiments, the transmembrane domain comprises the amino acid sequence of SEQ ID NO: 193 or 194.

In some embodiments according to any one of the CARs (including multivalent CARs) described above, the intracellular signaling domain comprises a primary intracellular signaling domain of an immune effector cell (such as a T cell). In some embodiments, the primary intracellular signaling domain is derived from CD3ζ. In some embodiments, the primary intracellular signaling domain comprises the amino acid sequence of SEQ ID NO: 197 or 198.

In some embodiments according to any one of the CARs (including multivalent CARs) described above, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the co-stimulatory signaling domain comprises a cytoplasmic domain of CD28 and/or a cytoplasmic domain of CD137. In some embodiments, the co-stimulatory signaling domain comprises the amino acid sequence of SEQ ID NO: 195 and/or SEQ ID NO: 196.

In some embodiments according to any one of the CARs (including multivalent CARs) described above, the CAR further comprises a hinge domain located between the C-terminus of the extracellular antigen binding domain and the N-terminus of the transmembrane domain. In some embodiments, the hinge domain is derived from CD8α. In some embodiments, the hinge domain comprises the amino acid sequence of SEQ ID NO: 192.

In some embodiments according to any one of the CARs (including multivalent CARs) described above, the CAR further comprises a signal peptide located at the N-terminus of the polypeptide. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide comprises the amino acid sequence of SEQ ID NO: 191.

One aspect of the present application provides a CAR as listed in Tables 4 and 5. In some embodiments, the CAR comprises an amino acid sequence selected from the group consisting of SEQ ID NOs: 216-256 and 298-335.

One aspect of the present application provides a polypeptide comprising an amino acid sequence selected from the group consisting of SEQ ID NOs: 115-152, 216-256 and 298-335.

One aspect of the present application provides an isolated nucleic acid comprising a nucleic acid sequence encoding any one of the anti-BCMA sdAbs or CARs (including multivalent CARs) described above. In some embodiments, the nucleic acid sequence is selected from the group consisting of SEQ ID NOs: 153-190, 257-297 and 336-373. In some embodiments, the isolated nucleic acid further comprises a first nucleic acid sequence encoding a first CAR, wherein the second nucleic acid sequence encoding second CAR is operably linked to the first nucleic acid sequence via a third nucleic acid sequence encoding a self-cleaving peptide, such as a T2A, P2A, or F2A peptide. Wherein the third nucleic acid sequence is SEQ ID NO: 385. In some embodiments, the isolated nucleic acid is a DNA molecule. In some embodiments, the isolated nucleic acid is an RNA molecule.

One aspect of the present application provides a vector comprising any one of the isolated nucleic acids described above. In some embodiments, the vector is an expression vector. In some embodiments, the vector is a viral vector. In some embodiments, the vector is a lentiviral vector. In some embodiments, the vector is a non-viral vector.

One aspect of the present application provides an engineered immune effector cell, comprising any one of the CARs (including multivalent CARs) provided above, or any one of the isolated nucleic acids described above, or any one of the vectors described above. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

One aspect of the present application provides a pharmaceutical composition comprising any one of the engineered immune effector cells described above and a pharmaceutically acceptable carrier. Further provided is a method of treating cancer in an individual, comprising administering to the individual an effective amount of any one of the pharmaceutical compositions described above. In some embodiments, the engineered immune effector cell is autologous. In some embodiments, the engineered immune effector cell is allogenic. In some embodiments, the cancer is a liquid cancer. In some embodiments, the cancer is multiple myeloma, acute lymphoblastic leukemia, or chronic lymphocytic leukemia. In some embodiments, the cancer is a solid cancer, such as glioblastoma. In some embodiments, the cancer is refractory or relapsed multiple myeloma.

One aspect of the present application provides a pharmaceutical composition comprising any one of the anti-BCMA sdAbs described above and a pharmaceutically acceptable carrier. In some embodiments, there is provided a method of treating a disease (such as cancer) in an individual, comprising administering to the individual an effective amount of the pharmaceutical composition.

Also provided are methods of use, kits, and articles of manufacture comprising any one of the anti-BCMA sdAbs, CARs (including multivalent CARs), engineered immune effector cells, isolated nucleic acids, or vectors described above.

BRIEF DESCRIPTION OF THE DRAWINGS

FIG. 8B shows BCMA epitope peptides.

FIG. 12B shows bioluminescence imaging data in LCAR-B38M CAR-T treated mice and untransduced T cell (UnT) treated mice. FIG. 12C shows the study design and bioluminescence images of mice in CAR-T group and UnT group. FIG. 12D shows images of livers from UnT-treated mice. FIG. 12E shows an ex vivo luciferase assay validating tumors in the livers of UnT-treated mice.

FIG. 14A shows the in vitro cytotoxicity results of LCAR-B38M CAR-T cells and LCAR-B27S CAR-T cells prepared from multiple myeloma patient A. FIG. 14B shows the in vitro cytotoxicity results of LCAR-B38M CAR-T cells and LCAR-B27S CAR-T cells prepared from multiple myeloma patient B. FIG. 14C shows the in vitro cytotoxicity results of LCAR-B38M CAR-T cells and LCAR-B27S CAR-T cells prepared from multiple myeloma patient C.

DETAILED DESCRIPTION OF THE PRESENT APPLICATION

Figure 1A:
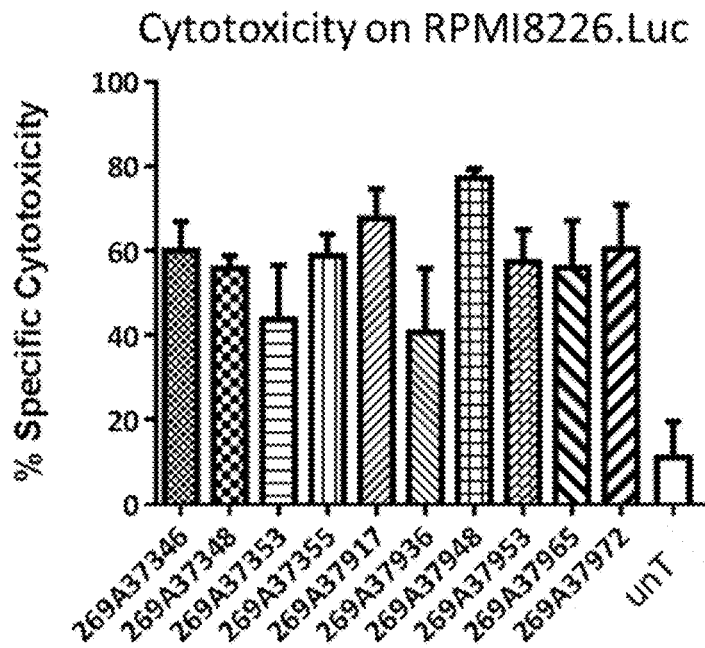
FIGS. 1A-1B show results of an in vitro cytotoxicity assay of T cells expressing exemplary monospecific CARs comprising various anti-BCMA sdAbs against RPMI8226. Luc cells (FIG. 1A), or U87MG.Luc cells (FIG. 1B).

The present application provides anti-BCMA single-domain antibodies (sdAb) and chimeric antigen receptors (CARs) comprising an extracellular antigen binding domain comprising one or more BCMA binding moieties (such as anti-BCMA sdAbs). Multivalent CARs comprising at least two binding moieties (such as sdAbs) that specifically bind to a single antigen are also provided. In some embodiments, the present application provides multivalent (such as bivalent or trivalent) CARs comprising at least two anti-BCMA sdAbs. In some embodiments, the at least two anti-BCMA sdAbs are different anti-BCMA sdAbs that specifically bind to different epitopes on BCMA. The anti-BCMA sdAbs, CARs and engineered immune cells expressing CARs described in the present application are useful agents for cancer treatment.

Notably, the present application has demonstrated superior efficacy of bivalent bi-epitope CARs comprising two anti-BCMA sdAbs targeting different BCMA epitopes (e.g., LCAR-B38M), in treating multiple myeloma among human patients. At an interim analysis of a Phase I/II clinical trial, 100% of patients with relapsed or refractory multiple myeloma responded to the LCAR-B38M CAR-T treatment. 94% of the patients had evident clinical remission of myeloma within two months of receiving the CAR-T treatment. Patients who reached Stringent Complete Response (sCR) criteria remained free of minimal residual disease after more than a year of receiving the CAR-T treatment. Additionally, the LCAR-B38M CAR-T treatment was well tolerated by the patients as most patients only experienced mild and manageable cytokine release syndrome, a common side effect of CAR-T cell-based therapy. No patients experienced neurological side effects. In comparison, a pilot clinical study of a monovalent CAR comprising a single anti-BCMA sdAb showed lower objective response rate and complete remission rate, and higher relapse rate among treated patients. Prior to this application, all BCMA CARs under clinical studies had only one BCMA binding moiety in the extracellular antigen binding domain. The improved clinical efficacy and safety of the multivalent BCMA CARs of the present application are unexpected.

Accordingly, one aspect of the present application provides a multivalent CAR comprising a polypeptide comprising: (a) an extracellular antigen binding domain comprising a plurality of a single-domain antibody (sdAb) specifically binding to BCMA; (b) a transmembrane domain; and (c) an intracellular signaling domain.

In another aspect, there is provided a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope is different from the second epitope.

Further provided are novel anti-BCMA sdAbs and CARs comprising any one or more of the anti-BCMA sdAbs described herein.

Engineered immune effector cells (such as T cells) comprising the CARs, pharmaceutical compositions, kits, articles of manufacture and methods of treating cancer using the engineered immune effectors cells or the sdAbs are also described herein.

I. Definitions

The term "antibody" includes monoclonal antibodies (including full length 4-chain antibodies or full length heavy-chain only antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody" herein. Antibodies contemplated herein include single-domain antibodies, such as heavy chain only antibodies.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. *Camelid* animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs". Some $V_H$Hs may also be known as Nanobodies. *Camelid* sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the *Camelid* species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein., Nature, 256: 495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and-binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, sdAbs comprise three HVRs (or CDRs): HVR1 (or CDR1), HVR2 (or CDR2), and HVR3 (or CDR3). HVR3 displays the most diversity of the three HVRs, and is believed to play a unique role in conferring fine specificity to antibodies. See, e.g., Hamers-Casterman et al., Nature 363:446-448 (1993); Sheriff et al., Nature Struct. Biol. 3:733-736 (1996).

The term "Complementarity Determining Region" or "CDR" are used to refer to hypervariable regions as defined by the Kabat system. See Kabat et al., Sequences of Proteins of Immunological Interest, 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kab at Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a sdAb (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein (such as a CAR or an sdAb), which is determinative of the presence of the target in the presence of a heterogeneous population of molecules including biological molecules. For example, an antigen binding protein (such as a CAR or an sdAb) that specifically binds a target (which can be an epitope) is an antigen binding protein (such as a CAR or an sdAb) that binds this target with greater affinity, avidity, more readily, and/or with greater duration than it binds other targets. In some embodiments, the extent of binding of an antigen binding protein (such as a CAR or an sdAb) to an unrelated target is less than about 10% of the binding of the antigen binding protein (such as a CAR or an sdAb) to the target as measured, e.g., by a radioimmunoassay (RIA). In some embodiments, an antigen binding protein (such as a CAR or an sdAb) that specifically binds a target has a dissociation constant (Kd) of ≤1, 100 nM, ≤10 nM, ≤1 nM, or ≤0.1 nM. In some embodiments, an antigen binding protein (such as a CAR or an sdAb) specifically binds an epitope on a protein that is conserved among the protein from different species. In some embodiments, specific binding can include, but does not require exclusive binding.

The term "specificity" refers to selective recognition of an antigen binding protein (such as a CAR or an sdAb) for a particular epitope of an antigen. Natural antibodies, for example, are monospecific. The term "multispecific" as used herein denotes that an antigen binding protein (such as a CAR or an sdAb) has two or more antigen-binding sites of which at least two bind different antigens. "Bispecific" as used herein denotes that an antigen binding protein (such as a CAR or an sdAb) has two different antigen-binding specificities. The term "monospecific" CAR as used herein denotes an antigen binding protein (such as a CAR or an sdAb) that has one or more binding sites each of which bind the same antigen.

The term "valent" as used herein denotes the presence of a specified number of binding sites in an antigen binding protein (such as a CAR or an sdAb). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an sdAb).

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRT, FcγRII and FcγRIII Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Binding affinity" generally refers to the strength of the sum total of non-covalent interactions between a single binding site of a molecule (e.g., an antibody or a CAR) and its binding partner (e.g., an antigen). Unless indicated otherwise, as used herein, "binding affinity" refers to intrinsic binding affinity that reflects a 1:1 interaction between members of a binding pair (e.g., antibody and antigen, or CAR and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T" refers to a T cell that expresses a CAR. "BCMA CAR" refers to a CAR having an extracellular binding domain specific for BCMA. "Bi-epitope CAR" refers to a CAR having an extracellular binding domain specific for two different epitopes on BCMA.

An "isolated" nucleic acid molecule encoding a CAR or an sdAb described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human.

The term "effective amount" used herein refers to an amount of an agent, such as a msdAb, an engineered immune effector cell, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, In some embodiments of the present application, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-BCMA Single-Domain Antibodies

One aspect of the present application provides isolated single-domain antibodies (referred herein as "anti-BCMA sdAbs") that specifically bind to BCMA, such as human BCMA. In some embodiments, the anti-BCMA sdAb modulates BCMA activity. In some embodiments, the anti-BCMA sdAb is an antagonist antibody. Further provided are antigen-binding ragments derived from any one of the anti-BCMA sdAbs described herein, and antigen binding proteins comprising any one of the anti-BCMA sdAbs described herein. Exemplary anti-BCMA sdAbs are listed in Table 2 below.

TABLE 2

Exemplary anti-BCMA sdAbs.

| SdAb | Ex. AA SEQ ID | Ex. NA SEQ ID | CDR1 | CDR2 | CDR3 |
|---|---|---|---|---|---|
| 269A37346 | 115 | 153 | DYYAIG (SEQ ID NO: 1) | CISRSDGSTYYADSVK G (SEQ ID NO: 39) | AGADCSGYLRDYEF (SEQ ID NO: 77) |
| 269A37348 | 116 | 154 | TYGMA (SEQ ID NO: 2) | SKASMNYSGRTYYAD SVKG (SEQ ID NO: 40) | AGTGCSTYGCFDAQI IDY (SEQ ID NO: 78) |
| 269A37917 | 117 | 155 | TFTMG (SEQ ID NO: 3) | AISLSPTLAYYAESVK G (SEQ ID NO: 41) | ADRKSVMSIRPDY (SEQ ID NO: 79) |
| 269A37355 | 118 | 156 | INAMG (SEQ ID NO: 4) | SIRGLGRTNYDDSVK G (SEQ ID NO: 42) | VYVTLLGGVNRDY (SEQ ID NO: 80) |
| 269A37915 | 119 | 157 | SIVMG (SEQ ID NO: 5) | AIMWNDGITYLQDSV KG (SEQ ID NO: 43) | ASKGRYSEYEY (SEQ ID NO: 81) |
| 269A37936 | 120 | 158 | RAVIV (SEQ ID NO: 6) | FIKPSDGTIYYIDSLKG (SEQ ID NO: 44) | ASPEDWYTDWIDW S IYR (SEQ ID NO: 82) |
| 269A37953 | 121 | 159 | SDVMG (SEQ ID NO: 7) | AIMWNDGITYLQDSV KG (SEQ ID NO: 45) | ASKGRYSEYEY (SEQ ID NO: 83) |
| 269A37965 | 122 | 160 | NDHMA (SEQ ID NO: 8) | AIDWSGRTTNYADPV EG (SEQ ID NO: 46) | VLRAWISYDNDY (SEQ ID NO: 84) |
| 269A37972 | 123 | 161 | KNTVA (SEQ ID NO: 9) | SITWDGRTTYYADSV KG (SEQ ID NO: 47) | DLGKWPAGPADY (SEQ ID NO: 85) |
| 269A37353 | 124 | 162 | SHVMG (SEQ ID NO: 10) | VIGWRDISTSYADSVK G (SEQ ID NO: 48) | ARRIDAADFDS (SEQ ID NO: 86) |
| 269A37948 | 125 | 163 | TYFMA (SEQ ID NO: 11) | GIAWSGGSTAYADSV KG (SEQ ID NO: 49) | SRGIEVEEFGA (SEQ ID NO: 87) |
| 269B005 | 126 | 164 | INVMA (SEQ ID NO: 12) | AVTRDGRKSCGDSVKG (SEQ ID NO: 50) | DGWGATTLDYTYGMD Y (SEQ ID NO: 88) |
| 269B023 | 127 | 165 | TFTMG (SEQ ID NO: 13) | SITWDGRSAYYAESVK G (SEQ ID NO: 51) | DRKSVMSIRPDY (SEQ ID NO: 89) |
| 269B024 | 128 | 166 | INAMG (SEQ ID NO: 14) | TITRGGSTNYGPSVKG (SEQ ID NO: 52) | ERLDGSGYGYEYDY (SEQ ID NO: 90) |
| 269B028 | 129 | 167 | KNTVA (SEQ ID NO: 15) | SITCDGRTTYYANSVNG (SEQ ID NO: 53) | YRKSIMSIQPDY (SEQ ID NO: 91) |
| 269B030 | 130 | 168 | SIVMG (SEQ ID NO: 16) | AIMWNDGLTYLQGSVK G (SEQ ID NO: 54) | DRKSVMSIRPDY (SEQ ID NO: 92) |
| 269B038 | 131 | 169 | TFTMG (SEQ ID NO: 17) | AISLSPTLAYYAESVKG (SEQ ID NO: 55) | RRIDAADFDS (SEQ ID NO: 93) |

TABLE 2-continued

Exemplary anti-BCMA sdAbs.

| SdAb | Ex. AA SEQ ID | Ex. NA SEQ ID | CDR1 | CDR2 | CDR3 |
|---|---|---|---|---|---|
| 269B054 | 132 | 170 | KNTVA (SEQ ID NO: 18) | SITWDGRTTYYADSVKG (SEQ ID NO: 56) | LGKWPAGPADY (SEQ ID NO: 94) |
| 269B059 | 133 | 171 | INTMD (SEQ ID NO: 19) | AISLSPTLAYYAESVKG (SEQ ID NO: 57) | DRKSVMSIRPDY (SEQ ID NO: 95) |
| 269B060 | 134 | 172 | KNTVA (SEQ ID NO: 20) | SITCDGRTTYYANSVKG (SEQ ID NO: 58) | LGKWPAGSADY (SEQ ID NO: 96) |
| 269B069 | 135 | 173 | DYWMH (SEQ ID NO: 21) | SIDTSGQTTYYADSLKG (SEQ ID NO: 59) | RYRGGTWYGMAN (SEQ ID NO: 97) |
| 269B074 | 136 | 174 | SNTMA (SEQ ID NO: 22) | STTWNGRSTYYADSVKG (SEQ ID NO: 60) | LGKWPAGPADY (SEQ ID NO: 98) |
| 269B076 | 137 | 175 | TFTMG (SEQ ID NO: 23) | DISGGRTNYADSVKG (SEQ ID NO: 61) | DRKSVMSIRPDY (SEQ ID NO: 99) |
| 269B079 | 138 | 176 | VAAISL (SEQ ID NO: 24) | FTISRDNAKNTVVLQMNSLKP (SEQ ID NO: 62) | DRKSVMSIRPDY (SEQ ID NO: 100) |
| 269B083 | 139 | 177 | KNTVA (SEQ ID NO: 25) | SITWDGRTTYYADSVKG (SEQ ID NO: 63) | TASCHLFGLGSGAFVS (SEQ ID NO: 101) |
| 269B085 | 140 | 178 | TFTMG (SEQ ID NO: 26) | AISLSPTLAYYAESVKG (SEQ ID NO: 64) | SKDRYSEYEY (SEQ ID NO: 102) |
| 269B093 | 141 | 179 | TFTMG (SEQ ID NO: 27) | AISLSPTLAYYAESVKG (SEQ ID NO: 65) | KNGGPVDY (SEQ ID NO: 103) |
| 269B094 | 142 | 180 | SIVMG (SEQ ID NO: 28) | AIMWNDGITYLQDSVKG (SEQ ID NO: 66) | SKGRYSEYEY (SEQ ID NO: 104) |
| 269B104 | 143 | 181 | TFTMG (SEQ ID NO: 29) | AINLSPTLTYYAESVKG (SEQ ID NO: 67) | ERKSVMAIPPDY (SEQ ID NO: 105) |
| 269B109 | 144 | 182 | TFTMG (SEQ ID NO: 30) | SITLIPTFPYYAYSVKG (SEQ ID NO: 68) | YRKYLMSILPDY (SEQ ID NO: 106) |
| 269B110 | 145 | 183 | TFTMG (SEQ ID NO: 31) | AISLSPTLAYYAESVKG (SEQ ID NO: 69) | NRNSQRVIAALSWIGMNY (SEQ ID NO: 107) |
| 269B113 | 146 | 184 | TFTMG (SEQ ID NO: 32) | AISLSPTLAYYAESVKG (SEQ ID NO: 70) | RRIDAADFDS (SEQ ID NO: 108) |
| 269B126 | 147 | 185 | TFTMG (SEQ ID NO: 33) | VIGWRDINASYADSVKG (SEQ ID NO: 71) | RRIDATDFDS (SEQ ID NO: 109) |
| 269B129 | 148 | 186 | NHVMG (SEQ ID NO: 34) | VIGWRDISTSYADSVKG (SEQ ID NO: 72) | RRIDAADFDS (SEQ ID NO: 110) |
| 269B131 | 149 | 187 | NYILA (SEQ ID NO: 35) | HISRSGGKSGYGDSVKG (SEQ ID NO: 73) | PLWYGSPTLIDY (SEQ ID NO: 111) |
| 269B135 | 150 | 188 | TFTMG (SEQ ID NO: 36) | AISLSPTLAYYAESVKG (SEQ ID NO: 74) | DRKSVMSIRPDY (SEQ ID NO: 112) |
| 269B136 | 151 | 189 | TFTMG (SEQ ID NO: 37) | AISLSPTLAYYAEPVKG (SEQ ID NO: 75) | DRKSVMSIRPDY (SEQ ID NO: 113) |
| 269B139 | 152 | 190 | NNFVMG (SEQ ID NO: 38) | AISLSPTLAYYVESVKG (SEQ ID NO: 76) | DRKSVMSIRPDY (SEQ ID NO: 114) |

B cell mature antigen (BCMA), also known as CD269, is a member of the tumor necrosis factor receptor superfamily, namely TNFRSF17 (Thompson et al., J. Exp. Medicine, 192 (1):129-135, 2000). Human BCMA is almost exclusively expressed in plasma cells and multiple myeloma cells (see e.g. Novak et al., Blood, 103(2): 689-694, 2004; Neri et al., Clinical Cancer Research, 73(19):5903-5909; Felix et al., Mol. Oncology, 9(7):1348-58, 2015). BCMA can bind B-cell activating factor (BAFF) and a proliferation including ligand (APRIL) (e.g. Mackay et al., 2003 and Kalled et al., Immunological Review, 204: 43-54, 2005). BCMA can be a suitable tumor antigen target for immunotherapeutic agents against multiple myeloma. Antibodies of high affinity can block the binding between BCMA and its native ligands BAFF and APRIL. The anti-BCMA sdAbs can be used in combination with cell immunotherapy using CAR-T cells, for example, to enhance cytotoxic effects against tumor cells.

In some embodiments, there is provided an anti-BCMA sdAb comprising one, two, or all three CDRs of the amino acid sequence of SEQ ID NO: 115. In some embodiments, there is provided an anti-BCMA sdAb comprising one, two, or all three CDRs of the amino acid sequence of SEQ ID NO: 116, In some embodiments, there is provided an anti-BCM A. sdAb comprising one, two, or all three CDRs of the amino acid sequence of SEQ ID NO: 117. In some embodiments, there is provided an anti-BCMA sdAb comprising one, two, or all three CDRs of the amino acid sequence of SEQ ID NO: 118. In some embodiments, there is provided an anti-BCMA sdAb comprising one, two, or all three CDRs of the amino acid sequence of SEQ ID NO: 119. In some embodiments, there is provided an anti-BCMA sdAb comprising one, two, or all three CDRs of the amino acid sequence of SEQ ID NO: 120. In some embodiments, there is provided an anti-BCMA sdAb comprising one, two, or all three CDRs of the amino acid sequence of SEQ ID NO: 121. In some embodiments, there is provided an anti-BCMA sdAb comprising one, two, or all three CDRs of the amino acid sequence of SEQ ID NO: 122. In some embodiments, there is provided an anti-BCMA sdAb comprising one, two, or all three CDRs of the amino acid sequence of SEQ ID NO: 123. In some embodiments, there is provided an anti-BCMA sdAb comprising one, two, or all three CDRs of the amino acid sequence of SEQ ID NO: 124. In some embodiments, there is provided an anti-BCMA sdAb comprising one, two, or all three CDRs of the amino acid sequence of SEQ ID NO: 125. In some embodiments, there is provided an anti-BCMA sdAb comprising one, two, or all three CDRs of the amino acid sequence of SEQ ID NO: 126. In some embodiments, there is provided an anti-BCMA sdAb comprising one, two, or all three CDRs of the amino acid sequence of SEQ ID NO: 127. In some embodiments, there is provided an anti-BCMA sdAb comprising one, two, or all three CDRs of the amino acid sequence of SEQ ID NO: 128. In some embodiments, there is provided an anti-BCMA sdAb comprising one, two, or all three CDRs of the amino acid sequence of SEQ ID NO: 129. In some embodiments, there is provided an anti-BCMA sdAb comprising one, two, or all three CDRs of the amino acid sequence of SEQ ID NO: 130. In some embodiments, there is provided an anti-BCMA sdAb comprising one, two, or all three CDRs of the amino acid sequence of SEQ ID NO: 131. In some embodiments, there is provided an anti-BCMA sdAb comprising one, two, or all three CDRs of the amino acid sequence of SEQ ID NO: 132. In some embodiments, there is provided an anti-BCMA sdAb comprising one, two, or all three CDRs of the amino acid sequence of SEQ ID NO: 133. In some embodiments, there is provided an anti-BCMA, sdAb comprising one, two, or all three CDRs of the amino acid sequence of SEQ ID NO: 134. In some embodiments, there is provided an anti-BCMA sdAb comprising one, two, or all three CDRs of the amino acid sequence of SEQ ID NO: 135. In some embodiments, there is provided an anti-BCMA sdAb comprising one, two, or all three CDRs of the amino acid sequence of SEQ ID NO: 136, In some embodiments, there is provided an anti-BCMA sdAb comprising one, two, or all three CDRs of the amino acid sequence of SEQ ID NO: 137. In some embodiments, there is provided an anti-BCMA sdAb comprising one, two, or all three CDRs of the amino acid sequence of SEQ ID NO: 138. In some embodiments, there is provided an anti-BCMA sdAb comprising one, two, or all three CDRs of the amino acid sequence of SEQ ID NO: 139. In some embodiments, there is provided an anti-BCMA sdAb comprising one, two, or all three CDRs of the amino acid sequence of SEQ ID NO: 140. In some embodiments, there is provided an anti-BCMA sdAb comprising one, two, or all three CDRs of the amino acid sequence of SEQ ID NO: 141. In some embodiments, there is provided an anti-BCMA sdAb comprising one, two, or all three CDRs of the amino acid sequence of SEQ ID NO: 142. In some embodiments, there is provided an anti-BCMA sdAb comprising one, two, or all three CDRs of the amino acid sequence of SEQ ID NO: 143. In some embodiments, there is provided an anti-BCMA sdAb comprising one, two, or all three CDRs of the amino acid sequence of SEQ:ID NO: 144. In some embodiments, there is provided an anti-BCMA sdAb comprising one, two, or all three CDRs of the amino acid sequence of SEQ ID NO: 145. In some embodiments, there is provided an anti-BCMA sdAb comprising one, two, or all three CDRs of the amino acid sequence of SEQ ID NO: 146. In some embodiments, there is provided an anti-BCMA sdAb comprising one, two, or all three CDRs of the amino acid sequence of SEQ ID NO: 147. In some embodiments, there is provided an anti-BCMA sdAb comprising one, two, or all three CDRs of the amino acid sequence of SEQ ID NO: 148. In some embodiments, there is provided an anti-BCMA sdAb comprising one, two, or all three CDRs of the amino acid sequence of SEQ ID NO: 149. In some embodiments, there is provided an anti-BCMA sdAb comprising one, two, or all three CDRs of the amino acid sequence of SEQ ID NO: 150, In some embodiments, there is provided an anti-BCMA sdAb comprising one, two, or all three CDRs of the amino acid sequence of SEQ ID NO: 151. In some embodiments, there is provided an anti-BCMA sdAb comprising one, two, or all three CDRs of the amino acid sequence of SEQ ID NO: 152. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising at least one, at least two, or all three CDRs selected from (a) a CDR1 comprising an amino acid sequence selected from SEQ ID NO: 1-38; (b) a. CDR2 comprising an amino acid sequence selected from SEQ ID NO: 39-76; and (c) a CDR3 comprising an amino acid sequence selected from SEQ ID NO: 77-114, In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:1-38; (b) a CDR2 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 39-76; and (c) a CDR3 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 77-114. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, there is provided an anti-BCMA sdAb comprising three CDRs comprising: (a) a CDR1 having about any one of 1, 2, 3, or 4 amino acid substitutions (e.g., conservative substitutions), insertions, or deletions to an amino acid sequence selected from SEQ ID NO:1-38; (b) a CDR2 having about any one of 1, 2, 3, or 4 amino acid substitutions (e.g., conservative substitutions), insertions, or deletions to an amino acid sequence selected from SEQ ID NO:39-76; and (c) a CDR3 having about any one of 1, 2, 3, or 4 amino acid substitutions (e.g., conservative substitutions), insertions, or deletions to an amino acid sequence selected from SEQ ID NO: 77-114. In some embodiments, the anti-BCMA sdAb is affinity matured. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising three CDRs comprising: (a) a CDR1 comprising the amino acid sequence of SEQ ID NO: 1; (b) a CDR2 comprising the amino acid sequence of SEQ ID NO: 39; and (c) a CDR3 comprising the amino acid sequence of SEQ ID NO: 77. In some embodiments, there is provided an anti-BCMA sdAb comprising three CDRs comprising: (a) a CDR1 comprising the amino acid sequence of SEQ ID NO: 2; (b) a CDR2 comprising the amino acid sequence of SEQ ID NO: 40; and (c) a CDR3 comprising the amino acid sequence of SEQ ID NO: 78. In some embodiments, there is provided an anti-BCMA, sdAb comprising three CDRs comprising: (a) a CDR1 comprising the amino acid sequence of SEQ ID NO: 3; (b) a CDR2 comprising the amino acid sequence of SEQ ID NO: 41; and (c) a CDR3 comprising the amino acid sequence of SEQ ID NO: 79. In some embodiments, there is provided an anti-BCMA sdAb comprising three CDRs comprising: (a) a CDR1 comprising the amino acid sequence of SEQ ID NO: 4; (b) a CDR2 comprising the amino acid sequence of SEQ ID NO: 42; and (c) a CDR3 comprising the amino acid sequence of SEQ ID NO: 80. In some embodiments, there is provided an anti-BCMA sdAb comprising three CDRs comprising: (a) a CDR1 comprising the amino acid sequence of SEQ ID NO: 5; (b) a CDR2 comprising the amino acid sequence of SEQ ID NO: 43; and (c) a. CDR3 comprising the amino acid sequence of SEQ ID NO: 81. In some embodiments, there is provided an anti-BCMA sdAb comprising three CDRs comprising: (a) a CDR1 comprising the amino acid sequence of SEQ ID NO: 6; (b) a CDR2 comprising the amino acid sequence of SEQ ID NO: 44; and (c) a CDR3 comprising the amino acid sequence of SEQ ID NO: 82. In some embodiments, there is provided anti-BCMA sdAb comprising three CDRs comprising: (a) a CDR1 comprising the amino acid sequence of SEQ ID NO: 7; (b) a CDR2 comprising the amino acid sequence of SEQ ID NO: 45; and (c) a CDR3 comprising the amino acid sequence of SEQ ID N0: 83. In some embodiments, there is provided an anti-BCMA sdAb comprising three CDRs comprising: (a) a CDR1 comprising the amino acid sequence of SEQ ID NO: 8; (b) a CDR2 comprising the amino acid sequence of SEQ ID NO: 46; and (c) a CDR3 comprising the amino acid sequence of SEQ ID NO: 84. In some embodiments, there is provided an anti-BCMA sdAb comprising three CDRs comprising: (a) a CDR1 comprising the amino acid sequence of SEQ ID NO: 9; (b) a CDR2 comprising the amino acid sequence of SEQ ID NO: 47; and (c) a CDR3 comprising the amino acid sequence of SEQ ID NO: 85. In some embodiments, there is provided an anti-BCSA sdAb comprising three CDRs comprising: (a) a CDR1 comprising the amino acid sequence of SEQ ID NO: 10; (b) a CDR2 comprising the amino acid sequence of SEQ ID NO: 48; and (c) a CDR3 comprising the amino acid sequence of SEQ ID NO: 86. In some embodiments, there is provided anti-BCMA sdAb comprising three CDRs comprising: (a) a CDR1 comprising the amino acid sequence of SEQ ID NO: 11; (b) a CDR2 comprising the amino acid sequence of SEQ ID NO: 49; and (c) a CDR3 comprising the amino acid sequence of SEQ ID NO: 87. In some embodiments, there is provided an anti-BCMA sdAb comprising three CDRs comprising: (a) a CDR1 comprising the amino acid sequence of SEQ ID NO: 12; (b) a CDR2 comprising the amino acid sequence of SEQ ID NO: 50; and (c) a CDR3 comprising the amino acid sequence of SEQ ID NO: 88, In some embodiments, there is provided an anti-BCMA sdAb comprising three CDRs comprising: (a) a CDR1 comprising the amino acid sequence of SEQ ID NO: 13; (b) a CDR2 comprising the amino acid sequence of SEQ ID NO: 51; and (c) a CDR3 comprising the amino acid sequence of SEQ ID NO: 89. In some embodiments, there is provided an anti-BCMA sdAb comprising three CDRs comprising: (a) a CDR1 comprising the amino acid sequence of SEQ ID NO: 14; (b) a CDR2 comprising the amino acid sequence of SEQ ID NO: 52; and (c) a CDR3 comprising the amino acid sequence of SEQ ID NO: 90. In some embodiments, there is provided an anti-BCMA sdAb comprising three CDRs comprising: (a) a CDR1 comprising the amino acid sequence of SEQ ID NO: 15; (b) a CDR2 comprising the amino acid sequence of SEQ ID NO: 53; and (c) a CDR3 comprising the amino acid sequence of SEQ ID NO: 91. In some embodiments, there is provided an anti-BCM A sdAb comprising three CDRs comprising: (a) a CDR1 comprising the amino acid sequence of SEQ ID NO: 16; (b) a CDR2 comprising the amino acid sequence of SEQ ID NO: 54; and (c) a. CDR3 comprising the amino acid sequence of SEQ ID NO: 92. In some embodiments, there is provided an anti-BCMA sdAb comprising three CDRs comprising: (a) a CDR1 comprising the amino acid sequence of SEQ ID NO: 17; (b) a CDR2 comprising the amino acid sequence of SEQ ID NO: 55; and (c) a CDR3 comprising the amino acid sequence of SEQ ID NO: 93, In some embodiments, there is provided an anti-BC:MA sdAb comprising three CDRs comprising: (a) a CDR1 comprising the amino acid sequence of SEQ ID NO: 18; (b) a CDR2 comprising the amino acid sequence of SEQ ID NO: 56; and (c) a CDR3 comprising the amino acid sequence of SEQ ID NO: 94. In some embodiments, there is provided an anti-BCMA sdAb comprising three CDRs comprising: (a) a CDR1 comprising the amino acid sequence of SEQ ID NO: 19; (b) a CDR2 comprising the amino acid sequence of SEQ ID NO: 57; and (c) a CDR3 comprising the amino acid sequence of SEQ ID NO: 95. In some embodiments, there is provided an anti-BCMA sdAb comprising three CDRs comprising: (a) a CDR1 comprising the amino acid sequence of SEQ ID NO: 20; (b) a CDR2 comprising the amino acid sequence of SEQ ID NO: 58; and (c) a. CDR3 comprising the amino acid sequence of SEQ ID NO: 96. In some embodiments, there is provided an anti-BCMA sdAb comprising three CDRs comprising: (a) a CDR1 comprising the amino acid sequence of SEQ ID NO: 21; (b) a CDR2 comprising the amino acid sequence of SEQ ID NO: 59; and (c) a CDR3 comprising the amino acid sequence of SEQ ID NO: 97, In some embodiments, there is provided an anti-BCMA sdAb comprising three CDRs comprising: (a) a CDR1 comprising the amino acid sequence of SEQ ID NO: 22; (b) a CDR2 comprising the amino acid sequence of SEQ ID NO: 60; and (c) a CDR3 comprising the amino acid sequence of SEQ ID NO: 98. In some embodiments, there is provided an anti-BCMA sdAb comprising three CDRs comprising: (a) a CDR1 comprising the amino acid sequence of SEQ ID NO: 23; (b) a CDR2 comprising the amino acid sequence of SEQ ID NO: 61; and (c) a CDR3 comprising the amino acid sequence of SEQ ID NO: 99. In some embodiments, there is provided an anti-BC MA sdAb comprising three CDRs comprising: (a) a CDR1 comprising the amino acid sequence of SEQ ID NO: 24; (b) a CDR2 comprising the amino acid sequence of SEQ ID NO: 62; and (c) a CDR3 comprising the amino acid sequence of SEQ ID NO: 100. In some embodiments, there is provided an anti-BCMA sdAb comprising three CDRs comprising: (a) a CDR1 comprising the amino acid sequence of SEQ ID NO: 25; (b) a CDR2 comprising the amino acid sequence of SEQ ID NO: 63; and (c) a CDR3 comprising the amino acid sequence of SEQ ID NO: 101. In some embodiments, there is provided an anti-BCMA, sdAb comprising three CDRs comprising: (a) a CDR1 comprising the amino acid sequence of SEQ ID NO: 26; (b) a CDR2 comprising the amino acid sequence of SEQ ID NO: 64; and (c) a CDR3 comprising the amino acid sequence of SEQ ID NO: 102. In some embodiments, there is provided an anti-BCMA sdAb comprising three CDRs comprising: (a) a CDR1 comprising the amino acid sequence of SEQ ID NO: 27; (b) a CDR2 comprising the amino acid sequence of SEQ ID NO: 65; and (c) a CDR3 comprising the amino acid sequence of SEQ ID NO: 103, in some embodiments, there is provided an anti-BC:MA sdAb comprising three CDRs comprising: (a) a CDR1 comprising the amino acid sequence of SEQ ID NO: 28; (b) a CDR2 comprising the amino acid sequence of SEQ ID NO: 66; and (c) a CDR3 comprising the amino acid sequence of SU) ID NO: 104, In some embodiments, there is provided an anti-BCMA sdAb comprising three CDRs comprising: (a) a CDR1 comprising the amino acid sequence of SEQ ID NO: 29; (b) a CDR2 comprising the amino acid sequence of SEQ ID NO: 67; and (c) a CDR3 comprising the amino acid sequence of SEQ ID NO: 105. In some embodiments, there is provided an anti-BCMA sdAb comprising three CDRs comprising: (a) a CDR1 comprising the amino acid sequence of SEQ ID NO: 30; (b) a CDR2 comprising the amino acid sequence of SEQ ID NO: 68; and (c) a CDR3 comprising the amino acid sequence of SEQ ID NO: 106. In some embodiments, there is provided an anti-BCMA sdAb comprising three CDRs comprising: (a) a CDR1 comprising the amino acid sequence of SEQ ID NO: 31; (b) a CDR2 comprising the amino acid sequence of SEQ ID NO: 69; and (c) a CDR3 comprising the amino acid sequence of SEQ ID NO: 107. In some embodiments, there is provided an anti-BCMA sdAb comprising three CDRs comprising: (a) a CDR1 comprising the amino acid sequence of SEQ ID NO: 32; (b) a CDR2 comprising the amino acid sequence of SEQ ID NO: 70; and (c) a CDR3 comprising the amino acid sequence of SEQ ID NO: 108. In some embodiments, there is provided an anti-BCMA sdAb comprising three CDRs comprising: (a) a CDR1 comprising the amino acid sequence of SEQ:ID NO: 33; (b) a CDR2 comprising the amino acid sequence of SEQ ID NO: 71; and (c) a CDR3 comprising the amino acid sequence of SEQ ID NO: 109. In some embodiments, there is provided an anti-BCMA sdAb comprising three CDRs comprising: (a) a CDR1 comprising the amino acid sequence of SEQ ID NO: 34; (b) a CDR2 comprising the amino acid sequence of SEQ ID NO: 72; and (c) a CDR3 comprising the amino acid sequence of SEQ ID NO: 110. In some embodiments, there is provided an anti-BCMA sdAb comprising three CDRs comprising: (a) a CDR1 comprising the amino acid sequence of SEQ ID NO: 35; (b) a CDR2 comprising the amino acid sequence of SEQ ID NO: 73; and (c) a CDR3 comprising the amino acid sequence of SEQ ID NO: 111. In some embodiments, there is provided an anti-BCMA sdAb comprising three CDRs comprising: (a) a CDR1 comprising the amino acid sequence of SEQ ID NO: 36; (b) a CDR2 comprising the amino acid sequence of SEQ ID NO: 74; and (c) a CDR3 comprising the amino acid sequence of SEQ ID NO: 112. In some embodiments, there is provided an anti-BCMA sdAb comprising three CDRs comprising: (a) a CDR1 comprising the amino acid sequence of SEQ ID NO: 37; (b) a CDR2 comprising the amino acid sequence of SEQ ID NO: 75; and (c) a CDR3 comprising the amino acid sequence of SEQ ID NO: 113. In some embodiments, there is provided an anti-BCMA, sdAb comprising three CDRs comprising: (a) a CDR1 comprising the amino acid sequence of SEQ ID NO: 38; (b) a CDR2 comprising the amino acid sequence of SEQ ID NO: 76; and (c) a CDR3 comprising the amino acid sequence of SEQ ID NO: 114. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, the anti-BCMA sdAb, including any of the embodiments described above (i.e., anti-BCMA sdAb comprising specific CDR1, CDR2, and/or CDR3) comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 115-152. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, a total of 1 to 10 amino acids have been substituted, inserted and/or deleted in an amino acid sequence selected from SEQ ID NO: 115-152. In some embodiments, substitutions, insertions, or deletions occur in regions outside the CDRs (i.e., in the FRs), Optionally, the anti-BCMA sdAb comprises an amino acid sequence selected from SEQ ID NO: 115-152, including post-translational modifications of that sequence.

In some embodiments, there is provided an isolated anti-BCMA sdAb comprising a $V_HH$ domain having an amino acid sequence selected from the group consisting of SEQ ID NOs: 115-152. In some embodiments, there is provided a polypeptide comprising an amino acid sequence selected from the group consisting of SEQ ID NOs: 115-152.

In some embodiments, functional epitopes can be mapped by combinatorial alanine scanning. In this process, a combinatorial alanine-scanning strategy can be used to identify amino acids in the BCMA protein that are necessary for interaction with anti-BCMA sdAbs. In some embodiments, the epitope is conformational and crystal structure of anti-BCMA sdAb bound to BCMA may be employed to identify the epitopes. In some embodiments, the present application provides an epitope of BCMA derived from an amino acid sequence selected from the group consisting of SEQ ID NOs: 388-394, In some embodiments, the present application provides an epitope of BCMA comprising an amino acid sequence selected from the group consisting of SEQ ID NOs: 388-394.

In some embodiments, the present application provides antibodies which compete with any one of the anti-BCMA sdAbs described herein for binding to BCMA. In some embodiments, the invention provides antibodies which compete with the anti-BCMA sdAbs provided herein for binding to an epitope on the BCMA. In some embodiments, an antibody is provided that binds to the same epitope as an anti-BCMA sdAb comprising an amino acid sequence selected from the group consisting of SEQ ID NOs: 115-152. In some embodiments, an antibody is provided that specifically binds to BCMA competitively with an anti-BC:MA sdAb comprising an amino acid sequence selected from the group consisting of SEQ ID NOs: 115-152.

In some embodiments, competition assays may be used to identify a monoclonal antibody that competes with an anti-BCMA sdAb described herein for binding to BCMA. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope (e.g., a BCMA epitope derived from an amino acid sequence selected from the group consisting of SEQ ID NOs: 388-394) that is bound by an antibody described herein. Exemplary competition assays include, but are not limited to, routine assays such as those provided in Harlow and Lane (1988) Antibodies: A Laboratory Manual ch.14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-BCMA sdAb described herein is a camelid, chimeric, humanized or human antibody. In some embodiments, the present application provides an antibody that competes with a camelid, chimeric, humanized, or human anti-BCMA sdAb as described herein.

In some embodiments, there is provided an anti-BCMA antibody or antigen binding protein comprising any one of the anti-BCMA sdAbs described above, in some embodiments, the anti-BCMA antibody is a monoclonal antibody, including a camelid, chimeric, humanized or human antibody. In some embodiments, the anti-BCMA antibody is an antibody fragment, e.g., a $V_HH$ fragment. In some embodiments, the anti-BCMA antibody is a full-length heavy chain only antibody comprising an Fc region of any antibody class or isotype, such as IgG1 or IgG4. In some embodiments, the Fc region has reduced or minimized effector function.

In some embodiments, the anti-BCMA antibody (such as anti-BCMA sdAb) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-BCMA antibodies (such as anti-BCMA sdAbs) described above. In some embodiments, an isolated nucleic acid encoding an anti-BCMA sdAb is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NO: 153-190. In some embodiments, there is provided an isolated nucleic acid comprising a nucleic acid sequence selected from the group consisting of SEQ ID NO: 153-190. In some embodiments, a vector (e.g., expression vector) comprising such nucleic acid are provided. In some embodiments, a host cell comprising such nucleic acid is provided. In some embodiments, a method of making an anti-BCMA antibody is provided, wherein the method comprises culturing a host cell comprising a nucleic acid encoding the anti-BCMA antibody, as provided above, under conditions suitable for expression of the anti-BCMA antibody, and optionally recovering the anti-BCMA antibody from the host cell (or host cell culture medium).

Features of Antibodies

1. Antibody Affinity

In some embodiments, an anti-BCMA antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In some embodiments, Kd is measured by a radiolabeled antigen binding assay (RIA) performed with the Fab version or $V_HH$ fragment of an antibody of interest and its antigen as described by the following assay. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)).

In some embodiments, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab or $V_HH$ of the antibody of interest (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In some embodiments, an antibody provided herein is an antibody fragment. Antibody fragments include, but are not limited to, Fab, Fab', Fab'-SH, F(ab')$_2$, Fv, and scFv fragments, V$_H$H, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In some embodiments, the antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., Methods 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the sdAbs are modified, such as humanized, without diminishing the native affinity of the domain for antigen and while reducing its immunogenicity with respect to a heterologous species. For example, the amino acid residues of the antibody variable domain (V$_H$H) of an llama antibody can be determined, and one or more of the *Camelid* amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of *Camelid* sdAbs requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

Single-domain antibodies comprising a V$_H$H domain can be humanized to have human-like sequences. In some embodiments, the FR regions of the V$_H$H domain used herein comprise at least about any one of 50%, 60%, 70%, 80%, 90%, 95% or more of amino acid sequence homology to human V$_H$ framework regions. One exemplary class of humanized V$_H$H domains is characterized in that the V$_H$Hs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human V$_H$ framework regions and said polypeptides might be administered to a human directly without expectation of an unwanted immune response therefrom, and without the burden of further humanization.

Another exemplary class of humanized *Camelid* sdAbs has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in V$_H$ from double-chain antibodies. As such, peptides belonging to these two classes show a high amino acid sequence homology to human V$_H$ framework regions and said peptides might be administered to a human directly without expectation of an unwanted immune response therefrom, and without the burden of further humanization.

4. Human Antibodies

In some embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human sdAbs are known in the art. See, e.g., US20090307787A1, U.S. Pat. No. 8,754,287, US20150289489A1, US20100122358A1, and WO2004049794, Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et at, *Proc. Natl. Acad. Sci. USA*, 1033557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Jans- sens et al., Proc. Natl. Acad. Sci. USA. 2006 Oct. 10; 103(40:15130-5 can be used. For example, such heavy chain antibody expressing mice can express heavy chain antibodies with any suitable (single) variable domain, such as (single) variable domains from natural sources (e.g. human (single) variable domains, *Camelid* (single) variable domains or shark (single) variable domains), as well as for example synthetic or semi-synthetic (single) variable domains.

5. Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing sdAb libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, an antibody provided herein is a multispecific antibody, e.g. a bispecific antibody. Multispecific antibodies are antibodies that have binding specificities for at least two different sites. In some embodiments, one of the binding specificities is for an antigen selected from the group consisting of CD19, CD20, BCMA, and CD38, and the other is for any other antigen. In some embodiments, bispecific antibodies may bind to two different epitopes of an antigen selected from the group consisting of CD19, CD20, BCMA, and CD38. Bispecific antibodies may also be used to localize cytotoxic agents to cells which express an antigen selected from the group consisting of CD19, CD20, BCMA, and CD38.

Bispecific antibodies can be prepared as full length antibodies or antibody fragments. Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991); and creating polypeptides comprising tandem single-domain antibodies (see, e.g, U.S. Patent Application No. 20110028695; and Conrath et al. J. Biol. Chem., 2001; 276(10):7346-50). Engineered antibodies with three or more functional antigen binding sites, including "Octopus antibodies," are also included herein (see, e.g., US 2006/0025576A1).

7. Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In some embodiments, antibody variants having one or more amino acid substitutions are provided. Sites of interest for substitutional mutagenesis include the HVRs and FRs. Conservative substitutions are shown in Table 3 under the heading of "Preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

| Amino Acid Substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |

TABLE 3-continued

| Amino Acid Substitutions | | |
|---|---|---|
| Original Residue | Exemplary Substitutions | Preferred Substitutions |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, *FUT*8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc region Variants

In some embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Methods of Preparation

The antibodies (such as sdAbs) described herein may be prepared using any methods known in the art or as described herein.

Methods of preparing sdAbs have been described. See, for example, Els Pardon et al, *Nature Protocol*, 2014; 9(3): 674. Single-domain antibodies (such as $V_H$Hs) may be obtained using methods known in the art such as by immunizing a *Camelid* species (such as camel or llama) and obtaining hybridomas therefrom, or by cloning a library of sdAbs using molecular biology techniques known in the art and subsequent selection by ELISA with individual clones of unselected libraries or by using phage display.

For recombinant production of the sdAbs, the nucleic acids encoding the sdAbs are isolated and inserted into a replicable vector for further cloning (amplification of the DNA) or for expression. DNA encoding the sdAb is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

1. Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 µg or 5 µg or the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

2. Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (coding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as FIAT medium, Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g, X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp, 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (coding, supra). Suitable culture media for this purpose include, for example, D-MEM or DPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g, by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5:256-262 (1993) and Pliickthun, Immunol, Revs. 130:151-188 (1992).

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively; using phage libraries. Subsequent publications describe the production of high affinity (nM range) human antibodies by chain shuffling (Marks et at., Bio/Technology, 10:779-783 (1992)), as well as combinatorial infection and in vivo recombination as a strategy for constructing very large phage libraries (Waterhouse et at., Nucl. Acids Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Recombinant Production in Prokaryotic Cells
a) Vector Construction

Polynucleotide sequences encoding the antibodies of the present application can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RB S), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as E. coli LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the—galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the antibodies according to the present application can occur in the cytoplasm of the host cell, and therefore does not require the presence of secretion signal sequences within each cistron. In some embodiments, polypeptide components, such as the polypeptide encoding the $V_H$ domain of the first antigen binding portion optionally fused to the second antigen binding portion, and the polypeptide encoding the $V_L$ domain of the first antigen binding portion optionally fused to the second antigen binding portion, are expressed, folded and assembled to form functional antibodies within the cytoplasm. Certain host strains (e.g., the *E. coli* trxB strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled the antibodies of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells.

Prokaryotic host cells suitable for expressing the antibodies of the present application include Archaebacteria and Eubacteria, such as Gram-negative or Gram-positive organisms. Examples of useful bacteria include *Escherichia*(e.g., *E. coli*), *Bacilli* (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.* In some embodiments, gram-negative cells are used. In some embodiments, *E. coli* cells are used as hosts for the invention. Examples of *E. coli* strains include strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells.

The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed antibodies of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

*E. coli* strains deficient for proteolytic enzymes and transformed with plasmids overexpressing one or more chaperone proteins may be used as host cells in the expression system encoding the antibodies of the present application.

d) Protein Purification

The antibodies produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibodies comprising an Fc region of the present application. Protein A is a 41kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

4. Recombinant Production in Eukaryotic Cells

For Eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. A the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, —lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S. D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

In some embodiments, the present application also provides immunoconjugates comprising any of the antibodies (such as sdAbs) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, sapaonaria *officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $A^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In some embodiments, any of the antibodies (such as sdAbs) provided herein is useful for detecting the presence of BCMA in a biological sample. The term "detecting" as used herein encompasses quantitative or qualitative detection. In certain embodiments, a biological sample is blood, serum or other liquid samples of biological origin. In some embodiments, a biological sample comprises a cell or tissue.

In some embodiments, an anti-BCMA antibody (such as any one of the anti-BCMA sdAbs described herein) for use in a method of diagnosis or detection is provided. In a further aspect, a method of detecting the presence of BCMA in a biological sample is provided. In certain embodiments, the method comprises detecting the presence of BCMA protein in a biological sample. In certain embodiments, BCMA is human BCMA. In certain embodiments, the method comprises contacting the biological sample with an anti-BCMA antibody as described herein under conditions permissive for binding of the anti-BCMA antibody to BCMA, and detecting whether a complex is formed between the anti-BCMA antibody and BCMA. Such method may be an in vitro or in vivo method. In some embodiments, an anti-BCMA antibody is used to select subjects eligible for therapy with an anti-BCMA antibody, e.g. where BCMA is a biomarker for selection of patients.

In certain embodiments, labeled anti-BCMA sdAbs are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Chimeric Antigen Receptors

One aspect of the present application provides a chimeric antigen receptor (CAR) comprising an extracellular antigen binding domain comprising one or more single-domain antibodies (such as $V_HHs$). Any one of the anti-BCMA sdAbs described in Section II can be used in the CARs described herein. Exemplary structures of CARs are shown in FIGS. 15A-15D.

In some embodiments, there is provided a CAR targeting BCMA (also referred herein as "BCMA CAR") comprising a polypeptide comprising: (a) an extracellular antigen binding domain comprising an anti-BCMA sdAb; (b) a transmembrane domain; and (c) an intracellular signaling domain. In some embodiments, the anti-BCMA sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb is camelid, chimeric, human, or humanized. In some embodiments, the anti-BCMA sdAb comprises a V$_H$H domain comprising an amino acid sequence selected from the group consisting of SEQ ID NO: 115-152. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 216-256 and 298-335. In some embodiments, there is provided a BCMA CAR comprising an amino acid sequence selected from the group consisting of SEQ ID NO: 216-256 and 298-335. Also provided is a polypeptide comprising an amino acid sequence selected from the group consisting of SEQ ID NO: 216-256 and 298-335.

In some embodiments, there is provided an isolated nucleic acid encoding any of the BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 257-297 and 336-373. In some embodiments, there is provided an isolated nucleic acid comprising a nucleic acid sequence selected from the group consisting of SEQ ID NO: 257-297 and 336-373. In some embodiments, the isolated nucleic acid is a DNA. In some embodiments, the isolated nucleic acid is an RNA. In some embodiments, there is provided a vector comprising any one of the nucleic acids encoding the BCMA CARs described above. In some embodiments, the vector is an expression vector. In some embodiments, the vector is a viral vector, such as a lentiviral vector. In some embodiments, the vector is a non-viral vector. Exemplary monovalent BCMA CARs are shown in Table 4 below.

TABLE 4

Exemplary monovalent BCMA CARs.

| Ex. Vector or CAR name | Ex. AA SEQ ID | Ex. NA SEQ ID | Extracellular | | | Intracellular signaling | | |
|---|---|---|---|---|---|---|---|---|
| | | | SP | sdAb | Hinge | TM | CO1 | CO2 | Prim. |
| PLLV-hEF1a-269A37346 | 216 | 257 | CD8α | 269A37346 | CD8α | CD28 | CD28 | CD137 | CD3ζ |
| PLLV-hEF1a-269A37348 | 217 | 258 | CD8α | 269A37348 | CD8α | CD28 | CD28 | CD137 | CD3ζ |
| PLLV-hEF1a-269A37917 | 218 | 259 | CD8α | 269A37917 | CD8α | CD28 | CD28 | CD137 | CD3ζ |

TABLE 4-continued

Exemplary monovalent BCMA CARs.

| Ex. Vector or CAR name | Ex. AA SEQ ID | Ex. NA SEQ ID | SP | Extra-cellular. sdAb | Hinge | TM | Intracellular signaling | | |
|---|---|---|---|---|---|---|---|---|---|
| | | | | | | | CO1 | CO2 | Prim. |
| PLLV-hEF1a-269A37355 | 219 | 260 | CD8α | 269A37355 | CD8α | CD28 | CD28 | CD137 | CD3ζ |
| PLLV-hEF1a-269A37915 | 220 | 261 | CD8α | 269A37915 | CD8α | CD28 | CD28 | CD137 | CD3ζ |
| PLLV-hEF1a-269A37936 | 221 | 262 | CD8α | 269A37936 | CD8α | CD28 | CD28 | CD137 | CD3ζ |
| PLLV-hEF1a-269A37953 | 222 | 263 | CD8α | 269A37953 | CD8α | CD28 | CD28 | CD137 | CD3ζ |
| PLLV-hEF1a-269A37965 | 223 | 264 | CD8α | 269A37965 | CD8α | CD28 | CD28 | CD137 | CD3ζ |
| PLLV-hEF1a-269A37972 | 224 | 265 | CD8α | 269A37972 | CD8α | CD28 | CD28 | CD137 | CD3ζ |
| PLLV-hEF1a-269A37353 | 225 | 266 | CD8α | 269A37353 | CD8α | CD28 | CD28 | CD137 | CD3ζ |
| PLLV-hEF1a-269A37948 | 226 | 267 | CD8α | 269A37948 | CD8α | CD28 | CD28 | CD137 | CD3ζ |
| GSI5011 CAR | 227 | 268 | CD8α | 269A37346 | CD8α | CD8α | CD137 | NA | CD3ζ |
| GSI5019 CAR | 228 | 269 | CD8α | 269A37353 | CD8α | CD8α | CD137 | NA | CD3ζ |
| GSI5020 CAR | 229 | 270 | CD8α | 269A37917 | CD8α | CD8α | CD137 | NA | CD3ζ |
| 269B005S | 230 | 271 | CD8α | 269B005 | CD8α | CD8α | CD137 | NA | CD3ζ |
| 269B023S | 231 | 272 | CD8α | 269B023 | CD8α | CD8α | CD137 | NA | CD3ζ |
| 269B024S | 232 | 273 | CD8α | 269B024 | CD8α | CD8α | CD137 | NA | CD3ζ |
| 269B028S | 233 | 274 | CD8α | 269B028 | CD8α | CD8α | CD137 | NA | CD3ζ |
| 269B030S | 234 | 275 | CD8α | 269B030 | CD8α | CD8α | CD137 | NA | CD3ζ |
| 269B038S | 235 | 276 | CD8α | 269B038 | CD8α | CD8α | CD137 | NA | CD3ζ |
| 269B054S | 236 | 277 | CD8α | 269B054 | CD8α | CD8α | CD137 | NA | CD3ζ |
| 269B059S | 237 | 278 | CD8α | 269B059 | CD8α | CD8α | CD137 | NA | CD3ζ |
| 269B060S | 238 | 279 | CD8α | 269B060 | CD8α | CD8α | CD137 | NA | CD3ζ |
| 269B069S | 239 | 280 | CD8α | 269B069 | CD8α | CD8α | CD137 | NA | CD3ζ |
| 269B074S | 240 | 281 | CD8α | 269B074 | CD8α | CD8α | CD137 | NA | CD3ζ |
| 269B076S | 241 | 282 | CD8α | 269B076 | CD8α | CD8α | CD137 | NA | CD3ζ |
| 269B079S | 242 | 283 | CD8α | 269B083 | CD8α | CD8α | CD137 | NA | CD3ζ |
| 269B083S | 243 | 284 | CD8α | 269B085 | CD8α | CD8α | CD137 | NA | CD3ζ |
| 269B085S | 244 | 285 | CD8α | 269B093 | CD8α | CD8α | CD137 | NA | CD3ζ |
| 269B093S | 245 | 286 | CD8α | 269B094 | CD8α | CD8α | CD137 | NA | CD3ζ |
| 269B094S | 246 | 287 | CD8α | 269B104 | CD8α | CD8α | CD137 | NA | CD3ζ |
| 269B104S | 247 | 288 | CD8α | 269B109 | CD8α | CD8α | CD137 | NA | CD3ζ |
| 269B109S | 248 | 289 | CD8α | 269B110 | CD8α | CD8α | CD137 | NA | CD3ζ |
| 269B110S | 249 | 290 | CD8α | 269B113 | CD8α | CD8α | CD137 | NA | CD3ζ |
| 269B113S | 250 | 291 | CD8α | 269B126 | CD8α | CD8α | CD137 | NA | CD3ζ |
| 269B126S | 251 | 292 | CD8α | 269B129 | CD8α | CD8α | CD137 | NA | CD3ζ |
| 269B129S | 252 | 293 | CD8α | 269B131 | CD8α | CD8α | CD137 | NA | CD3ζ |
| 269B131S | 253 | 294 | CD8α | 269B135 | CD8α | CD8α | CD137 | NA | CD3ζ |
| 269B135S | 254 | 295 | CD8α | 269B136 | CD8α | CD8α | CD137 | NA | CD3ζ |
| 269B136S | 255 | 296 | CD8α | 269B139 | CD8α | CD8α | CD137 | NA | CD3ζ |
| 269B139S | 256 | 297 | CD8α | 269B024 | CD8α | CD8α | CD137 | NA | CD3ζ |

Multivalent Chimeric Antigen Receptors

The present application also provides multivalent CARs that have two or more (such as about any one of 2, 3, 4, 5, 6, or more) binding moieties that specifically bind to an antigen, such as BCMA. In some embodiments, one or more of the binding moieties are antigen binding fragments. In some embodiments, one or more of the binding moieties comprise single-domain antibodies. In some embodiments, one or more of the binding moieties are derived from camelid antibodies. In some embodiments, one or more of the binding moieties are derived from a four-chain antibody. In some embodiments, one or more of the binding moieties are scFvs. In some embodiments, one or more of the binding moieties are derived from human antibodies. In some embodiments, one or more of the binding moieties are polypeptide ligands or other non-antibody polypeptides that specifically bind to the antigen. In some embodiments, the multivalent CAR is monospecific, i.e., the multivalent CAR targets a single antigen, and comprises two or more binding sites for the single antigen. In some embodiments, the multivalent CAR is multispecific, i.e., the multivalent CAR targets more than one antigen, and the multivalent CAR comprises two or more binding sites for at least one antigen. The binding moieties specific for the same antigen may bind to the same epitope of the antigen (i.e., "mono-epitope CAR") or bind to different epitopes (i.e., "multi-epitope CAR" such as bi-epitope CAR or tri-epitope CAR) of the antigen. The binding sites specific for the same antigen may comprise the same or different sdAbs.

In some embodiments, the present application provides a multivalent (such as bivalent, trivalent, or of higher number of valencies) chimeric antigen receptor comprising a polypeptide comprising: (a) an extracellular antigen binding domain comprising a plurality (such as at least about any one of 2, 3, 4, 5, 6, or more) of binding moieties specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the present application provides a multivalent (such as bivalent, trivalent, or of higher number of valencies) chimeric antigen receptor comprising a polypeptide comprising: (a) an extracellular antigen binding domain comprising a plurality (such as at least about any one of 2, 3, 4, 5, 6, or more) of single-domain antibodies (sdAbs) specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the present application provides a multivalent (such as bivalent, trivalent, or of higher number of valencies) chimeric antigen receptor comprising a polypeptide comprising: (a) an extracellular antigen binding domain comprising a first binding moiety specifically binding to a first epitope of an antigen (such as a tumor antigen), and a second binding moiety specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first binding moiety is an sdAb and the second binding moiety is derived from a human antibody (e.g., an scFv). In some embodiments, the first binding moiety is an sdAb and the second binding moiety is a polypeptide ligand. In some embodiments, the first epitope is the same as the second epitope. In some embodiments, the first epitope is different from the second epitope. In some embodiments, the multivalent CAR specifically binds to two different epitopes on an antigen. In some embodiments, the multivalent CAR specifically binds to three or more different epitopes on an antigen.

In some embodiments, the present application provides a multivalent (such as bivalent, trivalent, or of higher number of valencies) chimeric antigen receptor comprising a polypeptide comprising: (a) an extracellular antigen binding domain comprising a first sdAb specifically binding to a first epitope of an antigen (such as a tumor antigen), and a second sdAb specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the binding moieties, such as sdAbs (including the plurality of sdAbs, or the first sdAb and/or the second sdAb) are camelid, chimeric, human, or humanized. In some embodiments, the binding moieties or sdAbs are fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR is monospecific. In some embodiments, the multivalent CAR is multispecific, such as bispecific.

The multivalent CARs describe herein may be specially suitable for targeting multimeric antigens via synergistic binding by the different antigen binding sites, or for enhancing binding affinity or avidity to the antigen. Any of the anti-BCMA sdAbs described herein may be used in the extracellular antigen binding domain of the multivalent CARs described herein. A list of exemplary multivalent BCMA CARs, exemplary sequences, constructs and vectors thereof are shown in Table 5.

In some embodiments, there is provided a multivalent CAR targeting BCMA comprising: (a) an extracellular antigen binding domain comprising a plurality (such as at least about any one of 2, 3, 4 or more) of a BCMA binding moiety (e.g., an anti-BCMA sdAb); (b) a transmembrane domain; and (c) an intracellular signaling domain. Any of the anti-BCMA sdAbs can be used to construct the multivalent BCMA CAR. In some embodiments, the extracellular antigen binding domain specifically binds to a single epitope of BCMA, and these CARs are referred herein as mono-epitope multivalent BCMA CARs.

In some embodiments, there is provided a multivalent BCMA CAR comprising: (a) an extracellular antigen binding domain comprising a plurality (such as at least about any one of 2, 3, 4 or more) of an anti-BCMA sdAb; (b) a transmembrane domain; and (c) an intracellular signaling domain, wherein the anti-BCMA sdAb comprises a CDR1 comprising the amino acid sequence of SEQ ID NO:1, a CDR2 comprising the amino acid sequence of SEQ ID NO:39, and a CDR3 comprising the amino acid sequence of SEQ ID NO:77.

In some embodiments, there is provided a multivalent BCMA CAR (also referred herein as "multi-epitope multivalent CAR") comprising: (a) an extracellular antigen binding domain comprising at least two (such as any one of 2, 3, 4, or more) BCMA binding moieties; (b) a transmembrane domain; and (c) an intracellular signaling domain, wherein the at least two BCMA binding moieties specifically bind to at least two different epitopes on BCMA. In some embodiments, the extracellular antigen binding domain comprises a first BCMA binding moiety and a second BCMA binding moiety. In some embodiments, the first BCMA binding moiety is an anti-BCMA sdAb and the second BCMA binding moiety is derived from a human antibody (e.g., an scFv). In some embodiments, the first BCMA binding moiety is an sdAb and the second BCMA binding moiety is a BCMA polypeptide ligand. In some embodiments, the first anti-BCMA binding moiety and/or the second BCMA binding moiety specifically binds to an epitope on BCMA derived from an amino acid sequence selected from SEQ ID NOs: 388-394. In some embodiments, the first BCMA binding moiety specifically binds to an epitope derived from SEQ ID NO: 389 and/or 390. In some embodiments, the second BCMA binding moiety specifically binds to an epitope derived from SEQ ID NO: 391 and/or 392.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb and the second anti-BCMA sdAb specifically binds to different epitopes on BCMA. Any of the anti-BCMA sdAbs can be used to construct the multivalent BCMA CAR. In some embodiments, the first anti-BCMA sdAb and/or the second anti-BCMA sdAb specifically binds to an epitope on BCMA derived from an amino acid sequence selected from SEQ ID NOs: 388-394. In some embodiments, the first anti-BCMA sdAb specifically binds to an epitope derived from SEQ ID NO: 389 and/or 390. In some embodiments, the second anti-BCMA sdAb specifically binds to an epitope derived from SEQ ID NO: 391 and/or 392.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:3, a CDR2 comprising the amino acid sequence of SEQ ID NO:41, and a CDR3 comprising the amino acid sequence of SEQ ID NO:79; and wherein the second anti-BCMA sdAb comprises a CDR1 comprising the amino acid sequence of SEQ ID NO:10, a CDR2 comprising the amino acid sequence of SEQ ID NO:48, and a CDR3 comprising the amino acid sequence of SEQ ID NO:86. In some embodiments, the first anti-BCMA sdAb comprises a $V_HH$ domain comprising the amino acid sequence of SEQ ID NO: 117. In some embodiments, the second anti-BCMA sdAb comprises a $V_HH$ domain comprising the amino acid sequence of SEQ ID NO: 124. In some embodiments, the first anti-BCMA sdAb comprises a $V_HH$ domain comprising the amino acid sequence of SEQ ID NO: 124. In some embodiments, the second anti-BCMA sdAb comprises a $V_HH$ domain comprising the amino acid sequence of SEQ ID NO: 117.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:10, a CDR2 comprising the amino acid sequence of SEQ ID NO:48, and a CDR3 comprising the amino acid sequence of SEQ ID NO:86; and wherein anti-BCMA sdAb comprises a CDR1 comprising the amino acid sequence of SEQ ID NO:11, a CDR2 comprising the amino acid sequence of SEQ ID NO:49, and a CDR3 comprising the amino acid sequence of SEQ ID NO:87. In some embodiments, the first anti-BCMA sdAb comprises a $V_HH$ domain comprising the amino acid sequence of SEQ ID NO: 124. In some embodiments, the second anti-BCMA sdAb comprises a $V_HH$ domain comprising the amino acid sequence of SEQ ID NO: 125.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:7, a CDR2 comprising the amino acid sequence of SEQ ID NO:45, and a CDR3 comprising the amino acid sequence of SEQ ID NO:83; and wherein anti-BCMA sdAb comprises a CDR1 comprising the amino acid sequence of SEQ ID NO:11, a CDR2 comprising the amino acid sequence of SEQ ID NO:49, and a CDR3 comprising the amino acid sequence of SEQ ID NO:87. In some embodiments, the first anti-BCMA sdAb comprises a $V_HH$ domain comprising the amino acid sequence of SEQ ID NO: 121. In some embodiments, the second anti-BCMA sdAb comprises a $V_HH$ domain comprising the amino acid sequence of SEQ ID NO: 125.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:15, a CDR2 comprising the amino acid sequence of SEQ ID NO:53, and a CDR3 comprising the amino acid sequence of SEQ ID NO:91; and wherein anti-BCMA sdAb comprises a CDR1 comprising the amino acid sequence of SEQ ID NO:18, a CDR2 comprising the amino acid sequence of SEQ ID NO:56, and a CDR3 comprising the amino acid sequence of SEQ ID NO:94. In some embodiments, the first anti-BCMA sdAb comprises a $V_HH$ domain comprising the amino acid sequence of SEQ ID NO: 129. In some embodiments, the second anti-BCMA sdAb comprises a $V_HH$ domain comprising the amino acid sequence of SEQ ID NO: 132.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:18, a CDR2 comprising the amino acid sequence of SEQ ID NO:56, and a CDR3 comprising the amino acid sequence of SEQ ID NO:94; and wherein anti-BCMA sdAb comprises a CDR1 comprising the amino acid sequence of SEQ ID NO:20, a CDR2 comprising the amino acid sequence of SEQ ID NO:58, and a CDR3 comprising the amino acid sequence of SEQ ID NO:96. In some embodiments, the first anti-BCMA sdAb comprises a $V_HH$ domain comprising the amino acid sequence of SEQ ID NO: 132. In some embodiments, the second anti-BCMA sdAb comprises a $V_HH$ domain comprising the amino acid sequence of SEQ ID NO: 134.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti- BCMA sdAb comprises a CDR1 comprising the amino acid sequence of SEQ ID NO:20, a CDR2 comprising the amino acid sequence of SEQ ID NO:58, and a CDR3 comprising the amino acid sequence of SEQ ID NO:96; and wherein anti-BCMA sdAb comprises a CDR1 comprising the amino acid sequence of SEQ ID NO:28, a CDR2 comprising the amino acid sequence of SEQ ID NO:66, and a CDR3 comprising the amino acid sequence of SEQ ID NO:104. In some embodiments, the first anti-BCMA sdAb comprises a $V_HH$ domain comprising the amino acid sequence of SEQ ID NO: 134. In some embodiments, the second anti-BCMA sdAb comprises a $V_HH$ domain comprising the amino acid sequence of SEQ ID NO: 142.

In some embodiments, the first BCMA binding moiety (e.g., the first anti-BCMA sdAb) is located at the N-terminus of the second BCMA binding moiety (e.g., the second anti-BCMA sdAb). In some embodiments, the first BCMA binding moiety (e.g., the first anti-BCMA sdAb) is located at the C-terminus of the second BCMA binding moiety (e.g., the second anti-BCMA sdAb). In some embodiments, the first BCMA binding moiety (e.g., the first anti-BCMA sdAb) and the second BCMA binding moiety (e.g., the second anti-BCMA sdAb) are fused to each other via a peptide bond or a peptide linker. In some embodiments, the peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent. In some embodiments, the multivalent BCMA CAR is trivalent. In some embodiments, the multivalent BCMA CAR specifically binds to two different epitopes on BCMA. In some embodiments, the multivalent BCMA CAR specifically binds to three or more different epitopes on BCMA.

In some embodiments, there is provided a multivalent BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NOs: 298-335. In some embodiments, there is provided a multivalent BCMA CAR comprising an amino acid sequence selected from the group consisting of SEQ ID NOs: 298-335. Also provided is a polypeptide comprising an amino acid sequence selected from the group consisting of SEQ ID NOs: 298-335.

In some embodiments, there is provided an isolated nucleic acid encoding any of the multivalent BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 336-373. In some embodiments, there is provided an isolated nucleic acid comprising a nucleic acid sequence selected from the group consisting of SEQ ID NOs: 336-373. In some embodiments, the isolated nucleic acid is a DNA. In some embodiments, the isolated nucleic acid is an RNA. In some embodiments, there is provided a vector comprising any one of the nucleic acids encoding the multivalent BCMA CARs described above. In some embodiments, the vector is an expression vector. In some embodiments, the vector is a viral vector, such as a lentiviral vector. In some embodiments, the vector is a non-viral vector. Exemplary multivalent BCMA CARs are shown in Table 5 below.

TABLE 5

Exemplary multivalent BCMA CARs.

| | | | | Extracellular Antigen binding domain | | | | | | | | | |
|---|---|---|---|---|---|---|---|---|---|---|---|---|---|
| CAR | Ex. AA SEQ ID | Ex. NA SEQ ID | SP | sdAb #1 | Lnk. #1 SEQ ID | sdAb #2 | Lnk. #2 SEQ ID | sdAb #3 | Hinge | TM | CO1 | Intracellular signaling Prim. |
| GSI50 14 | 298 | 336 | CD8α | 269A 37346 | 208 | 269A 37346 | NA | NA | CD 8α | CD 8α | CD 137 | CD3ζ |
| GSI50 15 | 299 | 337 | CD8α | 269A 37346 | 208 | 269A 37346 | 208 | 269A 37346 | CD 8α | CD 8α | CD 137 | CD3ζ |
| GSI50 21 | 300 | 338 | CD8α | 269A 37353 | 208 | 269A 37917 | NA | NA | CD 8α | CD 8α | CD 137 | CD3ζ |
| GSI50 22 | 301 | 339 | CD8α | 269A 37353 | 213 | 269A 37917 | NA | NA | CD 8α | CD 8α | CD 137 | CD3ζ |
| GSI50 23 | 302 | 340 | CD8α | 269A 37353 | 215 | 269A 37917 | NA | NA | CD 8α | CD 8α | CD 137 | CD3ζ |
| GSI50 24 | 303 | 341 | CD8α | 269A 37917 | 209 | 269A 37353 | NA | NA | CD 8α | CD 8α | CD 137 | CD3ζ |
| GSI50 25 | 304 | 342 | CD8α | 269A 37917 | 213 | 269A 37353 | NA | NA | CD 8α | CD 8α | CD 137 | CD3ζ |
| GSI50 26 | 305 | 343 | CD8α | 269A 37917 | 214 | 269A 37353 | NA | NA | CD 8α | CD 8α | CD 137 | CD3ζ |

TABLE 5-continued

Exemplary multivalent BCMA CARs.

| CAR | Ex. AA SEQ ID | Ex. NA SEQ ID | SP | sdAb #1 | Lnk. #1 SEQ ID | sdAb #2 | Lnk. #2 SEQ ID | sdAb #3 | Hinge | TM | CO1 | Intracellular signaling Prim. |
|---|---|---|---|---|---|---|---|---|---|---|---|---|
| BCAR 001 | 306 | 344 | CD8α | 269A37353 | 208 | 269A37948 | NA | NA | CD8α | CD8α | CD137 | CD3ζ |
| BCAR 002 | 307 | 345 | CD8α | 269A37353 | 213 | 269A37948 | NA | NA | CD8α | CD8α | CD137 | CD3ζ |
| BCAR 003 | 308 | 346 | CD8α | 269A37353 | 215 | 269A37948 | NA | NA | CD8α | CD8α | CD137 | CD3ζ |
| BCAR 004 | 309 | 347 | CD8α | 269A37948 | 209 | 269A37353 | NA | NA | CD8α | CD8α | CD137 | CD3ζ |
| BCAR 005 | 310 | 348 | CD8α | 269A37948 | 213 | 269A37353 | NA | NA | CD8α | CD8α | CD137 | CD3ζ |
| BCAR 006 | 311 | 349 | CD8α | 269A37948 | 214 | 269A37353 | NA | NA | CD8α | CD8α | CD137 | CD3ζ |
| BCAR 007 | 312 | 350 | CD8α | 269A37953 | 208 | 269A37948 | NA | NA | CD8α | CD8α | CD137 | CD3ζ |
| BCAR 008 | 313 | 351 | CD8α | 269A37953 | 213 | 269A37948 | NA | NA | CD8α | CD8α | CD137 | CD3ζ |
| BCAR 009 | 314 | 352 | CD8α | 269A37953 | 215 | 269A37948 | NA | NA | CD8α | CD8α | CD137 | CD3ζ |
| BCAR 010 | 315 | 353 | CD8α | 269A37953 | 209 | 269A37948 | NA | NA | CD8α | CD8α | CD137 | CD3ζ |
| BCAR 011 | 316 | 354 | CD8α | 269A37953 | 213 | 269A37948 | NA | NA | CD8α | CD8α | CD137 | CD3ζ |
| BCAR 012 | 317 | 355 | CD8α | 269A37953 | 214 | 269A37948 | NA | NA | CD8α | CD8α | CD137 | CD3ζ |
| BCAR 013 | 318 | 356 | CD8α | 269B028 | 208 | 269B054 | NA | NA | CD8α | CD8α | CD137 | CD3ζ |
| BCAR 014 | 319 | 357 | CD8α | 269B028 | 213 | 269B054 | NA | NA | CD8α | CD8α | CD137 | CD3ζ |
| BCAR 015 | 320 | 358 | CD8α | 269B028 | 215 | 269B054 | NA | NA | CD8α | CD8α | CD137 | CD3ζ |
| BCAR 016 | 321 | 359 | CD8α | 269B028 | 209 | 269B054 | NA | NA | CD8α | CD8α | CD137 | CD3ζ |
| BCAR 017 | 322 | 360 | CD8α | 269B028 | 213 | 269B054 | NA | NA | CD8α | CD8α | CD137 | CD3ζ |
| BCAR 018 | 323 | 361 | CD8α | 269B028 | 214 | 269B054 | NA | NA | CD8α | CD8α | CD137 | CD3ζ |
| BCAR 019 | 324 | 362 | CD8α | 269B054 | 208 | 269B060 | NA | NA | CD8α | CD8α | CD137 | CD3ζ |
| BCAR 020 | 325 | 363 | CD8α | 269B054 | 213 | 269B060 | NA | NA | CD8α | CD8α | CD137 | CD3ζ |
| BCAR 021 | 326 | 364 | CD8α | 269B054 | 215 | 269B060 | NA | NA | CD8α | CD8α | CD137 | CD3ζ |
| BCAR 022 | 327 | 365 | CD8α | 269B054 | 209 | 269B060 | NA | NA | CD8α | CD8α | CD137 | CD3ζ |
| BCAR 023 | 328 | 366 | CD8α | 269B054 | 213 | 269B060 | NA | NA | CD8α | CD8α | CD137 | CD3ζ |
| BCAR 024 | 329 | 367 | CD8α | 269B054 | 214 | 269B060 | NA | NA | CD8α | CD8α | CD137 | CD3ζ |
| BCAR 025 | 330 | 368 | CD8α | 269B060 | 208 | 269B094 | NA | NA | CD8α | CD8α | CD137 | CD3ζ |
| BCAR 026 | 331 | 369 | CD8α | 269B060 | 213 | 269B094 | NA | NA | CD8α | CD8α | CD137 | CD3ζ |
| BCAR 027 | 332 | 370 | CD8α | 269B060S | 215 | 269B094 | NA | NA | CD8α | CD8α | CD137 | CD3ζ |
| BCAR 028 | 333 | 371 | CD8α | 269B060 | 209 | 269B094 | NA | NA | CD8α | CD8α | CD137 | CD3ζ |
| BCAR 029 | 334 | 372 | CD8α | 269B060 | 213 | 269B094 | NA | NA | CD8α | CD8α | CD137 | CD3ζ |
| BCAR 030 | 335 | 373 | CD8α | 269B060 | 214 | 269B094 | NA | NA | CD8α | CD8α | CD137 | CD3ζ |

Multispecific Chimeric Antigen Receptor

The present application further provides multispecific chimeric antigen receptors targeting two or more (such as about any one of 2, 3, 4, 5, 6, or more) different antigens. In some embodiments, the multispecific CAR has one antigen binding site for each antigen. In some embodiments, the multispecific CAR has more than two binding sites for at least one antigen. Each antigen binding site may comprise a sdAb. For example, in some embodiments, the multispecific CAR is a bispecific CAR comprising an extracellular antigen binding domain comprising two different sdAbs each specifically binding to an antigen. In some embodiments, the multispecific CAR is a trispecific CAR comprising an extracellular antigen binding domain comprising three different sdAbs each specifically binding to an antigen.

In some embodiments, there is provided a multispecific (such as bispecific) chimeric antigen receptor (CAR) comprising a polypeptide comprising: (a) an extracellular antigen binding domain comprising a first single-domain antibody (sdAb) specifically binding to BCMA and a second single-domain antibody (sdAb) specifically binding to a second antigen (such as a tumor antigen); (b) a transmembrane domain; and (c) an intracellular signaling domain, wherein the first antigen is different from the second antigen. In some embodiments, the second antigen is selected from the group consisting of CD19, CD20, CD22, CD33, CD38, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first sdAb and the second sdAb are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ.

Extracellular Antigen Binding Domain

The extracellular antigen binding domain of the CARs described herein comprises one or more (such as any one of 1, 2, 3, 4, 5, 6 or more) binding moieties, such as sdAbs. In some embodiments, the one or more binding moieties are antibodies or antigen-binding fragments thereof. In some embodiments, the one or more binding moieties are derived from four-chain antibodies. In some embodiments, the one or more binding moieties are derived from camelid antibodies. In some embodiments, the one or more binding moieties are derived from human antibodies. In some embodiments, the one or more binding moieties are non-antibody binding proteins, such as polypeptide ligands or engineered proteins that bind to an antigen. The binding moieties can be fused to each other directly via peptide bonds, or via peptide linkers.

1. Single-Domain Antibodies

In some embodiments, the CAR comprises an extracellular antigen binding domain comprising one or more sdAbs. The sdAbs may be of the same of different origins, and of the same or different sizes. Exemplary sdAbs include, but are not limited to, heavy chain variable domains from heavy-chain only antibodies (e.g., $V_HH$ or $V_{NAR}$), binding molecules naturally devoid of light chains, single domains (such as $V_H$ or $V_L$) derived from conventional 4-chain antibodies, humanized heavy-chain only antibodies, human sdAbs produced by transgenic mice or rats expressing human heavy chain segments, and engineered domains and single domain scaffolds other than those derived from antibodies. Any sdAbs known in the art or developed by the inventors, including the sdAbs described in Section II of the present application, may be used to construct the CARs described herein. The sdAbs may be derived from any species including, but not limited to mouse, rat, human, camel, llama, lamprey, fish, shark, goat, rabbit, and bovine. Single-domain antibodies contemplated herein also include naturally occurring sdAb molecules from species other than Camelidae and sharks.

In some embodiments, the sdAb is derived from a naturally occurring single-domain antigen binding molecule known as heavy chain antibody devoid of light chains (also referred herein as "heavy chain only antibodies"). Such single domain molecules are disclosed in WO 94/04678 and Hamers-Casterman, C. et al. (1993) Nature 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in Camelidae species, for example, camel, llama, vicuna, dromedary, alpaca and guanaco. Other species besides Camelidae may produce heavy chain molecules naturally devoid of light chain, and such $V_HH$s are within the scope of the present application.

$V_HH$ molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of $V_HH$ s produces high yield, properly folded functional $V_HH$s. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent CARs comprising one or more $V_HH$ domains may interact more efficiently with targets than multispecific or multivalent CARs comprising antigen binding fragments derived from conventional 4-chain antibodies. Since $V_H$Hs are known to bind into 'unusual' epitopes such as cavities or grooves, the affinity of CARs comprising such $V_H$Hs may be more suitable for therapeutic treatment than conventional multi-specific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_H$H domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called *Camelidae* hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. in some embodiments, the sdAb is affinity matured.

In some embodiments, naturally occurring $V_H$H domains against a particular antigen or target, can be obtained from (naïve or immune) libraries of *Camelid* $V_H$H sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naive or immune) $V_H$H libraries may be used, such as $V_H$H libraries obtained from (naive or immune) $V_H$H libraries by techniques such as random mutagenesis and/or CDR shuffling, as for example described in WO 00/43507.

In some embodiments, the sdAbs are generated from conventional four-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

2. Antigens

The antigen(s) targeted by the CARs of the present application are cell surface molecules. The binding moieties (such as sdAbs) may be chosen to recognize an antigen that acts as a cell surface marker on target cells associated with a special disease state. In some embodiments, the antigen (such as the first antigen and/or the second antigen) is a tumor antigen. In some embodiments, the multispecific CARs target two or more tumor antigens. In some embodiments, the tumor antigen is associated with a B cell malignancy. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases.

Tumor antigens are proteins that are produced by tumor cells that can elicit an immune response, particularly T-cell mediated immune responses. The selection of the targeted antigen of the invention will depend on the particular type of cancer to be treated. Exemplary tumor antigens include, for example, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD 19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCMA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

In some embodiments, the antigen (such as the first antigen and/or the second antigen) are selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

3. Peptide linkers

The various binding moieties (such as sdAbs) in the multispecific or multivalent CARs described herein may be fused to each other via peptide linkers. In some embodiments, the binding moieties (such as sdAbs) are directly fused to each other without any peptide linkers. The peptide linkers connecting different binding moieties (such as sdAbs) may be the same or different. Different domains of the CARs may also be fused to each other via peptide linkers.

Each peptide linker in a CAR may have the same or different length and/or sequence depending on the structural and/or functional features of the sdAbs and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. For example, in a multivalent or multispecific CAR of the present application that comprise sdAbs directed against a multimeric antigen, the length and flexibility of the peptide linkers are preferably such that it allows each sdAb in the multivalent CAR to bind to the antigenic determinant on each of the subunits of the multimer. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence GGGGS (SEQ ID NO: 208), $(GGGGS)_2$ (SEQ ID NO: 209), $(GGGS)_4$ (SEQ ID NO: 210), GGGGSGGGGSGGGGGGSGSGGGS (SEQ ID NO: 211), GGGGSGGGGSGGGGGGSGSGGGGSGGGGSGGGGS (SEQ ID NO: 212), $(GGGGS)_3$ (SEQ ID NO: 213), $(GGGGS)_4$ (SEQ ID NO: 214), or $(GGGGS)_5$ (SEQ ID NO: 215).

Transmembrane Domain

The CARs of the present application comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably a eukaryotic cell membrane. Transmembrane domains compatible for use in the CARs described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some embodiments, the transmembrane domain is derived from CD28. In some embodiments, the transmembrane domain is a transmembrane domain of CD28 comprising the amino acid sequence of SEQ ID NO: 194. In some embodiments, the transmembrane domain of CD28 is encoded by the nucleic acid sequence of SEQ ID NO: 203.

In some embodiments, the transmembrane domain is derived from CD8α. In some embodiments, the transmembrane domain is a transmembrane domain of CD8α comprising the amino acid sequence of SEQ ID NO: 193. In some embodiments, the transmembrane domain of CD8□ is encoded by the nucleic acid sequence of SEQ ID NO: 202.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of which are incorporated by reference herein.

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

Intracellular Signaling Domain

The CARs of the present application comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma(FCER1G), FcR beta (Fc Epsilon Rib), CD3 gamma, CD3 delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wildtype CD3ζ. In some embodiments, the primary intracellular signaling domain of wildtype CD3ζ comprises the amino acid sequence of SEQ ID NO: 197. In some embodiments, the primary intracellular signaling domain is a functional mutant of the cytoplasmic signaling domain of CD3ζ containing one or more mutations, such as Q65K. In some embodiments, the primary intracellular signaling domain of mutant CD3ζ comprises the amino acid sequence of SEQ ID NO: 198. In some embodiments, the primary intracellular signaling domain is encoded by the nucleic acid sequence of SEQ ID NO: 206 or 207.

Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains, for example, two copies of the co-stimulatory signaling domain of CD28. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g.,4-1BBITNFSF9/CD137, 4-1BB Ligand/TNFSF9, BAFF/BLyS/TNFSF13B, BAFF R/TNFRSF13C, CD27/TN-FRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TN-FRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLANIF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, 4-1BB, OX40, CD30, CD40, CD3, lymphocyte function-associated antigen-1(LFA-1), CD2, CD7, LIGHT, NKG2C, B7-H3 and ligands that specially bind to CD83.

In some embodiments, the intracellular signaling domain in the CAR of the present application comprises a co-stimulatory signaling domain derived from CD28. In some embodiments, the intracellular signaling domain comprises a cytoplasmic signaling domain of CD3ζ and a co-stimulatory signaling domain of CD28. In some embodiments, the intracellular signaling domain comprises a co-stimulatory signaling domain of CD28 comprising the amino acid sequence of SEQ ID NO: 195. In some embodiments, the co-stimulatory signaling domain of CD28 is encoded by the nucleic acid sequence of SEQ ID NO: 204.

In some embodiments, the intracellular signaling domain in the CAR of the present application comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 196. In some embodiments, the co-stimulatory signaling domain of CD137 is encoded by the nucleic acid sequence of SEQ ID NO: 205.

In some embodiments, the intracellular signaling domain in the CAR of the present application comprises a co-stimulatory signaling domain of CD28 and a co-stimulatory signaling domain of CD137. In some embodiments, the intracellular signaling domain comprises a cytoplasmic signaling domain of CD3ζ, a co-stimulatory signaling domain of CD28, and a co-stimulatory signaling domain of CD137. In some embodiments, the intracellular signaling domain comprises a polypeptide comprising from the N-terminus to the C-terminus: a co-stimulatory signaling domain of CD28, a co-stimulatory signaling domain of CD137, and a cytoplasmic signaling domain of CD3ζ. In some embodiments, the co-stimulatory signaling domain of CD28 comprising the amino acid sequence of SEQ ID NO: 195. In some embodiments, the co-stimulatory signaling domain of CD137 comprising the amino acid sequence of SEQ ID NO: 196.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

Hinge Region

The CARs of the present application may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 192. In some embodiments, the hinge domain of CD8α is encoded by the nucleic acid sequence of SEQ ID NO: 201.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N- terminus of the transmembrane domain is a peptide linker, such as a (GxS)n linker, wherein x and n, independently can be an integer between 3 and 12, including 3, 4, 5, 6, 7, 8, 9, 10, 11, 12, or more.

Signal Peptide

The CARs of the present application may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-C SF receptor α, and IgG1 heavy chain. In some embodiments, the signal peptide is derived from CD8α. In some embodiments, the signal peptide of CD8α comprises the amino acid sequence of SEQ ID NO: 191. In some embodiments, the signal peptide of CD8α is encoded by the nucleic acid sequence of SEQ ID NO: 199 or 200.

IV. Engineered Immune Effector Cells

Further provided in the present application are host cells (such as immune effector cells) comprising any one of the CARs described herein.

Thus, in some embodiments, there is provided an engineered immune effector cell (such as T cell) comprising a multivalent CAR comprising a polypeptide comprising: (a) an extracellular antigen binding domain comprising a first BCMA binding moiety specifically binding to a first epitope of BCMA, and a second BCMA binding moiety specifically binding to a second epitope of BCMA; (b) a transmembrane domain; and (c) an intracellular signaling domain, wherein the first epitope and the second epitope are different.

In some embodiments, there is provided an engineered immune effector cell (such as T cell) comprising a multivalent CAR comprising a polypeptide comprising: (a) an extracellular antigen binding domain comprising a first anti-BCMA sdAb specifically binding to a first epitope of BCMA, and a second anti-BCMA sdAb specifically binding to a second epitope of BCMA; (b) a transmembrane domain; and (c) an intracellular signaling domain, wherein the first epitope and the second epitope are different. In some embodiments, the first anti-BCMA sdAb and/or the second anti-BCMA sdAb is camelid, chimeric, human, or humanized. In some embodiments, the first anti-BCMA and the second anti-BCMA are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the extracellular antigen binding domain comprises at least two anti-BCMA sdAbs. In some embodiments, the anti-BCMA sdAb is camelid, chimeric, human, or humanized. In some embodiments, the anti-BCMA sdAb comprises a V$_H$H domain comprising an amino acid sequence selected from the group consisting of SEQ ID NO: 115-152. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the BCMA CAR comprises an amino acid sequence selected from the group consisting of SEQ ID NO: 216-256, 298-335. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Figure 15A:
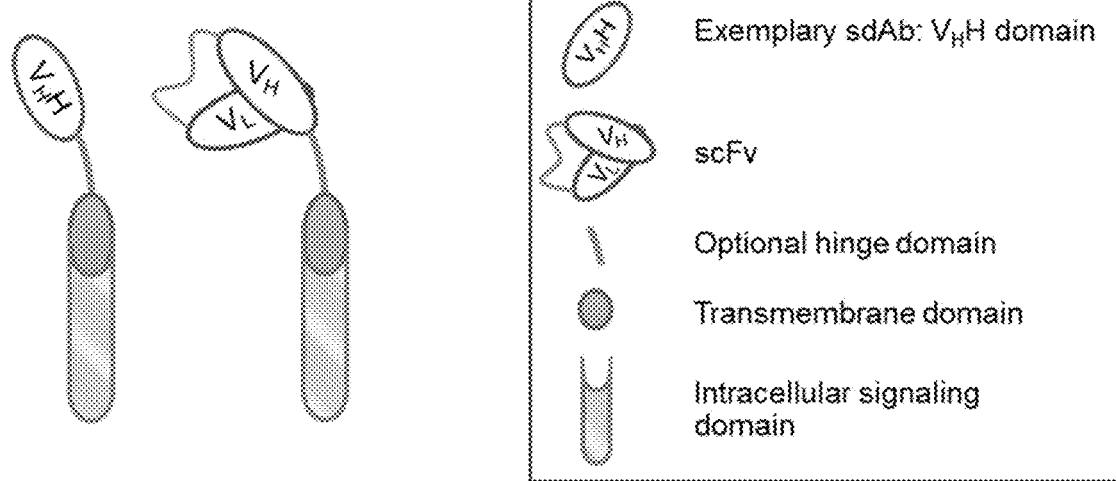
FIG. 15A compares the structures of a $V_HH$-based CAR and a conventional scFv-based CAR. The schematic structure on the left shows an exemplary monospecific monovalent CAR having an extracellular antigen binding domain comprising a VHH domain. The schematic structure on the right shows an exemplary monospecific monovalent CAR having an extracellular antigen binding domain comprising a scFv domain.
Figure 15B:
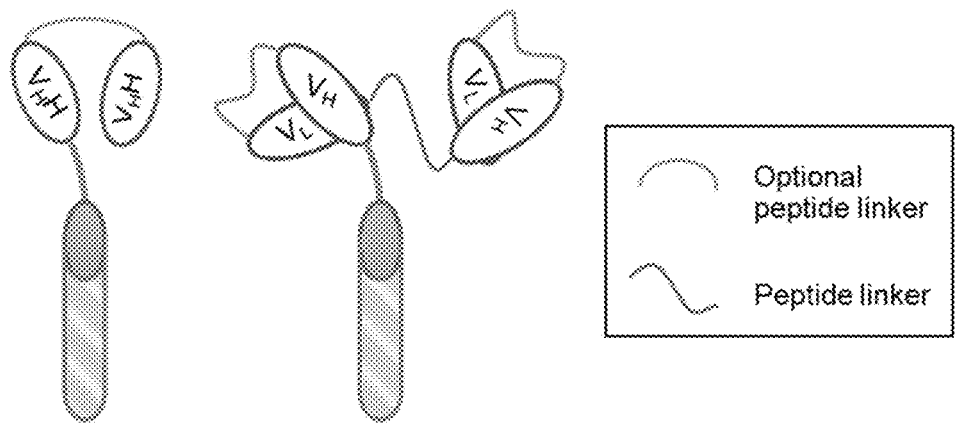
FIG. 15B compares the structures of a $V_HH$-based CAR having two antigen binding sites and a conventional scFv-based CAR having two antigen binding sites. The schematic structure on the left is an exemplary CAR having an extracellular antigen binding domain comprising two $V_HH$ domains. The two $V_HH$ domains may be the same or different. The schematic structure on the right shows an exemplary CAR having an extracellular antigen binding domain comprising two scFv domains. The two scFv domains may be the same or different.
Figure 15C:
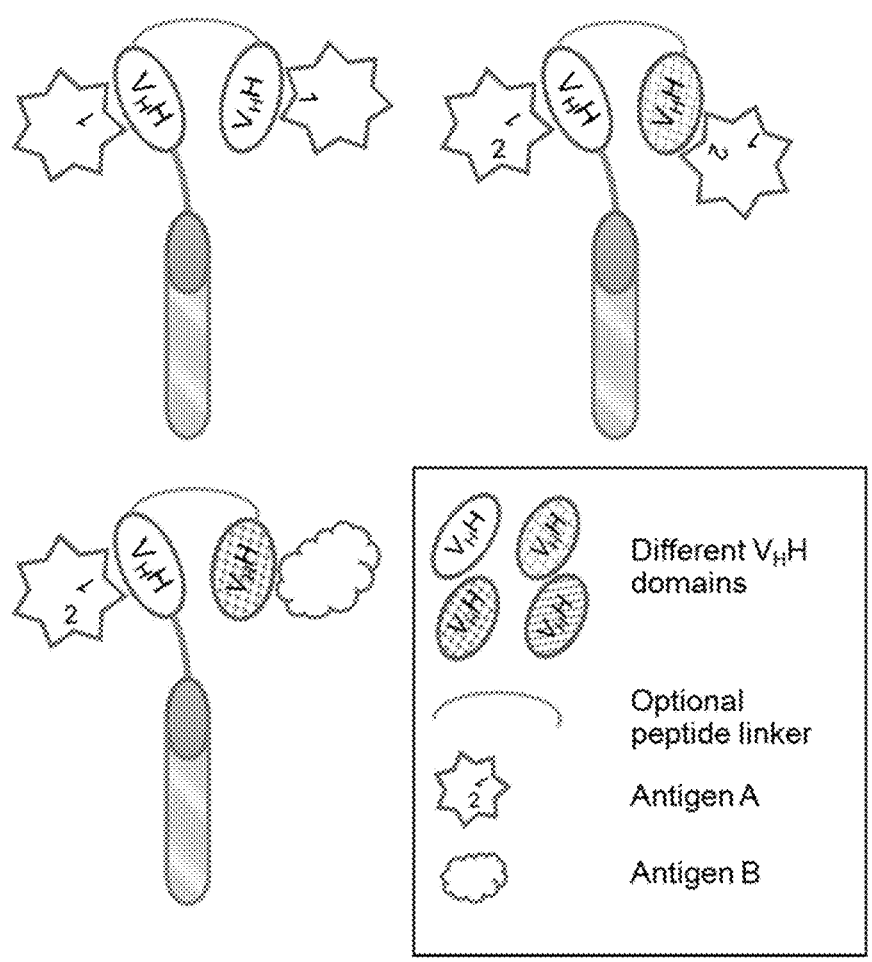
FIG. 15C shows schematic structures of exemplary bivalent and bispecific $V_HH$-based CARs. The schematic structure in the top left panel shows an exemplary mono-epitope, bivalent CAR having an extracellular antigen binding domain comprising two identical $V_HH$ domains, each of which specifically binds to epitope 1 of antigen A. The schematic structure in the top right panel shows an exemplary bi-epitope, bivalent CAR having an extracellular antigen binding domain comprising a first $V_HH$ domain specifically binding to epitope 1 of antigen A, and a second $V_HH$ domain specifically binding to epitope 2 of antigen A. Epitope 1 and epitope 2 of antigen A may be different in their structures and/or sequences. The schematic structure in the bottom left panel shows an exemplary bispecific CAR having an extracellular antigen binding domain comprising a first $V_HH$ domain specifically binding to antigen A, and a second $V_HH$ domain specifically binding to antigen B. Antigen A and antigen B are different antigens.
Figure 15D:
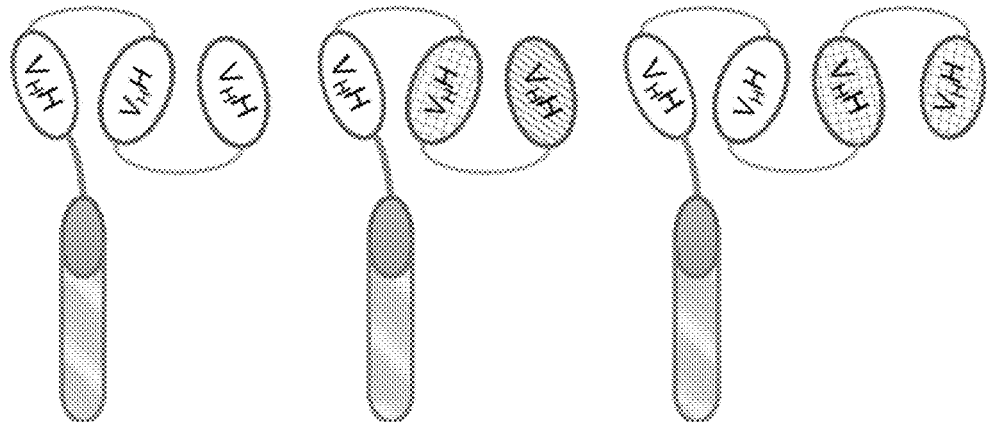
FIG. 15D shows schematic structures of exemplary $V_HH$-based CARs having three or more $V_HH$ domains. The CARs may have a plurality of $V_HH$ domains fused to each other directly or via peptide linkers. The $V_HH$ domains may be the same or different. Different $V_HH$ domains may specifically bind to different epitopes on the same antigen or different antigens.
Figure 15E:
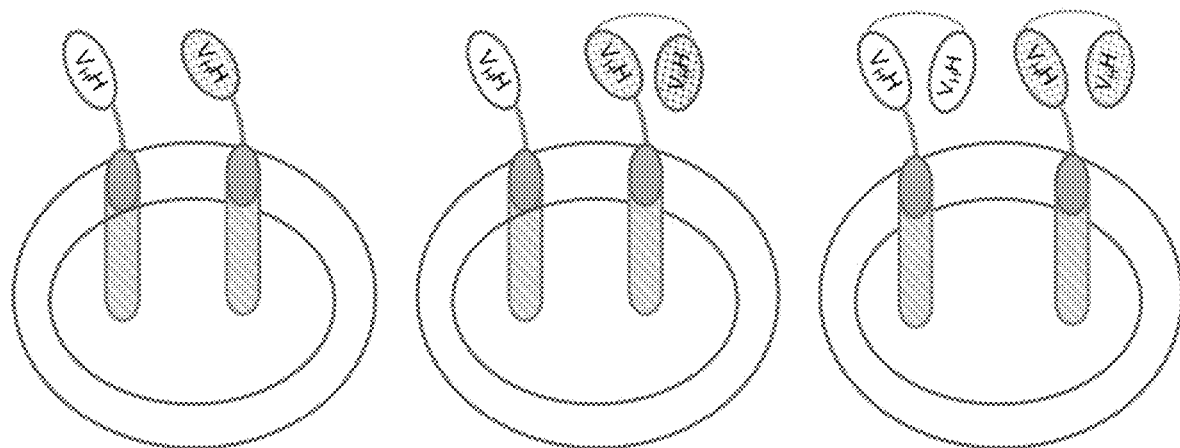
FIG. 15E shows exemplary engineered immune effector cells co-expressing two different $V_HH$-based CARs. The exemplary engineered immune effector cell in the left panel co-expresses two different monospecific, monovalent CARs. The exemplary engineered immune effector cell in the middle panel co-expresses a monospecific, monovalent CAR and a bispecific or bivalent CAR. The exemplary engineered immune effector cell in the right panel co-expresses two different bispecific or bivalent CARs. The CARs may recognize different antigens.

Also provided are engineered immune effector cells comprising (or expressing) two or more different CARs. Any two or more of the CARs described herein may be expressed in combination. The CARs may target different antigens, thereby providing synergistic or additive effects. As the single-domain antibodies in the extracellular antigen binding domains of the CARs have only single antigen variable chains (such as heavy chains), such CAR-expressing cells do not have variable chain mispairing problems, as seen in engineered immune effector cells co-expressing two or more scFv-based CARs. Exemplary engineered immune effector cells co-expressing two VHH-based CARs are illustrated in FIG. 15E. One of skill in the art would recognize that CARs based on other sdAbs or having other structures as described herein may be co-expressed in the engineered immune effector cells as well. The two or more CARs may be encoded on the same vector or different vectors.

The engineered immune effector cell may further express one or more therapeutic proteins and/or immunomodulators, such as immune checkpoint inhibitors. See, for example, International Patent Application NOs. PCT/CN2016/073489 and PCT/CN2016/087855, which are incorporated herein by reference in their entirety.

Vectors

The present application provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, N.Y.), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying CARs can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector is a non-viral vector. In some embodiments, the vector is a transposon, such as a Sleeping Beauty (SB) transposon system, or a PiggyBac transposon system. In some embodiments, the vector is a polymer-based non-viral vector, including for example, poly (lactic-co-glycolic acid) (PLGA) and poly lactic acid (PLA), poly(ethylene imine) (PEI), and dendrimers. In some embodiments, the vector is a cationic-lipid based non-viral vector, such as cationic liposome, lipid nanoemulsion, and solid lipid nanoparticle (SLN). In some embodiments, the vector is a peptide-based gene non-viral vector, such as poly-L-lysine. Any of the known non-viral vectors suitable for genome editing can be used for introducing the CAR-encoding nucleic acids to the engineered immune effector cells. See, for example, Yin H. et al. *Nature Rev. Genetics* (2014) 15:521-555; Aronovich EL et al. "The Sleeping Beauty transposon system: a non-viral vector for gene therapy." *Hum. Mol. Genet.* (2011) R1: R14-20; and Zhao S. et al. "PiggyBac transposon vectors: the tools of the human gene editing." *Transl. Lung Cancer Res.* (2016) 5(1): 120-125, which are incorporated herein by reference. In some embodiments, any one or more of the nucleic acids encoding a CAR is introduced to the engineered immune effector cells by a physical method, including, but not limited to electroporation, sonoporation, photoporation, magnetofection, hydroporation.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present invention. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive CAR expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof. In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A. In some embodiments, the T2A peptide has an amino acid sequence of SEQ ID NO: 385.

Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as CD20+ or CD19+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described in Section III. In some embodiments, the CAR is introduced to the immune effector cells by inserting proteins into the cell membrane while passing cells through a microfluidic system, such as CELL SQUEEZE® (see, for example, U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001) Molecular Cloning: A Laboratory Manual, Cold Spring Harbor Laboratory, N.Y. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035.

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

1. Sources of T Cells

Prior to expansion and genetic modification of the T cells, a source of T cells is obtained from an individual. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as FICOLL™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28- negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C., or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present application is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

2. Activation and Expansion of T Cells

Whether prior to or after genetic modification of the T cells with the CARs described herein, the T cells can be activated and expanded generally using methods as described, for example, in U.S. Pat. Nos. 6,352,694; 6,534, 055; 6,905,680; 6,692,964; 5,858,358; 6,887,466; 6,905, 681; 7,144,575; 7,067,318; 7,172,869; 7,232,566; 7,175, 843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

V. Pharmaceutical Compositions

Further provided by the present application are pharmaceutical compositions comprising any one of the anti-BCMA single-domain antibodies, or any one of the engineered immune effector cells comprising any one of the CARs (such as BCMA CARs) as described herein, and a pharmaceutically acceptable carrier. Pharmaceutical compositions can be prepared by mixing a sdAb, or a plurality of engineered immune effector cells having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, a-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

VI. Methods of Treatment

The present application further relates to methods and compositions for use in cell immunotherapy. In some embodiments, the cell immunotherapy is for treating cancer, including but not limited to hematological malignancies and solid tumors. Any of the anti-BCMA sdAbs, CARs, and engineered immune effector cells (such as CAR-T cells) described herein may be used in the method of treating cancer. The CARs described herein may be useful for treating tumors having antigen loss escape mutations, and for reducing resistance to existing therapies. In some embodiments, the methods and compositions described herein may be used for treating other diseases that are associated with the antigens specifically recognized by the single-domain antibodies or CARs, including, for example, autoimmune diseases.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety specifically binding to a first epitope of BCMA, and a second BCMA binding moiety specifically binding to a second epitope of BCMA; (b) a transmembrane domain; and (c) an intracellular signaling domain, wherein the first epitope and the second epitope are different; and (2) a pharmaceutically acceptable carrier. In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first anti-BCMA sdAb specifically binding to a first epitope of BCMA, and a second anti-BCMA sdAb specifically binding to a second epitope of BCMA; (b) a transmembrane domain; and (c) an intracellular signaling domain, wherein the first epitope and the second epitope are different; and (2) a pharmaceutically acceptable carrier. In some embodiments, the engineered immune effector cell is autologous. In some embodiments, the engineered immune effector cell is allogenic. In some embodiments, the engineered immune effector cells are CAR-T cells. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain; and (2) a pharmaceutically acceptable carrier, wherein the anti- BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the extracellular antigen binding domain comprises at least two anti-BCMA sdAbs. In some embodiments, the anti-BCMA sdAb is camelid, chimeric, human, or humanized. In some embodiments, the anti-BCMA sdAb comprises a $V_HH$ domain comprising an amino acid sequence selected from the group consisting of SEQ ID NO: 115-152. In some embodiments, the BCMA CAR comprises an amino acid sequence selected from the group consisting of SEQ ID NOs: 216-256 and 298-335. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of obtaining partial or complete clinical remission in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, the engineered immune effector cell is autologous. In some embodiments, the engineered immune effector cell is allogenic. In some embodiments, the engineered immune effector cells are CAR-T cells. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising an anti-BCMA sdAb and a pharmaceutically acceptable carrier, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb is camelid, chimeric, human, or humanized. In some embodiments, the anti-BCMA sdAb comprises an amino acid sequence selected from the group consisting of SEQ ID NO: 115-152. In some embodiments, the cancer is a liquid cancer, such as multiple myeloma, acute lymphoblastic leukemia, or chronic lymphocytic leukemia. In some embodiments, the cancer is refractory or relapsed multiple myeloma.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting.

In some embodiments, the cancer is multiple myeloma. In some embodiments, the cancer is stage I, stage II or stage III, and/or stage A or stage B multiple myeloma based on the Durie-Salmon staging system. In some embodiments, the cancer is stage I, stage II or stage III multiple myeloma based on the International staging system published by the International Myeloma Working Group (IMWG). In some embodiments, the cancer is monoclonal gammopathy of undetermined significance (MGUS). In some embodiments, the cancer is asymptomatic (smoldering/indolent) myeloma. In some embodiments, the cancer is symptomatic or active myeloma. In some embodiments, the cancer is refractory multiple myeloma. In some embodiments, the cancer is metastatic multiple myeloma. In some embodiments, the individual did not respond to a previous treatment for multiple myeloma. In some embodiments, the individual has progressive disease after a previous treatment of multiple myeloma. In some embodiments, the individual has previously received at least about any one of 2, 3, 4, or more treatment for multiple myeloma. In some embodiments, the cancer is relapsed multiple myeloma.

In some embodiments, the individual has active multiple myeloma. In some embodiments, the individual has clonal bone marrow plasma cells of at least 10%. In some embodiments, the individual has a biopsy-proven bony or extramedullary plasmacytoma. In some embodiments, the individual has evidence of end organ damage that can be attributed to the underlying plasma cell proliferative disorder. In some embodiments, the individual has hypercalcemia, e.g., serum calcium >0.25 mmol/L (>1 mg/dL) higher than the upper limit of normal or >2.75 mmol/L (>11 mg/dL). In some embodiments, the individual has renal insufficiency, e.g., creatinine clearance <40 mL per minute or serum creatinine >177 µmol/L (>2 mg/dL). In some embodiments, the individual has anemia, e.g., hemoglobin value of >20 g/L below the lowest limit of normal, or a hemoglobin value <100 g/L. In some embodiments, the individual has one or more bone lesions, e.g., one or more osteolytic lesion on skeletal radiography, CT, or PET/CT. In some embodiments, the individual has one or more of the following biomarkers of malignancy (MDEs): (1) 60% or greater clonal plasma cells on bone marrow examination; (2) serum involved/uninvolved free light chain ratio of 100 or greater, provided the absolute level of the involved light chain is at least 100 mg/L; and (3) more than one focal lesion on MRI that is at least 5 mm or greater in size.

Administration of the pharmaceutical compositions may be carried out in any convenient manner, including by injection, ingestion, transfusion, implantation or transplantation. The compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, N.Y. 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, wherein the pharmaceutical composition comprises any one of the sdAbs described herein, the pharmaceutical composition is administered at to dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212.

In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. In some embodiments, the pharmaceutical composition is administered at a dosage of any of about $10^4$ to about $10^5$, about $10^5$ to about $10^6$, about $10^6$ to about $10^7$, about $10^7$ to about $10^8$, about $10^8$ to about $10^9$, about $10^4$ to about $10^9$, about $10^4$ to about $10^6$, about $10^6$ to about $10^8$, or about $10^5$ to about $10^7$ cells/kg of body weight of the individual. In some embodiments, the pharmaceutical composition is administered at a dose of at least about any $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ cells/kg or more. In some embodiments, the pharmaceutical composition is administered at a dose of about $3\times10^5$ to about $7\times10^6$ cells/kg, or about $3\times10^6$ cells/kg.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between administrations is about any one of 1 week to 2 weeks, 2 weeks to 1 month, 2 weeks to 2 months, 1 month to 2 months, 1 month to 3 months, 3 months to 6 months, or 6 months to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. In some embodiments, the pharmaceutical composition is administered in split doses, such as about any one of 2, 3, 4, 5, or more doses. In some embodiments, the split doses are administered over about a week. In some embodiments, the dose is equally split. In some embodiments, the split doses are about 20%, about 30% and about 50% of the total dose. In some embodiments, the interval between consecutive split doses is about 1 day, 2 days, 3 days or longer. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the amount of the pharmaceutical composition is effective to cause an objective clinical response in the individual. In some embodiments, there is provided a method of obtaining an objective clinical response in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, Stringent Clinical Response (sCR) is obtained in the individual.

In some embodiments, the amount of the pharmaceutical composition is effective to cause disease remission (partial or complete) in the individual. In some embodiments, there is provided a method of causing disease remission (partial or complete) in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some the clinical remission is obtained after no more than about any one of 6 months, 5 months, 4 months, 3 months, 2 months, 1 months or less after the individual receives the pharmaceutical composition.

In some embodiments, the amount of the pharmaceutical composition is effective to prevent relapse or disease progression of the cancer in the individual. In some embodiments, there is provided a method of preventing relapse or disease progression in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, the relpase or disease progression is prevented for at least about 6 months, 1 year, 2 years, 3 years, 4 years, 5 years or more.

In some embodiments, the amount of the pharmaceutical composition is effective to prolong survival (such as disease free survival) in the individual. In some embodiments, the survival is prolonged for at least about 2, 3, 4, 5, 6, 12, or 24 months. In some embodiments, there is provided a method of prolonging survival of an individual having multiple myeloma (e.g., relapsed or refractory multiple myeloma), comprising: administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier.

In some embodiments, the pharmaceutical composition is effective to improve quality of life in the individual. In some embodiments, there is provided a method of improving quality of life of an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier.

In some embodiments, the amount of the pharmaceutical composition is effective to inhibit growth or reducing the size of a solid or lymphatic tumor. In some embodiments, the size of the solid or lymphatic tumor is reduced for at least about 10% (including for example at least about any of 20%, 30%, 40%, 60%, 70%, 80%, 90%, or 100%). In some embodiments, a method of inhibiting growth or reducing the size of a solid or lymphatic tumor in an individual is provided.

In some embodiments, the amount of the pharmaceutical composition is effective to inhibit tumor metastasis in the individual. In some embodiments, at least about 10% (including for example at least about any of 20%, 30%, 40%, 60%, 70%, 80%, 90%, or 100%) metastasis is inhibited. In some embodiments, there is provided a method of inhibiting tumor metastasis of an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, a method of inhibiting metastasis to lymph node is provided. In some embodiments, a method of inhibiting metastasis to the lung is provided. In some embodiments, a method of inhibiting metastasis to the liver is provided. Metastasis can be assessed by any known methods in the art, such as by blood tests, bone scans, x-ray scans, CT scans, PET scans, and biopsy.

VII. Kits and Articles of Manufacture

Further provided are kits, unit dosages, and articles of manufacture comprising any of the single-domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

The examples and exemplary embodiments below are intended to be purely exemplary of the invention and should therefore not be considered to limit the invention in any way. The following examples and exemplary embodiments are offered by way of illustration and not by way of limitation.

VIII. Exemplary Embodiments

The invention provides the following embodiments:

Embodiment 1. An anti-BCMA single-domain antibody (sdAb) comprising any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114.

Embodiment 2. The anti-BCMA sdAb of embodiment 1, wherein the anti-BCMA sdAb comprises an amino acid sequence selected from the group consisting of SEQ ID NOs: 115-152.

Embodiment 3. An anti-BCMA antibody that competes with the anti-BCMA sdAb of embodiment 1 or 2.

Embodiment 4. The anti-BCMA antibody of embodiment 3, wherein the anti-BCMA antibody is an sdAb.

Embodiment 5. The anti-BCMA sdAb of any one of embodiments 1, 2 and 4, wherein the anti-BCMA sdAb is a camelid antibody.

Embodiment 6. The anti-BCMA sdAb of any one of embodiments 1, 2 and 4, wherein the anti-BCMA sdAb is a chimeric antibody.

Embodiment 7. The anti-BCMA sdAb of any one of embodiments 1, 2 and 4, wherein the anti-BCMA sdAb is humanized.

Embodiment 8. The anti-BCMA sdAb of any one of embodiments 1-2 and 4-7, wherein the anti-BCMA sdAb is a $V_H H$ fragment.

Embodiment 9. A chimeric antigen receptor (CAR) comprising a polypeptide comprising: (a) an extracellular antigen binding domain comprising the anti-BCMA sdAb of any one of embodiments 1-2 and 4-7; (b) a transmembrane domain; and (c) an intracellular signaling domain.

Embodiment 10. The CAR of embodiment 9, wherein the extracellular antigen binding domain comprises at least two anti-BCMA sdAbs.

Embodiment 11. A multivalent chimeric antigen receptor (CAR) comprising a polypeptide comprising: (a) an extracellular antigen binding domain comprising at least two BCMA binding moieties; (b) a transmembrane domain; and (c) an intracellular signaling domain.

Embodiment 12. The multivalent CAR of embodiment 11, wherein the extracellular antigen binding domain comprises a first BCMA binding moiety and a second BCMA binding moiety.

Embodiment 13. The multivalent CAR of embodiment 12, wherein one or more of the first BCMA binding moiety and the second BCMA binding moiety is a sdAb.

Embodiment 14. The multivalent CAR of embodiment 12 or 13, wherein the first BCMA binding moiety is a first anti-BCMA sdAb and the second BCMA binding moiety is a second anti-BCMA sdAb.

Embodiment 15. The multivalent CAR of embodiment 12 or 13, wherein the first BCMA binding moiety is an anti-BCMA sdAb and the second BCMA binding moiety is derived from a human antibody.

Embodiment 16. The multivalent CAR of embodiment 12 or 13, wherein the first BCMA binding moiety is an anti-BCMA sdAb and the second BCMA binding moiety is a polypeptide ligand of BCMA.

Embodiment 17. The multivalent CAR of any one of embodiments 12-16, wherein the first BCMA binding moiety and the second BCMA binding moiety specifically bind to the same epitope on BCMA.

Embodiment 18. The multivalent CAR of any one of embodiments 12-16, wherein the first BCMA binding moiety and the second BCMA binding moiety specifically bind to different epitopes on BCMA.

Embodiment 19. The multivalent CAR of any one of embodiments 12-18, wherein the first BCMA binding moiety and/or the second BCMA binding moiety specifically binds to an epitope on BCMA derived from an amino acid sequence selected from SEQ ID NOs: 388-394.

Embodiment 20. The multivalent CAR of any one of embodiments 12-19, wherein one or more of the first BCMA binding moiety and the second BCMA binding moiety is the anti-BCMA sdAb of embodiment 1.

Embodiment 21. The multivalent CAR of any one of embodiments 12-20, wherein the first BCMA binding moiety is located at the N-terminus of the second BCMA binding moiety.

Embodiment 22. The multivalent CAR of any one of embodiments 12-20, wherein the first BCMA binding moiety is located at the C-terminus of the second BCMA binding moiety.

Embodiment 23. The multivalent CAR of any one of embodiments 12-22, wherein the first BCMA binding moiety and the second BCMA binding moiety are fused to each other via a peptide linker.

Embodiment 24. The multivalent CAR of embodiment 23, wherein the peptide linker is no more than about 50 amino acids long.

Embodiment 25. The multivalent CAR of embodiment 24, wherein the peptide linker comprises an amino acid sequence selected from the group consisting of SEQ ID NOs: 208-215.

Embodiment 26. The CAR or multivalent CAR of any one of embodiments 9-25, wherein the transmembrane domain is derived from a molecule selected from the group consisting of CD8α, CD4, CD28, CD137, CD80, CD86, CD152 and PD1.

Embodiment 27. The CAR or multivalent CAR of embodiment 26, wherein the transmembrane domain is derived from CD8α or CD28.

Embodiment 28. The CAR or multivalent CAR of embodiment 27, wherein the transmembrane domain comprises the amino acid sequence of SEQ ID NO: 193 or 194.

Embodiment 29. The CAR or multivalent CAR of any one of embodiments 9-28, wherein the intracellular signaling domain comprises a primary intracellular signaling domain of an immune effector cell.

Embodiment 30. The CAR or multivalent CAR of embodiment 29, wherein the primary intracellular signaling domain is derived from CD3ζ.

Embodiment 31. The CAR or multivalent CAR of embodiment 30, wherein the primary intracellular signaling domain comprises the amino acid sequence of SEQ ID NO: 197 or 198.

Embodiment 32. The CAR or multivalent CAR of any one of embodiments 9-31, wherein the intracellular signaling domain comprises a co-stimulatory signaling domain.

Embodiment 33. The CAR or multivalent CAR of embodiment 32, wherein the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof.

Embodiment 34. The CAR or multivalent CAR of embodiment 33, the co-stimulatory signaling domain comprises a cytoplasmic domain of CD28 and/or a cytoplasmic domain of CD137.

Embodiment 35. The CAR or multivalent CAR of embodiment 34, wherein the co-stimulatory signaling domain comprises the amino acid sequence of SEQ ID NO: 195 and/or SEQ ID NO: 196.

Embodiment 36. The CAR or multivalent CAR of any one of embodiments 32-35, wherein the intracellular signaling domain comprises at least two co-stimulatory signaling domains.

Embodiment 37. The CAR or multivalent CAR of any one of embodiments 9-36, further comprising a hinge domain located between the C-terminus of the extracellular antigen binding domain and the N-terminus of the transmembrane domain.

Embodiment 38. The CAR or multivalent CAR of embodiment 37, wherein the hinge domain is derived from CD8α.

Embodiment 39. The CAR or multivalent CAR of embodiment 38, wherein the hinge domain comprises the amino acid sequence of SEQ ID NO: 192.

Embodiment 40. The CAR or multivalent CAR of any one of embodiments 9-39, further comprising a signal peptide located at the N-terminus of the polypeptide.

Embodiment 41. The CAR or multivalent CAR of embodiment 40, wherein the signal peptide is derived from CD8α.

Embodiment 42. The CAR or multivalent CAR of embodiment 41, wherein the signal peptide comprises the amino acid sequence of SEQ ID NO: 191.

Embodiment 43. A chimeric antigen receptor comprising an amino acid sequence selected from the group consisting of SEQ ID NOs: 216-256 and 298-335.

Embodiment 44. An isolated nucleic acid comprising a nucleic acid sequence encoding the CAR or multivalent CAR of any one of embodiments 11-43.

Embodiment 45. The isolated nucleic acid of claim 44, comprising a nucleic acid sequence selected from the group consisting of SEQ ID NOs: 257-297 and 336-373.

Embodiment 46. The isolated nucleic acid of embodiment 45, further comprising a second nucleic acid sequence encoding a second CAR, wherein the nucleic acid sequence encoding the CAR is operably linked to the second nucleic acid sequence via a third nucleic acid sequence encoding a self-cleaving peptide.

Embodiment 47. The isolated nucleic acid of embodiment 46, the self-cleaving peptide is selected from the group consisting of T2A, P2A, and F2A.

Embodiment 48. The isolated nucleic acid of embodiment 47, the third nucleic acid sequence is SEQ ID NO: 385.

Embodiment 49. The isolated nucleic acid of any one of embodiments 44-48, the isolated nucleic acid is an RNA molecule.

Embodiment 50. A vector comprising the isolated nucleic acid of any one of embodiments 44-49.

Embodiment 51. The vector of embodiment 50, wherein the vector is an expression vector.

Embodiment 52. The vector of embodiment 50 or 51, wherein the vector is a viral vector.

Embodiment 53. The vector of embodiment 52, wherein the vector is a lentiviral vector.

Embodiment 54. The vector of embodiment 50 or 51, wherein the vector is a non-viral vector.

Embodiment 55. An engineered immune effector cell, comprising the CAR or multivalent CAR of any one of embodiments 9-43, the isolated nucleic acid of any one of embodiments 44-49, or the vector of any one of embodiments 50-54.

Embodiment 56. The engineered immune effector cell of embodiment 55, wherein the immune effector cell is a T cell, an NK cell, a peripheral blood mononuclear cell (PBMC), a hematopoietic stem cell, a pluripotent stem cell, or an embryonic stem cell.

Embodiment 57. The engineered immune effector cell of embodiment 56, wherein the immune effector cell is a T cell.

Embodiment 58. A pharmaceutical composition, comprising the engineered immune effector cell of any one of embodiments 55-57, and a pharmaceutically acceptable carrier.

Embodiment 59. A method of treating cancer in an individual, comprising administering to the individual an effective amount of the pharmaceutical composition of embodiment 58.

Embodiment 60. The method of embodiment 59, wherein the cancer is multiple myeloma.

Embodiment 61. The method of embodiment 60, wherein the cancer is refractory or relapsed multiple myeloma.

Embodiment 62. The method of any one of embodiments 59-61, wherein the engineered immune effector cell is autologous.

Embodiment 63. The method of any one of embodiments 59-61, wherein the engineered immune effector cell is allogenic.

Embodiment 64. The method of any one of embodiments 59-63, wherein the individual is human.

Embodiment 65. The method of any one of embodiments 59-64, wherein the pharmaceutical composition is administered intravenously.

Embodiment 66. The method of any one of embodiments 59-65, wherein the pharmaceutical composition is administered at a dose of about $1 \times 10^5$ to about $1 \times 10^7$ cells/kg.

Embodiment 67. The method of any one of embodiments, 59-66, wherein the pharmaceutical composition is administered in 3 split doses over about one week.

Embodiment 68. Use of the pharmaceutical composition of embodiment 58 for treating cancer in an individual.

Embodiment 69. Use of the pharmaceutical composition of embodiment 58 in the preparation of a medicament for treating cancer in an individual.

Embodiment 70. A pharmaceutical composition, comprising the anti-BCMA sdAb of any one of embodiments 1-8.

Embodiment 71. A method of treating a disease in an individual, comprising administering to the individual an effective amount of the pharmaceutical composition of embodiment 70.

Embodiment 72. The method of embodiment 71, wherein the disease is cancer.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example,

Example 1. Preparation of Anti-BCMA sdAbs

To develop sdAbs with high binding affinity to BCMA, llamas were immunized with a recombinant BCMA antigen. A phage-display library was then constructed to identify $V_HH$ leads. Distinct clones were picked at random and were classified according to the heavy chain complementarity determining region 3 (CDR3), a region that can play a major role in antigen binding. An exemplary protocol is described below. Other protocols for preparing sdAbs have been described. See, for example, Els Pardon et al, Nature Protocol, 2014; 9(3): 674.

1. Animal Immunization and Iimmune Response Assay 1.1 Animal Immunization

An immunogen comprising a recombinant human BCMA protein having a C-terminal Fc tag (ACRO Biosystems, Cat No.:BC7-H5254) was mixed with adjuvant or PBS and injected to llamas. The animals were immunized by service vendor (Cedarline) for seven times, typically with 200 μg immunogen and CFA (Complete Freund's Adjuvant) each time at about 1-week to 2-week intervals. Peripheral blood samples were collected at the pre-immunization stage and after the 5th and 7th immunization. After multiple rounds of immunization, immune reactions of the llamas against the target antigen were evaluated to confirm the titer of antigen-specific sdAbs. Lymphocytes were isolated by gradient centrifugation from about 100 ml of peripheral blood. The cells were supplemented with RNALATER™ and stored at −80° C. Sera were obtained by centrifugation of anti-coagulated blood samples and stored at −80° C.

1.2 IgG Fractionation

IgG-subclass fractionation was carried out according to GenScript's Standard Operating Procedure. The IgG subclasses were fractionated from terminal bleed serum using Protein G and Protein A resins. The 1 ml serum sample was loaded onto a 1 ml HITRAP® Protein G HP column, and the column was washed with 10 ml phosphate buffer (20 mM, pH 7.0). The IgG3 (MW 100,000 Da) fraction was eluted with 0.15 M NaCl, 0.58% acetic acid (pH 3.5), and the eluate was neutralized with 1 M Tris-HCl (pH 9.0) to pH 7.4. Subsequently, the IgG1 (MW 170,000 Da) fraction was eluted with 0.1 M glycine-HCl (pH 2.7), and the eluate was neutralized with 1 M Tris-HCl (pH 8.5) to pH 7.4. The flow-through of HITRAP® Protein G HP column was then loaded onto a 1 ml HITRAP® Protein A HP column, and the column was washed with 20 ml phosphate buffer (20 mM, pH 7.0). The IgG2 (MW 100,000 Da) fraction was eluted with 0.15 M NaCl, 0.58% acetic acid (pH 4.5), and the eluate was neutralized with 1M Tris-HCl (pH 9.0) to pH 7.4. The concentrations of the purified IgG1, IgG2 and IgG3 antibodies were determined by OD280, and the purity of each was assessed by both reducing and non-reducing SDS-PAGE analysis.

1.3 Immune Response Assay

Immune response of the llamas was evaluated by ELISA, in which the serum samples and purified IgGs were assayed for binding to immobilized immunogens. Sera collected pre-immunization, after 5th immunization and at terminal bleed were evaluated. The antigen (i.e., recombinant human antigen protein) was diluted in coating buffer at 4 μg/ml. The microtiter plate was coated with diluted antigen at 4° C. overnight. The plate was then washed 3 times with washing buffer followed by blocking at room temperature for 2 hours. The plate was subsequently washed 4 times with washing buffer. A series of diluted sera or IgGs were added to the plate and incubated at room temperature for 1.5 hours. The plate was then washed 4 times with washing buffer. HRP-conjugated anti-llama IgG secondary antibody was added to the plate and incubated at room temperature for 1 hour. After washing, the TMB substrate was added to each well and incubated for 10 minutes before stopping with 1 M HC1. To quantify binding, absorbance at 450 nm was measured for each well using a MK3 spectrometer.

2. $V_HH$ Phage Display Library Construction 2.1 RNA Extraction

Total RNA was extracted from the isolated lymphocytes (from 1.1.1) using TRIZOL® Reagent according to the manufacturer's protocol. Quantity and quality of the total RNA were assessed by gel electrophoresis and quantified by measuring absorbance at OD260/280.

2.2 RT-PCR and $V_HH$ Amplification

Total RNA was reverse transcribed into cDNA with an oligo(dT)$_{20}$ primer using PRIMESCRIPT™ 1st Strand cDNA Synthesis Kit according to the manufacturer's protocol. Six forward and two reverse specific degenerate primers were designed to amplify the $V_HH$ fragments, which had two BglI restriction sites introduced. The $V_HH$ fragments were amplified according to GenScript's standard operating procedure as described below.

The variable regions of the heavy-chain immunoglobulins (i.e., $V_HH$s) were amplified using a two-step polymerase chain reaction (PCR). In the first PCR, 100 ng of cDNA template was mixed with primers CALL001 (SEQ ID NO: 374) and CALL002 (SEQ ID NO: 375). The DNA products from the first PCR reaction were analyzed by agarose gel electrophoresis. After gel purification, the DNA products of the first PCR were used as templates in the second PCR. The second PCR was performed with the primers BACK-1 (SEQ ID NO: 376), BACK-2 (SEQ ID NO: 377) and PMCF (SEQ ID NO: 378). The amplified second PCR products containing $V_HH$ PCR fragments were gel purified and enzyme digested, and then inserted into phagemid plasmids. The recombinant plasmids with $V_HH$ gene fragments were electro-transferred into E. coli cells in order to generate the phage display $V_HH$ immune library.

The procedure of the PCR reaction has an initial denaturation step at 94° C. for 7 min, followed by 30 cycles of 94° C. for 1 min, 55° C. for 1 min, and 72° C. for 1 min; and followed by a final extension step at 72° C. for 7 min.

2.3 Phage Library Construction

The $V_HH$ PCR products were obtained by amplification using different primer pairs. The PCR products were then digested with BglI and gel purified. The gel purified fragments were inserted into GenScript's in-house phagemid vector. A pilot library was constructed to optimize the ligation and transformation conditions. The optimized ligation and transformation conditions were employed to develop the phagemid library. A small portion of the transformed cells was diluted and streaked on 2×YT plates supplemented with 100 μg/ml ampicillin. The colonies were counted to calculate the library size. Positive clones were randomly picked and sequenced to assess the quality of the library. The rest of the transformed cells were streaked onto YT plates supplemented with 100 μg/ml ampicillin and 2% glucose. Lawns of colonies were scraped off the plates. A small aliquot of the cells was used for library plasmid isolation. The rest was supplemented with glycerol and stored at −80° C. as stock.

3. Phage Display Panning
3.1 Bio-Panning

The constructed $V_HH$ phage library was panned against recombinant human BCMA protein and CHO cells expressing human BCMA (i.e., CHO-BCMA cells, prepared in house by Legend Biotec) respectively using a standard procedure developed by GenScript. The library stock was grown to log phase, and then the library was rescued with M13KO7 helper phage and was amplified overnight at 25° C. in a shaker. The phage was then precipitated with PEG/NaCl, re-suspended in PBS and stored at −80° C. For solid phase panning, microplate wells were coated with recombinant human BCMA protein in PBS at 4° C. overnight. For liquid phase panning, CHO-BCMA cells were blocked with blocking buffer at room temperature for 1 hour. During the coating or blocking step, phage particles were pre-incubated with the blocking buffer and Fc control protein in microplate wells. After pre-incubation, phage particles were added to the wells coated with BCMA proteins or CHO-BCMA solution respectively and incubated for 1 hour. After incubation, unbound and nonspecifically bound phages were washed away by rinsing the wells or the CHO-BCMA cells with PBST for six times supplemented with two additional PBS washes. The bound phage particles were eluted by 100 mM triethylamine(TEA), and the eluate was neutralized by 1 M Tris-HCl (pH 7.4). Half of the eluate was then used to infect exponentially growing *E. coli* TG1 cells ($OD_{600}$=0.4~0.6) for output titration.

3.2 Phage ELISA

Phage ELISA was performed to identify clones specific to the target antigens. Individual output phage clones were grown in 96-deep-well plate and rescued by M13KO7 helper phage overnight. To identify clones that bind to antigen proteins, 96-well ELISA microtiter plates were coated with recombinant human BCMA protein and Fc control protein respectively in coating buffer overnight at 4° C., and the plates were then blocked with blocking buffer. After blocking, approximately 50 µl per well of phage supernatant from the overnight cell culture was added to the plates for 1.5-hour incubation at 4° C. The plates were washed four times, and the HRP-conjugated anti-M13 monoclonal antibody was added to the plates for 45-minute incubation at 4° C. The plates were again washed five times and substrate solution was added to the wells for developing. Absorption at 450 nm was measured for each well.

To identify clones that bind CHO-BCMA cells, the CHO-BCMA cells were blocked with blocking buffer at room temperature for 1 hour. After blocking, approximately 20 µl per well of phage supernatant from the overnight cell culture was added to the cell solutions for 1-hour incubation at room temperature. After the cells were washed 4 times, the HRP-conjugated anti-M13 monoclonal antibody was added for 30-minute incubation at room temperature. The cells were washed five times and substrate solution was then added for developing. The absorption was measured at 450 nm. After panning, ELISA positive phage clones were randomly selected and DNA was prepared from output phage using a plasmid extraction kit. The anti-BCMA $V_HH$s in the plasmids were sequenced.

Example 2. Preparation of Exemplary Monovalent BCMA Chimeric Antigen Receptors

A nucleic acid sequence encoding a CAR backbone polypeptide comprising from the N-terminus to the C-terminus: a CD8α hinge domain, a CD28 transmembrane domain, a CD28 cytoplasmic domain, a CD137 cytoplasmic domain, and a CD3ζ cytoplasmic domain was chemically synthesized and cloned into a pre-modified lentiviral vector downstream and operably linked to a constitutive hEF1α promoter. The resulting CAR backbone vector was named "PLLV-hEF1α-8281373." Multi-cloning sites (MCS) in the vector allowed insertion of a nucleic acid sequence comprising a Kozak sequence (SEQ ID NO:379) operably linked to a nucleic acid sequence encoding a CD8α signal peptide fused to the N-terminus of a $V_HH$ fragment into the PLLV-hEF1α-8281373 vector, upstream and operably linked to the CAR backbone sequence.

To construct a monospecific CAR having a single $V_HH$ domain using the PLLV-hEF1α-8281373 backbone, the nucleic acid sequence encoding the $V_HH$ domain was operably linked to the 3' of the nucleic acid sequence encoding the CD8α signal peptide. The fusion nucleic acid sequence was chemically synthesized and cloned into the PLLV-hEF1α-8281373 CAR backbone via the EcoRI (SEQ ID NO: 380: 5'-GAATTC-3') and SpeI (SEQ ID NO: 381: 5'-ACTAGT-3') restriction sites by molecular cloning techniques known in the art. Table 4 lists the vectors that were constructed to express the exemplary monospecific, monovalent anti-BCMA CARs.

For ease of further inserting additional sequences, such as a nucleotide encoding a second $V_HH$, when designing a monospecific CAR construct, restriction sites including HpaI (SEQ ID NO: 382: 5'-GTTAAC-3'), MluI (SEQ ID NO: 383: 5'-ACGCGT-3'), NsiI (SEQ ID NO: 384: 5'-ATGCAT-3') sites were included between the CD8α signal peptide nucleic acid sequence and the $V_HH$ nucleic acid sequence.

The lentivirus packaging plasmid mixture including pCMV-ΔR-8.74 and pMD2. G (Addgene #12259) was pre-mixed with the vectors PLLV-hEF1α-8281373 having $V_HH$ fragments at a pre-optimized ratio with polyetherimide (PEI), then mixed properly and incubated at room temperature for 5 minutes. The transfection mix was then added dropwise to the HEK293 cells and mixed gently. Afterwards, cells were incubated overnight in a 37° C. and 5% $CO_2$ cell incubator. The supernatants were collected after centrifugation at 4° C., 500 g for 10 min.

The virus-containing supernatants were filtered through a 0.45 µm PES filter, followed by ultra-centrifugation for lentivirus concentration. After ultra-centrifugation, the supernatants were carefully discarded and the virus pellets were rinsed cautiously with pre-chilled DPB S. The virus was aliquoted properly, then stored at −80° C. immediately. The virus titer was determined by p24 based on HTRF kit developed by GenScript.

PBMC Preparation

Leukocytes were collected from healthy donors by apheresis, and cell concentration was adjusted to 5×10⁶ cells/ml in R10 medium. Leukocytes were then mixed with 0.9% NaCl solution at 1:1 (v/v) ratio. 3 ml lymphoprep medium was added to a 15 ml centrifuge tube, and 6 ml of diluted lymphocyte mix was slowly layered on top of the lymphoprep medium. The lymphocyte mix was centrifuged at 800 g for 30 minutes without brakes at 20° C. Lymphocyte buffy coat was then collected with a 200 µl pipette. The harvested fraction was diluted at least 6 folds with 0.9% NaCl or R10 to reduce density of the solution. The harvested fraction was then centrifuged at 250 g for 10 minutes at 20° C. The supernatant was aspirated completely, and 10 ml of R10 was added to the cell pellet to resuspend the cell pellet. The mixture was further centrifuged at 250 g for 10 minutes at 20° C. The supernatant was again aspirated. 2 ml of 37° C. pre-warmed R10 with 100 IU/ml IL-2 was added to the cell pellet, and the cell pellet was re-suspended softly. The cell number was determined following Trypan Blue staining, and this PBMC sample was ready for later experiments.

T Cell Purification

Human T cells were purified from PBMCs using Miltenyi Pan T cell isolation kit (Cat #130-096-535), following manufacturer's protocol as described below. Cell number was first determined and the cell suspension was centrifuged at 300 g for 10 minutes. The supernatant was then aspirated completely, and the cell pellets were re-suspended in 40 µl buffer per $10^7$ total cells. 10 µl of Pan T Cell Biotin-Antibody Cocktail was added per $10^7$ total cells, mixed thoroughly and incubated for about 5 minutes in the refrigerator (2~8° C.). 30 µl of buffer was then added per $10^7$ cells. 20 µl of Pan T Cell MicroBead Cocktail was added per $10^7$ cells. The cell suspension mixture was mixed well and incubated for an additional 10 minutes in the refrigerator (2~8° C.). A minimum of 500 µl is required for magnetic separation. For magnetic separation, an LS column was placed in the magnetic field of a suitable MACS Separator. The column was prepared by rinsing with 3 ml of buffer. The cell suspension was then applied onto the column, and flow-through containing the unlabeled cells was collected, which represented the enriched T cell fractions. Additional T cells were collected by washing the column with 3 ml of buffer and collecting unlabeled cells that pass through. These unlabeled cells again represented the enriched T cells, and were combined with the flow-through from previous step. The pooled enriched T cells were then centrifuged and re-suspended in R10+100 IU/ml IL-2.

The prepared T cells were subsequently pre-activated for 48-96 hours with human T cell activation/expansion kit (Miltenyi #130-091-441) according to manufacturer's protocol in which anti-CD3/CD28 MACSiBead particles were added at a bead-to-cell ratio of 1:2.

In Vitro Cytotoxicity Assay

The pre-activated T cells were transduced with lentivirus stock in the presence of 7 pg/ml polybrene with centrifugation at 1200 g, 32° C. for 1.5 h. The transduced cells were then transferred to the cell culture incubator for transgene expression under suitable conditions.

On day 3 or day 7 post-transduction, transduced T cells were harvested and co-incubated with tumor cells at an effector (CAR-T) to target cell ratio of 20:1 for 20 hours. Target cells were human multiple myeloma cell line RPMI8226. Luc, human cell line K562. BCMA.Luc cells which recombinantly expressed BCMA, K562. CD19. Luc cell line which recombinantly expressed CD19, or human glioblastoma cell line U87MG.Luc cells. All of the cell lines were engineered in house to express firefly luciferase. To assay the cytotoxicity of CAR-T on tumor cells, ONE-GLO™ luminescent luciferase assay reagents (Promega #E6110) were prepared according to manufacturer's protocol and added to the co-cultured cells to detect the remaining luciferase activity in the well. Since luciferase is expressed only in the target cells, the remaining luciferase activity in the well correlates directly to the number of viable target cells in the well. The maximum luciferase activity was obtained by adding culture media to target cells in the absence of effector cells. The minimum luciferase activity was determined by adding Triton X-100 at a final concentration of 1% at the time when the cytotoxicity assays were initiated. The specific cytotoxicity was calculated by the formula: Specific Cytotoxicity %=100%*(1-(RLUsample-RLUmin)/(RLUmax-RLUmin)).

Figure 1B:
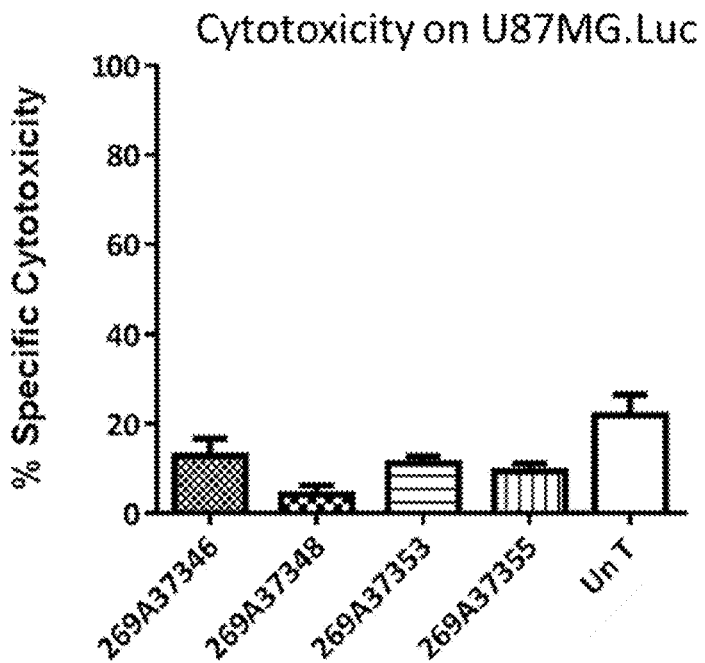

Exemplary monovalent CAR targeting BCMA (CD269) were selected and tested in the cytotoxicity assay. As shown in FIG. 1A, among a first group of monovalent BCMA CARs tested, the selected clones exhibited different levels of cytotoxicity against multiple myeloma cell line RPMI8226. Luc cells, with over 60% monovalent $V_HH$-based CAR-Ts showing >50% cytotoxicity against RPMI8226. Luc cells. Clones 269A37346, 269A37348, 269A37353, and 269A37355 based CAR-T were selected for further testing. In particular, clones 269A37346, 269A37348, 267A37353 and 269A37355 based CAR-T exhibited potent cytotoxicity against multiple myeloma cell line RPMI8226. Luc cells with more than 20%-30% increase in RPMI8226. Luc cell killing by CAR-T treatment as compared with untransduced control T cells (UnT). Nevertheless, such cytotoxicity increase did not occur against human glioblastoma cell line U87MG.Luc cells (see FIG. 1B). No significant cytotoxicity effects were detected against U87MG.Luc by these monovalent $V_HH$-based CAR-T cells as compared to UnT controls. The observation above indicated that some of these clones might be target specific and potent against BCMA positive cells.

Figure 2A:
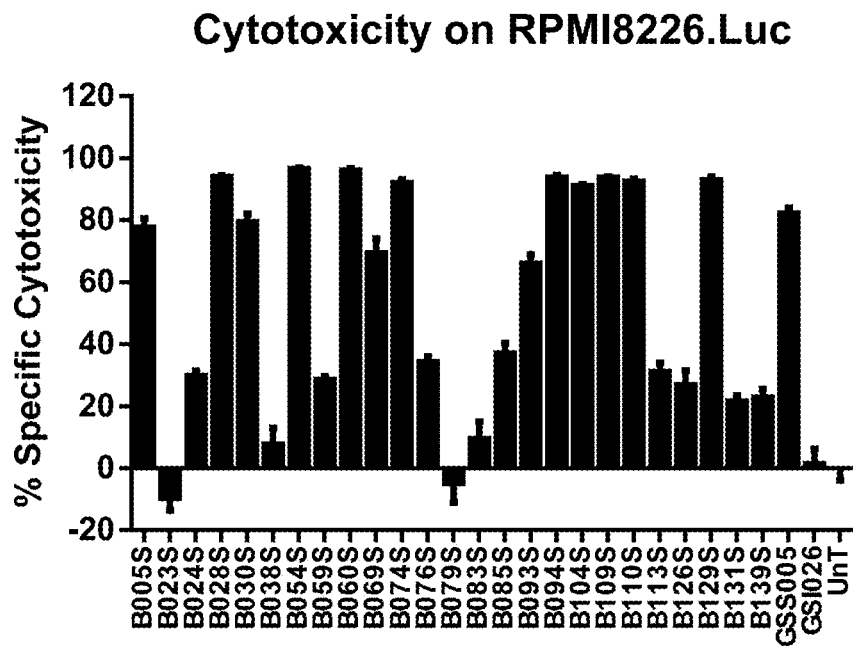
FIGS. 2A-2C show results of an in vitro cytotoxicity assay of T cells expressing exemplary monospecific CARs comprising various anti-BCMA sdAbs against RPMI8226. Luc cells (FIG. 2A), K562. BCMA.Luc cells (FIG. 2B), or K562. CD19. Luc cells (FIG. 2C).
Figure 2B:
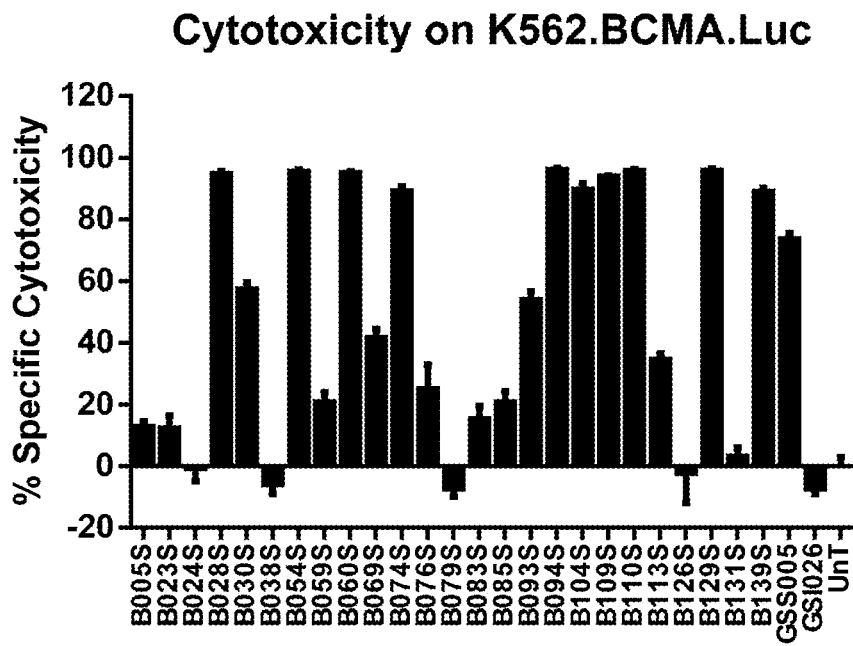
Figure 2C:
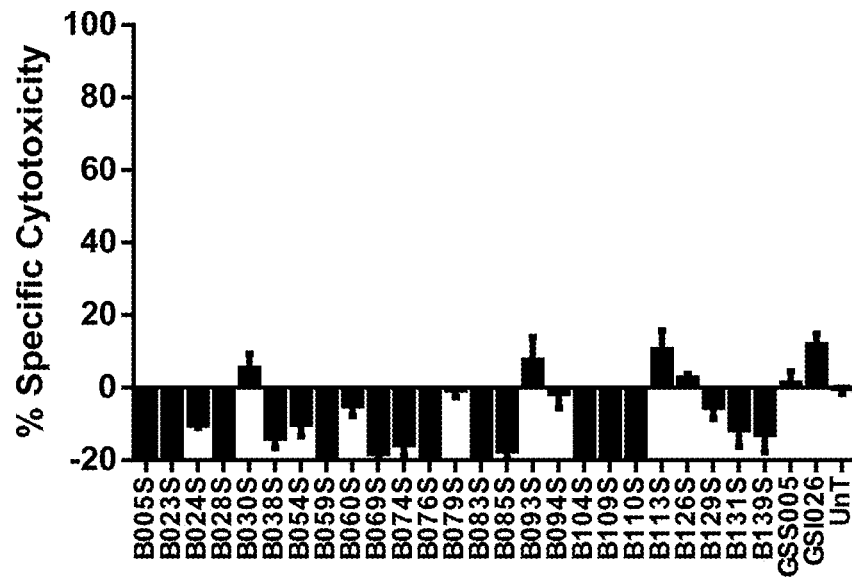

A second group of exemplary monovalent BCMA CARs were assessed for in vitro cytotoxicity. GSS005, a CAR comprising an anti-BMCA scFv, served as a positive control. GSI026, a CAR comprising an anti-EGFRvIII scFv, served as a negative control. As shown in FIGS. 2A-2B, the selected clones exhibited different levels of cytotoxicity against the multiple myeloma cells RPMI8226. Luc, and BCMA over-expressing stable cell line K562. BCMA.Luc. No clones showed potent cytotoxicity against BCMA negative cell line K562. CD19. Luc (FIG. 2C). Among these clones, 269B005S, 269B028S, 269B030S, 269B054S, 269B060S, 269B069S, 269B093S, 269B094S, 269B104S, 269B109S, 269B110S and 269B129S based CAR-T were most potent according to the cytotoxicity data.

IFNgamma Release

Figure 3:
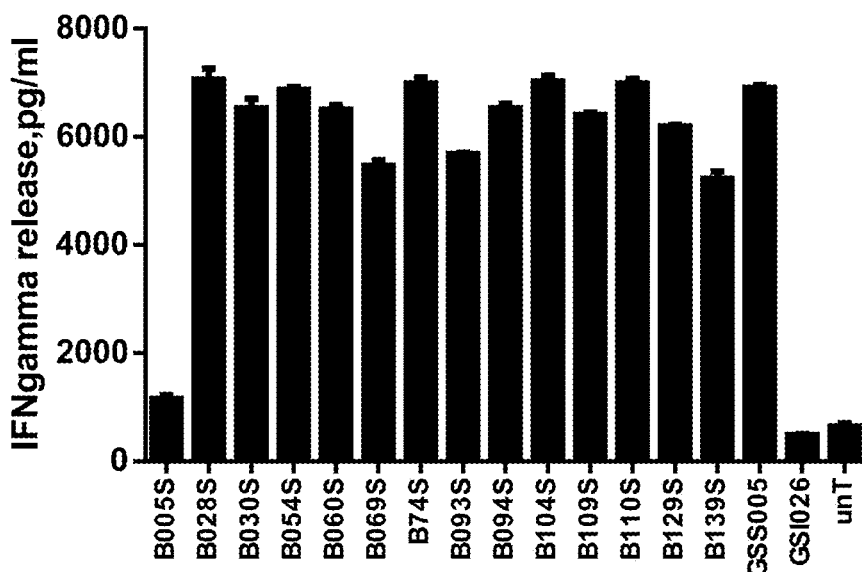
FIG. 3 shows results of an in vitro IFNγ release assay of T cells expressing exemplary monospecific CARs comprising various anti-BCMA sdAbs against K562. BCMA.Luc cells.

Additionally, supernatants from the in vitro co-culture assays were collected to assess CAR-induced cytokine release, e.g., interferon gamma (i.e, IFNγ) release. As shown in FIG. 3, T cells expressing selected monovalent BCMA CARs released high levels of IFNγ upon co-culturing with BCMA-expressing target cells K562. BCMA.Luc. Nonspecific CAR-Ts, such as GSI026, or untransduced T cells (UnT) did not induce release of IFNγ in the co-culture. The cytokine release data is consistent with the in vitro cytotoxicity data.

Example 3. Preparation of Exemplary Multivalent BCMA Chimeric Antigen Receptors

Multivalent $V_HH$-based CARs can be constructed by cloning a nucleic acid sequence encoding multiple copies of a $V_HH$, or multiple different $V_HHs$ fused to each other via peptide linkers into a CAR signal domain backbone vector. Exemplary multivalent BCMA CAR constructs are shown in Table 5. These constructs were prepared by fusing 2-3 anti-BCMA $V_HHs$ by Glycine-serine peptide linkers followed by directly synthesizing this fusion sequence in combination with a Kozak-CD8α signal peptide nucleic acid sequence, and cloning into the PLLV-hEF1α-81373 CAR backbone via EcoRI and SpeI restriction sites. Monovalent BCMA CAR constructs were also cloned into the same PLLV-hEF1α-81373 CAR backbone to serve as controls (e.g., GSI5011, GSI5019, and GSI5020, Table 4).

Lentiviral vectors carrying CAR genes were packaged and titrated with protocols as described in Example 2. Using protocols described in Example 2, human PBMCs were prepared from peripheral bloods of volunteers for further isolation of primary human T cells using Miltenyi human PanT cell isolation kits. The purified T cells were pre-activated and expanded using Miltenyi anti-CD3/CD28 micro-beads as described in Example 2. The pre-activated T cells were then transduced with lentivirus stock in the presence of 7 μg/ml polybrene by centrifugation at 1200 g, 32° C. for 1.5 h. The transduced cells were then transferred to the cell culture incubator for transgene expression under suitable conditions.

In Vitro Cytotoxicity Assay

On day 3 post transduction, transduced T cells were harvested and co-incubated with tumor cells. To assay the cytotoxicity of CAR-T on tumor cells, ONE-GLO™ luminescent luciferase assay reagents were added to the co-cultured cells and the specific cytotoxicity for each CAR-T was measured as described in Example 2.

Figure 4A:
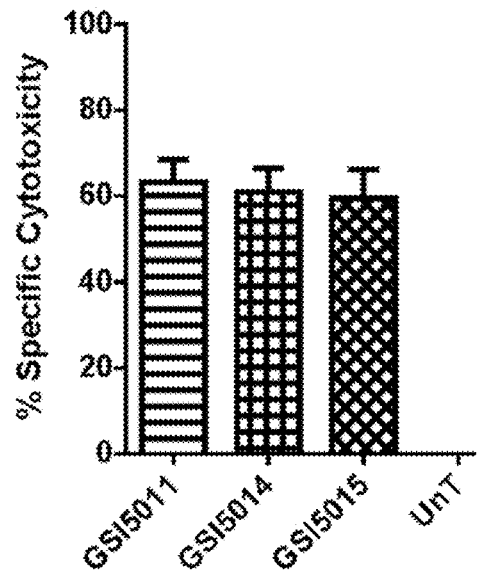
FIGS. 4A-4C show results of an in vitro cytotoxicity assay of T cells expressing exemplary multivalent BCMA CARs against RPMI8226. Luc cells (FIGS. 4A-4B) or U87MG.Luc cells (FIG. 4C).

In a first experiment, monovalent BCMA CAR (GSI5011), bivalent BCMA CAR (GSI5014), and trivalent BCMA CAR (GSI5015) expressing T cells were co-cultured with RPMI8226. Luc cells at an effector to target ratio of 20:1 for 20 hours. All three CAR constructs comprise anti-BCMA VHH domains of clone 269A37346. As shown in FIG. 4A, the specific percentage lysis of RPMI8226. Luc cells were 63.25±2.64% by GSI5011-expressing CAR-T cells, 61.04±2.75% by GSI5014-expressing CAR-T cells, and 59.57±2.64% by GSI5015-expressing CAR-T cells, as compared to 0.05%±2.33% by untransduced control T cells (UnT). The BCMA CARs tested having different antigen binding modalities had potent antitumor activity against BCMA positive cells.

Figure 4B:
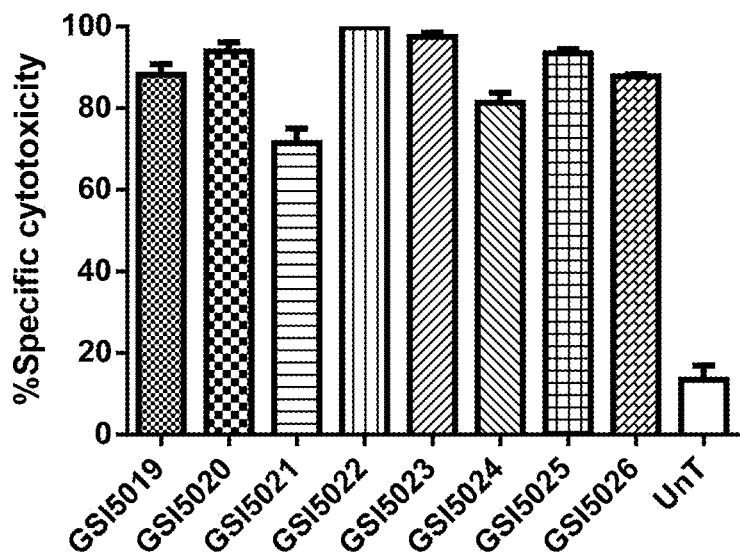
Figure 4C:
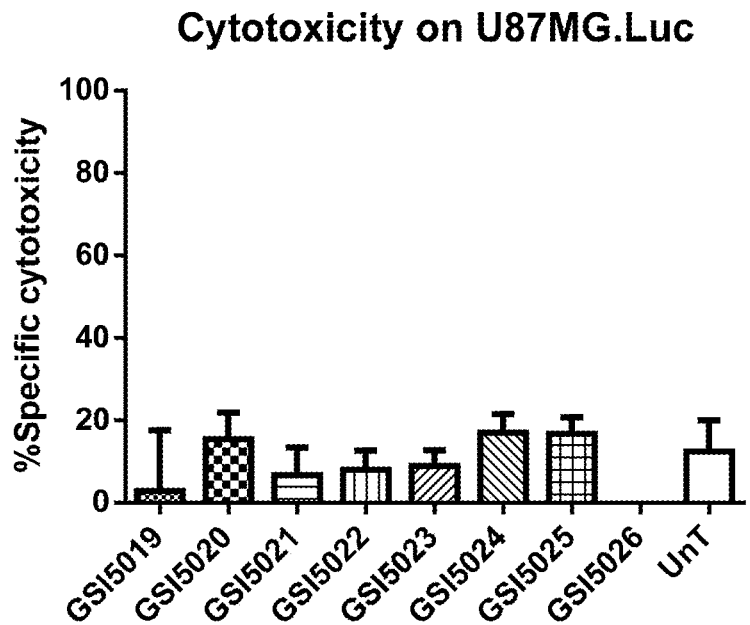

In a second experiment, exemplary bivalent BCMA CARs (GSI5021-GSI5026) having two different BCMA binding moieties 269A37353 and 269A37917 were tested. Engineered T cells expressing each bivalent BCMA CAR was co-cultured with RPMI8226. Luc cells at an effector to target ratio of 20:1 for 20 hours. Monovalent BCMA CARs, GSI5019 and GSI5020 were also tested for comparison. As shown in FIG. 4B, the specific percentage of lysis of RPMI8226. Luc cells were 88.21±1.29% by GSI5019-expressing CAR-T cells,93.84±1.13% by GSI5020-expressing CAR-T cells, 71.45±1.79% by GSI5021-expressing CAR-T cells, 99.80±0.45% by GSI5022-expressing CAR-T cells, 97.46±0.50% by GSI5023-expressing CAR-cells, 81.29±1.27% by GSI5024-expressing CAR-T cells, 93.50±0.47% by GSI5025-expressing CAR-T cells, 87.83±0.23% by GSI5026-expressing CAR-T cells, respectively, as compared to 13.49%±1.75% by untransduced control T cells (UnT). Also, as depicted in FIG. 4C, the specific percentage of lysis of BCMA-negative cell line U87MG.Luc was 2.84±7.41% by GSI5019-expressing CAR-T cells, 15.50±2.24% by GSI5020-expressing CAR-T cells, 6.74±3.37% by GSI5021-expressing CAR-T cells, 8.03±2.36% by GSI5022-expressing CAR-T cells, 9.00±1.88% by GSI5023-expressing CAR-T cells, 17.03±2.27% by GSI5024-expressing CAR-T cells, 16.81±1.98% by GSI5025-expressing CAR-T cells, −11.55±5.43% by GSI5026-expressing CAR-T cells, as compared to 12.49%±3.79% by untransduced control T cells (UnT). The data suggests that the bivalent CARs with different antigen-binding modalities had potent antitumor activity against BCMA positive cells, but not against BCMA negative cells.

Figure 5A:
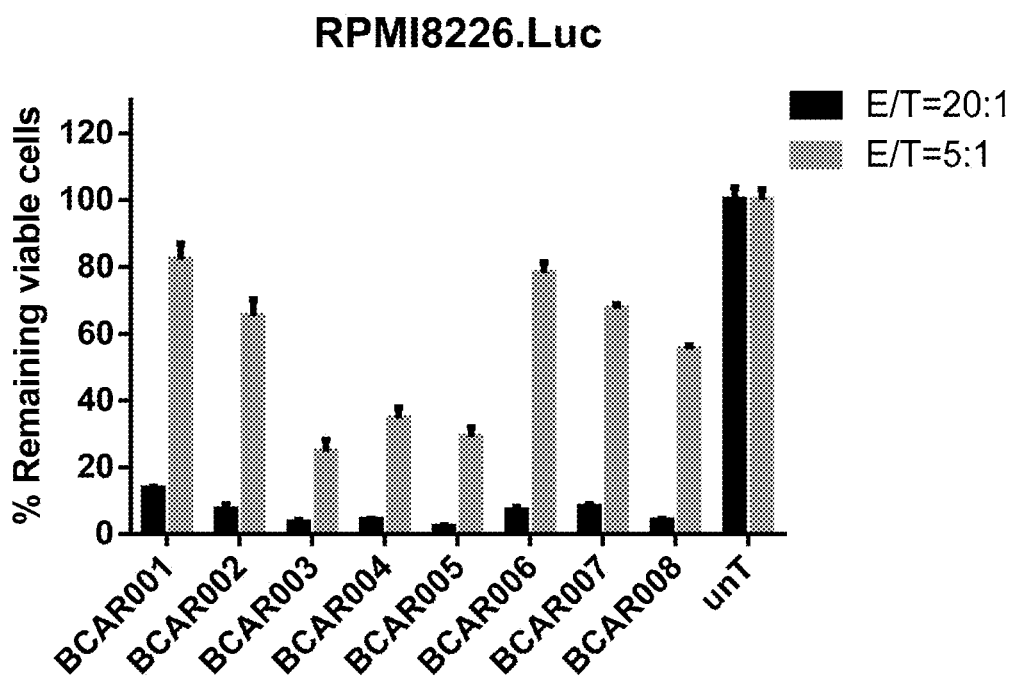
FIGS. 5A-5E show results of an in vitro cytotoxicity assay of T cells expressing exemplary bivalent BCMA CARs against RPMI8226. Luc cells (FIG. 5A), K562. CD19. Luc cells (FIG. 5B), A549. Luc cells (FIG. 5C), U87MG.Luc cells (FIG. 5D), or Raji.Luc cells (FIG. 5E).
Figure 5B:
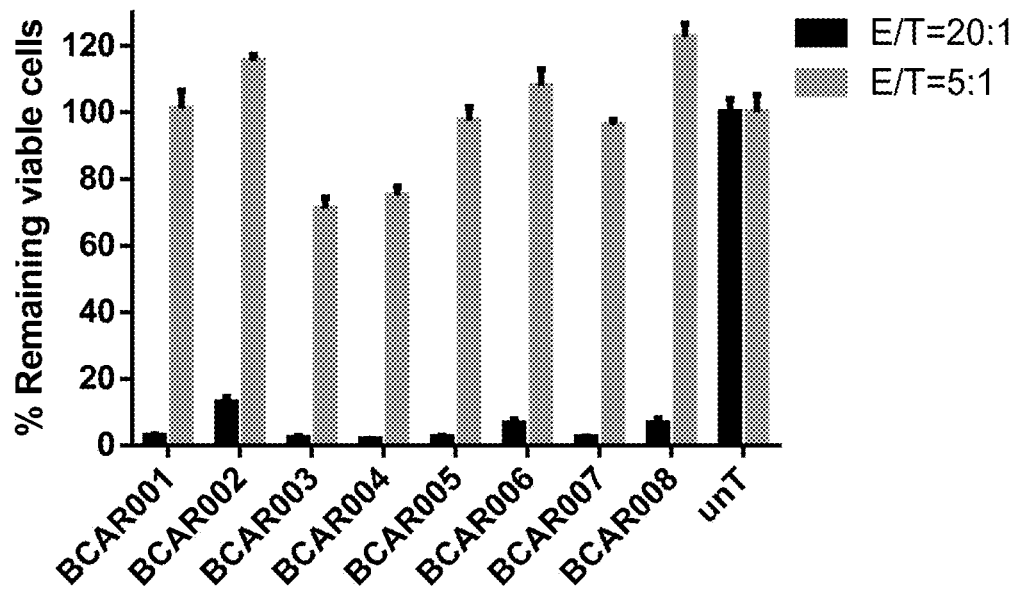
Figure 5C:
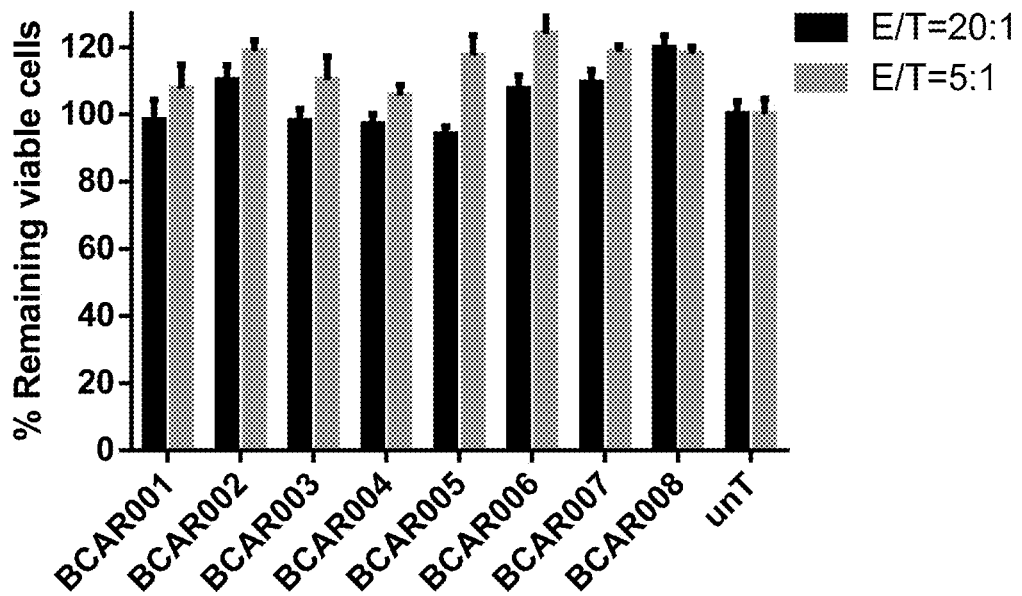
Figure 5D:
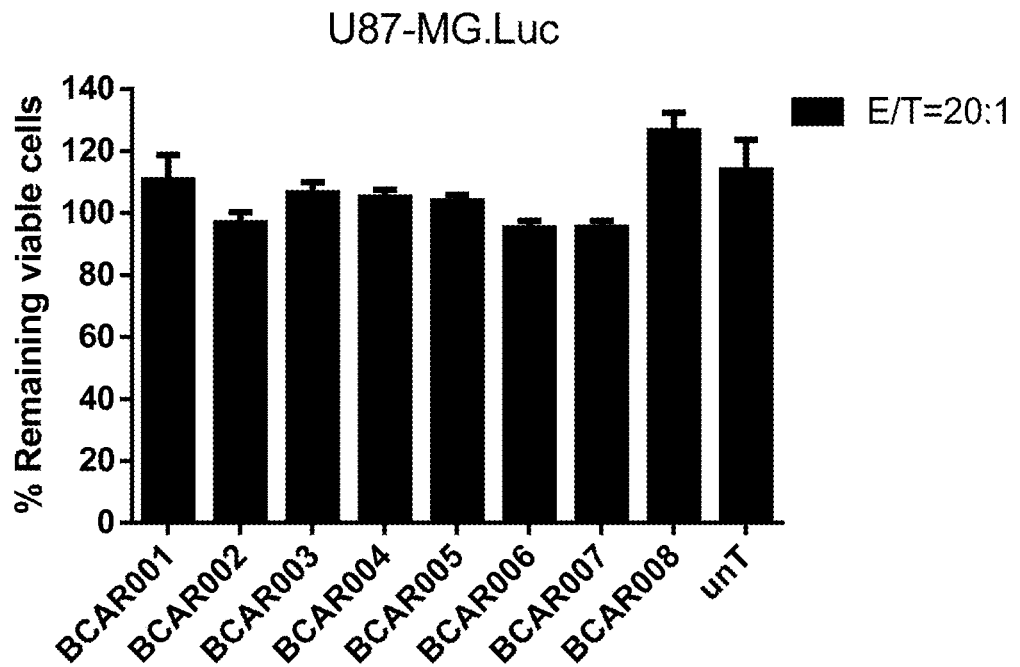
Figure 5E:
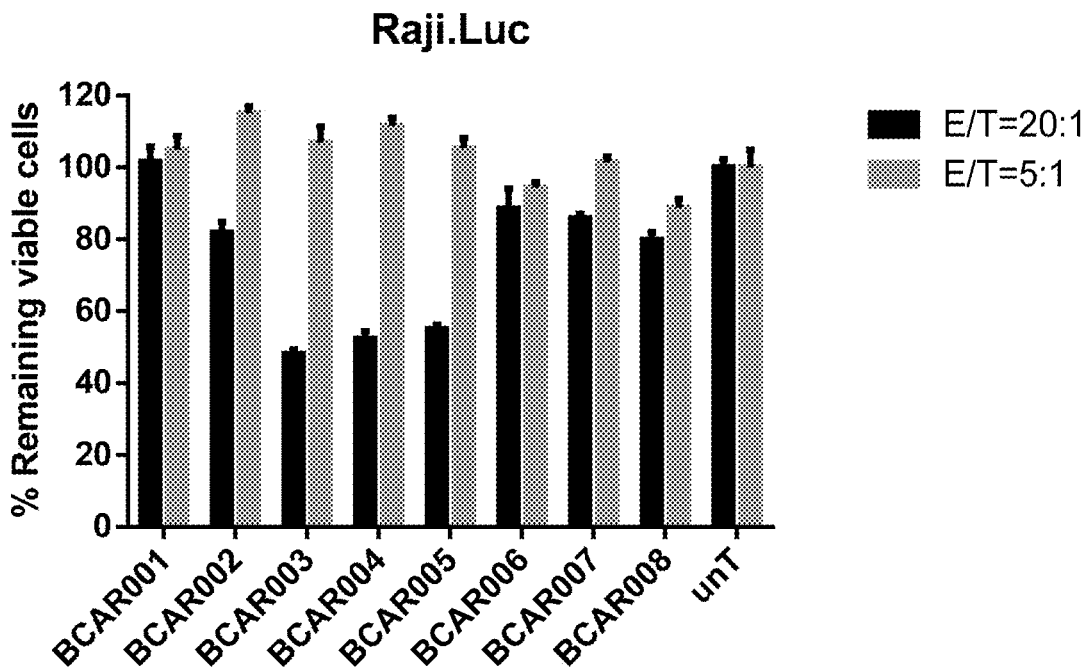
Figure 5F:
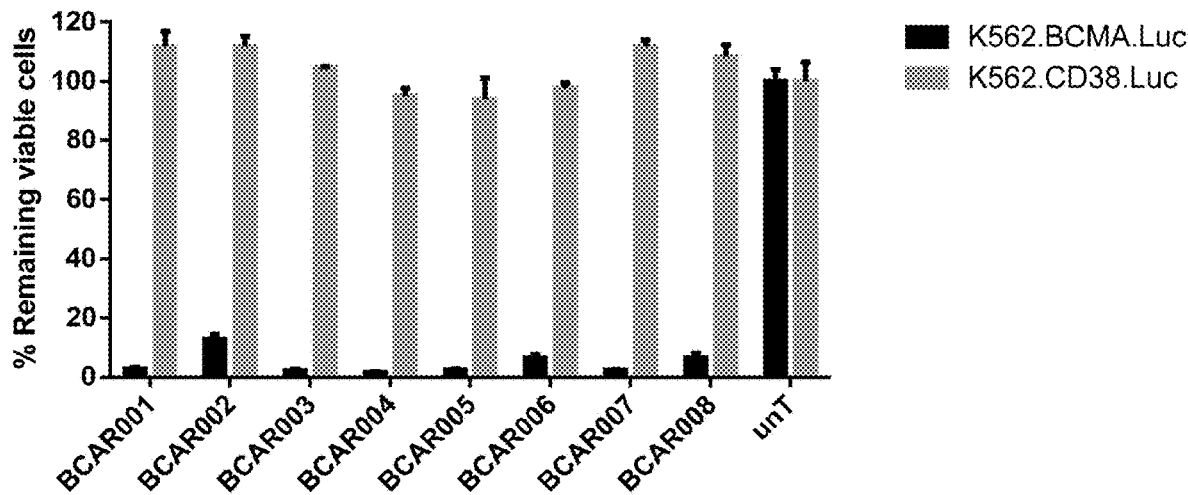
FIG. 5F shows results of an in vitro cytotoxicity assay of T cells expressing exemplary bivalent BCMA CARs against K562. BCMA.Luc cells and K562. CD38. Luc cells.

In a third experiment, exemplary bivalent BCMA CARs (i.e., BCMAR001-BCMAR008) having two different BCMA binding moieties were constructed, and engineered CAR-T cells expressing the bivalent BCMA CARs were prepared from primary T cells obtained from R/R MM patient donor #13. In-house developed firefly luciferase expressing cell lines including RPMI8226 (human multiple myeloma cell line), A549 (human lung cancer cell line), U87-MG (human glioblastoma cell line) and Raji (human Burkitt's lymphoma cell line) were used as target cells and co-cultured with each group of transduced T cells side by side (with Effector: target cell ratio of 20:1 or 5:1) for 20 hours in a 37° C./5% $CO_2$ cell incubator. Upon completion of co-culture, the remaining luciferase activities (relative light unit, RLU) were assayed with ONE-GLO™ luminescent luciferase assay kit (Promega) to assess the cytotoxicity of each CAR-T. As shown in FIGS. 5A-5E, the bivalent BCMA CAR-Ts had dose-dependent cytotoxicity against RPMI8226. Luc, K562. BCMA.Luc and Raji.Luc cells, but little cytotoxicity against BCMA negative A549. Luc and U87-MG.Luc cells. Data in FIG. 5F demonstrate that the cytotoxicity of the bivalent BCMA CAR-T cells against tumor cells are BCMA-specific as the CAR-T cells were not cytotoxic against K562. C38. Luc cells that were $CD38^+$/$BCMA^-$. K562. BCMA.Luc treated with BCMAR001-BCMAR008 CAR-T cells only showed limited residual Luciferase activities (i.e., viable cells) as compared to UnT treated target cells (2.88±0.45%, 12.84±1.67%, 2.22±0.56%, 1.77±0.14%, 2.59±0.28%, 6.58±1.19%, 2.47±0.20%, 6.61±1.47% for BCMAR001-BCMAR008 respectively, as compared to UnT of 100±3.95%, mean±standard error). These results demonstrate potent cytotoxicity of the bivalent BCMA CAR-T cells against K562. BCMA.Luc cells. BCMAR001-BCMAR008 CAR-T cells did not have significant cytotoxicity against K562. CD38. Luc cells as no significant decrease in Luciferase activity was detected as compared to UnT-treated target cells (111.82±5.11%, 111.72±3.43%, 104.74±0.24%, 95.04±2.70%, 93.93±7.23%, 97.72±1.86%, 111.90±2.01%, 108.33±4.05%, for BCMAR001-BCMAR008 respectively, as compared to UnT of 100±6.58%, mean±standard error). These data suggested the cytotoxicity of the bivalent BCMA CAR-T is BCMA dependent.

IFNgamma Release

Figure 6A:
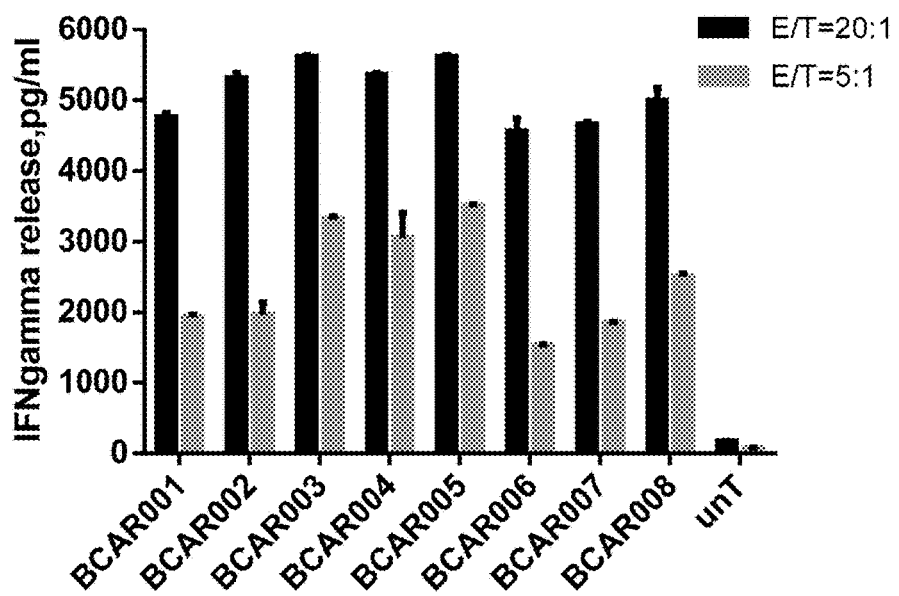
FIG. 6A shows results of an in vitro IFNγ release assay of T cells expressing exemplary bivalent BCMA CARs against K562. BCMA.Luc cells at two different effector cell to target cell ratios.
Figure 6B:
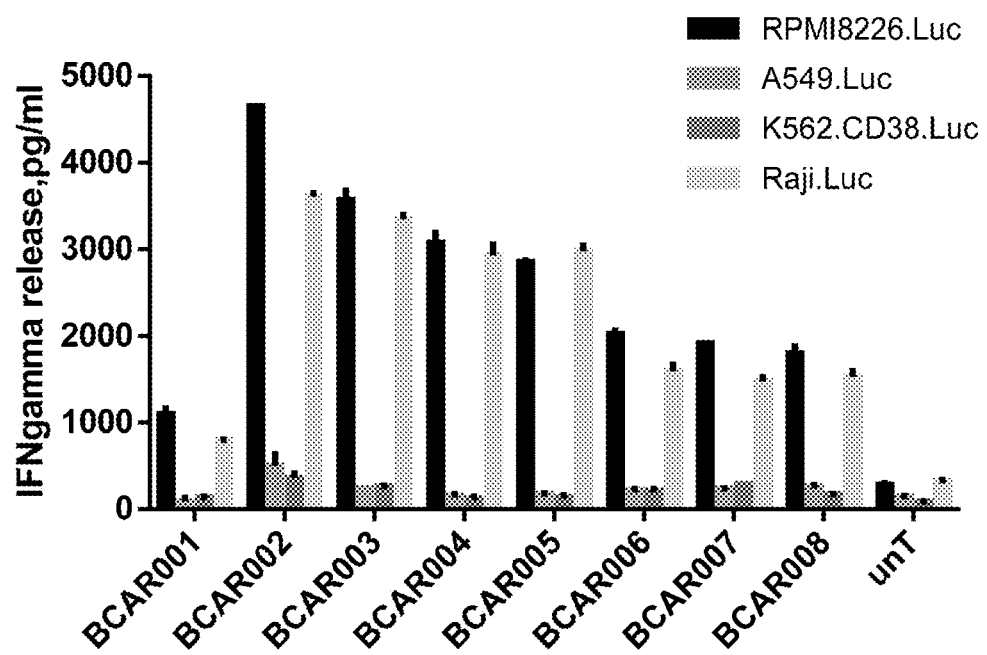
FIG. 6B shows results of an in vitro IFNγ release assay of T cells expressing exemplary bivalent BCMA CARs against RPMI8226. Luc, A549. Luc, K562. CD38. Luc and Raji.Luc cells.

Additionally, supernatants from in vitro co-culture assays were collected to assess CAR-induced cytokine release (e.g., interferon gamma, IFNγ release). As shown in FIGS. 6A-6B, IFNγ release in the co-culture assays was CAR-dependent and BCMA-specific, which is consistent with the in vitro cytotoxicity data (Table 6).

TABLE 6

IFN gamma release in co-culture assays by bivalent BCMA CAR-T

| | RPMI8226.Luc | | A549.Luc | | K562.CD38.Luc | | Raji.Luc | |
|---|---|---|---|---|---|---|---|---|
| | Mean, pg/ml | s.e. | Mean, pg/ml | se. | Mean, pg/ml. | s.e. | Mean, pg/ml | s.e. |
| BCAR001 | 1097.23 | 61.87 | 89.18 | 42.19 | 135.81 | 5.87 | 795.87 | 7.29 |
| BCAR002 | 4651.22 | 1.13 | 503.63 | 130.73 | 361.87 | 49.68 | 3613.30 | 34.04 |

TABLE 6-continued

IFN gamma release in co-culture assays by bivalent BCMA CAR-T

| | RPMI8226.Luc | | A549.Luc | | K562.CD38.Luc | | Raji.Luc | |
|---|---|---|---|---|---|---|---|---|
| | Mean, pg/ml | s.e. | Mean, pg/ml | se. | Mean, pg/ml. | s.e. | Mean, pg/ml | s.e. |
| BCAR003 | 3569.84 | 108.19 | 243.82 | 1.31 | 265.08 | 3.24 | 3348.66 | 49.80 |
| BCAR004 | 3077.41 | 110.82 | 161.70 | 12.97 | 128.50 | 17.08 | 2931.11 | 120.31 |
| BCAR005 | 2850.34 | 20.16 | 170.90 | 8.27 | 141.20 | 17.54 | 2976.27 | 67.22 |
| BCAR006 | 2023.71 | 37.61 | 223.96 | 6.21 | 215.00 | 17.87 | 1588.54 | 77.96 |
| BCAR007 | 1912.98 | 2.28 | 239.43 | 1.93 | 289.72 | 1.94 | 1472.87 | 49.76 |
| BCAR008 | 1798.90 | 76.85 | 258.71 | 19.39 | 171.89 | 6.51 | 1526.93 | 66.70 |
| UnT | 281.75 | 20.55 | 143.70 | 10.46 | 85.65 | 1.98 | 328.61 | 6.69 |

Copy Numbers of Integrated CAR Genes

The copy numbers of integrated CAR genes for each transduced T cell group was determined by a semi-quantitative PCR (q-PCR) assay. Briefly, genomic DNA from each group of CAR-T was prepared with Gentra Puregene Cell Kit (Qiagen). The concentration of genomic DNA was determined by Nanodrop, and 10 ng genomic DNA sample was processed for a standardized q-PCR assay with SYBR Green Realtime PCR Master mix plus (Toyobo) on ABI #7300 q-PCR instrument using CAR specific primers (forward primer 137P2F, SEQ ID NO: 398: 5'-GTCCTTCTCCTGTCACTGGTTAT-3'; and reverse primer 137P2R, SEQ ID NO: 399: 5'- TCTTCTTCTTCTG-GAAATCGGCA-3'). The relative copy number of each integrated CAR gene was calculated based on a standard curve established using plasmid containing target sequences.

As shown in Table 7, a high copy number of CAR vector was integrated into the genome of the T cells in each CAR-T preparation.

TABLE 7

Genome integration copy numbers.

| CAR-T cells with constructs | Copies/ng gDNA |
|---|---|
| GSI5019 | 35091.6 |
| GSI5020 | 27627.2 |
| GSI5021 | 24926.8 |
| GSI5022 | 26393.6 |
| GSI5023 | 32376.3 |
| GSI5024 | 39319.8 |
| GSI5025 | 22269.3 |
| GSI5026 | 34790.4 |
| UnT | 26.6 |

Example 4. Epitope Mapping and Differential Epitope Binding of Two $V_HH$ Domains in LCAR-B38M The epitopes of the four anti-BCMA $V_HH$ domains were mapped. An exemplary bivalent BCMA CAR having two different anti-BCMA $V_HH$ domains that specifically bind to different epitopes of BCMA was constructed. Bivalent/biepitope CAR comprising $V_H$H1 and $V_H$H2, named LCAR-B38M CAR, is one multivalent BCMA CAR listed in Table 5.

Surface Plasmon Resonance (SPR) Assay

Each of four exemplary anti-BCMA $V_HH$ sequences was cloned into a vector containing a human IgG1 Fc fragment (hIgG1Fc) sequence to facilitate recombinant expression of BCMA $V_HH$-hIgG1Fc. Recombinant proteins were obtained and purified for SPR assays.

The affinity of each $V_HH$-hIgG1Fc for BCMA was determined by SPR using a BIACORE® 2000 analytical system (GE Healthcare). Briefly, each $V_HH$-hIgG1Fc protein was covalently coupled to a CM5(s) sensor chip using 4 μg/ml $V_HH$-hIgG1Fc. Recombinant BCMA-His protein (ACRO Biosystems, Cat #BCMA-H522y) was serially diluted in running buffer (10 mM HEPES, 150 mM NaCl, 3 mM EDTA, 0.05% Tween-20, pH 7.4) and injected at a flowrate of 10 μl/min followed by dissociation. The association and dissociation rate constants were determined using the BIACORE® 2000 evaluation software version 3.0 (Langmuir binding, local fit, 1:1 binding model). The binding affinities of the four $V_HH$-hIgG1Fcs are shown in Table 8.

TABLE 8

Binding affinities of $V_HH$-hIgG1Fcs to human BCMA-His protein.

| Ligand | $k_a$ (1/Ms) | $k_d$ (1/s) | $K_D$ (M) |
|---|---|---|---|
| $V_H$H1-hIgG1Fc | 5.5E+04 | <1.0E−05* | <1.8E−10* |
| $V_H$H2-hIgG1Fc | 1.9E+06 | 1.5E−02 | 7.8E−09 |
| $V_H$H3-hIgG1Fc | 3.4E+04 | 1.7E−04 | 5.1E−09 |
| $V_H$H4-hIgG1Fc | 2.1E+06 | 9.4E−04 | 4.6E−10 |

Binding of Recombinant $V_HH$-His Proteins to Target Cells

Recombinant anti-BCMA $V_HH$-His proteins were constructed by fusing the anti-BCMA $V_HH$ sequence to a human albumin signal peptide sequence (N'-MKWVTFISLLFLF-SSAYS-C'; SEQ ID NO: 386) at the N terminus, and a 6×His-tag (N'-GSGHEIHEIHH-C'; SEQ ID NO: 387) at the C terminus. The codons were further optimized for optimal expression in mammalian host cells. The obtained nucleotide sequences were then cloned into a mammalian expression vector pTT5 via 5'-XbaI and 3'-HindIII restriction sites to provide plasmids, pTT5-LAB001 (for $V_H$H1), pTT5-LAB002 (for $V_H$H2) and pTT5-LAB003 (for $V_H$H1× $V_H$H2).

In order to obtain recombinant BCMA $V_HH$ proteins, HEK293T cells were transiently transfected with the plasmids. Briefly, 5×10⁶ HEK293T cells were seeded in 10 cm cell culture dishes one day prior to the transfection. On the next day, the cells were transfected with each plasmid using LIPOFECTAMINE™ 2000 Reagent (Thermofisher Scientific, Cat. No.: 11668-019) following the manufacturer's manual. Four days after transfection, supernatant was harvested and the expression levels of the antibodies were detected by ELSIA using HRP anti-His Tag (Biolegend, Cat. No.: 652504). The expression levels of LAB001, LAB002 and LAB003 were 109.31 ng/ml, 152.48 ng/ml and 396.62 ng/ml respectively.

Binding affinities of LAB001, LAB002 and LAB003 anti-BCMA $V_HH$-His proteins were determined using cell-based assays. Briefly, serially diluted anti-BCMA V$_H$H-His proteins were incubated with 1×10$^5$ target cells (either K562. BCMA.Luc or K562. CD38. Luc cells, which were in-house developed cell lines stably expressing BCMA or CD39 respectively) at 4° C. for 2 hours. Afterwards, cells were centrifuged at 300 g for 10 min, and the supernatant was discarded. The cell pellets were re-suspended with DPBS. The cell pellets were washed, centrifuged, and the supernantant was discarded for 2 more times. Then cell pellets were subsequently re-suspended with detection antibody (THE™ His tag Antibody [FITC], GenScript Cat: A01620) containing buffers for 45 min at 4° C. for 2 hours. Afterwards, cells were centrifuged at 300 g for 10 min, and the supernatant was discarded. The cell pellets were washed, centrifuged, and the supernatant was discarded for 2 more times. Binding affinities of LAB001, LAB002 and LAB003 to either K562. BCMA.Luc or K562. CD38. Luc cells were determined using an ATTUNE™ Nxt flow cytometer. Data was fitted by GraphPad PRISM™ version 6.0 using a "One site—Specific binding with Hill slope".

Figure 7A:
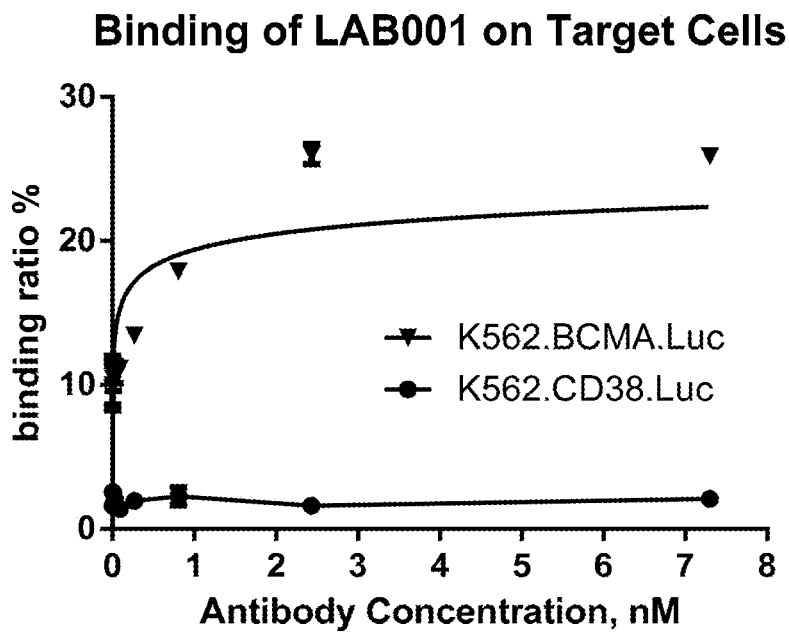
FIGS. 7A-7C show binding of three exemplary VHH fragments to K562. BCMA.Luc cells and K562. CD38. Luc cells (negative control).
Figure 7B:
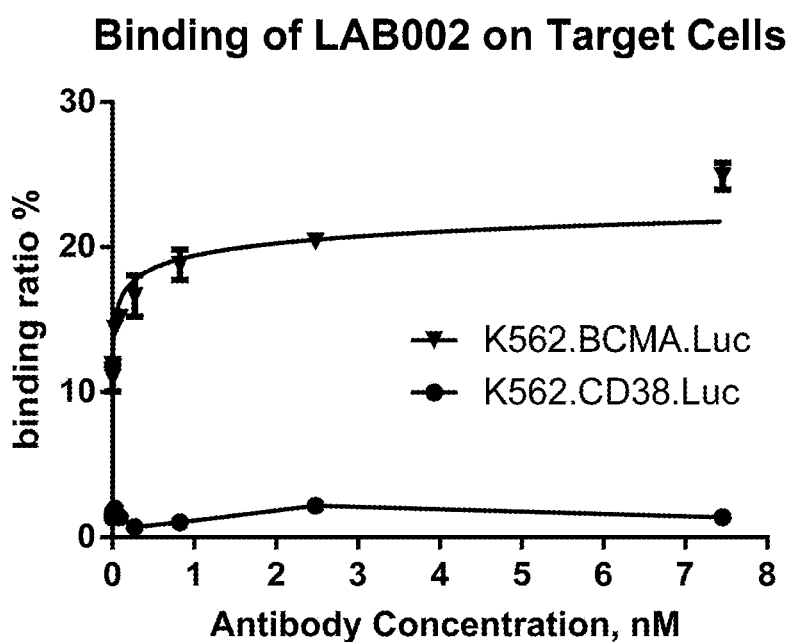
Figure 7C:
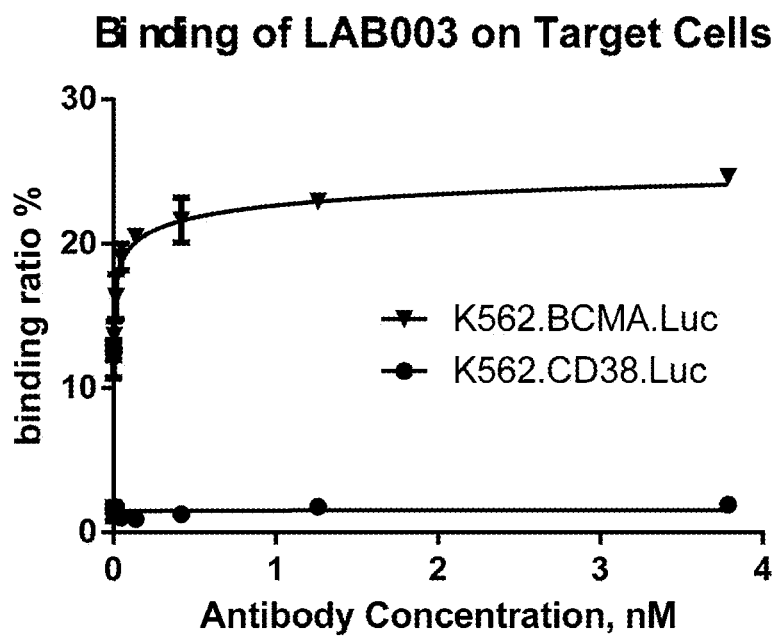

As shown in FIG. 7A-7C, LAB001, LAB002 and LAB003 specifically bind to K562. BCMA.Luc cells in a dose-dependent manner. The binding affinities are 0.079 nM, 0.035 nM and 0.0047 nM respectively. None of the antibodies showed significant binding to BCMA negative cell line K562. CD38. Luc. Moreover, LAB003 (V$_H$H1×V$_H$H2) showed significantly higher binding affinity (0.0047 nM) than either LAB001 (V$_H$H1) or LAB002 (V$_H$H2).

Epitope Binding

BCMA (NP_001183, UniProt #Q02223) is a transmembrane protein of 184 amino acids long. Human BCMA consists of an extracellular domain (ECD, amino residue number 1-54), a transmembrane domain (TM, amino residue number 55-77) and a cytoplasmic domain (CD, amino residue number 78-184). In addition, sequence analysis suggests that BCMA has no recognizable signal peptide at its N terminus (Laabi Y et al. (1992) EMBO J 11:3897-3904; Laabi Y et al. (1994) Nucleic Acids Res 22:1147-1154; Gras M P (1995) Int Immunol 7:1093-1106; Hong-Bing Shu and Holly Johnson (2000): Proc. Natl. Acad. Sci. USA, 10.1073).

Figure 8A:
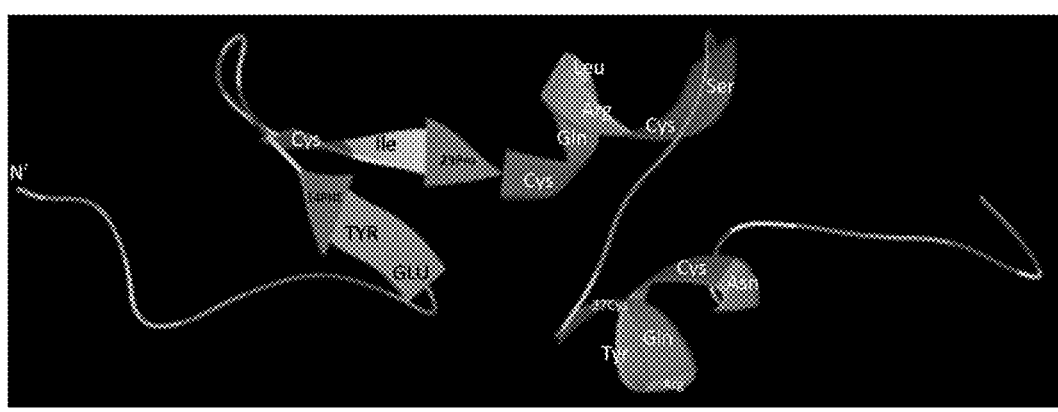
FIG. 8A shows a crystal structure of the extracellular domain of BCMA.

As also illustrated by the online database UniProt (worldwide web.uniprot.org/uniprot/Q02223), 3 disulfide bonds (Cys-Cys) are located in the ECD of BCMA, which are at positions 8↔21, 24↔37 and 28↔41 (Table 9). The secondary structure of the BCMA ECD from the N-terminus to the C-terminus consists of a beta strand (aa12-15), a turn (aa16-19), a beta strand (aa20-23), a helix (aa 24-27), a beta strand (aa30-32), a helix (aa35-37), a turn (aa38-40), and a turn (aa42-44). A structure of the BCMA ECD is shown in FIG. 8A, which is replicated from the structure from the PDB database worldwide web.ebi.ac.uk/pdbe/entry/pdb/2kn1/.

TABLE 9

Protein sequences of human BCMA.

| Position(s) | Description | Length | AA sequence |
|---|---|---|---|
| 1-54 | Extracellular domain | 54 | MLQMAGQCSQNEYFDSLLHACIPCQ LRCSSNTPPLTCQRYCNASVTNSVKG TNA (SEQ ID NO: 395) |
| 55-77 | Transmembrane domain | 23 | ILWTCLGLSLIISLAVFVLMFLL (SEQ ID NO: 396) |
| 78-184 | Cytoplasmic domain | 107 | RKINSEPLKDEFKNTGSGLLGMANID LEKSRTGDEIILPRGLEYTVEECTCED CIKSKPKVDSDHCFPLPAMEEGATIL VTTKTNDYCKSLPAALSATEIEKSISA R (SEQ ID NO: 397) |

BCMA epitope peptides (269EP001-269EP007) were designed as shown in FIG. 8B and TABLE 10, and chemically synthesized and biotinylated at the N-terminus. Binding affinities of V$_H$H1-hIgG1Fc or V$_H$H2-hIgG1Fc were determined using ELISA. Briefly, peptides described above were coated on MAXISORP™ ELISA plate at 1 μM overnight at 4° C. The next day, the plates were washed with PBST (add 0.5% TWEEN-20) twice, followed by plate blocking with 0.5% BSA at room temperature for 1h. The plates were then washed with PBST twice, followed by addition of serially diluted V$_H$H1-hIgG1Fc or V$_H$H2-hIgG1Fc at 10 nM in triplicates, then incubated at 4° C. for 2 h. The plates were then washed for 3 times with cold PBST, after which goat anti-Llama-HRP (1:1500, Bethyl Lab #A160) was added to each well and further incubated at room temperature for 1h. The plates were then washed for 4 times with PBST, and TMB substrates were added to each well and incubated at room temperature for 10-30 min. The plates were then read on TECAN® 10M microplate reader with absorbance at 450 nm.

TABLE 10

BCMA epitope peptide sequences.

| Epitope | Positions | Amino acid residue sequence | Length |
|---|---|---|---|
| 269EP001 | 1-10 | MLQMAGQCSQ (SEQ ID NO: 388) | 10 |
| 269EP002 | 8-21 | CSQNEYFDSLLHAC (SEQ ID NO: 389) | 14 |
| 269EP003 | 11-23 | NEYFDSLLHACIP (SEQ ID NO: 390) | 13 |
| 269EP004 | 20-30 | ACIPCQLRCSS (SEQ ID NO: 391) | 11 |
| 269EP005 | 24-42 | CQLRCSSNTPPLTCQRYCN (SEQ ID NO: 392) | 19 |
| 269EP006 | 36-43 | LTCQRYCNAS (SEQ ID NO: 393) | 10 |
| 269EP007 | 43-54 | ASVTNSVKGTNA (SEQ ID NO: 394) | 12 |

Figure 9A:
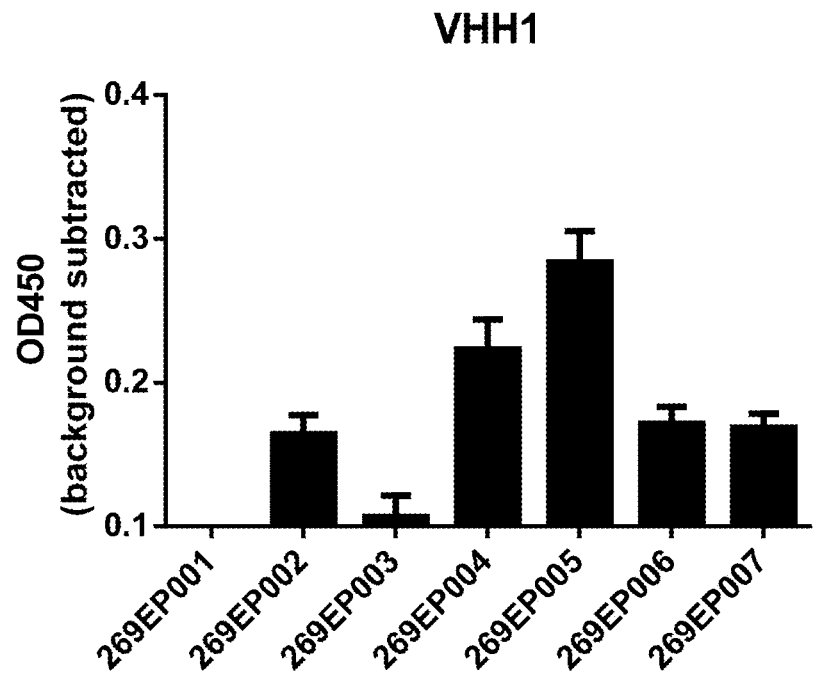
FIGS. 9A-9B show results of epitope mapping assays of VHH1 and VHH2.

As shown in FIG. 9A, $V_HH1$ showed strongest binding to the 269EP005 peptide followed by the 269EP004 peptide. However, binding of $V_HH1$ to 269EP003 and 269EP006 was relatively weak compared to 269EP005 and 269EP004. $V_HH1$ tends to bind an epitope located in the 269EP005 peptide (i.e., amino acid 24-36 of BCMA ECD), which contains the secondary structures of a helix (aa24-27), a beta strand (aa30-32), and a helix (aa35-37).

Figure 9B:
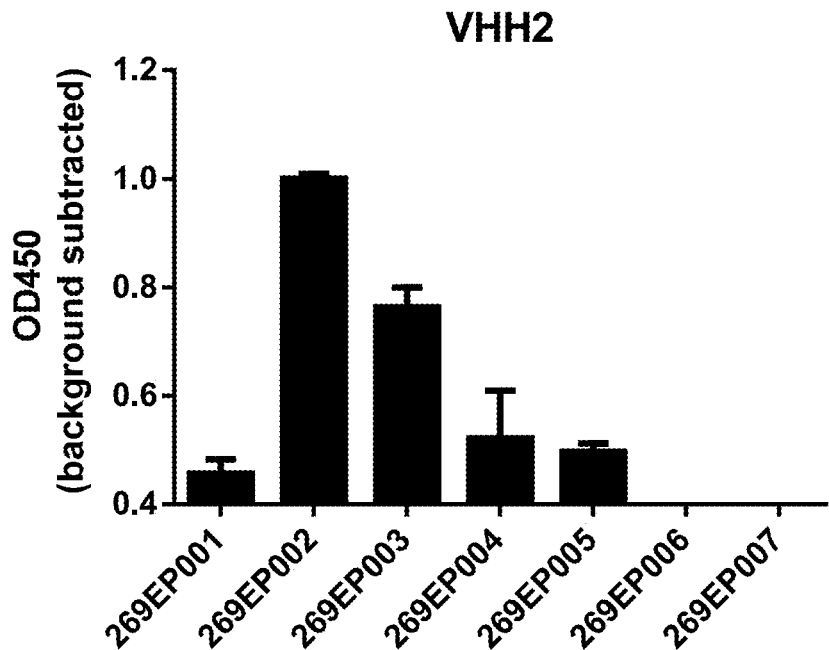

As shown in FIG. 9B, $V_HH2$ showed strongest binding to the 269EP002 peptide followed by the 269EP003 peptide. However, binding of $V_HH1$ to 269EP001 and 269EP004 was relatively weak compared to 269EP002 and 269EP003. While the first beta strand (aa12-15) and the beta strand (aa20-23) of the BCMA ECD are mainly located in the sequence covered by 269EP002 (aa8-21) and 269EP003 (aa1-23), $V_HH2$ tends to bind to an epitope located in the first two beta strands.

Competitive Binding Assay

Differential epitope binding of $V_HH1$ and $V_HH2$ was further validated by a cell-based competitive binding assay. A stable CHO cell line overexpressing human BCMA ("CHO-BCMA") was used in the assay.

Figure 10:
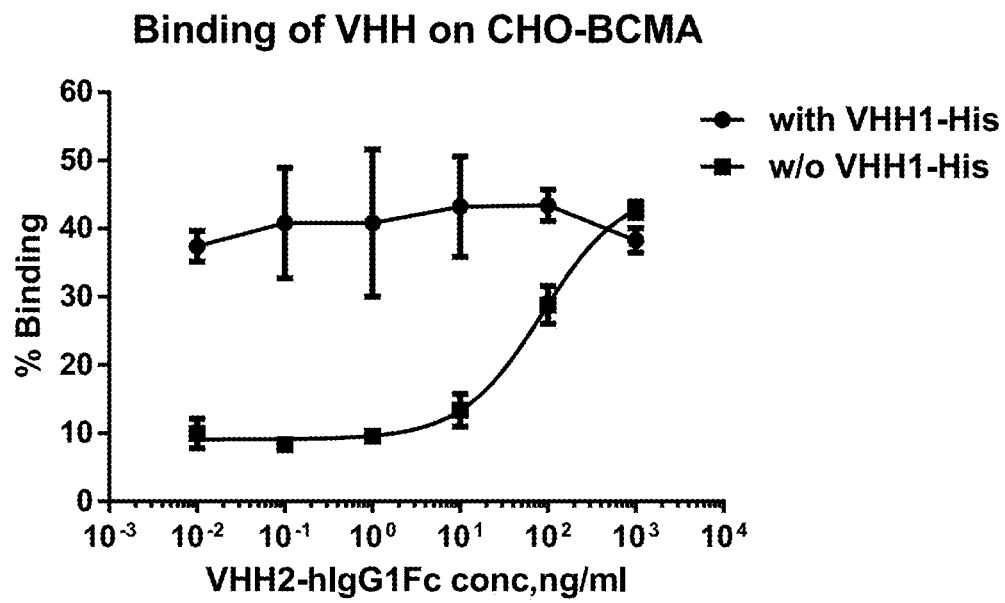
FIG. 10 shows results of a competitive binding assay using CHO-BCMA cells.

Briefly, $0.5 \times 10^6$ CHO-BCMA cells were pre-incubated with 12.5 ng/ml LAB001 (which contains 6xHis tag at the C terminus) at 4° C. for 0.5 h in duplicates. Then serially diluted $V_HH2$-hIgG1Fc recombinant antibody was added to each well of the plate and further incubated at 4° C. for another 1 h. After incubation, cells were washed with 500 µl DPBS and centrifuged at 300 g for 10 min. The cell pellets were re-suspended with DPBS containing anti-His tag-FITC (1:200, GenScript Cat: A16020), then cells were washed with 500 µl DPBS and centrifuged at 300 g for 10 min. The cell pellets were re-suspended with DPBS, and were then subject to FACS analysis on an ATTUNE Nxt flow cytometer. As an assay control, serially diluted $V_HH2$-hIgG1Fc was directly incubated with CHO-BCMA cells without the presence of LAB001 following identical procedures as above side-by-side. Goat anti- Human IgG (Fc specific)-FITC antibody (Sigma Aldrich Cat:F9512) was used to detect binding of $V_HH2$-hIgG1Fc to the CHO-BCMA cells. As shown in FIG. 10, $V_HH2$-hIgG1Fc alone binds to CHO-BCMA in a dose-dependent manner. However, $V_HH2$-hIgG1Fc was not able to compete with $V_HH1$-His binding to CHO-BCMA cells, which indicates different binding sites of $V_HH1$ and $V_HH2$ on BCMA.

Example 5. In Vivo Efficacy of LCAR-B38M CAR-T in Tumor Xenograft Mice

In vivo anti-tumor efficacy of LCAR-B38M CAR-T cells was evaluated in a NCG mouse model (NOD-Prkdc$^{em26Cd52}$IL2rg$^{em26Cd22}$/NjuCrl) having a multiple myeloma tumor xenograft. LCAR-B38M CAR is a bivalent BCMA CAR having two anti-BCMA $V_HH$ domains that target different BCMA epitopes.

The NCG mouse model was created by sequential CRISPR/Cas9 editing of the Prkdc and Il2rg loci in the NOD/Nju mouse, providing a mouse coisogenic to the NOD/Nju. The NOD/Nju mouse carries a mutation in the Sirpa (SIRP α) gene that allows for engrafting of foreign hematopoietic stem cells. The Prkdc knockout generates a SCID-like phenotype lacking proper T-cell and B-cell formation. The knockout of the Il2rg gene further exacerbates the SCID-like phenotype while additionally resulting in a decrease of NK cell production. Thus, the NCG mouse is a "triple-immunodeficient" mouse strain that is more immunocompromised than commonly used immunodeficient mouse strains including SCID and nude mice.

Prkdc and Il2rg are part of the SCID (severe combined immunodeficiency) family of genes affecting maturation and formation of T cells, B cells, NK cells and, to a lesser degree, dendritic cells. Prkdc encodes the catalytic subunit of the DNA-dependent protein kinase enzyme, which is required for V(D)J recombination, a necessary process to propagate antibody diversity in maturing T and B cells. Il2rg encodes the common gamma subunit found in IL-2 and multiple IL receptors (IL-4, IL-7, IL-9, IL-15 and IL-21), which are required to induce cytokine-mediated signaling for maturation of immature lymphocytes (e.g., T, B and NK cells) and other leukocytes.

Figure 11:
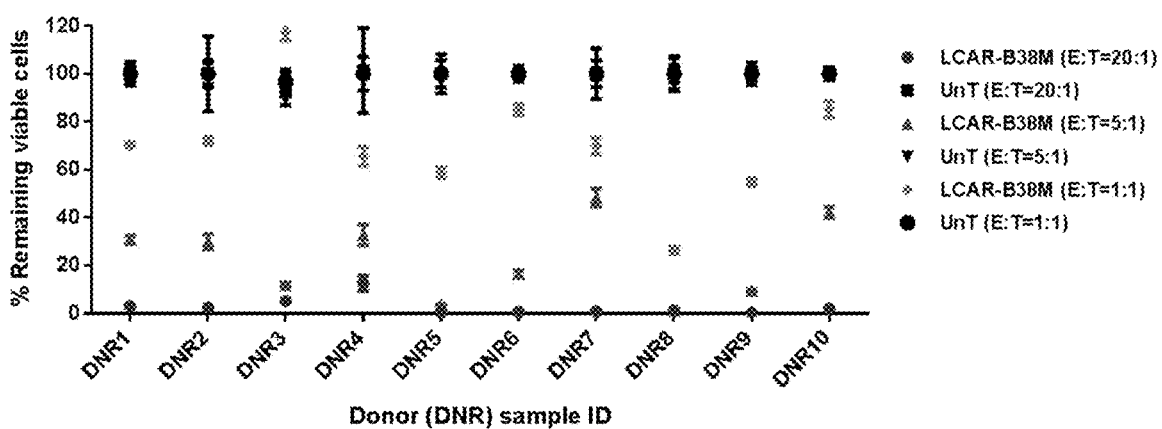
FIG. 11 shows in vitro cytotoxicity of donor-derived T cells expressing LCAR-B38M against RPMI8226. Luc cells.
Figure 12A:
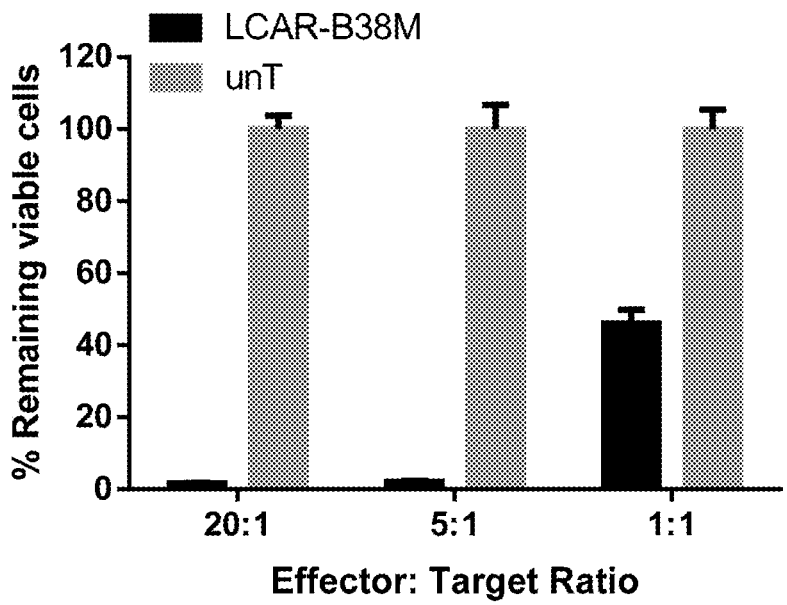
FIG. 12A shows in vitro cytotoxicity of LCAR-B38M CAR-T cells prepared from a selected donor against RPMI8226. Luc cells.

LCAR-B38M CAR-T cells were prepared using T cells from various donors to screen for T cell source yielding CAR-T with the highest efficacy of killing RPMI8226. Luc cells in vitro (FIG. 11). Based on the results of FIG. 11, LCAR-B38M CAR-T cells were prepared using T cells of the selected donor for in vivo animal assays. FIG. 12A shows dose-dependent in vitro cytotoxicity of this batch of LCAR-B38M CAR-T cells. To create the tumor xenograft, NCG mice were injected intravenously with RPMI8226. Luc cells. 14 days later, tumor engrafted mice were treated with the LCAR-B38M CAR-T cells or un-transduced T cells, followed by in vivo bioluminescence imaging (BLI).

Figure 12B:
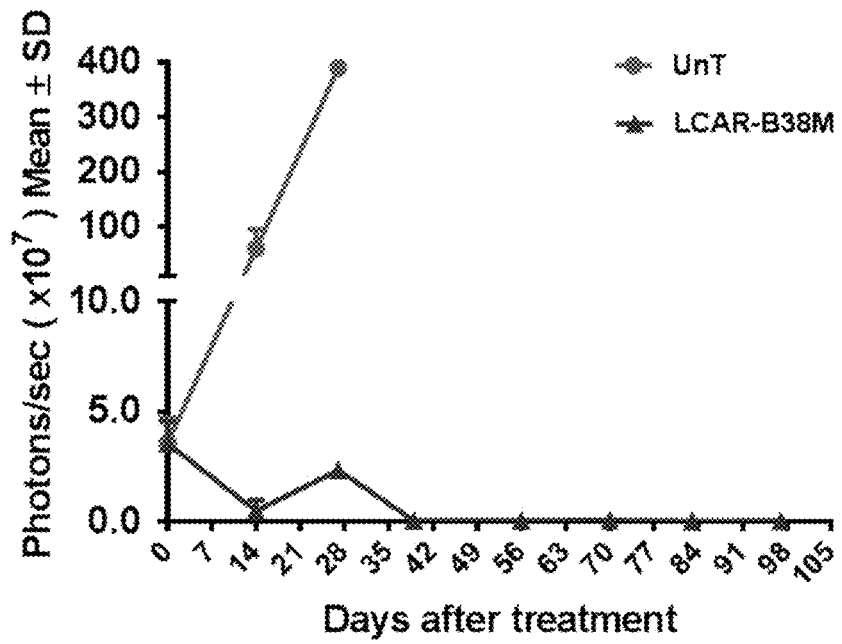
FIGS. 12B-12E show in vivo anti-tumor activity of LCAR-B38M CAR-T cells in tumor xenograft mice model.
Figure 12C:
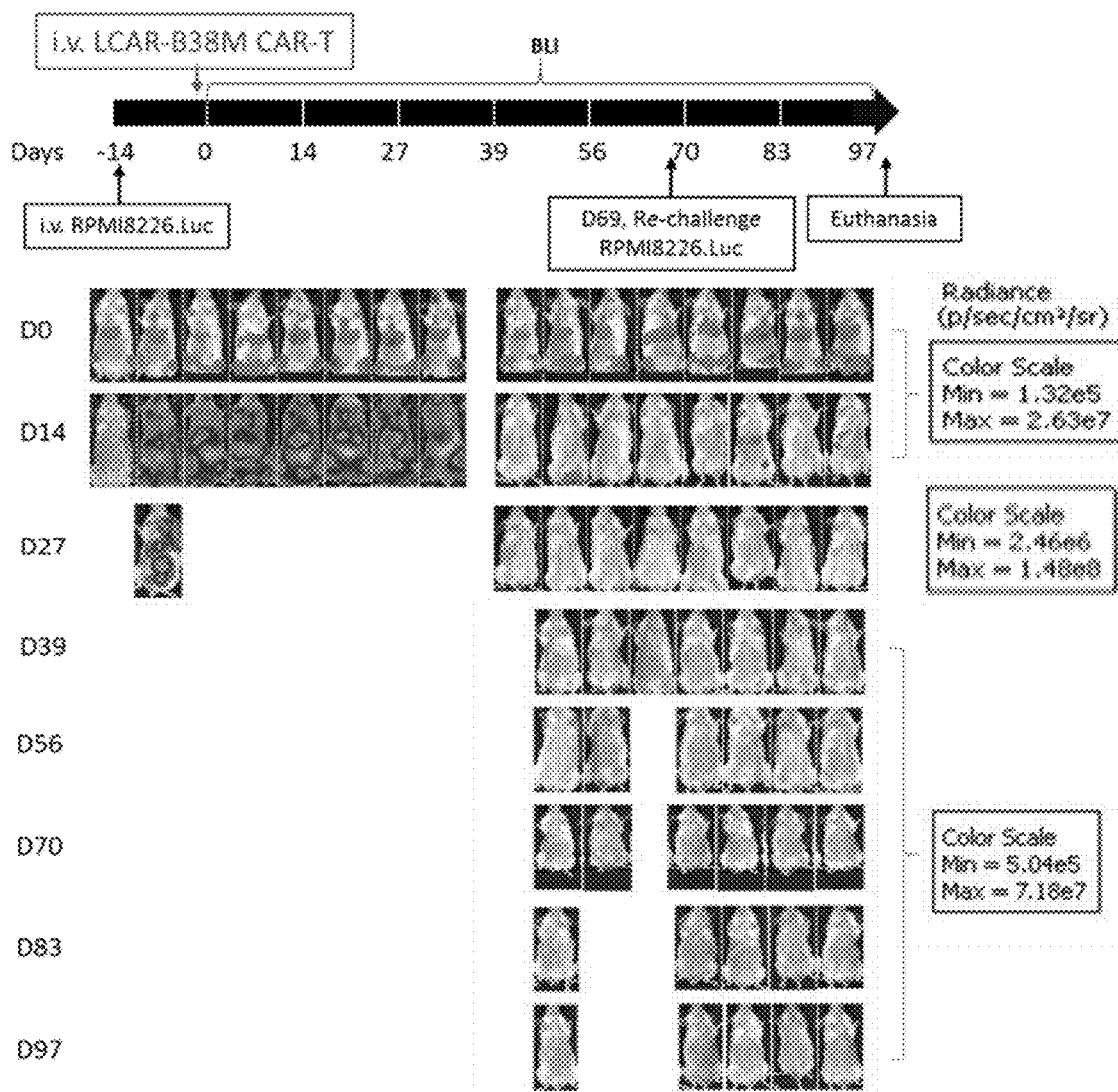
Figure 12D:
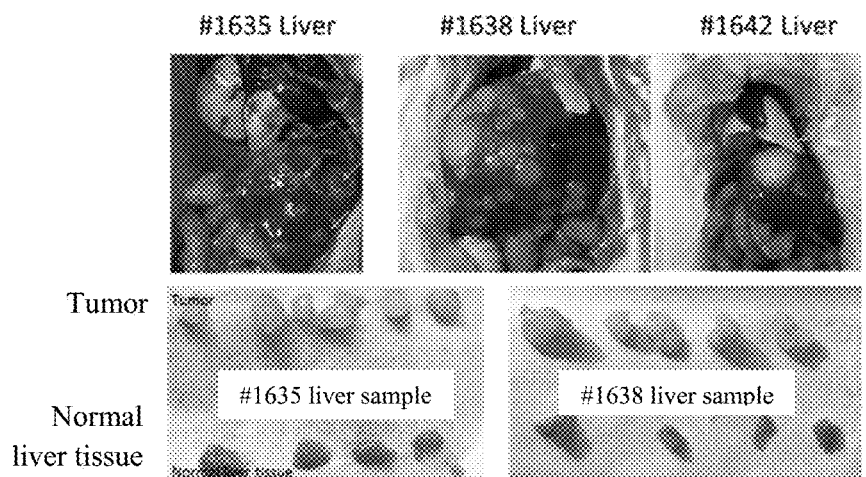
Figure 12E:
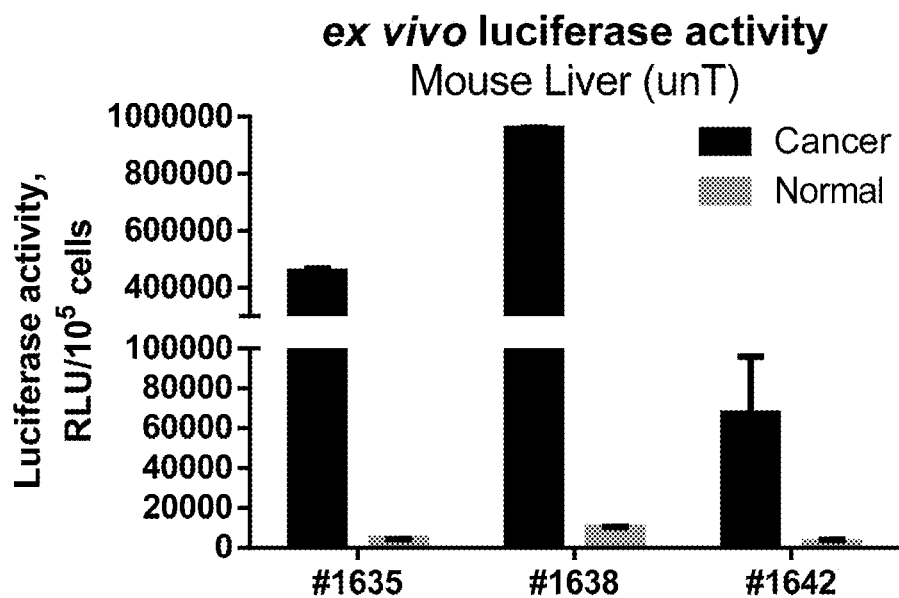
Figure 13A:
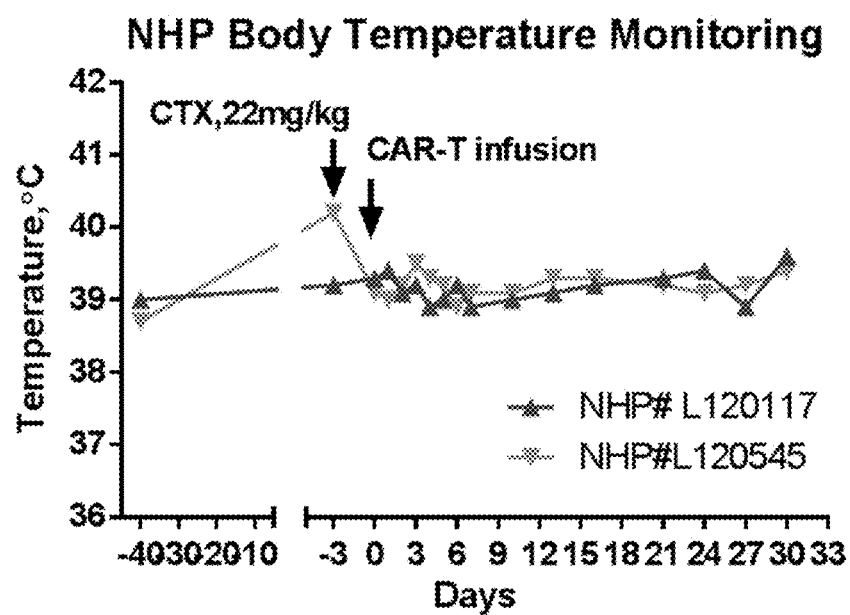
FIGS. 13A-13F show clinical parameters of two monkeys treated with LCAR-B38M CAR-T cells. The clinical parameters monitored in the study include body temperature (FIG. 13A), body weight (FIG. 13B), Complete Blood Count (CBC, FIGS. 13C and 13D), as well as serum chemistry and cytokine levels (FIGS. 13E and 13F).
Figure 13B:
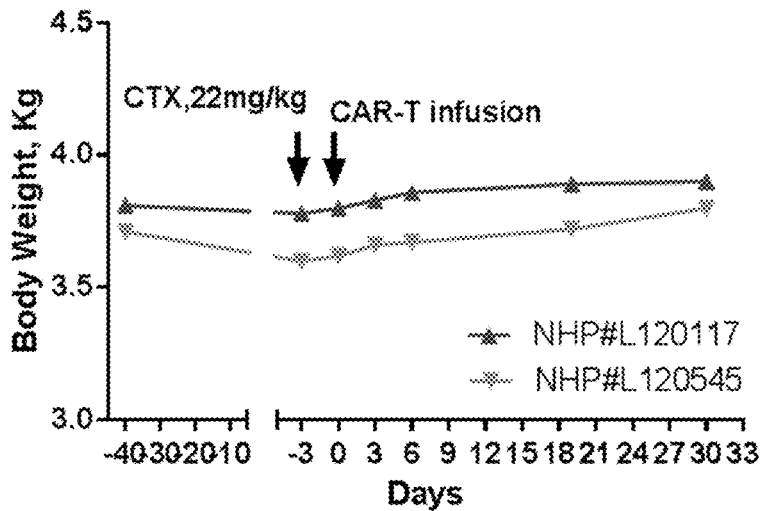
Figure 13C:
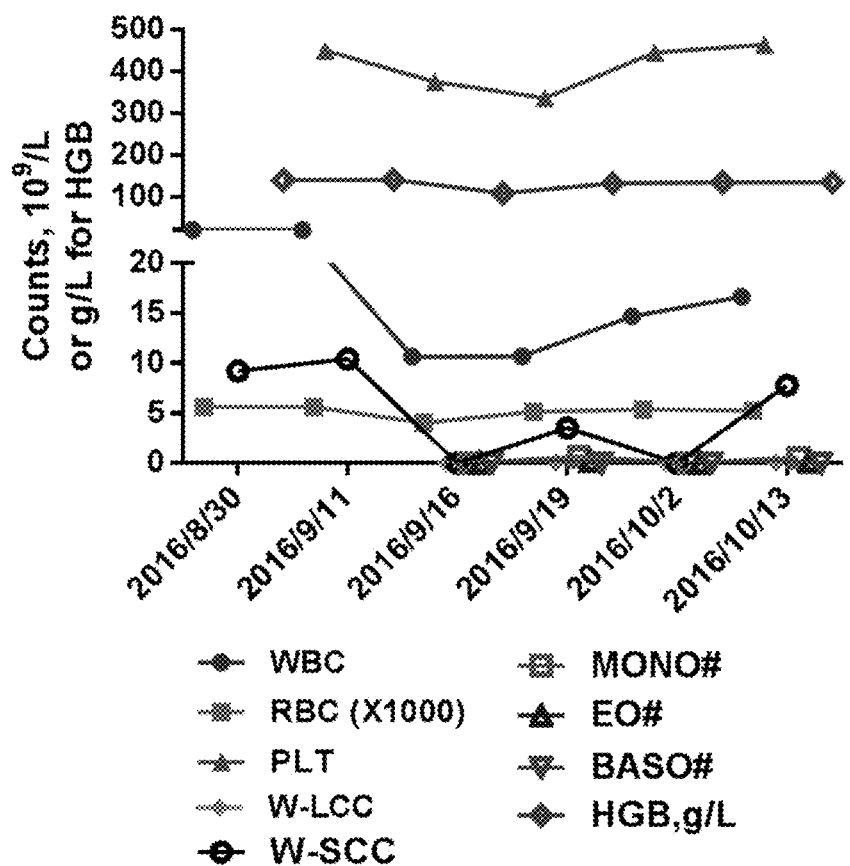
Figure 13D:
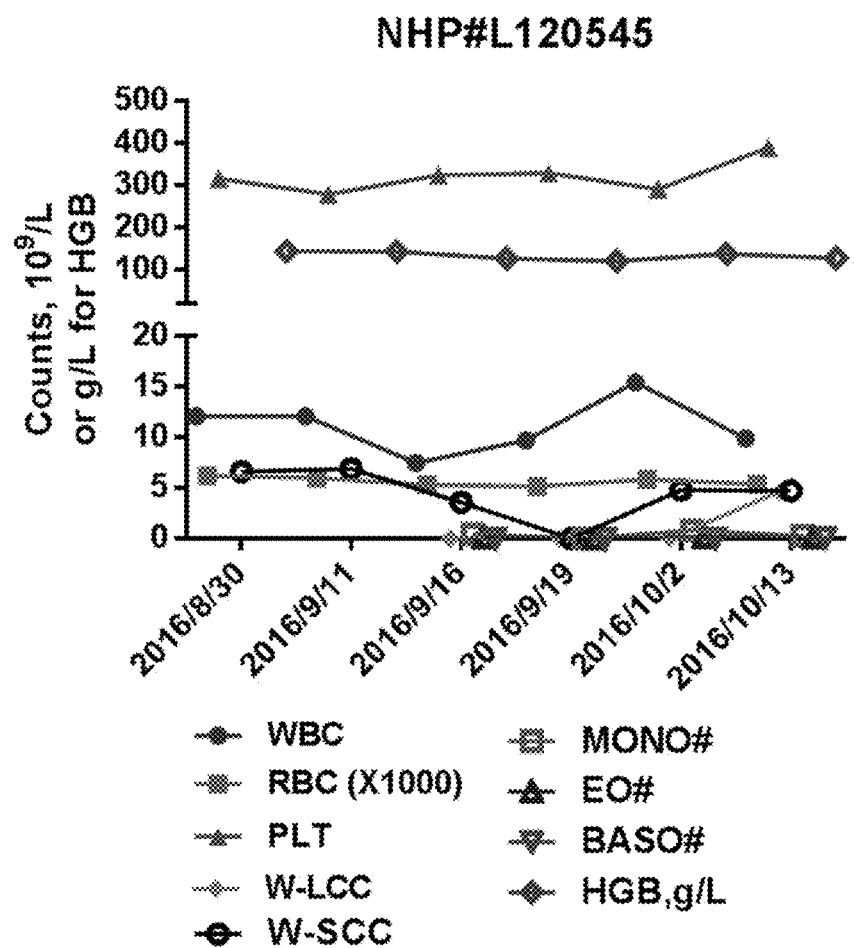
Figure 13E:
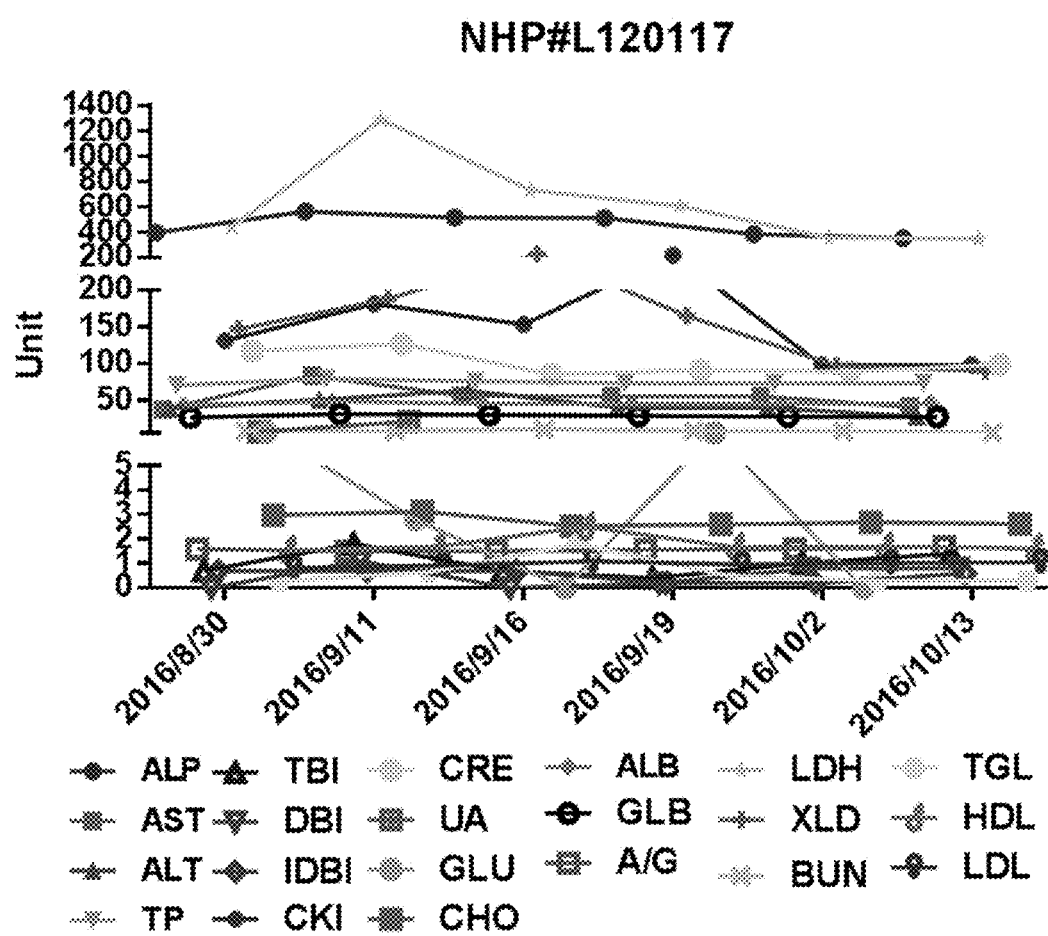
Figure 13F:
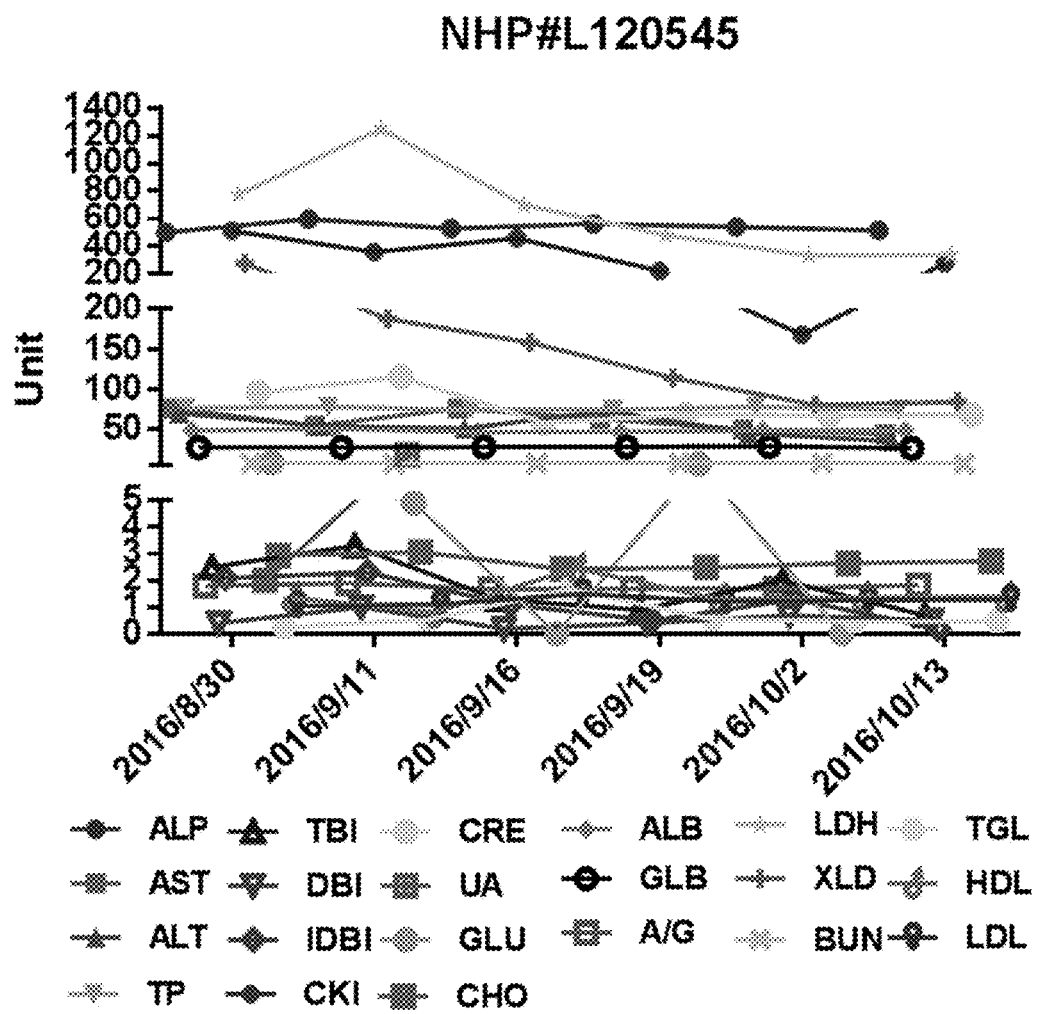

As shown in FIGS. 12B-12C, LCAR-B38M CAR-T cells were efficient to eradicate the engrafted RPMI8226. Luc tumor cells in NCG mice and rescue the mice, while most mice in the control (UnT) group died within 4 weeks. Interestingly, during autopsy, numerous metastatic tumors were observed in the liver of all mice in the UnT group. This observation was further validated by assessing ex vivo luciferase activities from the tumor samples (FIGS. 12D-12E). In contrast, the LCAR-B38M CAR-T treated mice did not have metastatic tumors in the livers. In summary, the in vivo study demonstrates the potency of LCAR-B38M CAR-T cells in eradication of multiple myeloma cells (e.g., RPMI8226. Luc) from NCG mice.

Example 6. Safety Study of LCAR-B38M CAR-T Treatment on Non-Human Primates

The in vivo safety of the LCAR-B38M CAR-T cells was evaluated in a cynomolgus monkey model. PBMC was obtained from peripheral blood samples of two monkeys (NHP #120117 and NHP #120545, both male, around 4 kg), and prepared by density gradient centrifugation. Cynomolgus monkey T cells were isolated from PBMC using non-human primate Pan T Cell Isolation Kit (Miltenyi #130-091-993) according to the manufacturer's manual. The prepared monkey T cells were pre-activated with non-human primate T Cell Activation/Expansion Kit (Miltenyi #130-092-919), human IL-2, and autologous monkey serum for 3 days. Afterwards, the pre-activated T cells were transduced with the LCAR-B38M lentivirus, followed by expansion for 10 additional days.

3 days prior to the infusion of autologous CAR-T cells, the monkeys were pre-treated with Cyclophosphamide at a dose of 22 mg/kg body weight by intravenous infusion. On the day of autologous infusion, cells were thawed in a 37° C. water bath by gentle swirling and immediately infused to the animals intravenously within 5 minutes. Monkey NHP #120117 was infused with $5 \times 10^6$/kg CAR-T cells, and monkey NHP #120545 was infused with $4 \times 10^7$/kg CAR-T cells.

The monkeys were monitored after the T-cell administration for fever, respiratory distress, change in appetite, diarrhea, and weight loss. Pre- and post-administration blood samples were obtained and examined for CBC, serum chemistry, and cytokine levels. As shown in FIGS. 13A-13F, the CAR-T cells had no significant toxicity in the monkeys.

Example 7. A Clinical Study of LCAR-B38M CAR-T in Human Patients with Refractory/Relapsed Multiple Myeloma A single-arm, open-label, multi-center, phase 1/2 clinical study was conducted to determine the safety and efficacy of LCAR-B38M CAR-T cells in treating human patients diagnosed with refractory or relapsed multiple myeloma ("r/r MM"). Information of the clinical trial can be found on worldwide web.clinicaltrials.gov, with identifier NCT03090659.

In the study, refractory/relapsed multiple myeloma patients were treated with LCAR-B38M CAR-T cells derived from autologous T cells of the patients. A total dose of $0.5 \times 10^6$-$5 \times 10^6$ cells/kg body weight was administered to each patient by intravenous injection in three split doses (20%, 30%, and 50% respectively) over the duration of a week (e.g., on Days 0, 2, and 6). During Days 1-30 of the study, patients were monitored for adverse events, and patient samples were obtained for laboratory assessment. All patients are followed up for at least 36 months after the CAR-T administration.

The primary outcome of the study measures occurrence of treatment related adverse events as assessed by Common Terminology Criteria for Adverse Events (CTCAE) v4.0 within 1-30 days after injection of the LCAR-B38M CAR-T cells. Secondary outcome assesses CAR-T induced anti-myeloma responses, e.g., by determining aberrant immunoglobulin levels in the serum, and number of multiple myeloma cells in the bone marrow of the patients before and after administration of the LCAR-B38M CAR-T cells. Efficacy objectives of the study include pathological Complete Response proportion, 3-year Disease Free Survival, 3-year Progression Free Survival.

Patients 18-75 years old are eligible for the study if: (1) the patient has a confirmed prior diagnosis of active multiple myeloma as defined by the updated IMWG criteria; (2) Clear BCMA expression is detected on malignant plasma cells from either bone marrow or a plasmacytoma by flow cytometry or immunohistochemistry; and (3) the patient has refractory multiple myeloma as defined by having received at least 3 prior treatment regimens including bortezomib, or otherwise identified by clinical doctors; or the patient has relapsed multiple myeloma as defined by in the NCCN clinical practice guidelines in Oncology: Multiple Myeloma (2016 V2).

The following patients are excluded from the study: (1) women of child-bearing potential or who are pregnant or breastfeeding; (2) patients who have any active and uncontrolled infection: hepatitis B, hepatitis C, HIV, or other fatal viral and bacterial infection; (3) patients who have received systemic corticosteroid steroid therapy of greater than 5 mg/day of prednisone or equivalent dose of another corticosteroid are not allowed within 2 weeks prior to either the required leukapheresis or the initiation of the conditioning chemotherapy regimen; (4) patients with any uncontrolled intercurrent illness or serious uncontrolled medical disorder; (5) patients with CNS metastases or symptomatic CNS involvement (including cranial neuropathies or mass lesions and spinal cord compression); (6) patients with a history of allogeneic stem cell transplantation, who have active acute or chronic graft-versus-host-disease (GVHD), or require immunosuppressant medications for GVHD, within 6 months of enrollment; or (7) patients with active autoimmune skin diseases such as psoriasis or other active autoimmune diseases such as rheumatoid arthritis.

At an interim analysis in May 2017, 35 patients with relapsed or treatment resistant (refractory) multiple myeloma received LCAR-B38M CAR-T treatment. First signs of treatment efficacy appeared as early as 10 days after initial injection of the CAR-T cells. Overall, the objective response rate was 100% and 33 out of 35 (94%) patients had an evident clinical remission of myeloma (complete response or very good partial response) within two months of receiving the CAR-T cells.

By the time of the analysis, 19 patients were followed for more than four months, a pre-set time for full efficacy assessment by the International Myeloma Working Group (IMWG) consensus criteria. One patient reached partial response and four patients achieved very good partial remission criteria (VgPR) in efficacy. No patients who reached the Stringent Complete Response ("sCR") criteria relapsed. Five patients who had been followed for over a year (12-14 months) remained at the sCR status and were free of minimal residual disease (i.e., no detectable cancer cells in the bone marrow).

Cytokine release syndrome ("CRS") is a common and potentially dangerous side effect of CAR T-cell therapy. Only transient CRS was experience by 85% of the 35 patients. CRS symptoms include fever, low blood pressure, difficulty of breathing, and problems with multiple organs. In a majority of the patients, CRS symptoms were mild and manageable. Only two patients experienced severe CRS (grade 3), but recovered upon receiving tocilizumab (an inflammation-reducing treatment commonly used to manage CRS in clinical trials of CAR-T cell therapy). No patients experienced neurologic side effects, another common and serious complication from CAR T-cell therapy.

The interim clinical trial data demonstrate potent efficacy and safety of the LCAR-B38M CAR-T treatment on patients with refractory/relapsed multiple myeloma.

In a pilot clinical study, 3 patients were treated with autologous T cells expressing a monovalent BCMA CAR, i.e., LCAR-B27S CAR-T cells. The LCAR-B27S CAR (one monovalent BCMA CAR listed in Table 4) has an antigen binding domain containing a single $V_H H$ fragment that recognizes a single epitope of the BCMA molecule. This $V_H H$ domain is identical to the second $V_H H$ domain of the bi-epitope/bivalent LCAR-B38M CAR.

Figure 14A:
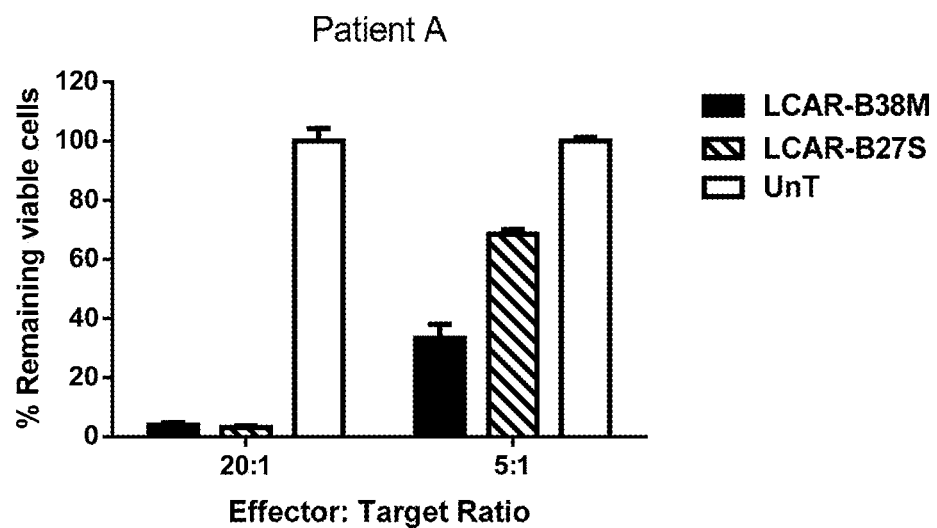
FIG. 14A-C show the in vitro cytotoxicity assays about LCAR-B38M CAR-T cells and LCAR-B27S CAR-T cells prepared from the same three multiple myeloma patients respectively.
Figure 14B:
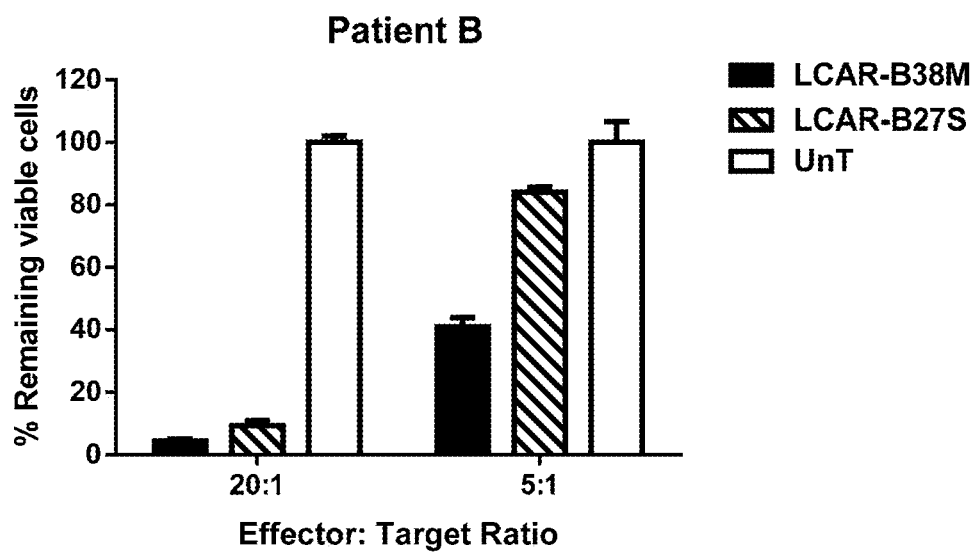
Figure 14C:
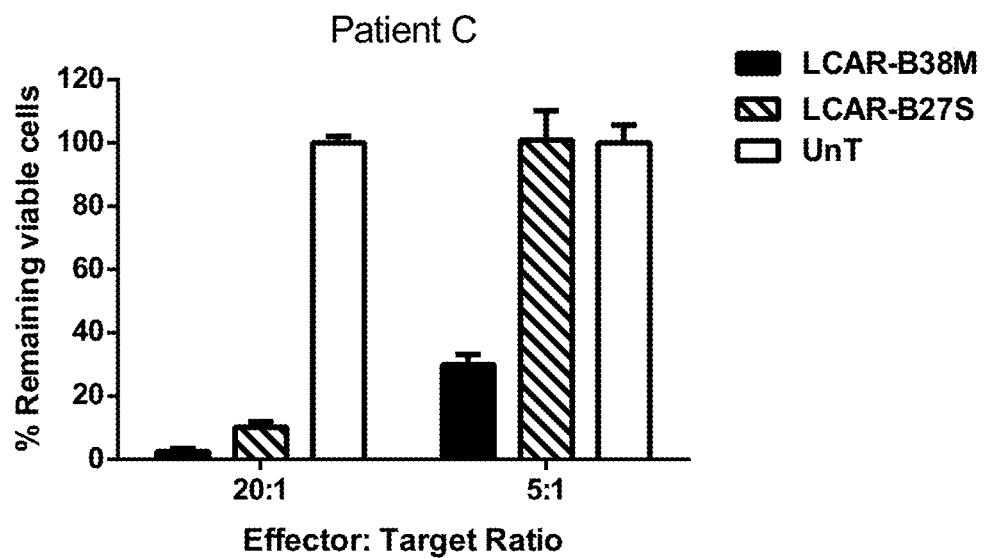

In an in vitro cytotoxicity assay, LCAR-B27S CAR-T cells were prepared from three multiple myeloma patients respectively, and LCAR-B38M CAR-T cells were also prepared respectively from the same three multiple myeloma patients as a control. Both CAR-T cells were co-cultured with RPMI8226. Luc cells at an effector to target ratio (E/T ratio) of 20:1 and 5:1 for 20 hours. As shown in FIG. 14A, CAR-T cells were prepared using T cells from patient A. The percentage of remaining viable cells, as assessed by remaining luciferase activity in RPMI8226. Luc cells, were 3.97±0.75% for LCAR-B38M and 3.17±0.57% for LCAR-B27S, when E/T ratio was 20:1. However, when E/T ratio was 5:1, LCAR-B38M showed higher potencies of killing RPMI8226. Luc cells as compared with LCAR-B27S (33.37±0.75% remaining viable cells for LCAR-B38M, 68.60±1.60% for LCAR-B27S). As shown in FIG. 14B, CAR-T cells were prepared using T cells from patient B. The percentage of remaining viable cells, as assessed by remaining luciferase activity in RPMI8226. Luc cells, were 4.45±0.57% for LCAR-B38M and 9.32±1.16% for LCAR-B27S, when E/T ratio was 20:1. However, when E/T ratio was 5:1, LCAR-B38M again showed higher potencies of killing RPMI8226. Luc cells as compared with LCAR-B27S (40.92±3.00% remaining viable cells for LCAR-B38M, 84.05±1.56% for LCAR-B27S). As shown in FIG. 14C, CAR-T cells were prepared using T cells from patient C. The percentage of remaining viable cells, as assessed by remaining luciferase activity in RPMI8226. Luc cells, were 2.56±0.88% for LCAR-B38M and 10.12±1.83% for LCAR-B27S, when E/T ratio was 20:1. However, when E/T ratio was 5:1, LCAR-B38M again showed higher potencies of killing RPMI8226. Luc cells as compared with LCAR-B27S (29.99±3.13% remaining viable cells for LCAR-B38M, 100.93±9.25% for LCAR-B27S).

In the pilot clinical study, 3 patients were treated with the LCAR-B27S CAR-T cells, in which all the preconditioning, injection and follow-up protocols were identical to those of the clinical study with the bivalent LCAR-B38M CAR. A total dose of $3\times10^6$ cells/kg (patient A), $5\times10^6$ cells/kg (patient B) and $7\times10^6$ cells/kg (patient C) body weight of autologous LCAR-B27S modified CAR-T cells were administered to each patient respectively by intravenous injection in three split doses (20%, 30%, and 50% respectively) over the duration of a week (e.g., on Days 0, 2, and 6). During Days 1-30 of the study, patients were monitored for adverse events, and patient samples were obtained for laboratory assessment. All patients were followed up for at least 36 months after the CAR-T administration.

2 patients among the three patients reached very good partial response (VgPR), but both patients relapsed within 6 months after the CAR-T infusion. The third patient did not show any clinical response. The pilot study with LCAR-B27S was consequently terminated by the IRB with no further patient enrollment.

Objective response rate, complete remission rate and relapse rate from this pilot monovalent BCMA CAR study (LCAR-B27S) and the bivalent BCMA CAR study (LCAR-B38M CAR-T) are shown in Table 11 below. The bivalent BCMA CAR-T had superior clinical efficacy in comparison to the monovalent BCMA CAR-T.

TABLE 11

Comparable clinical data of monovalent and bivalent/bi-epitope BCMA CAR-T therapies

| Agent | N | Dose (cells/kg) | Clinical trial | Objective Response Rate (ORR) | Complete Remission (CR) rate | Relapse Rate (>6 mon) |
|---|---|---|---|---|---|---|
| Monovalent BCMA CAR-T (LCAR-B27S) | 3 | 3, 5, 7 × $10^6$ respectively | Pilot study | 67% | 0% | 67% |
| Bivalent/Bi-epitope BCMA CAR-T (LCAR-B38M) | 35 | 0.3 × $10^6$ – 5.6 × $10^6$ (median = 2.9 × $10^6$) | NCT03 090659 | 100% | 57.1% | 7.5% |

What is claimed is:

1. A chimeric antigen receptor (CAR) comprising a polypeptide comprising:
   (a) an extracellular antigen binding domain comprising a first anti-BCMA single domain antibody (sdAb), and a second anti-BCMA sdAb; and wherein each of the first and second sdAb is a VHH domain;
   (b) a transmembrane domain; and
   (c) an intracellular signaling domain,
   wherein:
   (i) the first anti-BCMA sdAb comprises a CDR1, a CDR2 and a CDR3 as set forth in the VHH domain comprising the amino acid sequence of SEQ ID NO: 124, and
   (ii) the second anti-BCMA sdAb comprises a CDR1, a CDR2, and a CDR3 as set forth in the VHH domain comprising the amino acid sequence of SEQ ID NO: 117.

2. The CAR of claim 1, wherein the first anti-BCMA sdAb is located at the N-terminus of the second anti-BCMA sdAb, or wherein the first anti-BCMA sdAb is located at the C-terminus of the second anti-BCMA sdAb.

3. The CAR of claim 1, wherein the first anti-BCMA sdAb and the second anti-BCMA sdAb are directly fused to each other via a peptide bond or linked to each other via a peptide linker.

4. The CAR of claim 3, wherein the first anti-BCMA sdAb and the second anti-BCMA sdAb are linked to each other via a peptide linker and the peptide linker comprises no more than 50 amino acid residues.

5. The CAR of claim 1, wherein the transmembrane domain is derived from a molecule selected from the group consisting of CD8a, CD4, CD28, CD137, CD80, CD86, CD152 and PD1.

6. The CAR of claim 5, wherein the transmembrane domain is derived from CD8α or CD28.

7. The CAR of claim 1, wherein the intracellular signaling domain comprises a primary intracellular signaling domain of an immune effector cell.

8. The CAR of claim 7, wherein the primary intracellular signaling domain is derived from CD3ζ.

9. The CAR of claim 1, wherein the intracellular signaling domain comprises a co-stimulatory signaling domain.

10. The CAR of claim 9, wherein the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, ligands of CD83 and combinations thereof.

11. The CAR of claim 10, wherein the co-stimulatory signaling domain comprises a cytoplasmic domain of CD28 or a cytoplasmic domain of CD137.

12. The CAR of claim 1, further comprising a hinge domain located between the C-terminus of the extracellular antigen binding domain and the N-terminus of the transmembrane domain.

13. The CAR of claim 12, wherein the hinge domain is derived from CD8α.

14. The CAR of claim 1, further comprising a signal peptide located at the N-terminus of the polypeptide.

15. The CAR of claim 14, wherein the signal peptide is derived from CD8α.

16. An engineered immune effector cell, comprising the CAR of claim 1.

17. The engineered immune effector cell of claim 16, wherein the immune effector cell is a T cell.

18. A pharmaceutical composition, comprising the engineered immune effector cell of claim 17, and a pharmaceutically acceptable carrier.

19. A method of treating a cancer that expresses BCMA in an individual, comprising administering to the individual an effective amount of the pharmaceutical composition of claim 18.

20. The method of claim 19, wherein the cancer is multiple myeloma.

21. The method of claim 19, wherein the cancer is refractory or relapsed multiple myeloma.

* * * * *